US012721891B2

(12) United States Patent
Xue et al.

(10) Patent No.: US 12,721,891 B2
(45) Date of Patent: Sep. 1, 2026

(54) MOLECULAR ENGINEERING TO ENHANCE CAR-T MEDIATED TUMOR IMMUNOTHERAPY

(71) Applicant: HACKENSACK MERIDIAN HEALTH, INC., Edison, NJ (US)

(72) Inventors: Hai-Hui Xue, Nutely, NJ (US); Yi Zhang, Wallingford, PA (US); David Perlin, New York, NY (US); Xin Zhao, Clifton, NJ (US); Wei Hu, Union City, NJ (US)

(73) Assignee: HACKENSACK MERIDIAN HEALTH, INC., Edison, NJ (US)

( * ) Notice: Subject to any disclaimer, the term of this patent is extended or adjusted under 35 U.S.C. 154(b) by 0 days.

(21) Appl. No.: 19/084,311

(22) Filed: Mar. 19, 2025

(65) Prior Publication Data

US 2026/0102494 A1 Apr. 16, 2026

Related U.S. Application Data

(60) Provisional application No. 63/765,909, filed on Mar. 3, 2025, provisional application No. 63/707,903, filed on Oct. 16, 2024.

(51) Int. Cl.

| | |
|---|---|
| ***A61K 40/31*** | (2025.01) |
| ***A61K 40/11*** | (2025.01) |
| ***A61K 40/42*** | (2025.01) |
| ***A61P 35/02*** | (2006.01) |
| ***C07K 14/705*** | (2006.01) |
| ***C07K 16/28*** | (2006.01) |

(52) U.S. Cl.
CPC .............. *A61K 40/31* (2025.01); *A61K 40/11* (2025.01); *A61K 40/4211* (2025.01); *A61P 35/02* (2018.01); *C07K 14/7051* (2013.01); *C07K 16/2803* (2013.01); *A61K 2239/28* (2023.05); *C07K 2317/622* (2013.01)

(58) Field of Classification Search
None
See application file for complete search history.

(56) References Cited

U.S. PATENT DOCUMENTS 11,446,398 B2 9/2022 Barrett et al.

FOREIGN PATENT DOCUMENTS

WO WO-2016168595 A1 * 10/2016 .......... C07K 14/705

OTHER PUBLICATIONS

Lopez-Cantillo et al (Fron. Immun., 13:878209, pp. 1-16, 2022).*
Xing et al (J. Exp. Med., 215(8):2211-2226, 2018).*
Prager, I. et al., "NK cells switch from granzyme B to death receptor-mediated cytotoxicity during serial killing", J Exp Med, vol. 216 Issue No. 9, pp. 2113-2127, Sep. 2, 2019.
Prete, A. D. et al., "Leukocyte trafficking in tumor microenvironment", Curr Opin Pharmacol, vol. 35, pp. 40-47, Aug. 2017.
Prinzing, B. et al., "Deleting DNMT3A in CAR T cells prevents exhaustion and enhances antitumor activity", Sci Transl Med, vol. 13 Issue No. 620, eabh0272, Nov. 17, 2021 (Abstract Only).
Probst, H. C. et al., "Histological analysis of CD11c-DTR/GFP mice after in vivo depletion of dendritic cells", Clin Exp Immunol, vol. 141 Issue No. 3, pp. 398-404, Sep. 2005.
Pungsrinont, T. et al., "Role of PI3K-AKT-mTOR Pathway as a Pro-Survival Signaling and Resistance-Mediating Mechanism to Therapy of Prostate Cancer", Int J Mol Sci, vol. 22 Issue No. 20, pp. 1-25, Oct. 14, 2021.
Qian, B-Z. et al., "Macrophage diversity enhances tumor progression and metastasis", Cell, vol. 141 Issue No. 1, pp. 39-51, Apr. 2, 2010.
Qin, Y. et al., "III-10, a newly synthesized flavonoid, induced differentiation of human U937 leukemia cells via PKCδ activation", Eur J Pharm Sci, vol. 45 Issue No. 5, pp. 648-656, Apr. 11, 2012.
Queirolo, P. et al., "Efficacy and safety of ipilimumab in patients with advanced melanoma and brain metastases", Journal of Neuro-Oncology, vol. 118 Issue No. 1, pp. 109-116, Feb. 16, 2014.
Quigley, M. et al., "Transcriptional analysis of HIV-specific CD8+ T cells shows that PD-1 inhibits T cell function by upregulating BATF", Nat Med, vol. 16 Issue No. 10, pp. 1147-1151, Oct. 2010.
Rafiq, S. et al., "Targeted delivery of a PD-1-blocking scFv by CAR-T cells enhances anti-tumor efficacy in vivo", Nature Biotechnology, vol. 36, pp. 847-856, 2018.
Rajkumar, S. V. et al., "International Myeloma Working Group updated criteria for the diagnosis of multiple myeloma", Lancet Oncol, vol. 15 Issue No. 12, pp. e538-e548, Nov. 2014.

(Continued)

*Primary Examiner* — Brad Duffy
(74) *Attorney, Agent, or Firm* — Bochner PLLC; Beverly W. Lubit

(57) ABSTRACT

The present disclosure provides a chimeric antigen receptor (CAR) immunotherapy for treating a hematologic cancer comprising (a) genetically modifying a population of immune effector cells comprising T cell receptors (TCRs) to stably express at least one CAR, wherein the ectodomain of the CAR specifically binds a cancer antigen; (b) expanding the population of CAR-containing immune effector cells in the presence of one or more cytokines in vitro to achieve a therapeutic dose, wherein the population of CAR-containing immune effector cells exhibits a nonexhausted memory T cell phenotype; and (c) infusing eligible subjects with the CAR-containing immune effector memory T cell phenotype population of cells as needed until the hematologic cancer in the body is destroyed. The intracellular signal transduction domain of the CAR includes 4-1BB, a CD3ζ T cell activation chain and a genetically engineered TLE3, which can be ectopically expressed. The immune effector cell population engineered to express the CAR comprising the engineered TLE3 construct by lentiviral transduction is a CD3+ T cell population or an NK cell. Expression of the engineered TLE3 construct in stimulated CAR-containing immune effector cells in vitro and in vivo xenograft preclinical models promotes activation of genes that promote anti-tumor activity and also represses genes involved in excessive effector function, exhaustion or both.

12 Claims, 19 Drawing Sheets
(19 of 19 Drawing Sheet(s) Filed in Color)

(56) References Cited

OTHER PUBLICATIONS

Ramazi, S. et al., "Posttranslational modifications in proteins: resources, tools and prediction methods", vol. 00 Issue No. baab012, pp. 1-20, Apr. 7, 2021.
Raulet, D. H. "Roles of the NKG2D immunoreceptor and its ligands", Nat Rev Immunol, vol. 3 Issue No. 10, pp. 781-790, Oct. 2003.
Raulet, D. H. et al., "Regulation of ligands for the NKG2D activating receptor", Annu Rev Immunol, vol. 31, pp. 413-441, 2013.
Ren, B. et al., "PRDI-BF1/Blimp-1 repression is mediated by corepressors of the Groucho family of proteins", Genes & Dev. vol. 13, pp. 125-137, 1999.
Reth, M., "Antigen receptor tail clue", Nature, vol. 338 Issue No. 6214, pp. 383-384, Mar. 30, 1989.
Rich, J. T. et al., "A practical guide to understanding Kaplan-Meier curves", Otolaryngol Head Neck Surg, vol. 143 Issue No. 3, pp. 331-336, Sep. 2010.
Rivière, I. et al., "Chimeric Antigen Receptors: A Cell and Gene Therapy Perspective", Molecular Therapy, vol. 25 Issue No. 5, pp. 1117-1124, May 3, 2017.
Robey, E., "Selective Events in T Cell Development", Annual Review of Immunology, vol. 12, pp. 675-705, 1994.
Roeder, R. G. "The role of general initiation factors in transcription by RNA polymerase II", Trends Biochem Sci, vol. 21 Issue No. 9, pp. 327-335, Sep. 1996.
Röllig, C. et al., "Multiple myeloma", Lancet, vol. 385 Issue No. 9983, pp. 2197-2208, May 30, 2015.
Romee, R. et al., "Cytokine-induced memory-like natural killer cells exhibit enhanced responses against myeloid leukemia", Sci Transl Med, vol. 8 Issue No. 357, pp. 1-13, Sep. 21, 2016.
Romeo, C. et al., "Cellular immunity to HIV activated by CD4 fused to T cell or Fc receptor polypeptides", Cell, vol. 64 Issue No. 5, pp. 1037-1046, Mar. 8, 1991.
Romeo, C. et al., "Sequence requirements for induction of cytolysis by the T cell antigenFc receptor ζ chain", Cell, vol. 68 Issue No. 5, pp. p889-p897, Mar. 6, 1992.
Rosa, S. C. D. et al., "11-color, 13-parameter flow cytometry: identification of human naive T cells by phenotype, function, and T-cell receptor diversity", Nat Med, vol. 7(2):245-248, Feb. 2001.
Roybal, K. T. et al., "Precision Tumor Recognition by T Cells With Combinatorial Antigen-Sensing Circuits", Cell, vol. 164 Issue No. 4, pp. 770-779, Feb. 11, 2016.
Royball, K. T. et al., "Engineering T Cells with Customized Therapeutic Response Programs Using Synthetic Notch Receptors", Cell vol. 167 Issue No. 2, pp. 419-432, Oct. 6, 2016.
Rubtsov, A. V. et al., "Toll-like receptor 7 (TLR7)-driven accumulation of a novel CD11c B-cell population is important for the development of autoimmunity", Blood vol. 118 Issue No. 5, pp. 1305-1315, Aug. 4, 2011.
Ruella, M. et al., "Mechanisms of resistance to chimeric antigen receptor-T cells in haematological malignancies", Nat Rev Drug Discov, vol. 22 Issue No. 12, pp. 976-995, Dec. 2023 (Abstract Only).
Ruggeri, L. et al., "Effectiveness of donor natural killer cell alloreactivity in mismatched hematopoietic transplants", Science, vol. 295 Issue No. 5562, pp. 2097-2100, Mar. 15, 2002.
Rycaj, K. et al., "Cell-of-Origin of Cancer versus Cancer Stem Cells: Assays and Interpretations", Cancer Research, vol. 75 Issue No. 19, pp. 4003-4011, Oct. 1, 2015.
Sadelain, M. "CAR therapy: the CD19 paradigm", The Journal of Clinical Investigation, vol. 125 Issue No. 9, pp. 3392-3400, Sep. 1, 2015.
Sadelain, M. et al., "Targeting tumours with genetically enhanced T lymphocytes", Nature Reviews Cancer, vol. 3 Issue No. 1, pp. 35-45, Jan. 2003.
Sadelain, M. et al., "The promise and potential pitfalls of chimeric antigen receptors", Current Opinion in Immunology, vol. 21 Issue No. 2, pp. 215-223, Apr. 2009.
Sak, K. et al., "Established Human Cell Lines as Models to Study Anti-leukemic Effects of Flavonoids", Curr Genomics, vol. 18 Issue No. 1, pp. 3-26, Feb. 2017.
Sallusto, F. et al., "The Role of Chemokine Receptors in Primary, Effector, and Memory Immune Responses", Annu. Rev. Immunol., vol. 18, pp. 593-620, 2000.
Sallusto, F. et al., "Two subsets of memory T lymphocytes with distinct homing potentials and effector functions", Nature, vol. 401 Issue No. 6754, pp. 708-712, Oct. 14, 1999.
Samelson, L. E. et al., "Tyrosine kinases and tyrosine-based activation motifs. Current research on activation via the T cell antigen receptor", J Biol Chem, vol. 267 Issue No. 35, pp. 24913-24916, Dec. 15, 1992.
Santi, A. et al., "Cancer Associated Fibroblasts: The Architects of Stroma Remodeling", Proteomics, vol. 18 Issue No. 5-6, pp. 1-15, Mar. 2018.
Saoulli, K. et al., "CD28-independent, TRAF2-dependent Costimulation of Resting T Cells by 4-1BB Ligand", J Exp Med., vol. 187 Issue No. 11, pp. 1849-1862, Jun. 1, 1998.
Schietinger, A. et al., "Tolerance and exhaustion: defining mechanisms of T cell dysfunction", Trends in Immunology, vol. 35 Issue No. 2, pp. 51-60, Feb. 2014.
Schietinger, A. et al., "Tumor-Specific T Cell Dysfunction Is a Dynamic Antigen-Driven Differentiation Program Initiated Early during Tumorigenesis", Immunity, vol. 45 Issue No. 2, pp. 389-401, Aug. 16, 2016.
Schluns, K. S. et al., "Cytokine control of memory T-cell development and survival", vol. 3 Issue No. 4, pp. 269-279, Apr. 2003.
Schluns, K. S. et al., "Interleukin-7 mediates the homeostasis of naïve and memory CD8 T cells in vivo", Nat Immunol, vol. 1 Issue No. 5, pp. 426-432, Nov. 2000.
Schraml, B. U. et al., "Genetic tracing via DNGR-1 expression history defines dendritic cells as a hematopoietic lineage", Cell, vol. 154 Issue No. 4, pp. 843-858, Aug. 15, 2013.
Schraml, B. U. et al., "The AP-1 transcription factor Batf controls T(H)17 differentiation", Nature, vol. 460 Issue No. 7253, pp. 405-409, Jul. 16, 2009.
Schulz, C. et al., "A lineage of myeloid cells independent of Myb and hematopoietic stem cells", Science, vol. 336 Issue No. 6077, pp. 86-90, Apr. 6, 2012.
Schwartz, R. H. "A cell culture model for T lymphocyte clonal anergy", Science, vol. 248 Issue No. 4961, pp. 1349-1356, Jun. 15, 1990.
Schwartz, R. H. "T cell anergy", Annual Review of Immunology, vol. 21, pp. 305-334, 2003.
Schwarz, H. et al., "ILA, the human 4-1BB homologue, is inducible in lymphoid and other cell lineages", Blood, vol. 85 Issue No. 4, pp. 1043-1052, Feb. 15, 1995.
Montfoort, N. V. et al., "Antigen storage compartments in mature dendritic cells facilitate prolonged cytotoxic T lymphocyte cross-priming capacity", Proc Natl Acad Sci USA., vol. 106 Issue No. 16, pp. 6730-6735, Apr. 21, 2009.
Moon, E. K. et al., "Multifactorial T-cell hypofunction that is reversible can limit the efficacy of chimeric antigen receptor-transduced human T cells in solid tumors", Clinical Cancer Research, vol. 20 Issue No. 16, pp. 4262-4273, Aug. 15, 2014.
Morello, A. et al., "Mesothelin-Targeted CARs: Driving T Cells to Solid Tumors", Cancer Discovery, vol. 6 Issue No. 2, pp. 133-146, Feb. 2016.
Morgan, G. J. et al., "The genetic architecture of multiple myeloma", Nat Rev Cancer, vol. 12 Issue No. 5, pp. 335-348, Apr. 12, 2012.
Morgan, R. A. et al., "Case report of a serious adverse event following the administration of T cells transduced with a chimeric antigen receptor recognizing ERBB2", Mol Ther, vol. 18 Issue No. 4, pp. 843-851, Apr. 2010.
Morris, G. P. et al., "How the TCR balances sensitivity and specificity for the recognition of self and pathogens", Nat Immunol, vol. 13 Issue No. 2, pp. 121-128, Jan. 19, 2012.
Morsut, L. et al., "Engineering Customized Cell Sensing and Response Behaviors Using Synthetic Notch Receptors", Cell, vol. 164 Issue No. 4, pp. 780-791, Feb. 2016.

(56) References Cited

OTHER PUBLICATIONS

Motzer, R. J. et al., "Nivolumab versus Everolimus in Advanced Renal-Cell Carcinoma", The New England Journal of Medicine, vol. 373 Issue No. 19, pp. 1-11, Nov. 5, 2015.
Mueller, D. L., "E3 ubiquitin ligases as T cell anergy factors", Nature Immunology, vol. 5, pp. 883-890, Aug. 27, 2004.
Munter, S. D. et al., "Nanobody Based Dual Specific CARs", Int. J. Mol. Sci. 2018, vol. 19 Issue No. 2, 2018, 11 pages.
Murphy, T. L. et al., "Specificity through cooperation: BATF-IRF interactions control immune-regulatory networks", Nat Rev Immunol, vol. 13 Issue No. 7, pp. 499-509, Jul. 2013.
Murray, P. J. et al., "Protective and pathogenic functions of macrophage subsets", Nature Reviews Immunology, vol. 11, pp. 723-737, Oct. 14, 2011.
Nagarsheth, N. B. et al., "TCR-engineered T cells targeting E7 for patients with metastatic HPV-associated epithelial cancers", Nature Medicine, vol. 27, pp. 419-425, Feb. 8, 2021.
Nagarsheth, N. et al., "Chemokines in the cancer microenvironment and their relevance in cancer immunotherapy", Nat Rev Immunol, vol. 17 Issue No. 9, pp. 559-572, Sep. 2017.
Naik, S. H. et al., "Diverse and heritable lineage imprinting of early haematopoietic progenitors", Nature, pp. 496 Issue No. 7444, pp. 229-232, Apr. 11, 2013.
Nazareth, M. R. et al., "Characterization of human lung tumor-associated fibroblasts and their ability to modulate the activation of tumor-associated T cells", Journal of Immunology, vol. 178(9):5552-5562.
Nibbs, R. J. B. et al., "Immune regulation by atypical chemokine receptors", Nat Rev Immunol, vol. 13 Issue No. 11, pp. 815-829, Nov. 2013.
Nishio, N. et al., "Armed Oncolytic Virus Enhances Immune Functions of Chimeric Antigen Receptor-Modified T Cells in Solid Tumors", Cancer Res., vol. 74 Issue No. 18, pp. 5195-5205, Jul. 24, 2014.
Nowacki, T. M. et al., "Granzyme B production distinguishes recently activated CD8(+) memory cells from resting memory cells", Cell Immunol, vol. 247 Issue No. 1, pp. 36-48, May 2007.
Nozaki, T. et al., "Chemical Catalysis Intervening to Histone Epigenetics", Acc. Che. Res., vol. 54 Issue No. 9, pp. 2313-2322, Apr. 13, 2021.
Odorizzi, P. M. et al., "Inhibitory receptors on lymphocytes: insights from infections", Journal of Immunology, vol. 188 Issue No. 7, pp. 2957-2965, Apr. 1, 2012.
Ogawa, S. et al., "Physical and functional interactions between STAT5 and Runx transcription factors", J Biochem, vol. 143 Issue No. 5, pp. 695-709, Jun. 2008 (Abstract Only).
Ohtsubo, K. et al., "Glycosylation in cellular mechanisms of health and disease", Cell, vol. 126 Issue No. 5, pp. 855-867, Sep. 8, 2006.
Okazaki, T. et al., "A rheostat for immune responses: the unique properties of PD-1 and their advantages for clinical application", Nature Immunology, vol. 14 Issue No. 12, pp. 1-35, Dec. 2013.
Olson, J. A. et al., "NK cells mediate reduction of GVHD by inhibiting activated, alloreactive T cells while retaining GVT effects", Blood, vol. 115 Issue No. 21, pp. 4293-4301, May 27, 2010.
Orian, A. et al., "A Myc-Groucho complex integrates EGF and Notch signaling to regulate neural development", PNAS, vol. 104 Issue No. 40, pp. 15771-15776, Oct. 2, 2007.
Orlando, E. J. et al., "Genetic mechanisms of target antigen loss in CAR19 therapy of acute lymphoblastic leukemia", Nature Medicine, vol. 24 Issue No. 10, pp. 1504-1506, Oct. 2018.
O'Shea, J. J. et al., "JAKs and STATs in immunity, immunodeficiency, and cancer", N Engl J Med, vol. 368 Issue No. 2, pp. 161-170, Jan. 10, 2013.
Owen-Hughes, T. et al., "Persistent Site-Specific Remodeling of a Nucleosome Array by Transient Action of the SWI/SNF Complex", Science, vol. 273 Issue No. 5274, pp. 513-516, Jul. 26, 1996.
Pai-Scherf, L. et al., "FDA Approval Summary: Pembrolizumab for Treatment of Metastatic Non-Small Cell Lung Cancer: First-Line Therapy and Beyond", Oncologist, vol. 22 Issue No. 11, pp. 1392-1399, Nov. 2017.
Palazón, A. et al., "Agonist anti-CD137 mAb act on tumor endothelial cells to enhance recruitment of activated T lymphocytes", Cancer Res, vol. 71 Issue No. 3, pp. 801-811, Feb. 1, 2011.
Paley, M. A. et al., "Progenitor and terminal subsets of CD8+ T cells cooperate to contain chronic viral infection", Science, vol. 338 Issue No. 6111, pp. 1220-1225, Nov. 30, 2012.
Pardoll, D. M. "The blockade of immune checkpoints in cancer immunotherapy", Nat Rev Cancer, vol. 12 Issue No. 4, pp. 252-264, Mar. 22, 2012.
Pardoll, D. M. "The blockade of immune checkpoints in cancer immunotherapy", Nature Reviews Cancer, vol. 12, pp. 252-264, Mar. 22, 2012.
Parker, K. R. et al., "Single-Cell Analyses Identify Brain Mural Cells Expressing CD19 as Potential Off-Tumor Targets for CAR-T Immunotherapies", Cell, vol. 183 Issue No. 1, pp. 126-142, Oct. 1, 2020.
Parry, R. V. et al., "CTLA-4 and PD-1 receptors inhibit T-cell activation by distinct mechanisms", Molecular and Cellular Biology, vol. 25 Issue No. 21, pp. 9543-9553, Nov. 2005.
Patente, T. A. et al., "Human Dendritic Cells: Their Heterogeneity and Clinical Application Potential in Cancer Immunotherapy", Front. Immunol., vol. 9 Issue No. 3176, pp. 1-18, Jan. 2019.
Paul, M. R. et al., "Treatment of Recurrent Refractory Pediatric Pre-B Acute Lymphoblastic Leukemia Using Inotuzumab Ozogamicin Monotherapy Resulting in CD22 Antigen Expression Loss as a Mechanism of Therapy Resistance", Journal of Pediatric Hematology/Oncology, vol. 41 Issue No. 8, pp. e546-e549, Nov. 2019.
Paulson, A. G. et al., "Acquired cancer resistance to combination immunotherapy from transcriptional loss of class I HLA", Nature Communications, vol. 9 Issue No. 1, pp. 1-10, Sep. 24, 2018.
Pavlasova, G. et al., "The regulation and function of CD20: an "enigma" of B-cell biology and targeted therapy", Haematologica, vol. 105 Issue No. 6, pp. 1494-1506, Jun. 2020.
Pawlyn, C. et al., "Coexistent hyperdiploidy does not abrogate poor prognosis in myeloma with adverse cytogenetics and may precede IGH translocations", Blood, vol. 125 Issue No. 5, pp. 831-840, Jan. 29, 2015.
Pereira, B. I. et al., "Senescent cells evade immune clearance via HLA-E-mediated NK and CD8+ T cell inhibition", Nat Commun, vol. 10 Issue No. 1, pp. 1-13, Jun. 3, 2019.
Pereira, B. I. et al., "Sestrins induce natural killer function in senescent-like CD8+ T cells", Nature Immunology, vol. 21 Issue No. 6, pp. 684-694, Jun. 2020.
Philip, M. et al., "CD8+ T cell differentiation and dysfunction in cancer", Nat Rev Immunol, vol. 22 Issue No. 4, pp. 209-223, Apr. 2022.
Pipkin, M. E. "Runx proteins and transcriptional mechanisms that govern memory CD8 T cell development", Immunol Rev, vol. 300 Issue No. 1, pp. 100-124, Mar. 2021.
Plesner, T. et al., "Controversy in the Use of CD38 Antibody for Treatment of Myeloma: Is High CD38 Expression Good or Bad?", Cells, vol. 9 Issue No. 2, 2020, 5 pages.
Poljak, R.J. "Production and structure of diabodies", Structure, vol. 2 Issue No. 12, pp. 1121-1131, Dec. 15, 1994.
Polletta, L. et al., "SIRT5 regulation of ammonia-induced autophagy and mitophagy", Autophagy, vol. 11 Issue No. 2, pp. 253-270, 2015.
Pollok, K. E. et al., "4-1BB T-cell antigen binds to mature B cells and macrophages, and costimulates anti-mu-primed splenic B cells", Eur J Immunol, vol. 24 Issue No. 2, pp. 367-374, Feb. 1994.
Porter, D. L. et al., "Chimeric Antigen Receptor-Modified T Cells in Chronic Lymphoid Leukemia", N Engl J Med, vol. 365, pp. 725-733, 2011.
Sen, D. R. et al, "The epigenetic landscape of T cell exhaustion" Science, vol. 354 Issue No. 6316, pp. 1165-1169, Dec. 2, 2016.
Seo, H. et al., "BATF and IRF4 cooperate to counter exhaustion in tumor-infiltrating CAR T cells", Nature Immunology, vol. 22, pp. 983-995, Jul. 19, 2021.
Seo, W. et al., "The Roles of RUNX Family Proteins in Development of Immune Cells", Mol Cells, vol. 43 Issue No. 2, pp. 107-113, Jan. 10, 2020.
Serrels, A. et al., "Nuclear FAK controls chemokine transcription, Tregs, and evasion of anti-tumor immunity", Cell, vol. 163 Issue No. 1, pp. 160-173, Sep. 24, 2015.

(56) References Cited

OTHER PUBLICATIONS

Shah, N. et al., "Phase I study of cord blood-derived natural killer cells combined with autologous stem cell transplantation in multiple myeloma", Br J Haematol, vol. 177 Issue No. 3, pp. 457-466, May 2017.
Shalabi, H. et al., "Chapter 12—Cell-Based Therapies: A New Frontier of Personalized Medicine", Novel Designs of Early Phase Trials for Cancer Therapeutics, pp. 175-191, 2018.
Shan, Q. et al., "Ectopic Tcf1 expression instills a stem-like program in exhausted CD8+ T cells to enhance viral and tumor immunity", Cell Mol Immunol, vol. 18 Issue No. 5, pp. 1262-1277, May 2021.
Shan, Q. et al., "Tcf1 and Lef1 provide constant supervision to mature CD8+ T cell identity and function by organizing genomic architecture", Nat Commun, vol. 12 Issue No. 1, pp. 1-20, Oct. 6, 2021.
Shan, Q. et al., "Tcf1 preprograms the mobilization of glycolysis in central memory CD8+ T cells during recall responses", Nat Immunol, vol. 23 Issue No. 3, pp. 386-398, Mar. 2022.
Shan, Q. et al., "The transcription factor Runx3 guards cytotoxic CD8+ effector T cells against deviation towards follicular helper T cell lineage", Nat Immunol, vol. 18 Issue No. 8, pp. 931-939, Aug. 2017.
Shaw, A. R. et al., "Adenovirotherapy Delivering Cytokine and Checkpoint Inhibitor Augments CAR T Cells against Metastatic Head and Neck Cancer", Mol Ther, vol. 25 Issue No. 11, pp. 2440-2451, Nov. 1, 2017.
Shimasaki, N. et al., "NK cells for cancer immunotherapy", Nat Rev Drug Discov, vol. 19 Issue No. 3, pp. 200-218, Mar. 2020.
Shores, E. W. et al., "Role of the Multiple T Cell Receptor (TCR)-ζ Chain Signaling Motifs in Selection of the T Cell Repertoire", J Exp Med, vol. 185 Issue No. 5, pp. 893-900, Mar. 3, 1997.
Shuai, K. et al., "Regulation of JAK-STAT signalling in the immune system", Nat Rev Immunol, vol. 3 Issue No. 11, pp. 900-911, Nov. 2003.
Shvedunova, M. et al., "Modulation of cellular processes by histone and non-histone protein acetylation", Nat Rev Mol Cell Biol, vol. 23 Issue No. 5, pp. 329-349, May 2022 (Abstract Only).
Siddiqui, I. et al., "Intratumoral Tcf1+PD-1+CD8+ T Cells with Stem-like Properties Promote Tumor Control in Response to Vaccination and Checkpoint Blockade Immunotherapy", Immunity, vol. 50 Issue No. 1, pp. 195-211, Jan. 15, 2019.
Sionov R.V. et al., "Regulation of Bim in Health and Disease", Oncotarget (2015), vol. 6 pp. 23058-23134 (Abstract Only).
Sivori, S. et al., "Human NK cells: surface receptors, inhibitory checkpoints, and translational applications", Cell Mol Immunol, vol. 16 Issue No. 5, pp. 430-441, May 2019.
Smith, C. C. et al., "Alternative tumour-specific antigens", Nature Reviews Cancer, vol. 19, pp. 465-478, 2019.
Smith, S. E. et al., "Signals through 4-1BB inhibit T regulatory cells by blocking IL-9 production enhancing antitumor responses", Cancer Immunol Immunother., vol. 60 Issue No. 12, pp. 1775-1787, Jul. 26, 2011.
Socovich, A. M. et al., "The cancer matrisome: From comprehensive characterization to biomarker discovery", Semin Cell Dev Biol., vol. 89, pp. 157-166, May 2019.
Song, Y. et al., "T-cell Immunoglobulin and ITIM Domain Contributes to CD8+ T-cell Immunosenescence", Aging Cell, vol. 17 Issue No. 2, pp. 1-12, Apr. 2018.
Soto-Nieves, N. et al., "Transcriptional complexes formed by NFAT dimers regulate the induction of T cell tolerance", J Exp Med , vol. 206 Issue No. 4, pp. 867-876, 2009.
Spill, F. et al., "Impact of the physical microenvironment on tumor progression and metastasis", Curr Opin Biotechnol., vol. 40, pp. 41-48, Aug. 2016.
Spitz, F. et al., "Transcription factors: from enhancer binding to developmental control", Nature Reviews Genetics, vol. 13, pp. 613-626, Aug. 7, 2012.
Staal, F. J. T. et al., "The canonical Wnt signaling pathway plays an important role in lymphopoiesis and hematopoiesis", Eur J Immunol., vol. 38 Issue No. 7, pp. 1788-1794, Jul. 2008.
Stamatiou, K. et al., "Ki-67 is necessary during DNA replication for fork protection and genome stability", Genome Biology, vol. 25 Issue No. 105, pp. 1-33, Apr. 22, 2024.
Stegen, S. J. C. V. et al., "The pharmacology of second-generation chimeric antigen receptors", Nature Reviews Drug Discovery, vol. 14 Issue No. 7, pp. 499-509, Jul. 2015.
Steinke, F. C. et al., "From inception to output, Tcf1 and Lef1 safeguard development of T cells and innate immune cells", Immunology at the University of Iowa, vol. 59, pp. 45-55, May 22, 2014.
Stephens, H. A. "MICA and MICB genes: can the enigma of their polymorphism be resolved?", Trends Immunol, vol. 22 Issue No. 7, pp. 378-385, Jul. 2001.
Stinchcombe, J. C. et al., "Centrosome polarization delivers secretory granules to the immunological synapse", Nature, vol. 443 Issue No. 7110, pp. 462-465, Sep. 28, 2006.
Stoeckius, M. et al., "Simultaneous epitope and transcriptome measurement in single cells", Nature Methods, vol. 14, pp. 865-868, Jul. 31, 2017.
Sun, J. C. et al., "Adaptive immune features of natural killer cells", Nature, vol. 457 Issue No. 7229, pp. 557-561, Jan. 29, 2009.
Sun, W-W. et al., "Characteristics of circulating tumor cells in organ metastases, prognosis, and T lymphocyte mediated immune response", OncoTargets and Therapy, vol. 10, pp. 2413-2424, 2017.
Sutton, V. R. et al., "Initiation of Apoptosis by Granzyme B Requires Direct Cleavage of Bid, but Not Direct Granzyme B-Mediated Caspase Activation", J Exp Med, vol. 192 Issue No. 10, pp. 1403-1414, Nov. 13, 2000.
Taggart, D. et al., "Anti-PD-1/anti-CTLA-4 efficacy in melanoma brain metastases depends on extracranial disease and augmentation of CD8+ T cell trafficking", Proceedings of the National Academy of Sciences of the United States of America, vol. 115 Issue No. 7, pp. E1540-E1549, Feb. 13, 2018.
Takahashi, C. et al., "Cutting Edge: 4-1BB Is a Bona Fide CD8 T Cell Survival Signal", The Journal of Immunology, vol. 162 Issue No. 9, pp. 5037-5040, May 1999 (Abstract Only).
Tanaka, T. et al., "The Extracellular Signal-Regulated Kinase Pathway Phosphorylates AML1, an Acute Myeloid Leukemia Gene Product, and Potentially Regulates Its Transactivation Ability", Molecular and Cellular Biology, vol. 16 Issue No. 7, pp. 3967-3979, 1996.
Taniuchi, I. et al., "Epigenetic gene silencing by Runx proteins", Oncogene, vol. 23 Issue No. 24, pp. 4341-4345, May 24, 2004.
Taraseviciute, A. et al., "Chimeric Antigen Receptor T Cell-Mediated Neurotoxicity in Nonhuman Primates", Cancer Discov, vol. 8 Issue No. 6, pp. 750-763, Jun. 2018.
Tay, S. L. et al., "RUNX Poly(ADP-Ribosyl)ation and BLM Interaction Facilitate the Fanconi Anemia Pathway of DNA Repair", Cell Reports, vol. 24 Issue No. 7, pp. 1747-1755, Aug. 14, 2018.
Tchou, J. et al., "Safety and Efficacy of Intratumoral Injections of Chimeric Antigen Receptor (CAR) T Cells in Metastatic Breast Cancer", Cancer Immunol Res vol. 5 Issue No. 12, pp. 1152-1161, Dec. 2017.
Teijeira, A. et al., "CD137 on inflamed lymphatic endothelial cells enhances CCL21-guided migration of dendritic cells", The FASEB Journal, vol. 26 Issue No. 8, pp. 3380-3392, Aug. 2012.
Tesmer, L. A. et al., "Th17 cells in human disease", Immunol Rev, vol. 223, pp. 87-113, Jun. 2008.
Textor, A. et al., "Efficacy of CAR T-cell Therapy in Large Tumors Relies upon Stromal Targeting by IFN gamma", Cancer Research, vol. 74 Issue No. 23, pp. 6796-6805, Dec. 1, 2014.
Titov, A. et al., "The biological basis and clinical symptoms of CAR-T therapy-associated toxicites", Cell Death & Disease, vol. 9 Issue No. 9, 2018, 15 pages.
Topalian, S. L. et al., "Immune Checkpoint Blockade: A Common Denominator Approach to Cancer Therapy", Cancer Cell, vol. 27 Issue No. 4, pp. 450-461, Apr. 13, 2015.
Tran, E. et al., "Immune targeting of fibroblast activation protein triggers recognition of multipotent bone marrow stromal cells and cachexia", J Exp Med vol. 210 Issue No. 6, pp. 1125-1135, Jun. 3, 2013.
Tsun, A. et al., "Centrosome docking at the immunological synapse is controlled by Lck signaling", J Cell Biol, vol. 192 Issue No. 4, pp. 663-674, Feb. 21, 2011.

(56) References Cited

OTHER PUBLICATIONS

Turki-Judeh, W. et al., "Groucho: a corepressor with instructive roles in development", Curr Top Dev Biol, vol. 98, pp. 65-96, 2012.
Lareau, C. A. et al., "Charting the tumor antigen maps drawn by single-cell genomics", Cancer Cell, vol. 39 Issue No. 12, pp. 1553-1557, Dec. 13, 2021.
Leblay, N. et al., "Deregulation of Adaptive T Cell Immunity in Multiple Myeloma: Insights Into Mechanisms and Therapeutic Opportunities", Frontiers in Oncology, vol. 10, pp. 1-36, May 5, 2020.
Lee, D. W. et al., "ASTCT Consensus Grading for Cytokine Release Syndrome and Neurologic Toxicity Associated with Immune Effector Cells", Biol Blood Marrow Transplant, vol. 25 Issue No. 4, pp. 625-638, Apr. 2019.
Lee, D. Y. et al., "4-1BB Signaling Activates the T Cell Factor 1 Effector/β-Catenin Pathway with Delayed Kinetics via ERK Signaling and Delayed PI3K/AKT Activation to Promote the Proliferation of CD8+ T Cells", PLOS One, vol. 8 Issue No. 7, pp. 1-11, Jul. 2013.
Lee, H-W. et al., "4-1BB promotes the survival of CD8+ T lymphocytes by increasing expression of Bcl-xL and Bfl-1", J Immunol, vol. 169 Issue No. 9, pp. 4882-4888, Nov. 1, 2002.
Lee, J-W. et al., "RUNX3 and p53: How Two Tumor Suppressors Cooperate Against Oncogenic Ras?", Advances in Exptl Med & Biol., vol. 962, pp. 321-332, Mar. 16, 2017.
Lee, S-H. et al., "The effects of agonistic α-4-1BB antibody on natural killer cell function", J Immunol, vol. 196 Issue No. (1_Supplement) 61.4, 2016, 1 page (Abstract Only).
Letourneur, F. et al., "T-cell and basophil activation through the cytoplasmic tail of T-cell-receptor zeta family proteins", Proceedings of the National Academy of Sciences of the United States of America, vol. 88 Issue No. 20, pp. 8905-8909, Oct. 15, 1991.
Levanon, D. et al., "Transcriptional repression by AML1 and LEF-1 is mediated by the TLE/Groucho corepressors", PNAS, vol. 95 Issue No. 20, pp. 11590-11595, Sep. 29, 1998.
Levine, B. L. et al., "Global Manufacturing of CAR T Cell Therapy", Molecular Therapy Methods & Clinical Development, vol. 4, pp. 92-101, Dec. 31, 2016.
Li, P. et al., "BATF-JUN is critical for IRF4-mediated transcription in T cells", Nature, vol. 490 Issue No. 7421, pp. 543-546, Oct. 25, 2012.
Li, Y. et al., "Id2 epigenetically controls CD8+ T-cell exhaustion by disrupting the assembly of the Tcf3-LSD1 complex", Cellular & Molecular Immunology, vol. 21, pp. 292-308, 2024.
Liang, C. et al., "TOX as a potential target for immunotherapy in lymphocytic malignancies", Biomarker Research, vol. 9 Issue No. 20, Mar. 20, 2021, 8 pages.
Liddy, K. A. et al., "Functional decorations: post-translational modifications and heart disease delineated by targeted proteomics", Genome Medicine, vol. 5 Issue No. 20, 2013, 12 pages.
Lim, W. A. et al., "The Principles of Engineering Immune Cells to Treat Cancer", Cell, vol. 168 Issue No. 4, pp. 724-740, Feb. 9, 2017.
Liu, E. et al., "Use of CAR-Transduced Natural Killer Cells in CD19-Positive Lymphoid Tumors", N Engl J Med, vol. 382, pp. 545-553, Feb. 5, 2020.
Liu, J. et al., "Post-Translational Modification Control of Innate Immunity", Immunity, vol. 45 Issue No. 1, pp. 15-30, Jul. 19, 2016.
Liu, S. et al., "RUNX1 inhibits proliferation and induces apoptosis of t(8;21) leukemia cells via KLF4-mediated transactivation of P57", Haematologica, vol. 104 Issue No. 8, pp. 1-44, Aug. 2019.
Loberg, R. D. et al., "Enhanced Glycogen Synthase Kinase-3 Activity Mediates Hypoxia-induced Apoptosis of Vascular Smooth Muscle Cells and Is Prevented by Glucose Transport and Metabolism", J. Biol. Chem., vol. 277 Issue No. 44, pp. 41667-41673, 2002.
Loeb, L. A. et al., "Advances in chemical carcinogenesis: a historical review and prospective", Cancer Research, vol. 68 Issue No. 17, pp. 6863-6872, Sep. 1, 2008.
Long, A. H. et al., "4-1BB costimulation ameliorates T cell exhaustion induced by tonic signaling of chimeric antigen receptors", Nature Medicine, vol. 21 Issue No. 6, pp. 581-590, Jun. 2015.
López-Soto, A. et al., "Control of Metastasis by NK Cells", Cancer Cell, vol. 32 Issue No. 2, pp. 135-154, Aug. 14, 2017.
Lorsbach, R. B. et al., "Plasma Cell Myeloma and Related Neoplasms", American Journal of Clinical Pathology, vol. 136 Issue No. 2, pp. 168-182, Aug. 2011.
Love, J. J. et al., "Structural basis for DNA bending by the architectural transcription factor LEF-1", Nature, vol. 376, pp. 791-795, Aug. 31, 1995.
Lynn, R. C. et al., "c-Jun overexpression in CAR T cells induces exhaustion resistance", Nature, vol. 576, pp. 293-300, Dec. 4, 2019.
Ma, M. et al., "NKG2C+NKG2A—Natural Killer Cells are Associated with a Lower Viral Set Point and may Predict Disease Progression in Individuals with Primary HIV Infection", Front Immunol, vol. 8, Issue No. 1176, pp. 1-12, Sep. 2017.
Macek, B. et al., "Protein post-translational modifications in bacteria", Nat Rev Microbiol, vol. 17 Issue No. 11, pp. 651-664, Nov. 2019.
Machuldova, A. et al., "Role of Polymorphisms of NKG2D Receptor and Its Ligands in Acute Myeloid Leukemia and Human Stem Cell Transplantation", Front Immunol, vol. 12 Issue No. 651751, Mar. 30, 2021.
Mahbub, A. A. et al., "Differential Effects of Polyphenols on Proliferation and Apoptosis in Human Myeloid and Lymphoid Leukemia Cell Lines", Anticancer Agents med. Chem., vol. 13 Issue No. 10, pp. 1601-1613, 2013.
Maher, J. et al., "Human T-lymphocyte cytotoxicity and proliferation directed by a single chimeric TCRzeta /CD28 receptor", Nature Biotechnology, vol. 20 Issue No. 1, pp. 70-75, Jan. 2002.
Majzner, R. G. et al., "Clinical lessons learned from the first leg of the CAR T cell journey", Nature Medicine, vol. 25 Issue No. 9, pp. 1341-1355, Sep. 2019.
Mancuso, S. et al., "Immunosenescence and lymphomagenesis", Immun Ageing, vol. 15 Issue No. 22, Sep. 21, 2018, 7 pages.
Martin, M. D. et al., "Defining Memory CD8 T Cell", Front Immunol, vol. 9 Issue No. 2692, pp. 1-10, Nov. 2018.
Martinez, M. et al., "CAR T Cells for Solid Tumors: New Strategies for Finding, Infiltrating, and Surviving in the Tumor Microenvironment", Frontiers in Immunology, vol. 10 Issue No. 128, pp. 1-21, Feb. 2019.
Mattei, F. et al., "Trogocytosis in innate immunity to cancer is an intimate relationship with unexpected outcomes", iScience, vol. 25 Issue No. 105110, pp. 1-21, Oct. 21, 2022.
Maude, S. L. et al., "Chimeric antigen receptor T cells for sustained remissions in leukemia", The New England Journal of Medicine, vol. 371 Issue No. 16, pp. 1507-1517, Oct. 16, 2014.
Maus, M. V. et al., "Ex vivo expansion of polyclonal and antigen-specific cytotoxic T lymphocytes by artificial APCs expressing ligands for the T-cell receptor, CD28 and 4-1BB", Nat Biotechnol, vol. 20 Issue No. 2, pp. 143-148, Feb. 2002.
Maus, M. V. et al., "Making Better Chimeric Antigen Receptors for Adoptive T-cell Therapy", Clinical Cancer Research, vol. 22 Issue No. 8, pp. 1875-1884, Apr. 15, 2016.
Mcarthur, E. et al., "Topologically associating domain boundaries that are stable across diverse cell types are evolutionarily constrained and enriched for heritability", Am J Hum Genet, vol. 108 Issue No. 2, pp. 269-283, Feb. 4, 2021.
Mcgovern, N. et al., "Human dermal CD14 cells are a transient population of monocyte-derived macrophages", Immunity, vol. 41 Issue No. 3, pp. 465-477, Sep. 18, 2014.
Mclane, L. M. et al., "CD8 T Cell Exhaustion During Chronic Viral Infection and Cancer", Annu Rev Immunol, vol. 37, pp. 457-495, Apr. 26, 2019.
Mcmillin, D. W. et al., "Compartment-Specific Bioluminescence Imaging platform for the high-throughput evaluation of antitumor immune function", Blood, vol. 119 Issue No. 15, pp. e131-e138, Apr. 12, 2012.
Mego, M. et al., "Circulating Tumor Cells (CTC) Are Associated with Defects in Adaptive Immunity in Patients with Inflammatory Breast Cancer", Journal of Cancer, vol. 7 Issue No. 9, pp. 1095-1104.
Melsen, J. E. et al., "Human Circulating and Tissue-Resident CD56(bright) Natural Killer Cell Populations", Front Immunol, vol. 7 Issue No. 262, pp. 1-10, Jun. 2016.

(56) References Cited

OTHER PUBLICATIONS

Menter, T. et al., "Lymphomas and Their Microenvironment: A Multifaceted Relationship", Pathobiology, vol. 86 Issue No. 5-6, pp. 225-236, 2019.

Metelli, A. et al., "Surface Expression of TGFB Docking Receptor GARP Promotes Oncogenesis and Immune Tolerance in Breast Cancer", Cancer Research, vol. 76 Issue No. 24, pp. 7106-7117, Dec. 15, 2016.

Meyer-Schwesinger, C. et al., "The ubiquitin-proteasome system in kidney physiology and disease", Nat Rev Nephrol, vol. 15 Issue No. 7, pp. 393-411, Jul. 2019.

Milner, J. D. et al., "Early-onset lymphoproliferation and autoimmunity caused by germline STAT3 gain-of-function mutations", Blood, vol. 125 Issue No. 4, pp. 591-599, Jan. 22, 2015.

Minegishi, Y. et al., "Dominant-negative mutations in the DNA-binding domain of STAT3 cause hyper-IgE syndrome", Nature, vol. 448 Issue No. 7157, pp. 1058-1062, Aug. 30, 2007.

Mognol, G. P. et al., "Exhaustion-associated regulatory regions in CD8+ tumor-infiltrating T cells", Proc Natl Acad Sci USA, vol. 114 Issue No. 13, pp. E2776-E2785, Mar. 28, 2017.

Tyagarajan, S. et al., "Optimizing CAR-T Cell Manufacturing Processes during Pivotal Clinical Trials", Mol Ther Methods Clin Dev, vol. 16, pp. 136-144, Nov. 29, 2019.

Ubersax, J. A. et al., "Mechanisms of specificity in protein phosphorylation", Nat Rev Mol Cell Biol, vol. 8 Issue No. 7, pp. 530-541, Jul. 2007.

Unsoeld, H. et al., "Cutting Edge: CCR7+ and CCR7− Memory T Cells Do Not Differ in Immediate Effector Cell Function", The Journal of Immunology, vol. 169 Issue No. 2, pp. 638-641, Jul. 2002.

Utzschneider, D. T. et al., "Early precursor T cells establish and propagate T cell exhaustion in chronic infection", Nat Immunol, vol. 21 Issue No. 10, pp. 1256-1266, Oct. 2020.

Valeri, A. et al., "Overcoming tumor resistance mechanisms in CAR-NK cell therapy", Front Immunol, vol. 13 Issue No. 953849, pp. 1-28, Aug. 3, 2022.

Vermaelen, K. et al., "Accurate and simple discrimination of mouse pulmonary dendritic cell and macrophage populations by flow cytometry: methodology and new insights", Cytometry A, vol. 61 Issue No. 2, pp. 170-177, Oct. 2004.

Vezys, V. et al., "4-1BB Signaling Synergizes with Programmed Death Ligand 1 Blockade To Augment CD8 T Cell Responses during Chronic Viral Infection", Journal of Immunology, vol. 187 Issue No. 4, pp. 1634-1642, 2011.

Vilgelm, A. E. et al., "Chemokines Modulate Immune Surveillance in Tumorigenesis, Metastasis, and Response to Immunotherapy", Front Immunol, vol. 10, Issue No. 333, pp. 1-14, Feb. 2019.

Vinay, D. S. et al., "Role of 4-1BB in immune responses", Semin Immunol, vol. 10 Issue No. 6, pp. 481-489, Dec. 1998.

Voisinne, G. et al., "CD5, an Undercover Regulator of TCR Signaling", Front. Immunol., vol. 9, Dec. 7, 2018.

Wagner, D. L. et al., "Immunogenicity of CAR T cells in cancer therapy", Nat Rev Clin Oncol, vol. 18 Issue No. 6, pp. 379-393, Jun. 2021.

Wakim, L. M. et al., "Cross-dressed dendritic cells drive memory CD8+ T-cell activation after viral infection", Nature, vol. 471 Issue No. 7340, pp. 629-632, Mar. 31, 2011.

Walker, L. S.K. et al., "Confusing signals: recent progress in CTLA-4 biology", Trends in Immunology, vol. 36 Issue No. 2, pp. 63-70, Feb. 2015.

Wang, H. et al., "Protein post-translational modifications in the regulation of cancer hallmarks", Cancer Gene Ther, vol. 30 Issue No. 4, pp. 529-547, Apr. 2023 (Abstract Only).

Wang, J. et al., "A differentiation checkpoint limits hematopoietic stem cell self-renewal in response to DNA damage", Cell, vol. 148 Issue No. 5, pp. 1001-1014, Mar. 2, 2012.

Wang, J. et al., "Discrimination of the heterogeneity of bone marrow-derived dendritic cells", Mol Med Rep, vol. 16 Issue No. 5, pp. 6787-6793, Nov. 2017.

Wang, J. et al., "The presence of tumour-infiltrating lymphocytes (TILs) and the ratios between different subsets serve as prognostic factors in advanced hypopharyngeal squamous cell carcinoma", BMC Cancer, vol. 20 Issue No. 731, pp. 1-12, 2020.

Wang, K. et al., "CD19: a biomarker for B cell development, lymphoma diagnosis and therapy", Experimental Hematology & Oncology, vol. 1 Issue No. 36, 2012, 7 pages.

Wang, L-C. S. et al., "Targeting fibroblast activation protein in tumor stroma with chimeric antigen receptor T cells can inhibit tumor growth and augment host immunity without severe toxicity", Cancer Immunol Res, vol. 2 Issue No. 2, pp. 154-166, Feb. 2014.

Wang, Q. et al., "Intratumoral regulatory T cells are associated with suppression of colorectal carcinoma metastasis after resection through overcoming IL-17 producing T cells", Cellular Immunology, vol. 287, Issue No. 2, pp. 100-105, Feb. 2014.

Wang, S. et al., "Cloning and characterization of subunits of the T-cell receptor and murine leukemia virus enhancer core-binding factor", Mol Cell Biol, vol. 13 Issue No. 6, pp. 3324-3339, Jun. 1993.

Wang, W. et al., "Purification and biochemical heterogeneity of the mammalian SWI-SNF complex", EMBO J, vol. 15 Issue No. 19, pp. 5370-5382, Oct. 1, 1996.

Wang, X. et al., "Clinical manufacturing of CAR T cells: foundation of a promising therapy", Molecular Therapy Oncology, vol. 3 Issue No. 16015, Jun. 15, 2016, 7 pages.

Wang, X. et al., "Manufacture of tumor- and virus-specific T lymphocytes for adoptive cell therapies", Cancer Gene Therapy, vol. 22 Issue No. 2, Mar. 2015, 22 pages.

Ward-Hartstonge, K. A. et al., "Regulatory T-cell heterogeneity and the cancer immune response", Clinical & Translational Immunology, vol. 6 Issue No. 9, pp. 1-5, Sep. 15, 2017.

Watanabe, K. et al., "Expanding the Therapeutic Window for CAR T Cell Therapy in Solid Tumors: The Knowns and Unknowns of CAR T Cell Biology", Frontiers in Immunology, vol. 9 Issue No. 2486, pp. 1-12, Oct. 26, 2018.

Watanabe, K. et al., "Pancreatic cancer therapy with combined mesothelin-redirected chimeric antigen receptor T cells and cytokine-armed oncolytic adenoviruses", Therapeutics, vol. 3 Issue No. 7, pp. 1-18, 2018.

Watanabe, K. et al., "Target antigen density governs the efficacy of anti-CD20-CD28-CD3 ζ chimeric antigen receptor-modified effector CD8+ T cells", Journal of Immunology, vol. 194 Issue No. 3, pp. 911-920, Feb. 1, 2015.

Weber, E. W. et al., "The Emerging Landscape of Immune Cell Therapies", Cell, vol. 181 Issue No. 1, pp. 46-62, Apr. 2, 2020.

Weiss, A. et al., "Signal transduction by lymphocyte antigen receptors", Cell, vol. 76 Issue No. 2, pp. 263-274, Jan. 28, 1994.

Wells, A. D., "New insights into the molecular basis of T cell anergy: anergy factors, avoidance sensors, and epigenetic imprinting", J Immunol., vol. 182 Issue No. 12, pp. 7331-7341, Jun. 15, 2009.

Wheat, J. C. et al., "The Corepressor Tle4 Is a Novel Regulator of Murine Hematopoiesis and Bone Development", PLOS One, vol. 9 Issue No. 8, pp. 1-16, Aug. 25, 2014.

Wherry, E. J. et al., "Molecular and cellular insights into T cell exhaustion", Nature Reviews Immunology, vol. 15 Issue No. 8, pp. 486-499, Aug. 2015.

Wilcox, R. A. et al., "Cutting edge: Expression of functional CD137 receptor by dendritic cells", J Immunol, vol. 168 Issue No. 9, pp. 4262-4267, May 1, 2002.

Wilkie, S. et al., "Dual targeting of ErbB2 and MUC1 in breast cancer using chimeric antigen receptors engineered to provide complementary signaling", J Clin Immunol, vol. 32 Issue No. 5, pp. 1059-1070, Oct. 2012.

Williams, J. B. et al., "The EGR2 targets LAG-3 and 4-1BB describe and regulate dysfunctional antigen-specific CD8 + T cells in the tumor microenvironment", J Exp Med, vol. 214 Issue No. 2, pp. 381-400, Feb. 2017.

Wing, A. et al., "Improving CART-Cell Therapy of Solid Tumors with Oncolytic Virus-Driven Production of a Bispecific T-cell Engager", Cancer Immunol Res, vol. 6 Issue No. 5, pp. 605-616, May 2018.

(56) References Cited

OTHER PUBLICATIONS

Wosen, W. E. et al., "Epithelial MHC Class II Expression and Its Role in Antigen Presentation in the Gastrointestinal and Respiratory Tracts", Front. Immunol., vol. 9 Issue No. 2144, pp. 1-14, Sep. 2018.
Wu, J. et al., "An activating immunoreceptor complex formed by NKG2D and DAP10", Science, vol. 285 Issue No. 5428, pp. 730-732, Jul. 30, 1999.
Wu, Q. et al., "Protein arginine methylation: from enigmatic functions to therapeutic targeting", Nat Rev Drug Discov, vol. 20 Issue No. 7, pp. 509-530, Jul. 2021.
Xia, Y. et al., "Immune checkpoint blockade: Releasing the brake towards hematological malignancies", Blood Reviews, vol. 30 Issue No. 3, pp. 189-200, May 2016.
Xie, G. et al., "CAR-NK cells: A promising cellular immunotherapy for cancer", EBioMedicine, vol. 59 Issue No. 102975, pp. 1-10, Sep. 2020.
Xing, S. et al., "Tcf1 and Lef1 transcription factors establish CD8(+) T cell identity through intrinsic HDAC activity", Nat Immunol, vol. 17 Issue No. 6, pp. 695-703, Jun. 2016.
Xing, S. et al., "Tle corepressors are differentially partitioned to instruct CD8+ T cell lineage choice and identity", J Exp Med, vol. 215 Issue No. 8, pp. 2211-2226, Aug. 6, 2018.
Xiong, W. et al., "Immunological Synapse Predicts Effectiveness of Chimeric Antigen Receptor Cells", Mol Ther, vol. 26 Issue No. 4, pp. 963-975, Apr. 4, 2018.
Xue, H-H. et al., "Regulation of mature T cell responses by the Wnt signaling pathway", The Year in Immunology, vol. 1247, Issue No. 1, pp. 16-33, Jan. 2012.
Yamauchi, T. et al., "T-cell CX3CR1 expression as a dynamic blood-based biomarker of response to immune checkpoint inhibitors", Nature Communications, vol. 12 Issue No. 1402, pp. 1-14, Mar. 3, 2021.
Yan, Q. et al., "Structural basis for activation of ZAP-70 by phosphorylation of the SH2-kinase linker", Molecular and Cellular Biology, vol. 33 Issue No. 11, pp. 2188-2201, Jun. 2013.
Yan, S. et al., "Tumor-associated macrophages in immunotherapy", The FEBS Journal, vol. 288 Issue No. 21, pp. 6174-6186, Nov. 2021.
Yang, C. Y. et al., "The transcriptional regulators Id2 and Id3 control the formation of distinct memory CD8+ T cell subsets", Nat Immunol, vol. 12 Issue No. 12, pp. 1221-1229, Nov. 6, 2011.
Yang, X. et al., "Functions and clinical significance of KLRG1 in the development of lung adenocarcinoma and immunotherapy", BMC Cancer, vol. 21 Issue No. 752, 2021, 16 pages.
Ye, J. et al., "Human regulatory T cells induce T-lymphocyte senescence", Blood, vol. 120 Issue No. 10, pp. 2021-2031, Sep. 6, 2012.
Ye, L-Y. et al., "Hypoxia-Induced Epithelial-to-Mesenchymal Transition in Hepatocellular Carcinoma Induces an Immunosuppressive Tumor Microenvironment to Promote Metastasis", Cancer Research, vol. 76 Issue No. 4, pp. 818-830, Feb. 15, 2016.
Yewdell, J. W. et al., "Immunology: Cross-dressers turn on T cells", Nature, vol. 471 Issue No. 7340, pp. 581-582, Mar. 31, 2011.
Yin, Y. et al., "Checkpoint Blockade Reverses Anergy in IL-13Rα2 Humanized scFv-Based CAR T Cells to Treat Murine and Canine Gliomas", Mol Ther Oncolytics, vol. 11, pp. 20-38, Aug. 28, 2018.
Yokosuka, T. et al., "Programmed cell death 1 forms negative costimulatory microclusters that directly inhibit T cell receptor signaling by recruiting phosphatase SHP2", Journal of Experimental Medicine, vol. 209 Issue No. 6, pp. 1201-1217, Jun. 4, 2012.
Yokosuka, T. et al., "Spatiotemporal basis of CTLA-4 costimulatory molecule-mediated negative regulation of T cell activation", Immunity, vol. 33 Issue No. 3, pp. 326-339, Sep. 24, 2010.
Yona, S. et al., "Fate mapping reveals origins and dynamics of monocytes and tissue macrophages under homeostasis", Immunity, vol. 38 Issue No. 1, pp. 79-91, Jan. 24, 2013.
Yu, W-L. et al., "Chimeric Antigen Receptor T-cell (CAR T) Therapy for Hematologic and Solid Malignancies: Efficacy and Safety—A Systematic Review with Meta-Analysis", Cancers, vol. 11 Issue No. 1, pp. 1-27, 2019.
Zabidi, M. A. et al., "Regulatory enhancer-core-promoter communication via transcription factors and cofactors", Trends Genet., vol. 32 Issue No. 12, pp. 801-814, Nov. 2, 2016.
Zah, E. et al., "T Cells Expressing CD19/CD20 Bispecific Chimeric Antigen Receptors Prevent Antigen Escape by Malignant B Cells", Cancer Immunol Res, vol. 4 Issue No. 6, pp. 498-508, Jun. 2016.
Zhang, J. et al., "Senescent T cells: a potential biomarker and target for cancer therapy", EBioMedicine, vol. 68 Issue No. 103409, pp. 1-8, Jun. 2021.
Zhang, M. et al., "PTHrP prevents chondrocyte premature hypertrophy by inducing cyclin-D1-dependent Runx2 and Runx3 phosphorylation, ubiquitylation and proteasomal degradation", J Cell Sci., vol. 122 Issue No. 9, pp. 1382-1389, Apr. 7, 2009.
Zhang, P. et al., "Agonistic Anti-4-1BB Antibody Promotes the Expansion of Natural Regulatory T Cells While Maintaining Foxp3 Expression", Scandinavian Journal of Immunology, vol. 66 Issue No. 4, pp. 435-440, Oct. 2007.
Zhang, Y. et al., "In vivo kinetics of human natural killer cells: the effects of ageing and acute and chronic viral infection", Immunology, vol. 121 Issue No. 2, pp. 258-265, Jun. 2007.
Zhang, Y. et al., "TH1/TH2 cell differentiation and molecular signals", Adv Exp Med Biol, vol. 841, pp. 15-44, 2014.
Zhang, Z. et al., "Neoantigen: A New Breakthrough in Tumor Immunotherapy", Front Immunol, vol. 12 Issue No. 672356, pp. 1-9, Apr. 2021.
Zhang, Z. et al., "T Cell Dysfunction and Exhaustion in Cancer", Front. Cell Dev. Biol., vol. 8, Issue No. 17, pp. 1-13, Feb. 2020.
Zhao, X. et al., "Methylation of RUNX1 by PRMT1 abrogates SIN3A binding and potentiates its transcriptional activity", Genes & Dev., vol. 22, pp. 640-653, 2008.
Zhao, X. et al., "TCF1 in T cell immunity: a broadened frontier", Nature Reviews Immunology, vol. 22, pp. 147-157, Jun. 14, 2021 (Abstract Only).
Zhao, X. et al., "The transcriptional cofactor Tle3 reciprocally controls effector and central memory CD8+ T cell fates", Nat Immunol, vol. 25 Issue No. 2, pp. 294-306, Feb. 2024 (Abstract Only).
Zhao, Z. et al., "Structural Design of Engineered Costimulation Determines Tumor Rejection Kinetics and Persistence of Car T Cells", Cancer Cell, vol. 28 Issue No. 4, pp. 415-428, Oct. 12, 2015.
Zheng, Y. et al., "Transcriptional regulator early growth response gene 2 (Egr2) is required for T cell anergy in vitro and in vivo", Journal of Experimental Medicine, vol. 209 Issue No. 12, pp. 2157-2163, 2012.
Zhong, Q. et al., "Protein posttranslational modifications in health and diseases: Functions, regulatory mechanisms, and therapeutic implications", MedComm, vol. 4 Issue No. 3, pp. e261, Jun. 2023.
Zhou, X. et al., "Differentiation and persistence of memory CD8(+) T cells depend on T cell factor 1", Immunity, vol. 33 Issue No. 2, pp. 229-240, Aug. 27, 2010.
Zou, W. "Immunosuppressive networks in the tumour environment and their therapeutic relevance", Nature Reviews Cancer, vol. 5 Issue No. 4, pp. 263-274, Apr. 2005.
Zou, W. et al., "Inhibitory B7-family molecules in the tumour microenvironment", Nature Reviews Immunology, vol. 8 Issue No. 6, pp. 467-477, Jun. 2008.
Fundamental Immunology, 4th Ed., William E. Paul, ed. Lippincott-Raven Publishers, Philadelphia (1999) at 1051-1053.
Pauken, KE et al., "Epigenetic stabiligy of exhausted T cells limits durability of reinvigoration by PD-1 blockade," Science (2016) 342: 1242454.
Khaghanzadeh, N. et al., "CTLA4 gene variations and haplotypes in patients with lunch cancer," (2010) Cancer Genetocs and Cytogenetics 196: 171-174.
Waqas, SFH et al. in Nuclear Receptors: Methods and Experimental Protocols, MZ Badr. Ed., Springer, New York, NY, pp. 211-224.
Likanan, I. et al., "Hypoxia-inducible factor activity promotes antitumor effector function and tissue residency by CD8+ T cells," J. Clin. Invest. (2021) 131.

(56) References Cited

OTHER PUBLICATIONS

Mak, TW et al., Ch. 20—Hematopoietic cancers, in Primer to the Immune response (2014) Elsevier, Inc., pp. 573-574.
Malik, N. et al., "The transcription factor CBFB suppresses breast cancer through orchestrating translation and transcription," Nat. Commun. (2019) 10: 1-15.
Mao, S. et al., "Functional and Physical Interactions between AML1 Proteins and an ETS Protein, MEF: Implications for Pathogenesis of t(8;21)-Positive Leukemias," Mol. Cell Biol. (1999) 19: 3635-3644.
Qian J. et al. (2011) Immune Escape. In: Schwab M. (eds) Encyclopedia of Cancer. Springer, Berlin, Heidelberg. https://doi.org/10.1007/978-3-642-16483-5_2975.
Rasche, L. et al. N. Kroger, et al, eds., "Tumour Escape from CAR-T Cells," Chapter 4 in The EBMT/EHA CAR-T Cell Handbook (2002) doi.org/10.1007/978-3-030-94353-0_4.
Shlyueva, D. et al., "Transcriptional enhancers: from properties to genome-wide predictions," Nat. Rev. Genet. (2014) 13: 613-626.
Lin, Y. et al., "Lower T cell inhibitory receptor level in mononuclear cells from cord blood compared with peripheral blood," Stem Cell Invest. (2019) 6: 35.
International Search Report and Written Opinion of the International Searching Authority in relation to International Application No. PCT/US2025/025517, dated Jun. 23, 2025, 14 pages.
Kokabu, S. et al., "The transcriptional co-repressor TLE3 regulates myogenic differentiation by repressing the activity of the MyoD transcription factor", J Biol Chem, vol. 292 Issue No. 31, pp. 12885-12894, Aug. 4, 2017.
Ogawa, M. et al., "Transducin-like enhancer of split 3 regulates proliferation of melanoma cells via histone deacetylase activity", Oncotarget, vol. 10 Issue No. 3, pp. 404-414, 2019.
Adusumilli, P. S. et al., "A Phase I Trial of Regional Mesothelin-Targeted CAR T-cell Therapy in Patients with Malignant Pleural Disease, in Combination with the Anti-PD-1 Agent Pembrolizumab", Cancer Discov, vol. 11 Issue No. 11, pp. 2748-2763.
Alderson, M. R. et al., "Molecular and biological characterization of human 4-1BB and its ligand", Eur J Immunol, vol. 24 Issue No. 9, pp. 2219-2227, Sep. 1994.
Allaoui, R. et al., "Infiltration of γδ T cells, IL-17 + T cells and FoxP3 + T cells in human breast cancer", Cancer Biomarkers, vol. 20 Issue No. 4, pp. 395-409, 2017.
Anandasabapathy, N. et al., "GRAIL: an E3 ubiquitin ligase that inhibits cytokine gene transcription is expressed in anergic CD4+ T cells", Immunity, vol. 18 Issue No. 4, pp. 535-547, Apr. 2003.
Annala, M. J. et al., "Fusion genes and their discovery using high throughput sequencing", Cancer Lett, vol. 340 Issue No. 2, pp. 192-200, Nov. 1, 2013.
Araki, K. et al., "Programmed Cell Death 1-Directed Immunotherapy for Enhancing T-Cell Function", Cold Spring Harbor Symposia on Quantitative Biology, vol. 78, pp. 239-247, 2013.
Arce,L. et al., "Groucho binds two conserved regions of LEF-1 for HDAC-dependent repression", BMC Cancer, vol. 9 Issue No. 159, 2009, 14 pages.
Armitage, J. O., "The aggressive peripheral T-cell lymphomas: 2017", Am J Hematol, vol. 92 Issue No. 7, pp. 706-715, Jul. 2017.
Arneth, B., "Tumor Microenvironment", Medicina (Kaunas)., vol. 56 Issue No. 1, Dec. 30, 2019, 21 pages.
Au-Yeung, B. B. et al., "A sharp T-cell antigen receptor signaling threshold for T-cell proliferation", Proceedings of the National Academy of Sciences of the United States of America, vol. 111 Issue No. 35, pp. E3679-E3688, Sep. 2, 2014.
Balani, S. et al., "Modeling the process of human tumorigenesis", Nature Communications, vol. 8 Issue No. 15422, pp. 1-10, May 25, 2017.
Bandyopadhyay, S. et al., "Interleukin 2 gene transcription is regulated by Ikaros-induced changes in histone acetylation in anergic T cells", Blood, vol. 109 Issue No. 7, pp. 2878-2886, Dec. 5, 2006.
Banerji, J. et al., "Expression of a beta-globin gene is enhanced by remote SV40 DNA sequences", Cell, vol. 27 Issue No. 2 Pt 1, pp. 299-308, Dec. 1981.
Bannerji, R. et al., "Emerging Clinical Activity of REGN1979, an Anti-CD20×Anti-CD3 Bispecific Antibody, in Patients with Relapsed/Refractory Follicular Lymphoma (FL), Diffuse Large B-Cell Lymphoma (DLBCL), and Other B-Cell Non-Hodgkin Lymphoma (B-NHL) Subtypes", Blood, vol. 132, Issue No. Supplement 1, Nov. 29, 2018, 6 pages.
Barbari, C. et al., "Immunotherapies and Combination Strategies for Immuno-Oncology", Int J Mol Sci, vol. 21 Issue No. 14, pp. 1-28, Jul. 15, 2020.
Barbarin, A. et al., "Phenotype of NK-Like CD8(+) T Cells with Innate Features in Humans and Their Relevance in Cancer Diseases", Frontiers in Immunology, vol. 8 Issue No. 316, pp. 1-16, Mar. 27, 2017.
Barlogie, B. et al., "Treatment of multiple myeloma", Blood, vol. 103 Issue No. 1, pp. 20-32, Jan. 1, 2004.
Beltra, J-C. et al., "Developmental Relationships of Four Exhausted CD8+ T Cell Subsets Reveals Underlying Transcriptional and Epigenetic Landscape Control Mechanisms", Immunity, vol. 52 Issue No. 5, pp. 825-841, May 19, 2020.
Berenson, J. R. et al., "Monoclonal gammopathy of undetermined significance: a consensus statement", British Journal of Haematology, vol. 150, Issue 1, pp. 28-38, 2010.
Betz, B. C. et al., "Batf coordinates multiple aspects of B and T cell function required for normal antibody response", J Exp Med, vol. 207 Issue No. 5, pp. 933-942, Apr. 26, 2010.
Bidwell, B. N. et al., "Silencing of lrf7 pathways in breast cancer cells promotes bone metastasis through immune escape", Nature Medicine, vol. 18 Issue No. 8, pp. 1224-1231, Aug. 2012.
Björkström, N. K. et al., "CD8 T cells express randomly selected KIRs with distinct specificities compared with NK cells", Blood, vol. 120 Issue No. 17, pp. 3455-3465, Oct. 25, 2012.
Blackburn, S. D. et al., "Coregulation of CD8+ T cell exhaustion by multiple inhibitory receptors during chronic viral infection", Nature Immunology, vol. 10 Issue No. 1, pp. 29-37, Jan. 2009.
Blank, C. et al., "PD-L1/B7H-1 inhibits the effector phase of tumor rejection by T cell receptor (TCR) transgenic CD8+ T cells", Cancer Research, vol. 64 Isssue No. 3, pp. 1140-1145, Feb. 1, 2004.
Blank, C. U. et al., "Defining 'T cell exhaustion'", Nat Rev Immunol, vol. 19 Issue No. 11, pp. 665-674, Nov. 2019.
Bos, P. D. et al., "Transient regulatory T cell ablation deters oncogene-driven breast cancer and enhances radiotherapy", Journal of Experimental Medicine, vol. 210 Issue No. 11, pp. 2435-2466, Oct. 21, 2013.
Böttcher, J. P. et al., "Functional classification of memory CD8+ T cells by CX3CR1 expression", Nature Communications, vol. 6 Issue No. 8306, pp. 1-17, Sep. 25, 2015.
Boussiotis, V. A. et al., "Maintenance of Human T Cell Anergy: Blocking of IL-2 Gene Transcription by Activated Rap1", Science, vol. 278 Issue No. 5335, pp. 124-128, Oct. 3, 1997.
Bouwhuis, M. G. et al., "Polymorphisms in the CD28/CTLA4/ICOS genes: role in malignant melanoma susceptibility and prognosis?", Cancer Immunology Immunotherapy, vol. 59 Issue No. 2, pp. 303-312, Feb. 2010.
Bowie, J. U. et al., "A method to identify protein sequences that fold into a known three-dimensional structure", Science, vol. 253 Issue No. 5016, pp. 164-170, Jul. 12, 1991.
Bradley, J. R. et al., "Tumor necrosis factor receptor-associated factors (TRAFs)", Oncogene, vol. 20 Issue No. 44, pp. 6482-6491, Oct. 1, 2001.
Brantjes, H. et al., "All Tcf HMG box transcription factors interact with Groucho-related co-repressors", Nucleic Acids Research, vol. 29 Issue No. 7, pp. 1410-1419, Apr. 1, 2001.
Brassart-Pasco, S. et al., "Tumor Microenvironment: Extracellular Matrix Alterations Influence Tumor Progression", Front Oncol., vol. 10 Issue No. 397, pp. 1-13, Apr. 2020.
Britanova, O. V. et al., "Age-related decrease in TCR repertoire diversity measured with deep and normalized sequence profiling", Journal of Immunology, vol. 192 Issue No. 6, pp. 2689-2698, Mar. 15, 2014.
Brocker, T. "Chimeric Fv-zeta or Fv-epsilon receptors are not sufficient to induce activation or cytokine production in peripheral T cells", Blood, vol. 96 Issue No. 5, pp. 1999-2001, Sep. 1, 2000.

(56) References Cited

OTHER PUBLICATIONS

Brocker, T. et al., "New simplified molecular design for functional T cell receptor", European Journal of Immunology, vol. 23 Issue No. 7, pp. 1435-1439, Jul. 1993.
Brocker, T. et al., "Signals through T cell receptor-zeta chain alone are insufficient to prime resting T lymphocytes", Journal of Experimental Medicine, vol. 181 Issue No. 5, pp. 1653-1659, May 1, 1995.
Broderick, L. et al., "IL-12 reverses anergy to T cell receptor triggering in human lung tumor-associated memory T cells", Clinical Immunology, vol. 118, Issue No. 2-3, pp. 159-169, Feb.-Mar. 2006.
Broll, K. et al., "CD137 Expression in Tumor Vessel Walls: High Correlation With Malignant Tumors", American Journal of Clinical Pathology, vol. 115 Issue No. 4, pp. 543-549, Apr. 2001.
Brown, C. E. et al., "Bioactivity and Safety of IL13Rα2-Redirected Chimeric Antigen Receptor CD8+ T Cells in Patients with Recurrent Glioblastoma", Clin Cancer Res, vol. 21 Issue No. 18, pp. 4062-4072, Sep. 15, 2015.
Brown, I. E. et al., "Homeostatic Proliferation as an Isolated Variable Reverses CD8+ T Cell Anergy and Promotes Tumor Rejection1", Journal of Immunology, vol. 177 Issue No. 7, pp. 4521-4529, 2006.
Buscarlet, M. et al., "The 'Marx' of Groucho on development and disease", Trends Cell Biol, vol. 17 Issue No. 7, pp. 353-361, Jul. 2007.
Bussard, K. M. et al., "Tumor-associated stromal cells as key contributors to the tumor microenvironment", Breast Cancer Res., vol. 18 Issue No. 1, pp. 1-11, Aug. 11, 2016.
Butcher, E. C. et al., "Lymphocyte Trafficking and Regional Immunity", Advances in Immunology, vol. 72, pp. 209-253, 1999.
Caël, B. et al., "Umbilical Cord Blood as a Source of Less Differentiated T Cells to Produce CD123 CAR-T Cells", Cancers, vol. 14 Issue No. 3168, pp. 1-16, Jun. 2022.
Cai, X. et al., "Runx1 Deficiency Decreases Ribosome Biogenesis and Confers Stress Resistance to Hematopoietic Stem and Progenitor Cells", Cell Stem Cell, vol. 17 Issue No. 2, pp. 165-177, Aug. 6, 2015.
Call, M. E. et al., "The structural basis for intramembrane assembly of an activating immunoreceptor complex", Nature Immunology, vol. 11 Issue No. 11, pp. 1023-1029, Nov. 2010.
Campbell, D. J. et al., "Control of Regulatory T Cell Migration, Function, and Homeostasis", Journal of Immunology, vol. 195 Issue No. 6, pp. 2507-2513, Sep. 15, 2015.
Cappell, K. M. et al., "Long-term outcomes following CAR T cell therapy: what we know so far", Nat Rev Clin Oncol, vol. 20 Issue No. 6, pp. 359-371, Jun. 2023 (Abstract Only).
Carlens, J. et al., "Common gamma-chain-dependent signals confer selective survival of eosinophils in the murine small intestine", J Immunol, vol. 183 Issue No. 9, pp. 5600-5607, Nov. 1, 2009.
Carneiro, B. A. et al., "Targeting apoptosis in cancer therapy", Nat Rev Clin Oncol., vol. 17 Issue No. 7, pp. 395-417, Jul. 2020.
Caserta, S. et al., "Reduced Functional Avidity Promotes Central and Effector Memory CD4 T Cell Responses to Tumor-Associated Antigens", J Immunol, vol. 185 Issue No. 11, pp. 6545-6554, 2010.
Chaffer, C. L. et al., "How does multistep tumorigenesis really proceed?", Cancer Discovery, vol. 5 Issue No. 1, pp. 22-24, Jan. 2015.
Champsaur, M. et al., "Effect of NKG2D ligand expression on host immune responses", Immunological, vol. 235 Issue No. 1, pp. 267-285, May 2010.
Chan, J. D. et al., "FOXO1 enhances CAR T cell stemness, metabolic fitness and efficacy", Nature, vol. 629, pp. pp. 201-210, Apr. 10, 2024.
Chen, G. et al., "A functional interaction between the histone deacetylase Rpd3 and the corepressor Groucho in *Drosophila* development", Genes & development, vol. 13, pp. 2218-2230, Jul. 19, 1999.
Chen, J. et al., "NR4A transcription factors limit CAR T cell function in solid tumours", Nature, vol. 567 Issue No. 7749, pp. 530-534, Mar. 2019.
Chen, L. et al., "Costimulation of antitumor immunity by the B7 counterreceptor for the T lymphocyte molecules CD28 and CTLA-4", Cell, vol. 71 Issue No. 7, pp. 1093-1102, Dec. 24, 1992.
Chen, L. et al., "Regulating tumor suppressor genes: post-translational modifications", Signal Transduct Target Ther, vol. 5 Issue No. 1, Jun. 10, 2020, 25 pages.
Chen, Z. et al., "TCF-1-Centered Transcriptional Network Drives an Effector versus Exhausted CD8 T Cell-Fate Decision", Immunity, vol. 51 Issue No. 5, pp. 840-855, Nov. 19, 2019.
Chester, C. et al., "4-1BB agonism: adding the accelerator to cancer immunotherapy", Cancer Immunol Immunother, vol. 65 Issue No. 10, pp. 1243-1248, Oct. 2016.
Chester, C. et al., "Immunotherapy targeting 4-1BB: mechanistic rationale, clinical results, and future strategies", Blood, vol. 131 Issue No. 1, pp. 49-57, Jan. 4, 2018.
Chodaparambil, J. V. et al., "Molecular functions of the TLE tetramerization domain in Wnt target gene repression", EMBO J, vol. 33, pp. 719-731, 2014.
Choi, B. D. et al., "CAR-T cells secreting BiTEs circumvent antigen escape without detectable toxicity", Nat Biotechnol, vol. 37 Issue No. 9, pp. 1049-1058, Sep. 2019.
Choi, B. K. et al., "Peripheral 4-1BB signaling negatively regulates NK cell development through IFN-gamma", J Immunol, vol. 185 Issue No. 3, pp. 1404-1411, Aug. 1, 2010.
Choudhary, C. et al., "Lysine acetylation targets protein complexes and co-regulates major cellular functions", Science, vol. 325 Issue No. 5942, pp. 834-840, Aug. 14, 2009.
Church, M. C. et al., "The SWI/SNF chromatin remodeling complex: a critical regulator of metabolism", Biochem Soc Trans, vol. 52 Issue No. 3, pp. 1327-1337, 2024.
Ciofani, M. et al., "A validated regulatory network for Th17 cell specification", Cell, vol. 151 Issue No. 2, pp. 289-303, Oct. 12, 2012.
Clayton, K. L. et al., "T cell Ig and mucin domain-containing protein 3 is recruited to the immune synapse, disrupts stable synapse formation, and associates with receptor phosphatases", Journal of Immunology, vol. 192 Issue No. 2, pp. 782-791, Jan. 15, 2014.
Colpitt, S. L. et al., "IL-7 Receptor Expression Provides the Potential for Long-Term Survival of Both CD62Lhigh Central Memory T Cells and Th1 Effector Cells during Leishmania major Infection", J Immunol, vol. 182 Issue No. 9, pp. 5702-5711, 2009.
Conibear, A. C. et al., "Deciphering protein post-translational modifications using chemical biology tools", Nat Rev Chem, vol. 4 Issue No. 12, pp. 674-695, Dec. 2020.
Côté, J. et al., "Stimulation of GAL4 derivative binding to nucleosomal DNA by the yeast SWI/SNF complex", Science, vol. 265 Issue No. 5168, pp. 53-60, Jul. 1, 1994.
Covre, L. P. et al., "The role of senescent T cells in immunopathology", Aging Cell, vol. 19 Issue No. e13272, pp. 1-9, 2020.
Crespo, J. et al., "T cell anergy, exhaustion, senescence, and stemness in the tumor microenvironment", Curr Opin Immunol, vol. 25 Issue No. 2, pp. 214-221, 2013.
Cullen, S. P. et al., "Granzymes in cancer and immunity", Cell Death & Differentiation, vol. 17, pp. 616-623, Jan. 15, 2010.
Curiel, T. J. et al., "Blockade of B7-H1 improves myeloid dendritic cell-mediated antitumor immunity", Nature Medicine, vol. 9 Issue No. 5, pp. 562-567, May 2003.
Cyster, J. G. "Chemokines and cell migration in secondary lymphoid organs", Science, vol. 286 Issue No. 5447, pp. 2098-2102, Dec. 10, 1999.
Da Vià, M. C. et al., "Homozygous BCMA gene deletion in response to anti-BCMA CAR T cells in a patient with multiple myeloma", Nature Medicine, vol. 27, pp. 616-619, Feb. 22, 2021.
Dai, S. et al., "Toward a mechanistic understanding of DNA binding by forkhead transcription factors and its perturbation by pathogenic mutations", Nucleic Acids Research, vol. 49 Issue No. 118, pp. 10235-10249, Oct. 11, 2021.
D'Alonzo, R. C. et al., "Physical Interaction of the Activator Protein-1 Factors c-Fos and c-Jun with Cbfa1 for Collagenase-3 Promoter Activation", J. Biol. Chem, vol. 277 Issue No. 1, pp. 816-822, Jan. 4, 2002.

(56) References Cited

OTHER PUBLICATIONS

Daniels, D. A. et al., "Beta-catenin directly displaces Groucho/TLE repressors from Tcf/Lef in Wnt-mediated transcription activation", Nat Struct Mol Biol, vol. 12 Issue No. 4, pp. 364-371, Apr. 2005.
Davenport, A. J. et al., "Chimeric antigen receptor T cells form nonclassical and potent immune synapses driving rapid cytotoxicity", Proc Natl Acad Sci USA vol. 115 Issue No. 9, pp. E2068-E2076, Feb. 27, 2018.
Debenedette, M. A. et al., "Costimulation of CD28-T lymphocytes by 4-1BB ligand", J Immunol, vol. 158 Issue No. 2, pp. 551-559, Jan. 15, 1997.
Deenick, E. K. et al., "Signal Transducer and Activator of Transcription 3 Control of Human T and B Cell Responses", Front. Immunol., vol. 9 Issue No. 168, pp. 1-7, Feb. 2018.
Delamarre, L. et al., "Differential lysosomal proteolysis in antigen-presenting cells determines antigen fate", Science, vol. 307 Issue No. 5715, pp. 1630-1634, Mar. 11, 2025.
Deshpande, D. et al., "RNA-seq data science: From raw data to effective interpretation", Front. Genet., vol. 14, pp. 1-12, Mar. 13, 2023.
Di Giacomo, A. M. et al., "Immunotherapy targeting immune check-point(s) in brain metastases", Cytokine & Growth Factor Reviews, vol. 36, pp. 33-38, Aug. 2017.
Diefenbach, A. et al., "Strategies for target cell recognition by natural killer cells", Immunol Rev, vol. 181, pp. 170-184, Jun. 2001.
Dilmec, F. et al., "Investigation of CTLA-4 and CD28 gene polymorphisms in a group of Turkish patients with colorectal cancer", International Journal of Immunogenetics, vol. 35 Issue No. 4-5, pp. 317-321, Aug. 2008.
Doan, A. E. et al., "FOXO1 is a master regulator of memory programming in CAR T cells", Nature, vol. 629, pp. 211-218, Apr. 10, 2024.
Dolmetsch, R. E. et al., "Calcium oscillations increase the efficiency and specificity of gene expression", Nature, vol. 392 Issue No. 6679, pp. 933-936, Apr. 30, 1998.
Drake, M. T., "unveiling skeletal fragility in patients diagnosed with MGUS: no longer a condition of undetermined significance?", J Bone Miner Res, vol. 29 Issue No. 12, pp. 2529-2533, Dec. 2014.
Drenkard, D. et al., "CD137 is expressed on blood vessel walls at sites of inflammation and enhances monocyte migratory activity", The FASEB Journal, vol. 21 Issue No. 2, pp. 456-463, Feb. 2007.
Drutman, S. B. et al., "Inflammatory Spleen Monocytes Can Upregulate CD11c Expression Without Converting into Dendritic Cells", J Immunol, vol. 188 Issue No. 8, pp. 3603-3610, 2012.
Duarte, J. D. G. et al., "The good, the (not so) bad and the ugly of immune homeostasis in melanoma", Immunology and Cell Biology, vol. 96 Issue No. 5, pp. 497-506, May 2018.
Dunn, G. P. et al., "Interferons, immunity and cancer immunoediting", Nat Rev Immunol, vol. 6 Issue No. 11, pp. 836-848, Nov. 2006.
Eagle, R. A. et al., "Promiscuity and the single receptor: NKG2D", Nat Rev Immunol, vol. 7 Issue No. 9, pp. 737-744, Sep. 2007.
Ehrlich, L. I. R. et al., "Dynamics of p56lck translocation to the T cell immunological synapse following agonist and antagonist stimulation", Immunity, vol. 17 Issue No. 6, pp. 809-822, Dec. 2002.
Engels, B. et al., "Long-term Persistence of CD4+ but Rapid Disappearance of CD8+ T Cells Expressing an MHC Class I-restricted TCR of Nanomolar Affinity", Molecular Therapy, vol. 20 Issue No. 3, pp. p652-p660, Mar. 2012.
Erfani, N. et al., "Cytotoxic T lymphocyte antigen-4 promoter variants in breast cancer", Cancer Genetics and Cytogenetics, vol. 165 Issue No. 2, pp. 114-120, Mar. 2006.
Erfani, N. et al., "Increase of regulatory T cells in metastatic stage and CTLA-4 over expression in lymphocytes of patients with non-small cell lung cancer (NSCLC)", Lung Cancer, vol. 77 Issue No. 2, pp. 306-311, Aug. 2012.
Eshhar, Z. et al., "Specific activation and targeting of cytotoxic lymphocytes through chimeric single chains consisting of antibody-binding domains and the gamma or zeta subunits of the immunoglobulin and T-cell receptors", Proceedings of the National Academy of Sciences of the United States of America, vol. 90 Issue No. 2, pp. 720-724, Jan. 15, 1993.
Eshhar, Z. et al., "The T-body approach: potential for cancer immunotherapy", Seminars in Immunopathology, vol. 18 Issue No. 2, pp. 199-209, 1996.
Fairfield, H. et al., "Multiple myeloma in the marrow: pathogenesis and treatments", Ann N Y Acad Sci, vol. 1364 Issue No. 1, pp. 32-51, Jan. 2016.
Falschlehner, C. et al., "Following TRAIL's path in the immune system", Immunology, vol. 127, pp. 145-154, 2009.
Fedorov, V. D. et al., "PD-1- and CTLA-4-based inhibitory chimeric antigen receptors (iCARs) divert off-target immunotherapy responses", Sci Transl Med, vol. 5 Issue No. 215, pp. 215ra172, Dec. 11, 2013.
Fei, F. et al., "Targeting HLA-DR loss in hematologic malignancies with an inhibitory chimeric antigen receptor", Mol Ther, vol. 30 Issue No. 3, pp. 1215-1226, Nov. 18, 2021.
Finck, A. V. et al., "Engineered cellular immunotherapies in cancer and beyond", Nat Med, vol. 28 Issue No. 4, pp. 678-689, Apr. 2022 (Abstract Only).
Flanagan, S. E. et al., "Activating germline mutations in STAT3 cause early-onset multi-organ autoimmune disease", Nat Genet, vol. 46 Issue No. 8, pp. 812-814, Aug. 2014.
Foley, B. et al., "Cytomegalovirus reactivation after allogeneic transplantation promotes a lasting increase in educated NKG2C+ natural killer cells with potent function", Blood, vol. 119 Issue No. 11, pp. 2665-2674, Mar. 15, 2012.
Förster, R. et al., "CCR7 coordinates the primary immune response by establishing functional microenvironments in secondary lymphoid organs", Cell, vol. 99 Issue No. 1, pp. 23-33, Oct. 1, 1999.
Fraietta, J. A. et al., "Disruption of TET2 promotes the therapeutic efficacy of CD19-targeted T cells", Nature, vol. 558, pp. 307-312, Jun. 14, 2018.
Francisco, L. M. et al., "PD-L1 regulates the development, maintenance, and function of induced regulatory T cells", Journal of Experimental Medicine, vol. 206( Issue No. 13, pp. 3015-3029, Dec. 21, 2009.
Freud, A. G. et al., "The Broad Spectrum of Human Natural Killer Cell Diversity", Immunity, vol. 47 Issue No. 5, pp. 820-833, Nov. 21, 2017.
Frigault, M. J. et al., "Identification of chimeric antigen receptors that mediate constitutive or inducible proliferation of T cells", Cancer Immunology Research, vol. 3 Issue No. 4, pp. 356-367, Apr. 2015.
Fry, T. J. et al., "CD22-targeted CAR T cells induce remission in B-ALL that is naive or resistant to CD19-targeted CAR immunotherapy", Nat Med, vol. 24 Issue No. 1, pp. 20-28, Jan. 2018.
Furudate, S. et al., "Sequential Therapy with Nivolumab Followed by Ipilimumab Induces Complete Response in Metastatic Melanoma of the Lung but with Severe Hepatotoxicities", Case Reports in Oncology, vol. 9 Issue No. 3, pp. 644-649, Oct. 17, 2016.
Futagawa, T. et al., "Expression and function of 4-1BB and 4-1BB ligand on murine dendritic cells", Int Immunol, vol. 14 Issue No. 3, pp. 275-286, Mar. 2002.
Gabriel, C. H. et al., "Identification of Novel Nuclear Factor of Activated T Cell (NFAT)-associated Proteins in T Cells*", J Biol Chem, vol. 291 Issue No. 46, pp. 24172-24187, Sep. 16, 2016.
Gajewski, T. F. et al., "B7-1 but not B7-2 efficiently costimulates CD8+ T lymphocytes in the P815 tumor system in vitro", Journal of Immunology, vol. 156 Issue No. 2, pp. 465-472, Jan. 15, 1996.
Gao, B. et al., "Analysis of sirtuin 1 expression reveals a molecular explanation of IL-2-mediated reversal of T-cell tolerance", PNAS, vol. 109 Issue No. 3, pp. 899-904, Jan. 17, 2012.
Gao,F. et al., "Heterozygous Mutations in SMARCA2 Reprogram the Enhancer Landscape by Global Retargeting of SMARCA4", Molecular Cell, vol. 75, pp. 891-904, Sep. 5, 2019.
Garnett, C. T. et al., "Sublethal irradiation of human tumor cells modulates phenotype resulting in enhanced killing by cytotoxic T lymphocytes", Cancer Res, vol. 64 Issue No. 21, pp. 7985-7994, Nov. 1, 2004.

(56) References Cited

OTHER PUBLICATIONS

Gasperowicz, M. et al., "Mammalian Groucho homologs: redundancy or specificity?", J Cell Biochem, vol. 95 Issue No. 4, pp. 670-687, Jul. 1, 2005.
Gattinoni, L. et al., "Paths to stemness: building the ultimate antitumour T cell", Nat Rev Cancer, vol. 12 Issue No. 10, pp. 671-684, Oct. 2012.
Gavriil, A. et al., "Engineering Solutions for Mitigation of Chimeric Antigen Receptor T-Cell Dysfunction", Cancers 2020, vol. 12 Issue No. 8, 2020, 24 pages.
Geissmann, F. et al., "Development of monocytes, macrophages, and dendritic cells", Science, vol. 327 Issue No. 5966, pp. 656-661, Feb. 5, 2010.
Gensous , N. et al., "T Follicular Helper Cells in Autoimmune Disorders", Front Immunol, vol. 9 Issue No. 1637, Jul. 17, 2018.
Gerberick, G. F. et al., "Selective modulation of T cell memory markers CD62L and CD44 on murine draining lymph node cells following allergen and irritant treatment", Toxicol Appl Pharmacol, vol. 146 Issue No. 1, pp. 1-10, Sep. 1997.
Gerlach, C. et al., "The Chemokine Receptor CX3CR1 Defines Three Antigen-Experienced CD8 T Cell Subsets with Distinct Roles in Immune Surveillance and Homeostasis", Immunity, vol. 45 Issue No. 6, pp. 1270-1284, Dec. 20, 2016.
Ghaleb, A. M. et al., "Krüppel-like factor 4 (KLF4): What we currently know", Gene, vol. 611, pp. 27-37, May 5, 2017.
Giacomo, A. M. D. et al., "Ipilimumab and fotemustine in patients with advanced melanoma (NIBIT-M1): an open-label, single-arm phase 2 trial", The Lancet Oncology, vol. 13 Issue No. 9, pp. 879-886, Sep. 2012.
Giese, K. et al., "Assembly and function of a TCR enhancer complex is dependent on LEF-I-induced DNA bending and multiple protein-protein interactions", Genes & development, vol. 9, pp. 995-1008, 1995.
Glasmacher, E. et al., "A genomic regulatory element that directs assembly and function of immune-specific AP-1-IRF complexes", Science, vol. 338 Issue No. 6109, pp. 975-980, Nov. 16, 2012.
Glavey, S. V. et al., "American Society of Hematology Annual Meeting 2014: highlights in multiple myeloma", Expert Review of Hematology, vol. 8 Issue No. 3, pp. 273-275, Mar. 24, 2015.
Goh, Y. M. et al., "Src kinase phosphorylates RUNX3 at tyrosine residues and localizes the protein in the cytoplasm", J Biol Chem, vol. 285 Issue No. 13, pp. 10122-10129, Mar. 26, 2010.
Goldberg, S. B. et al., "Pembrolizumab for patients with melanoma or non-small-cell lung cancer and untreated brain metastases: early analysis of a non-randomised, open-label, phase 2 trial", The Lancet Oncology, vol. 17 Issue No. 7, pp. 976-983, Jul. 2016.
Gong, M. C. et al., "Cancer Patient T Cells Genetically Targeted to Prostate-Specific Membrane Antigen Specifically Lyse Prostate Cancer Cells and Release Cytokines in Response to Prostate-Specific Membrane Antigen", Neoplasia, vol. 1 Issue No. 2, pp. 123-127, Jun. 1999.
Gonzalez, H. et al., "Roles of the immune system in cancer: from tumor initiation to metastatic progression", Genes & Development, vol. 32 Issue No. 19-20, pp. 1267-1284, Oct. 1, 2018.
Goodwin, R. G. et al., "Molecular cloning of a ligand for the inducible T cell gene 4-1BB: a member of an emerging family of cytokines with homology to tumor necrosis factor", Eur J Immunol, vol. 23 Issue No. 10, pp. 2631-2641, Oct. 1993.
Gotwals, P. et al., "Prospects for combining targeted and conventional cancer therapy with immunotherapy", Nature Reviews Cancer, vol. 17, pp. 286-301, Mar. 24, 2017.
Grada, Z. et al., "TanCAR: A Novel Bispecific Chimeric Antigen Receptor for Cancer Immunotherapy", Molecular Therapy—Nucleic Acids, vol. 2 Issue No. e105, pp. 1-11, Jul. 9, 2013.
Grahovac, J. et al., "Matrikine and matricellular regulators of EGF receptor signaling on cancer cell migration and invasion", Laboratory Investigation, vol. 94, pp. 31-40, 2014.
Greenwald, R. J. et al., "CTLA-4 regulates induction of anergy in vivo", Immunity, vol. 14 Issue No. 2, pp. 145-155, Feb. 2001.
Griffith, J. W. et al., "Chemokines and chemokine receptors: positioning cells for host defense and immunity", Annu Rev Immunol, vol. 32, pp. 659-702, 2014.
Grigoryan, G. et al., "Design of protein-interaction specificity gives selective bZIP-binding peptides", Nature, vol. 458 Issue No. 7240, pp. 859-864, Apr. 16, 2009.
Grosschedl, R. et al., "HMG domain proteins: architectural elements in the assembly of nucleoprotein structures", Trends Genet, vol. 10 Issue No. 3, pp. 94-100, Mar. 1994.
Guccione, E. et al., "The regulation, functions and clinical relevance of arginine methylation", Nat Rev Mol Cell Biol, vol. 20 Issue No. 10, pp. 642-657, Oct. 2019.
Guertin, D.A et al. "Cell Growth," in The Molecular Basis of Cancer (4th Edn) Mendelsohn, J et al Eds, Saunders (2015), 179-190.
Gunn, M. D. et al., "Mice Lacking Expression of Secondary Lymphoid Organ Chemokine Have Defects in Lymphocyte Homing and Dendritic Cell Localization", J Exp Med, vol. 189 Issue No. 3, pp. 451-460, Feb. 1, 1999.
Haapaniemi, E. M. et al., "Autoimmunity, hypogammaglobulinemia, lymphoproliferation, and mycobacterial disease in patients with activating mutations in STAT3", Blood, vol. 125 Issue No. 4, pp. 639-648, Jan. 22, 2015.
Haart, S. J. D. et al., "Accessory cells of the microenvironment protect multiple myeloma from T-cell cytotoxicity through cell adhesion-mediated immune resistance", Clin Cancer Res., vol. 19 Issue No. 20, pp. 5591-5601, Oct. 15, 2013.
Haart, S. J. D. et al., "Sepantronium bromide (YM155) improves daratumumab-mediated cellular lysis of multiple myeloma cells by abrogation of bone marrow stromal cell-induced resistance", Haematologica, vol. 101 Issue No. 8, pp. e339-e342, Aug. 2016.
Hadinia, A. et al., "CTLA-4 gene promoter and exon 1 polymorphisms in Iranian patients with gastric and colorectal cancers", Journal of Gastroenterology and Hepatology, vol. 22 Issue No. 12, pp. 2283-2287, Dec. 2007.
Hamid, O. et al., "Safety and tumor responses with lambrolizumab (anti-PD-1) in melanoma", The New England Journal of Medicine, vol. 369 Issue No. 2, pp. 134-144, Jul. 11, 2013.
Hamieh, M. et al., "CAR T cell trogocytosis and cooperative killing regulate tumour antigen escape", Nature, vol. 568 Issue No. 7750, pp. 112-116, Mar. 27, 2019.
Han, X. et al., "Multi-antigen-targeted chimeric antigen receptor T cells for cancer therapy", J Hematol Oncol, vol. 12 Issue No. 128, 2019, 10 pages.
Hanabuchi, S. et al., "Fas and its ligand in a general mechanism of T-cell-mediated cytotoxicity", Proc. Natl. Acad. Sci. USA, vol. 91, pp. 4930-4934, May 1994.
Hanahan, D. "Hallmarks of Cancer: New Dimensions", Cancer Discovery, vol. 12 Issue No. 1, pp. 31-46, Jan. 12, 2022.
Haniffa, M. et al., "Ontogeny and functional specialization of dendritic cells in human and mouse", Adv Immunol, vol. 120, pp. 1-49, 2013.
Haring, J. S. et al., "Inflaming the CD8+ T Cell Response", Immunity, vol. 25 Issue No. 1, pp. 19-29, Jul. 2006.
Hashimoto, D. et al., "Tissue-resident macrophages self-maintain locally throughout adult life with minimal contribution from circulating monocytes", Immunity, vol. 38 Issue No. 4, pp. 792-804, Apr. 18, 2013.
Hashimoto, M. et al., "CD8 T Cell Exhaustion in Chronic Infection and Cancer: Opportunities for Interventions", Annual Review of Medicine, vol. 69, pp. 301-318, Jan. 2018.
Hegde, M. et al., "Combinational targeting offsets antigen escape and enhances effector functions of adoptively transferred T cells in glioblastoma", Mol Ther, vol. 21 Issue No. 11, pp. 2087-2101, Nov. 2013.
Hegde, M. et al., "Tandem CAR T cells targeting HER2 and IL13Rα2 mitigate tumor antigen escape", J Clin Invest, vol. 126 Issue No. 8, pp. 3036-3052, Aug. 1, 2016.
Heinisch, I. V. et al., "CD137 activation abrogates granulocyte-macrophage colony-stimulating factor-mediated anti-apoptosis in neutrophils", Eur J Immunol, vol. 30 Issue No. 12, pp. 3441-3446, Dec. 2000.
Henson, S. M. et al., "Blockade of PD-1 or p38 MAP kinase signaling enhances senescent human CD8(+) T-cell proliferation by

(56) References Cited

OTHER PUBLICATIONS distinct pathways", European Journal of Immunology, vol. 45 Issue No. 5, pp. 1441-1451, May 2015.
Henson, S. M. et al., "p38 signaling inhibits mTORC1-independent autophagy in senescent human CD8 T cells", Journal of Clinical Investigation, vol. 124 Issue No. 9, pp. 4004-4016, Sep. 2014.
Herbst, R. S. et al., "Predictive correlates of response to the anti-PD-L1 antibody MPDL3280A in cancer patients", Nature, vol. 515, pp. 563-567, 2014.
Herglotz, J. et al., "Histone arginine methylation keeps RUNX1 target genes in an intermediate state", Oncogene, vol. 32, pp. 2565-2575, 2013 (Abstract Only).
Herrera, Q. B . et al., "A novel pathway of alloantigen presentation by dendritic cells", J Immunol, vol. 173 Issue No. 8, pp. 4828-4837, Oct. 15, 2004.
Hertel, C. B. et al., "Loss of B cell identity correlates with loss of B cell-specific transcription factors in Hodgkin/Reed-Sternberg cells of classical Hodgkin lymphoma", Oncogene, vol. 21, pp. 4908-4920, Jul. 16, 2022 (Abstract Only).
Hess, J. et al. "AP-1 and Cbfa/Runt Physically Interact and Regulate Parathyroid Hormone-dependent MMP13 Expression in Osteoblasts through a New Osteoblast-specific Element 2/AP-1 Composite Element", The Journal of Biological Chemistry, vol. 276, Issue No. 23, pp. 20029-200238, 2001.
Hettinger, J. et al., "Origin of monocytes and macrophages in a committed progenitor", Nat Immunol, vol. 14 Issue No. 8, pp. 1-12, Aug. 2013.
Hilpert, J. et al., "Comprehensive analysis of NKG2D ligand expression and release in leukemia: implications for NKG2D-mediated NK cell responses", J Immunol vol. 189 Issue No. 3, pp. 1360-1371, Aug. 1, 2012.
Hinrichs, C. S. et al., "Reassessing target antigens for adoptive T-cell therapy", Nature Biotechnology, vol. 31 Issue No. 11, Nov. 2013, 24 pages.
Hiraga, J. et al., Down-regulation of CD20 expression in B-cell lymphoma cells after treatment with rituximab-containing combination chemotherapies: its prevalence and clinical significance, Blood, vol. 113 Issue No. 20, pp. 4885-4893, May 14, 2009.
Hirschhorn, J. N. et al., "Evidence that SNF2/SWI2 and SNF5 activate transcription in yeast by altering chromatin structure", Genes & development, vol. 6, pp. 2288-2298, 1992.
Hochweller, K. et al., "Dendritic cells control T cell tonic signaling required for responsiveness to foreign antigen", Proc Natl Acad Sci USA, vol. 107 Issue No. 13, pp. 5931-5936, Mar. 15, 2010.
Hodges, C. et al., "The Many Roles of BAF (mSWI/SNF) and PBAF Complexes in Cancer", Cold Spring Harb Perspect Med, vol. 6 Issue No. 8, pp. 1-25, Aug. 1, 2016.
Holland, S. M. et al., "STAT3 mutations in the hyper-IgE syndrome", N Engl J Med, vol. 357 Issue No. 16, pp. 1608-1619, Oct. 18, 2007.
Holliger, P. et al., "Diabodies: small bivalent and bispecific antibody fragments", Proc Natl Acad Sci USA, vol. 90 Issue No. 14, pp. 6444-6448, Jul. 15, 1993.
Holthof, L. C. et al., "Bone Marrow Mesenchymal Stromal Cells Can Render Multiple Myeloma Cells Resistant to Cytotoxic Machinery of CAR T Cells through Inhibition of Apoptosis", Clin Cancer Res, vol. 27 Issue No. 13, pp. 3793-3803, 2021 (Abstract Only).
Horsley, V. et al., "NFAT: ubiquitous regulator of cell differentiation and adaptation", J Cell Biol, vol. 156 Issue No. 5, pp. 771-774, Mar. 4, 2002.
Huang, G. et al., "Dimerization with PEBP2beta protects RUNX1/AML1 from ubiquitin-proteasome-mediated degradation", EMBO J, vol. 20 Issue No. 4, pp. 723-733, Feb. 15, 2001.
Huang, X-Z. et al., "Efficacy of immune checkpoint inhibitorsand age in cancer patients", Immunotherapy, vol. 12 Issue No. 8, pp. 587-603, 2020.
Huleatt, J. W. et al., "Antigen-driven induction of CD11c on intestinal intraepithelial lymphocytes and CD8+ T cells in vivo", J Immunol, vol. 154 Issue No. 11, pp. 5684-5693, Jun. 1, 1995 (Abstract Only).
Humphrey, S. J. et al., "Protein Phosphorylation: A Major Switch Mechanism for Metabolic Regulation", Trends Endocrinol Metab, vol. 26 Issue No. 12, pp. 676-687, Dec. 2015.
Hurtado, J. C. et al., "Signals through 4-1BB are costimulatory to previously activated splenic T cells and inhibit activation-induced cell death", J Immunol, vol. 158 Issue No. 6, pp. 2600-2609, 1997.
Huster, K. M. et al., "Selective expression of IL-7 receptor on memory T cells identifies early CD40L-dependent generation of distinct CD8+ memory T cell subsets", Proc Natl Acad Sci USA, vol. 101 Issue No. 15, pp. 5610-5615, Apr. 13, 2004.
Ikebuchi, R. et al., "Functional Phenotypic Diversity of Regulatory T Cells Remaining in Inflamed Skin", Front. Immunol., vol. 10 Issue No. 1098, pp. 1-14, May 2019.
Im, S. J. et al., "Defining CD8+ T cells that provide the proliferative burst after PD-1 therapy", Nature, vol. 537 Issue No. 7620, pp. 417-421, Sep. 15, 2016.
Imbalzano, A. N. et al., "Facilitated binding of TATA-binding protein to nucleosomal DNA", Nature, vol. 370, pp. 481-485, Aug. 11, 1994 (Abstract Only).
Intlekofer, A. M. et al., "Effector and memory CD8+ T cell fate coupled by T-bet and eomesodermin", Nat Immunol, vol. 6 Issue No. 12, pp. 1236-1244, Dec. 2005.
Irving, B. A. et al., "The cytoplasmic domain of the T cell receptor zeta chain is sufficient to couple to receptor-associated signal transduction pathways", Cell, vol. 64 Issue No. 5, pp. 891-901, Mar. 8, 1991.
Ise, W. et al., "The transcription factor BATF controls the global regulators of class-switch recombination in both B cells and T cells", Nat Immunol, vol. 12 Issue No. 6, pp. 536-543, Jun. 2011.
Jain, N. et al., "Disruption of SUV39H1-Mediated H3K9 Methylation Sustains CAR T-cell Function", Cancer Discov, vol. 14 Issue No. 1, pp. 142-157, Jan. 12, 2024.
Jain, N. et al., "TET2 guards against unchecked BATF3-induced CAR T cell expansion", Nature, vol. 615 Issue No. 7951, pp. 315-322, Mar. 2023 (Abstract Only).
Jameson, S. C. et al., "Understanding Subset Diversity in T Cell Memory", Immunity, vol. 48 Issue No. 2, pp. 214-226, Feb. 20, 2018.
Janeway, C. A., "The priming of helper T cells", Semin Immunol, vol. 1 Issue No. 1, pp. 13-20, Sep. 1989 (Abstract Only).
Janeway's Immunobiology, "Chapter 6: Antigen Presentation to T Lymphocytes", 9th ed., GS, Garland Science, Taylor & Francis Group, pp. 232-233, 2017.
Janeway's Immunobiology, 9th Ed. Kenneth Murphy & Casey Weaver, Garland Science, New York, NY (2017), at pp. 717-719.
Jemal, A. et al., "Cancer statistics, 2009", CA Cancer J Clin, vol. 59 Issue No. 4, pp. 225-249, Jul.-Aug. 2009.
Jennings, B. H. et al., "The Groucho/TLE/Grg family of transcriptional co-repressors", Genome Biology, vol. 9 Issue No. 205, 2008, 7 pages.
Jensen, M. C. et al., "Designing chimeric antigen receptors to effectively and safely target tumors", Current Opinion in Immunology, vol. 33, pp. 9-15, Apr. 2015.
Jeon, M. S. et al., "Essential role of the E3 ubiquitin ligase Cbl-b in T cell anergy induction", Immunity, vol. 21 Issue No. 2, pp. 167-177, Aug. 2004.
Jilani, I. et al., "Transient down-modulation of CD20 by rituximab in patients with chronic lymphocytic leukemia", Blood, vol. 102 Issue No. 10, pp. 3514-3520, Nov. 15, 2003.
Jinushi, M. et al., "MHC class I chain-related protein A antibodies and shedding are associated with the progression of multiple myeloma", Proc. Natl Acad. Sci. USA, vol. 105 Issue No. 4, pp. 1285-1290, Jan. 29, 2008.
Johnson, D. G. et al., "Role of E2F in cell cycle control and cancer", Front. Biosci. (Landmark Ed), vol. 3 Issue No. 4, pp. 447-458, Apr. 27, 1998.
Joly, E. et al., "What is trogocytosis and what is its purpose?", Nat Immunol, vol. 4 Issue No. 9, pp. 815, Sep. 2003.
Joshi, N. S. et al., "Regulatory T Cells in Tumor-Associated Tertiary Lymphoid Structures Suppress Anti-tumor T Cell Responses", Immunity, vol. 43 Issue No. 3, pp. 579-590, Sep. 15, 2015.

(56) References Cited

OTHER PUBLICATIONS

Jung, I. Y. et al., "BLIMP1 and NR4A3 transcription factors reciprocally regulate antitumor CAR T cell stemness and exhaustion", Sci Transl Med, vol. 14 Issue No. 670, eabn7336, Nov. 9, 2022 (Abstract Only).
Kaczorowski, K. J. et al. "Continuous immunotypes describe human immune variation and predict diverse responses", Proc. Nat. Acad. Sci. USA, vol. 114 Issue No. 30, pp. E6097-E6106, Jul. 10, 2017.
Kaech, S. M. et al., "Selective expression of the interleukin 7 receptor identifies effector CD8 T cells that give rise to long-lived memory cells", Nat Immunol, vol. 4 Issue No. 12, pp. 1191-1198, Dec. 2003.
Kaech, S. M. et al., "Transcriptional control of effector and memory CD8+ T cell differentiation", Nature Reviews Immunology, vol. 12, pp. 749-761, Oct. 19, 2012 (Abstract Only).
Kakarla, S. et al., "Antitumor effects of chimeric receptor engineered human T cells directed to tumor stroma", Mol Ther, vol. 21 Issue No. 8, pp. 1611-1620, Aug. 2013.
Kar, A. et al., "Molecular mechanisms of ETS transcription factor-mediated tumorigenesis", Crit Rev Biochem Mol Biol, vol. 48 Issue No. 6, pp. 522-543, Nov.-Dec. 2013.
Karlsson, H. et al., "Evaluation of Intracellular Signaling Downstream Chimeric Antigen Receptors", PLOS One, vol. 10, pp. 1-20, Dec. 23, 2015.
Kartikasari, A. E. R. et al., "Therapeutic Cancer Vaccines—T Cell Responses and Epigenetic Modulation", Front. Immunol., vol. 9 Issue No. 3109, pp. 1-15, Jan. 25, 2019.
Katz, S. C. et al., "Phase I Hepatic Immunotherapy for Metastases Study of Intra-Arterial Chimeric Antigen Receptor-Modified T-cell Therapy for CEA+ Liver Metastases", Clin Cancer Res, vol. 21 Issue No. 14, pp. 3149-3159, Jul. 15, 2015.
Kaufman, H. L. et al., "General Principles of Tumor Immunotherapy", Basic and Clinical Applications of Tumor Immunology, Chapter 5, pp. 67-121, 2007.
Khavari, P. A. et al., "BRG1 contains a conserved domain of the SWI2/SNF2 family necessary for normal mitotic growth and transcription", Nature, vol. 366, pp. 170-174, 1993.
Kikuchi, H. et al., "Cytotoxicity of Vitex agnus-castus fruit extract and its major component, casticin, correlates with differentiation status in leukemia cell lines", International Journal of Oncology, vol. 43 Issue No. 6, pp. 1976-1984, Dec. 2013.
Kim, C. M. et al., "Crystal structure of TRAF1 TRAF domain and its implications in the TRAF1-mediated intracellular signaling pathway", Scientific Reports, vol. 6 Issue No. 25526, pp. 1-10, May 6, 2016.
Kim, H-R. et al., "Pim-1 kinase phosphorylates and stabilizes RUNX3 and alters its subcellular localization", J. Cell Biochem., vol. 105 Issue No. 4, pp. 1048-1058, Nov. 1, 2008.
Kim, S. et al., "CTCF as a multifunctional protein in genome regulation and gene expression", Exp Mol Med, vol. 47 Issue No. 6, Jun. 5, 2015, 4 pages.
Klampatsa, A. et al., "Chimeric Antigen Receptor (CAR) T Cell Therapy for Malignant Pleural Mesothelioma (MPM)", Cancers, vol. 9 Issue No. 9, 2017, 10 pages.
Klingemann, H. "Are natural killer cells superior CAR drivers?", Oncoimmunology, vol. 3, pp. e28147-1-e28147-4, Apr. 15, 2014.
Kloss, C. C. et al., "Combinatorial antigen recognition with balanced signaling promotes selective tumor eradication by engineered T cells", Nat Biotechnol, vol. 31 Issue No. 1, pp. 71-75, Jan. 2013.
Kochenderfer, J. N. et al., "Chemotherapy-refractory diffuse large B-cell lymphoma and indolent B-cell malignancies can be effectively treated with autologous T cells expressing an anti-CD19 chimeric antigen receptor", J Clin Oncol, vol. 33 Issue No. 6, pp. 540-549, Feb. 20, 2015.
Kohrt, H. E. et al., "CD137 stimulation enhances the antilymphoma activity of anti-CD20 antibodies", Blood, vol. 117 Issue No. 8, pp. 2423-2432, Feb. 24, 2011.
Kohrt, H. E. et al., "Stimulation of natural killer cells with a CD137-specific antibody enhances trastuzumab efficacy in xenotransplant models of breast cancer", J Clin Invest, vol. 122 Issue No. 3, pp. 1066-1075, Mar. 2012.
Kohrt, H. E. et al., "Targeting CD137 enhances the efficacy of cetuximab", J Clin Invest, vol. 124 Issue No. 6, pp. 2668-2682, Jun. 2014.
Kong, J. C. et al., "Chimeric antigen receptor-natural killer cell therapy: current advancements and strategies to overcome challenges", Front. Immunol., vol. 15, pp. 1-15, Apr. 25, 2024.
Korinfskaya, S. et al., "Runx Transcription Factors in T Cells—What Is Beyond Thymic Development?", Front. Immunol., vol. 12 Issue No. 701924, pp. 1-16, Aug. 2021.
Korneev, K. V. et al., "TLR-signaling and proinflammatory cytokines as drivers of tumorigenesis", Cytokine, vol. 89, pp. 127-135, Jan. 2017.
Kozani, P. S. et al., "Recent Advances in Solid Tumor CAR-T Cell Therapy: Driving Tumor Cells From Hero to Zero?", Frontiers in Immunology, vol. 13 Issue No. 795164, pp. 1-22, May 2022.
Krause, A. et al., "Antigen-dependent CD28 signaling selectively enhances survival and proliferation in genetically modified activated human primary T lymphocytes", Journal of Experimental Medicine, vol. 188 Issue No. 4, pp. 619-626, Aug. 17, 1998.
Kruger, W. et al., "Amino acid substitutions in the structured domains of histones H3 and H4 partially relieve the requirement of the yeast SWI/SNF complex for transcription", Genes Dev, vol. 9 Issue No. 22, pp. 2770-2779, Nov. 15, 1995.
Kryczek, I. et al., "B7-H4 expression identifies a novel suppressive macrophage population in human ovarian carcinoma", Journal of Experimental Medicine, vol. 203 Issue No. 4, pp. 871-881, Apr. 17, 2006.
Kunert, A. et al., "CD45RA+CCR7−CD8 T cells lacking co-stimulatory receptors demonstrate enhanced frequency in peripheral blood of NSCLC patients responding to nivolumab", The Journal for Immuno Therapy of Cancer, vol. 7 Issue No. 1, 2019, 13 pages.
Kurachi, M. et al., "The transcription factor BATF operates as an essential differentiation checkpoint in early effector CD8+ T cells", Nature Immunology, vol. 15 Issue No. 4, pp. 373-383, Mar. 2, 2014.
Kwoczek, J. et al., "Cord blood-derived T cells allow the generation of a more naïve tumor-reactive cytotoxic T-cell phenotype", Transfusion, vol. 58 Issue No. 1, pp. 88-99, Jan. 2018.
Kwon, H. et al., "Nucleosome disruption and enhancement of activator binding by a human SW1/SNF complex", Nature, vol. 370, pp. 477-481, Aug. 11, 1994 (Abstract Only).
Lamers, C. H. J. et al., "Treatment of metastatic renal cell carcinoma with autologous T-lymphocytes genetically retargeted against carbonic anhydrase IX: first clinical experience", J Clin Oncol, vol. 24 Issue No. 13, pp. e20-e22, May 1, 2006.
Lanier, L. L. "NK cell receptors", Annual Review of Immunology, vol. 16, pp. 359-393, 1998.
Lanitis, E. et al., "Chimeric antigen receptor T Cells with dissociated signaling domains exhibit focused antitumor activity with reduced potential for toxicity in vivo", Cancer Immunol Res, vol. 1 Issue No. 1, pp. 43-53, Jul. 2013.
Lanna, A. et al., "IFN-α Inhibits Telomerase in Human CD8+ T Cells by Both hTERT Downregulation and Induction of p38 MAPK Signaling", Journal of Immunology, vol. 191 Issue No. 7, pp. 3744-3752, 2013.
Lanna, A. et al., "The kinase p38 activated by the metabolic regulator AMPK and scaffold TAB1 drives the senescence of human T cells", Nature Immunology, vol. 15 Issue No. 10, Oct. 2014, 10 pages.
Lanza, F. et al., "CD22 Expression in B-Cell Acute Lymphoblastic Leukemia: Biological Significance and Implications for Inotuzumab Therapy in Adults", Cancers (Basel), vol. 12 Issue No. 2, 2020, 15 pages.

* cited by examiner

FIG. 1A

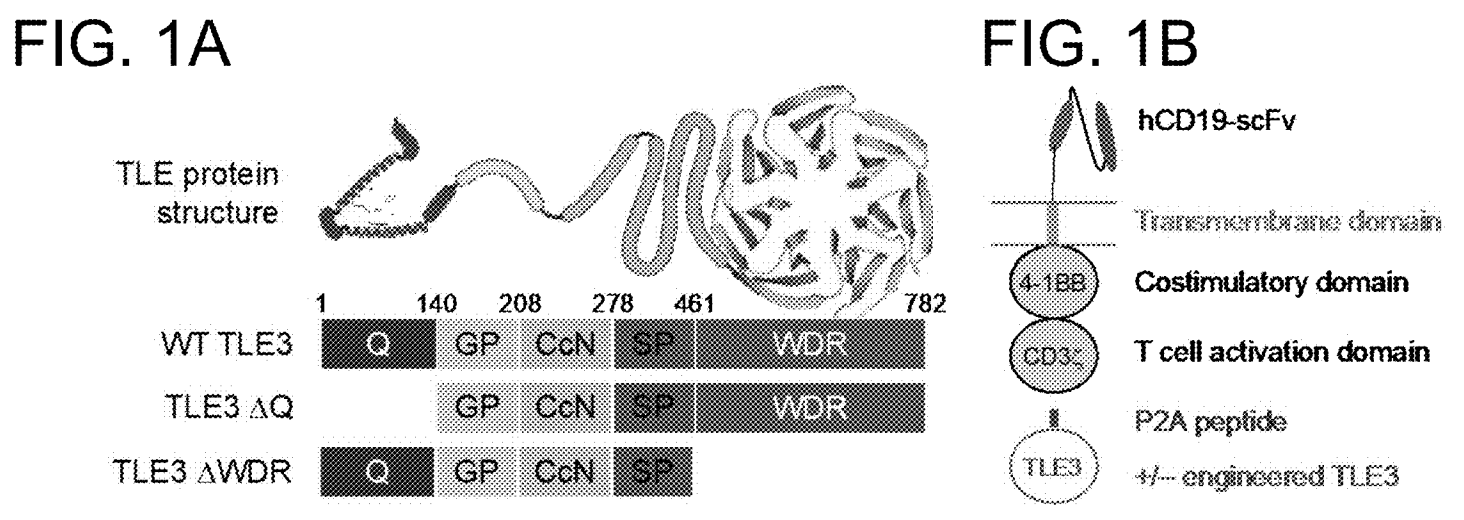

TLE protein structure

WT TLE3

TLE3 ΔQ

TLE3 ΔWDR 1 140 208 278 461 782

Q GP CcN SP WDR

FIG. 1B hCD19-scFv

Transmembrane domain

Costimulatory domain

T cell activation domain

P2A peptide

+/− engineered TLE3

4-1BB

CD3ζ

TLE3

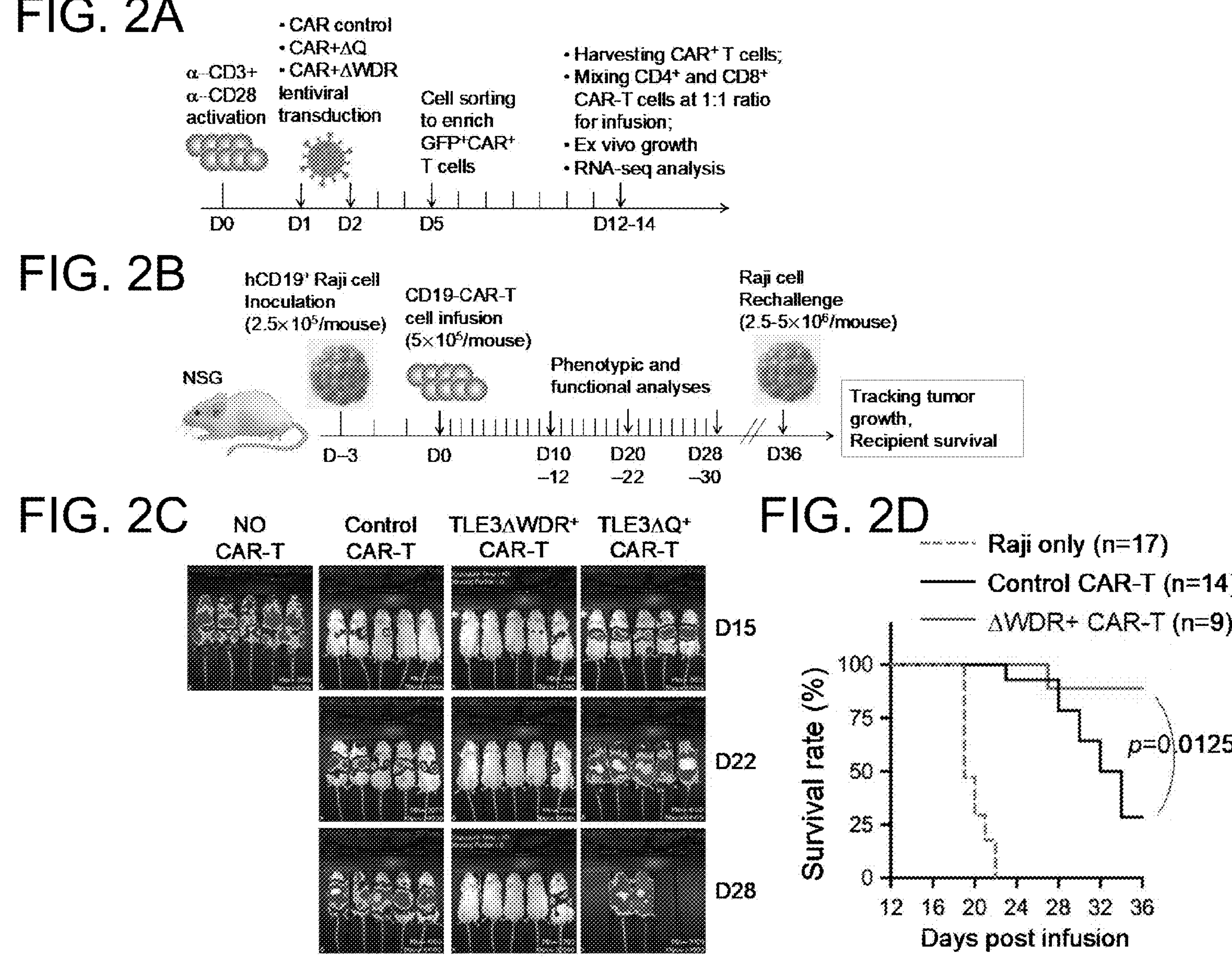

FIG. 2A
α-CD3+
α-CD28
activation
• CAR control
• CAR+ΔQ
• CAR+ΔWDR
lentiviral
transduction
Cell sorting
to enrich
GFP+CAR+
T cells
• Harvesting CAR+ T cells;
• Mixing CD4+ and CD8+
CAR-T cells at 1:1 ratio
for infusion;
• Ex vivo growth
• RNA-seq analysis
D0
D1
D2
D5
D12-14
FIG. 2B
NSG
hCD19+ Raji cell
Inoculation
(2.5×10^5/mouse)
CD19-CAR-T
cell infusion
(5×10^5/mouse)
Phenotypic and
functional analyses
Raji cell
Rechallenge
(2.5-5×10^6/mouse)
Tracking tumor
growth,
Recipient survival
D-3
D0
D10
-12
D20
-22
D28
-30
D36
FIG. 2C
NO
CAR-T
Control
CAR-T
TLE3ΔWDR+
CAR-T
TLE3ΔQ+
CAR-T
D15
D22
D28
FIG. 2D
Raji only (n=17)
Control CAR-T (n=14)
ΔWDR+ CAR-T (n=9)
Survival rate (%)
100
75
50
25
0
p=0.0125
12
16
20
24
28
32
36
Days post infusion

FIG. 3A

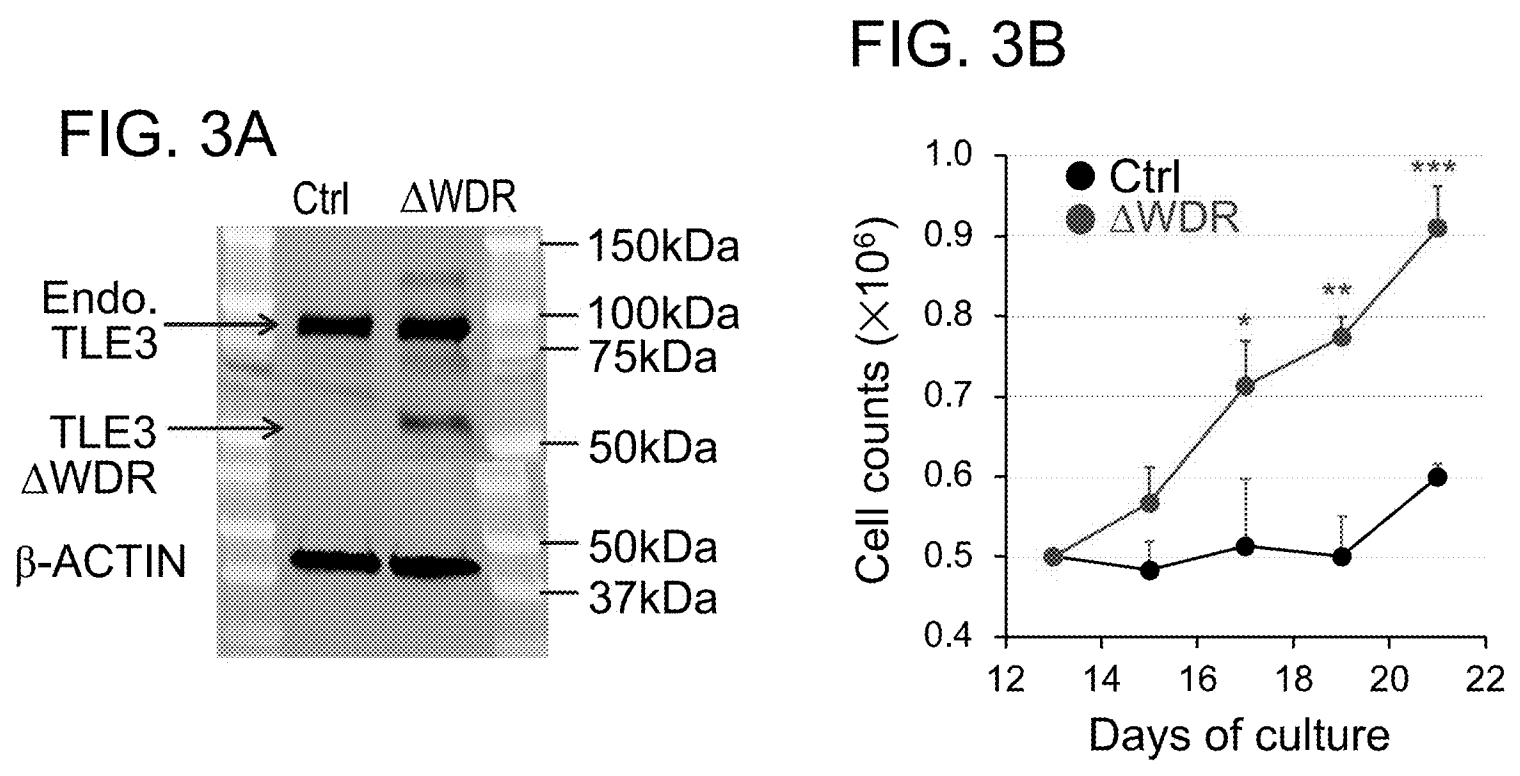

Ctrl ΔWDR

Endo. TLE3

TLE3 ΔWDR

β-ACTIN

150kDa
100kDa
75kDa
50kDa
50kDa
37kDa

FIG. 3B

Ctrl
ΔWDR

Cell counts (×10^6)

1.0
0.9
0.8
0.7
0.6
0.5
0.4

*
**
***

12 14 16 18 20 22

Days of culture

Donor1
Ctrl
w/o stim
Ctrl
w/ stim
ΔWDR
w/o stim
ΔWDR
w/ stim
PC1: 33.8% variance
PC2: 9.4% variance
Donor2
Ctrl
w/o stim
Ctrl
w/ stim
ΔWDR
w/o stim
ΔWDR
w/ stim
PC1: 45% variance
PC2: 10.8% variance ctrl_stim_r1
ctrl_stim_r2
ctrl_stim_r3
dWDR_stim_r1
dWDR_stim_r2
dWDR_stim_r3
TLE3
AEBP1
ARRB1
EPAS1
MYBL1
TCEA3
ZNF629
E2F2
SMARCA2
ITGAX
FGFR1
PAGFRB
COL6A2
PIK3R6
BCL2L11
BMF
NEK6
PIM3
SRGN
ETS2
TBX21
ID2
PLAGL2
NUS1
ACSL6
PAM
-1.5:1.5
b1stim glist1
b1stim glist2
b2stim glist1
b2stim glist2
Row level Z-Score
-1.5
-1.0
-0.5
0.0
0.5
1.0
1.5

CAR-T+ in blood (%)
10^2
10^1
10^0
10^-1
10^-2
10^-3
**
***
***
10
20
30
Days post-infusion
Ctrl
ΔWDR CD4+ or CD8+ freq in CAR-T cells (%)
120
100
80
60
40
20
0
NRD
NRD
CD4+
CD8+
D10
D20
D30
***
***
Ctrl
ΔWDR

FIG. 5A

CAR-T cell numbers $10^6$ $10^5$ $10^4$ $10^3$

CD4+ CD8+ CD4+ CD8+

Donor2

$10^7$ $10^6$ $10^5$ $10^4$ $10^3$

*

CD4+ CD8+ CD4+ CD8+

Donor3

Ctrl

ΔWDR

FIG. 5B

High
Cured
Ctrl
ΔWDR
23
18
3
0%
20%
40%
60%
80%
100%
Case distribution

CAR-T cell numbers
$10^6$
$10^5$
$10^4$
$10^3$
Ctrl
ΔWDR

Control
ΔWDR
CD8⁺ CAR-T
CD4⁺ CAR-T
9.5
84
1.4
5.2
7.3
48.9
7.7
36.1
2.1
0.3
85.5
12.1
0.1
0.2
95.1
4.6
TIM3
PD1 PE CD8⁺ CAR-T
CD4⁺ CAR-T
Relative expression
1.5
1
0.5
0
PD1
TIM3
LAG3
**
***
Ctrl
ΔWDR Control CAR-T (n=4)
ΔWDR+ CAR-T (n=6)
Survival rate (%)
100
75
50
25
0
p=0.0039
0
10
20
30
Days post rechallenge 0
6
10
17
Days post-rechallenge TIM3hiPD1+ subset (%)
50
40
30
20
10
0
0
5
10
15
Days post-rechallenge

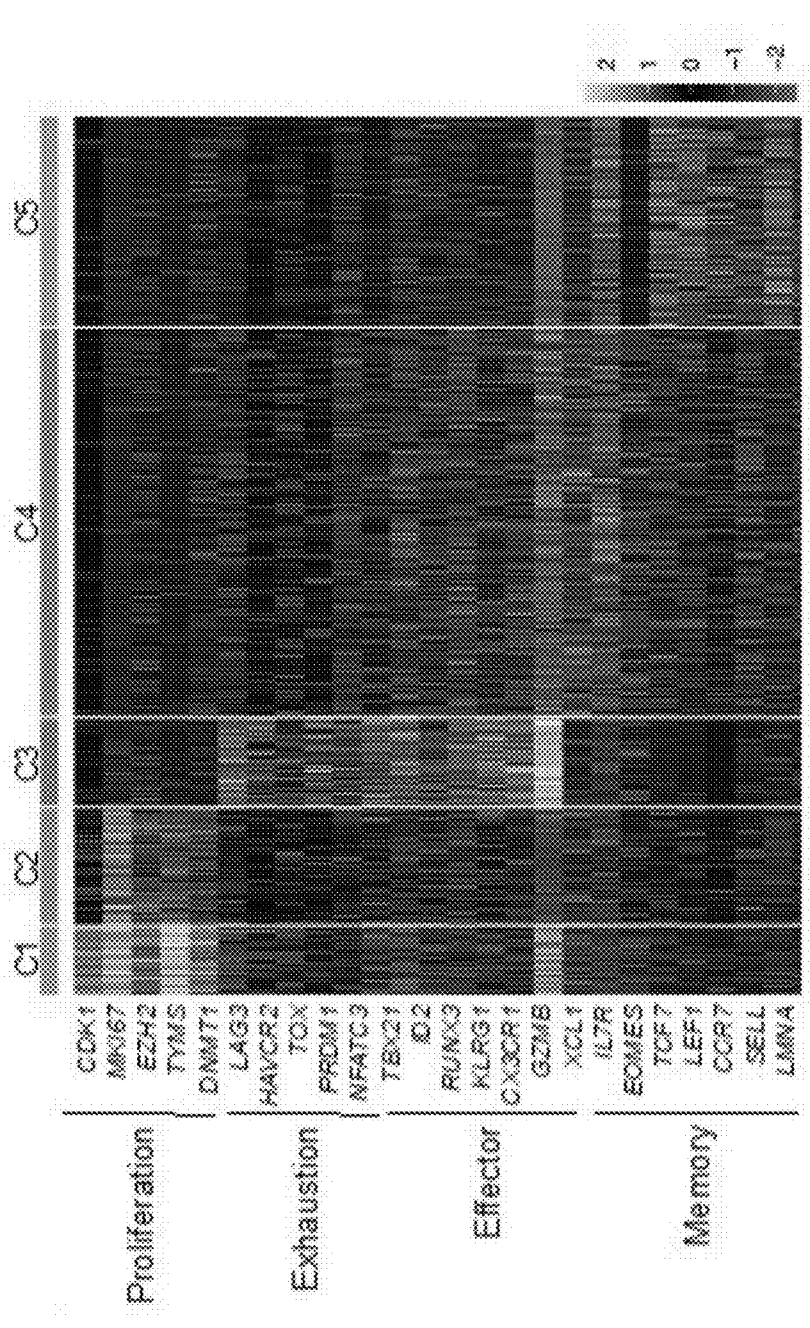
FIG. 11C

MOLECULAR ENGINEERING TO ENHANCE CAR-T MEDIATED TUMOR IMMUNOTHERAPY

CROSS REFERENCE TO RELATED APPLICATIONS

This application claims the benefit of priority to U.S. provisional application 63/707,903 (filed Oct. 16, 2024) and U.S. provisional application 63/765,909 (filed Mar. 3, 2025). The contents of each of these applications are incorporated herein by reference.

FIELD OF THE INVENTION

The present invention relates to methods for improving persistence and decreasing exhaustion of genetically engineered immune effector cells for treating hematological cancers.

BACKGROUND OF THE INVENTION

The Relationship Between the Immune System and Cancer

A tumor originates from a normal cell that has undergone tumorigenic transformation. This transformed cell is the cell-of-origin (COO) for the tumor. Tumorigenesis consists of four stages [Bi, Q. J. Immunology Res. (2022) (2022) article 3128933, citing Balani, S. et al. Nature Communic. (2017) 8 (1): article 15422; Chaffer, C L and Weinberg, RA. Cancer Discovery (2015) 5 (10): 22-24; Loeb, LA and Harris, CC. Cancer Res. (2008) 68 (17): 6863-71]: (1) tumor initiation, the initial stage of tumorigenesis, is the stage in which normal cells undergo irreversible genetic alterations under the influence of oncogenic factors, thus transforming into COOs with the possibility of malignant transformation; (2) tumor promotion is the period during which COOs clone selectively and transform into premalignant cells under the influence of protumor factors and other specific conditions; (3) malignant conversion is the stage in which premalignant cells start expressing malignant phenotypes; and (4) tumor progression is the final stage of tumorigenesis, in which premalignant cells develop into real tumor cells, obtain a series of new biological characteristics (including sustaining proliferative signaling, evading growth suppressors, resisting cell death, enabling replicative immortality, inducing or accessing vasculature, activating invasion and metastasis, deregulating cellular metabolism, avoiding immune destruction, and unlocking phenotypic plasticity, nonmutational epigenetic reprogramming, polymorphic microbiomes, and senescent cells) [Id., citing Hanahan, D. Cancer Discovery (2022) 12 (1): 31-46], and undergo more invasion and metastasis. These characteristics are the result of the superposition of various factors, particularly the tumor microenvironment (TME).

Tumors are edited by the immune system as they evolve and can escape rejection in many ways. In the elimination phase, when tumors arise in a tissue, a number of immune cells (e.g., NK cells, CD4 T cells, CD8 T cells, and γδT cells) can recognize and destroy potential tumor cells. If elimination is not completely successful, what follows is an equilibrium phase, in which, according to the cancer immunoediting hypothesis, tumor cells undergo changes or mutations that aid their survival because of the selection pressure imposed by the immune system so that a variety of different tumor cells develop. In the escape phase, tumor cells that have acquired the ability to elude the attentions of the immune system, by either escaping the killing mechanism or recruiting regulatory cells to protect it, spread unchallenged and become clinically detectable. [Janeway's Immunobiology, 9th Ed. Kenneth Murphy & Casey Weaver, Garland Science, New York, NY (2017), at pp 717].

Tumors can avoid stimulating an immune response or can evade it when it occurs by numerous mechanisms. For example, spontaneous tumors may initially lack mutations that produce new tumor-specific antigens that elicit T cell responses. Even when a tumor specific antigen is expressed and is taken up and presented by APCs, if co-stimulatory signals are absent the APC will tend to treat the tumor as self, rather than activating T cells. Some tumors lose the expression of a particular MHC class I molecule perhaps through immune selection by T cells specific for a peptide presented by that MHC class I molecule; such tumors that have lost such antigens are no longer eliminated by the immune system, a process termed "antigenic modulation". Tumors also seem able to evade immune attack by creating a generally immunosuppressive microenvironment. Many tumors make immunosuppressive cytokines, such as transforming growth factor beta (TGFβ), which tends to suppress the inflammatory T cell responses and cell mediated immunity needed to control tumor growth. For example, TGFβ induces the development of inducible regulatory T cells (Tregs). Some tumors, such as melanoma, ovarian carcinoma, and B-cell lymphoma, produce the immunosuppressive cytokine IL-10, which can reduce dendritic cell activity and inhibit T cell activation. The microenvironment of some tumors also contains populations of myeloid-derived suppressor cells (MDSCs), which can inhibit T-cell activation within the tumor. Some tumors express immune checkpoints, which directly inhibit immune responses. Tumors also can produce enzymes that act to suppress local immune responses. For example, the enzyme indoleamine 2,3-dioxygenase (IDO) catabolizes tryptophan, an essential amino acid, to produce the immunosuppressive metabolite kynurenine. Tumor cells also can produce materials, such as collagen, which create a physical barrier around the tumor, preventing interaction with cells of the immune system. [Janeway's Immunobiology, 9th Ed. Kenneth Murphy & Casey Weaver, Garland Science, New York, NY (2017), at pp 718-19]. An established clinical tumor can be sustained by subpopulations of self-renewing cancer cells operationally termed cancer stem cells (CSCs) that can generate, intraclonally, both tumorigenic and non-tumorigenic cells. [Rycaj, K. and Tang, DG, Cancer Res. (2015) 75 (19): 4003-11].

Immune checkpoints. During immune homeostasis, a crucial mechanism of peripheral tolerance is the regulation of an effector T-cell response via immune checkpoints on cytotoxic lymphocytes (CTLs) and activated CD4+ T cells to protect tissue from inflammatory damage. For example, two checkpoint molecules, CTLA-4 and PD-1, act as negative regulators of T-cell function and have been associated with immune evasion in cancer [Gonzalez, H. et al. Genes & Development (2018) 32:1267-84, citing Pardoll, DM (2012) Nat Rev Cancer 12:252-264]. The involvement of CTLA-4 signaling in cancer has been described in melanoma ([Id., citing Bouwhuis, M G et al. (2010) Cancer Immunol Immunother 59:303-312], lung ([Id., citing Khaghanzadeh, N. et al. (2010) Cancer Genet Cytogenet 196:171-174], breast ([Id., citing Erfani N. et al. Cancer Genet. Cytogenet. (2006) 165 (2): 114-20], gastric [Id., citing Hadinia, A. et al. (2007) J Gastroenterol Hepatol 22:2283-2287], and colorectal ([Id., citing Hadinia, A. et al. (2007) J Gastroenterol Hepatol 22:2283-2287; Dilmec, F. et al. (2008). Int J Immunogenet 35:317-321] cancers. Furthermore, the engagement of PD-1 with its coreceptor, PD-L1 (expressed by other immune cells, mesenchymal cells, vascular cells, and cancer cells), results in the down-regulation of T-cell activity, which inhibits their anti-tumor activities, such as T-cell migration, proliferation, secretion of cytotoxic mediators, and restriction of cell killing ([Id., citing Topalian, S L et al. (2015) Cancer Cell 27:450-461]. The use of immune checkpoint inhibitors such as anti-PD-1 (e.g., lambrolizumab, pembrolizumab (KEYTRUDA®) and nivolumab (OPDIVO®), anti-PD-L1 (MPDL3280A, Atezolizumab, TECENTRIQ®), and anti-CTLA4 (ipilimumab, YERVOY®) has had success enhancing the effector anti-tumor response in different malignancies ([Id., citing Gotwals, P. et al. (2017). Nat Rev Cancer 17:286-301], especially in melanoma and lung cancer ([Id., citing Hamid, O. et al. (2013) N Engl J Med 369:134-144; Herbst, R S et al. (2014). Nature 515:563-567; Topalian, S L et al. (2015) Cancer Cell 27:450-461].

As the tumor grows and the TME changes, new antigens are produced, and the ability of the immune system to prime new repertoires of T cells and direct them toward the tumor changes, thus altering the efficacy of tumor containment. As the immune system functions to stall tumor growth, cancer cells and the TME simultaneously suppress anti-tumor function by engaging immune checkpoints and the recruitment of regulatory CD4+ T cells (Tregs). Tregs are responsible for suppressing the priming, activation, and cytotoxicity of other effector immune cells, such as $T_H1$ CD4 T cells, CTLs, macrophages, NK cells, and neutrophils ([Id., citing Ward-Hartstonge K A, Kemp R A. (2017). Clin Transl Immunology 6: e154]. The Treg-mediated immunosuppression is orchestrated by contact-dependent mechanisms such as the expression of PD-L1, LAG-3, CD39/73, CTLA-4, or PD-1, with CTLA-4 and PD-1 even enhancing suppressive activity ([Id., citing Walker L S, Sansom D M. (2015) Trends Immunol 36:63-70], and by contact-independent mechanisms, which involve the sequestration of IL-2 and production of immune-suppressive molecules such as IL-10, TGF-β, prostaglandin E2, adenosine, and galectin-1 [Id., citing Francisco, L M et al. (2009). J Exp Med 206:3015-3029; Campbell, DJ (2015) Eur J Immunol 195:2507-2513]. In squamous cell carcinoma, the inhibition of focal adhesion kinase (FAK)—a cell contact-independent mechanism—results in CCL5 secretion by cancer cells that induces the recruitment of Tregs to the tumor site, where they suppress cytotoxic anti-tumor CD8+ T cells ([Id., citing Serrels, A. et al. (2015) Cell 163:160-173]. In breast and lung adenocarcinoma, Tregs suppress T-cell activation and the anti-tumor immune response in tumor-associated tertiary structures. Specific Treg depletion results in tumor cell death and increased production of IFN-γ ([Id., citing Bos, P D et al. (2013) J Exp Med 210:2435-2466; Joshi, N S et al. (2015) Immunity 43:579-590]. In breast cancer, infiltration of Tregs was correlated with worse patient outcome [Id., citing Allaoui, R. et al. (2017) Cancer Biomark 20:395-409].

In metastasis, CTLs exert an anti-metastatic effect in bone metastasis [Id., citing Bidwell, B N et al. (2012) Nat Med 18:1224-1231], while prospective analyses of lung and breast cancer patients established an opposite correlation between the level of circulating cancer cells and T cells in peripheral blood [Id., citing Mego, M et al. (2016) Circulating tumor cells (CTC) are associated with defects in adaptive immunity in patients with inflammatory breast cancer. J Cancer 7:1095-1104; Sun, W W et al. (2017) Onco Targets Ther 10:2413-2424].

These data extend to clinical trials reporting the therapeutic efficacy of immune checkpoint inhibition in metastatic carcinomas [Id., citing Di Giacomo, A M et al. (2012) Lancet Oncol 13:879-886; Queirolo, P. et al. (2014) J Neurooncol 118:109-116; Motzer, R J et al. (2015) N Engl J Med 373:1803-1813; Furudate, S. et al. (2016) Case Rep Oncol 9:644-649; Goldberg, S B et al. (2016) Lancet Oncol 17:976-983; Pai-Scherf, L. et al. (2017) Oncologist 22:1392-1399]. Checkpoint inhibitors are significantly effective in treating brain metastatic tumors from melanoma and lung cancer [Id., citing Queirolo, P. et al. (2014). J Neurooncol 118:109-116; Goldberg, S B et al. (2016) Lancet Oncol 17:976-983; Di Giacomo, A M et al. (2017) Cytokine Growth Factor Rev 36:33-38]. Evidence suggests that the effectiveness of checkpoint inhibition in melanoma brain metastasis depends on extracranial disease and peripheral activation of CD8+ T cells [Id., citing Taggart, D. et al. (2018) Proc Natl Acad Sci 115: E1540-E1549]. On the other hand, a high level of circulating Tregs has been associated with a higher risk of metastasis in non-small lung carcinoma patients. [Id., citing Erfani, N. et al. (2012) Lung Cancer 77:306-311]. Similar associations have been described in breast cancer [Id., citing Metelli, A. et al. (2016) Cancer Res 76:7106-7117], colorectal carcinoma metastasis [Id., citing Wang, Q. et al. (2014) Cell Immunol 287:100-105, and hepatocellular carcinoma [Id., citing Ye, L Y et al. (2016) Cancer Res 76:818-830].

Chimeric Antigen Receptor Immunotherapy

T cell receptors (TCRs) expressed on the surface of T lymphocytes can only recognize the peptide antigens presented to them through major histocompatibility complexes (MHCs) by antigen-presenting cells (APCs). For example, human T cells genetically engineered to express a high-avidity TCR that targets HPV-16 E7 through recognition of the $E7_{(11-19)}$ epitope complexed with HLA-A*02:01 demonstrated clinical activity in a phase 1 clinical trial for the treatment of metastatic human papilloma virus-associated epithelial cancers (NCT02858310). [Naagarasheth, N B et al. Nature Med. (2021) 27 (30:419-425). However, transcriptional loss of the specific HLA genes presenting the targeted viral epitope under CD8+ T cell pressure leading to a late acquired resistance to immunotherapy has been reported in metastatic Merkel cell carcinoma. [Paulson, K G et al. Nature Communic. (2018) 9:3868].

Monoclonal antibodies can recognize and bind cell surface-expressed antigens that are not presented by MHCs. This ability has been utilized to redirect the cytotoxicity of various kinds of immune cells toward tumor surface-expressed antigens of interest that can be either tumor-specific antigens (TSAs) or tumor-associated antigens (TAAs). [Kozani, P S et al. Front. Immunol. (2022) 13:795164].

The term "chimeric antigen receptor" or "CAR" as used herein refers to a synthetic MHC-independent receptor that targets T cells to a chosen antigen and reprograms T cell function, metabolism, and persistence [Riviere, I. and Sadelain, M. Mol. Ther. (2017) 25 (5): 1117-24, citing Eshhar, Z. et al. Springer Semin. Immunopathol. (1996) 18:199-209; Sadalain, M. et al. Nat. Rev. Cancer (2003) 3:35-45]. A CAR is mainly composed of three parts: an extracellular antigen recognition domain, usually a single-chain variable fragment (scFv) derived from a monoclonal antibody; a spacer/hinge region and transmembrane domain; and an intracellular signal transduction domain.

In first generation CARs, the intracellular signal transduction domain included a CD3ζ chain. In a second-generation CAR, the intracellular signal transduction domain included a CD3 ζ chain and one costimulatory molecule. In a third generation CAR, the intracellular signal transduction domain included a CD3ζ chain and two costimulatory molecules. The intracellular signal transduction domain of a fourth generation CAR includes a CD3 ζ chain and one costimulatory molecule and expresses a cytokine, such as IL-12.

An optimal CAR will specifically bind an antigen expressed in high abundance in tumor cells to form an effective immunological synapse leading to downstream T-cell signaling and a potent and specific anti-tumor effect.

Through their extracellular domain, CARs bind cell surface molecules independently of the major histocompatibility complex (MHC), in contrast to the physiological T cell receptor, which engages MHC/peptide complexes. CARs may thus target proteins, carbohydrates, or glycolipids and function independently of patient HLA haplotype. Binding to antigen triggers T cell activation, which is commonly mediated by the cytoplasmic domain of the CD3-ζ chain. [Riviere, I. and Sadelain, M. Mol. Ther. (2017) 25 (5): 1117-24, citing Irving, B A and Weiss, A. Cell (1991) 64:891-901; Romeo, C., Seed, B. Cell (1991) 64:1037-46; Letourneur, F. and Klausner, RD. Proc. Natl. Acad. Sci. USA (1991) 88:8905-9; Eshhar, Z. et al. Proc. Natl Acad. Sci. USA (1993) 90:720-24; Brocker, T. et al. Eur. J. Immunol. (1993) 23:1435-1439].

Merely providing T cell activation is, however, not sufficient to direct a productive immune response. [Id., citing Brocher, T. and Karjalainen, K. J. Exp. Med. (1995) 181: 1653-1659; Gong, M M C et al. Neoplasia (1999) 1:123-7; Brocker, T. Blood (2000) 96:1999-2001]. The CARs that have provided tangible clinical benefits incorporate a costimulatory domain [Id., citing Krause, A. et al. J. Exp. Med. (1998) 188:619-26;] which enables T cells to expand and retain their functionality upon repeated exposure to antigen [Id., citing Maher, J. et al. Nat. Biotechnol. (2002) 20:70-75]. These receptors have been dubbed second generation CARs [Id., citing Sadelain, M. et al. Curr. Opinion. Immunol. (2009) 21:215-233] and are key to the design of persisting engineered T cells that can attack tumors as long as they retain their functionality. Several reviews have addressed CAR design [Id., citing Jensen, M C and Riddell, SR. Curr. Opinion. Immunol. (2015) 33:9-15; van der Stegan, S J et al. Nat. Rev. Drug Discov. (2015) 14:499-509; Sadelain, M. J. Clin. Invest. (2015) 125:3392-3400; Maus, M V and June, C H. Clin. Cancer Res. (2016) 22:1875-1884], CAR prospects for solid tumors [Id., citing Hinrichs, C S and Restifo, N P Nat. Biotechnol. (2013) 999-1008; Morello, A. et al. Cancer Discov. (2016) 6:133-46], and T cell manufacturing [Id., citing Wang, X. and Riviere I., Mol. Ther. Oncolytics. (2016) 3:16015; Levine, B L et al. Mol. Ther. Methods Clin. Dev. (2016) 4:92-101; Wang, X., Riviere, I. Cancer Gene Ther. (2015) 22:85-94].

Clinical trials of CAR-T cells targeting the B cell antigen CD19 have shown sustained complete responses in patients with refractory relapsed B cell cancers, although with associated toxicity [Gavriil, A. et al. Cancers (2020) 12:2326, citing Maude, S L et al. N. Engl. J. Med. (2014) 371:1507-17; Titov, A. et al. Cell Death Dis. (2018) 9:897]. Solid tumors have been generally refractory for diverse reasons, including physical barriers to access of T cells, the presence of suppressive immune cells and tumor cells, the variability of expression of the target antigen, and in many tumors, low mutational burden limiting antigen spreading and generation of memory responses [Id., citing Majzner, R G and Mackall, CL. Nat. Med. (2019) 25:1341-1355; Martinez, M. et al. Front. Immunol. (2019) 10:128; Yu, W-L et al. Cancers (2019) 11:47].

Tumor Escape from CAR-T Cell Therapy.

To date, antigen loss, immune dysfunction, exhaustion and microenvironment-mediated upregulation of anti-apoptotic pathways have been identified as major modes of escape by solid tumors from CAR-T cell immunotherapy.

Antigen loss. Loss of expression of the antigen on tumor cells targeted by the CAR extracellular domain via the selective immune pressure of CAR-T cells is a major mechanism of CAR-T cell therapy failure. While antigen downregulation or dim expression is a well-known event in lymphoma and myeloma treated with therapeutic IgG antibodies [Rasche, L. et al. N. Kroger, et al, eds. Chapter 4 in The EBMT/EHA CAR-T Cell Handbook (2002) doi.org/10.1007/978-3-030-94353-0_4, citing Plesner, T. et al. Cell (2020) 9 (2): 378; Jilani, I. et al. (2003) Blood (2003) 102 (10): 3514-20], complete target loss is a phenomenon typically occurring after T-cell based therapy, such as CAR-T cell or T cell engaging bispecific antibodies (TCE) therapy, and rarely after treatment with antibody-drug conjugates. For example, antigen loss is a key mechanism of resistance to B cell immunotherapies targeting CD19, CD20 and CD22. [Id., citing Orlando, E J, et al. Nat. Med. (2018) 24 (10): 1504-6; Bannerji, R. et al. Blood (2018) 132 (Suppl. 1): 1690, Paul, M R et al. J. Pediatr. Hematol. Oncol. (2019) 41 (8): e546-e9]. Case reports also have described irreversible B cell maturation antigen (BCMA) loss after anti-BCMA CAR-T cell treatment of multiple myeloma (MM) [Id., citing Da Via, M C et al. Nat. Med. (2021) 27:616-619; Leblay, N. et al. Blood (2020) 136 (Suppl. 1) 11-2].

In addition to antigen loss, there are other mechanisms that limit or abrogate the effective recognition of cancer cells by CAR-T cells; these mechanisms are either conveyed directly by tumor cells or through a rewiring of the microenvironment. In preclinical models, especially in solid tumors, it was shown that tumor-infiltrating CAR-T cells undergo rapid loss of functionality, limiting their therapeutic efficacy. This hyporesponsiveness appears to be reversible when the T cells are isolated away from the tumor and is associated with upregulation of intrinsic T cell inhibitory enzymes [diacylglycerol kinase and SHP-1, an SH2 domain-containing protein tyrosine phosphatase] and with the expression of surface inhibitory receptors (e.g., PD-1, LAG3, TIM3, and 2B4) [Id., citing Moon, E K et al. Clin. Cancer Res. (2014) 20 (16): 4262-4273].

Dysfunctional T Cell States

Although TCR and CAR signaling are different, most of the framework for understanding the influence of CAR signaling on CAR-T function and differentiation is derived from work in the TCR field.

TCRs have a hierarchical threshold of antigen density for induction of cell lysis, proliferation and cytokine product [Watanabe, K., et al. Front. Immunol. (2018) 9:2486, citing Au-Yeung, B B et al. Proc. Nat. Acad. Sci. USA (2014) 111: E3679-88], where less antigen density is required for cell lysis than for cytokine production. CAR-T cells can recognize target cells with considerably lower levels of target antigen and have hierarchical T cell signaling thresholds for cell lysis, proliferation and individual cytokine production. Watanabe demonstrated that the target antigen density required to induce T cell proliferation and cytokine production was higher than that required to induce CAR mediated lysis. [Id., citing Watanabe, K. et al. J. Immunol. (2015) 194:911-920].

Functional T cells perform a range of activities upon stimulation with their cognate antigen. They can (1) expand, (2) secrete effector cytokines, and lyse target cells; (3) survive after removal of antigen stimulation and (4) do all the above upon secondary antigen challenge. A T cell is considered dysfunctional if at least one of these activities is not met.

Some studies suggest that the efficacy of immunotherapy is limited by the generation of dysfunctional T cells in the tumor microenvironment (TME).

T Cell Exhaustion

T cell exhaustion is a state of T cell dysfunction that arises during many chronic infections and cancer. It is defined by poor effector function, sustained expression of inhibitory receptors and a transcriptional state distinct from that of functional effector or memory T cells.

Exhausted T cells become dysfunctional via a progressive loss of functionality that is mainly mediated by upregulation of multiple inhibitory receptors, including the inhibitory pathways mediated by PD-1 in response to binding of PD1 ligand 1 (PD-L1) and/or PD-L2. [Wherry E J and Kurachi, M. Nature (2015) 15:486-499, citing Okazaki T, et al., Nature Immunol. (2013) 14:1212-1218, Odorizzi P M, Wherry E J. J. Immunol. (2012) 188:2957-2965, Araki K, et al. Cold Spring Harb. Symp. Quant. Biol. (2013) 78:239-247]. Exhausted T cells can co-express PD-1 together with lymphocyte activation gene 3 protein (LAG3), 2B4 (also known as CD244), CD160, T cell immunoglobulin domain and mucin domain-containing protein 3 (TIM3; encoded by HAVCR2), CTLA-4 and many other inhibitory receptors [Id., citing Blackburn S D, et al. Nat. Immunol. (2009) 10:29-37]. Typically, the higher the number of inhibitory receptors co-expressed by exhausted T cells, the more severe the exhaustion. It has been suggested that inhibitory receptors such as PD-1 might regulate T cell function in several ways [Id., citing Schietinger A, Greenberg P D. Trends Immunol. (2014) 35:51-60; Odorizzi P M, Wherry E J. J. Immunol. (2012) 188:2957-2965], e.g., first, by ectodomain competition, which refers to inhibitory receptors sequestering target receptors or ligands and/or preventing the optimal formation of microclusters and lipid rafts (for example, CTLA-4); second, through modulation of intracellular mediators, which can cause local and transient intracellular attenuation of positive signals from activating receptors such as the TCR and co-stimulatory receptors [Id., citing Parry R V, et al. Molec. Cell. Biol. (2005) 25:9543-9553; Yokosuka T, et al. J. Exp. Med. (2012) 209:1201-1217; Clayton K L, et al. J. Immunol. (2014) 192:782-791]; and third, through the induction of inhibitory genes [Id., citing Quigley M, et al. Nat. Med. (2010) 16:1147-1151]. Co-stimulatory receptors also are involved in T cell exhaustion [Id., citing Odorizzi P M, Wherry E J. J. Immunol. (2012) 188:2957-2965.]. It has also been possible to exploit the potential beneficial role of co-stimulation to reverse exhaustion by combining agonistic antibodies to positive co-stimulatory pathways with blockade of inhibitory pathways. 4-1BB (also known as CD137, encoded by TNFRSF9) is a TNFR family member and positive co-stimulatory molecule that is expressed on activated T cells. Combining PD-1 blockade and treatment with an agonistic antibody to 4-1BB dramatically improved exhausted T cell function and viral control [Id, citing Vezys V, et al. J. Immunol. (2011) 187:1634-1642]. Soluble molecules are a second class of signals that regulate T cell exhaustion; these include immunosuppressive cytokines such as IL-10 and transforming growth factor-β (TGFβ) and inflammatory cytokines, such as type I interferons (IFNs) and IL-6. [Wherry E J and Kurachi, M. Nature (2015) 15:486-499.]

Antigen-independent (tonic) signaling of a CAR-T cell also can result in an exhausted phenotype. [Gavriil, A. et al. Cancers (2020) 12:2326, citing Long, A H et al. Nat. Med. (2015) 21]. Long et al showed that second generation CAR-T cells with scFvs targeting 2-ganglioside (G(D2)) derived from antibody 14g2a, CD22, and ErbB2 plus a CD28-CD35 endodomain, in contrast to CD19 CARs, signal constitutively during their in vitro expansion. These CARs had enhanced T cell exhaustion and diminished anti-tumor activity in vivo. The authors demonstrated that scFv clustering, due to interaction between scFv framework regions, was responsible. Similarly, Frigault et al. have shown that high level expression of certain scFv-containing CARs leads to long term antigen-independent signaling and functional exhaustion. [Id., citing Frigault, M J et al., Cancer Immunol. Res. (2015) 3:356-67].

Beltra, et al. [Beltra, J C, et al. Immunity (2020) 19:825-41] identified a four-cell stage developmental framework for T cell exhaustion during chronic lymphocytic choriomeningitis virus (LCMV) infection in mice with complementary analysis in human tumors. A similar pattern of four Tex subsets was found in mouse B16 tumors and for tumor-infiltrating lymphocytes from human melanoma. The four distinct Tex subsets were based on Ly208 (Slamf6) and CD69 expression. Two interconverting TCF-1+ progenitor states were identified, one quiescent and blood inaccessible and a second that initiated robust cell cycling and gained access to circulation. This second TCF-1+Tex subset gave rise to a TCF-1−Tbet$^{hi}$ intermediate Tex subset that (re) acquired some effector-like features. These intermediate Tex cells ultimately became terminally differentiated, losing T-bet (and gaining Eomes) and permanently exiting the cell cycle. This final transition was coordinated by TOX-mediated antagonism of T-bet. PD-1 pathway blockage preferentially expanded the second progenitor and the T-bet$^{hi}$ intermediate Tex subsets. These cell subset transitions were regulated by the transcription factors TCF-1, T-bet and TOX in a hierarchical developmental pathway. The level and duration of chronic antigen stimulation and infection seemed to be key factors that lead to T cell exhaustion and correlated with the severity of dysfunction during chronic infection.

T Cell Senescence

Another dysfunctional state is senescence, which occurs when T cells permanently arrest their cell cycle and proliferation while retaining cytotoxic capability. Senescent T cells have a distinct phenotype including downregulated expression of the costimulatory molecules CD27 and CD28, and high expression of CD57, killer cell lectin-like receptor subfamily G member 1 (KLRG-1), and CD45RA [Zhang, J. et al. EBioMedicine (2021) 68:103409, citing Barbarin, A. et al. Front. Immunol. (2017) 8:316; Covre, L P et al. Aging Cell (2020) 19: e13272; Liu, W. et al. Cancers (2020): 12]. Senescent T cells also show a terminally differentiated phenotype with downregulation of chemokine receptors CCR7 and CD45RO but upregulation of CD45RA [Id., citing Henson, S M et al. J. Clin. Invest. (2014) 124:4004-4016; Huang, B. et al. J. Immunotherapy Cancer (2020) 8; Kunert, A. et al. J. Immunother. Cancer (2019) 7:149]. In senescent T cells, the efficiency of TCR signaling is compromised in that the expression of key components of TCR signaling (CD3, Lck, Zap70, SLP-76, LAT, and PLCγ1) [Id., citing Pereira, B I et al. Nature Immunol. (2020) 21:684-694; Lanna, A. et al. Nature Immunol. (2014) 15:965-972], as well as the costimulatory molecules CD27 and CD28 [Id., citing Ye, J. et al. Blood (2012) 120:2021-2031; Lanna, A. et al. J. Immunol. (2013) 191:3744-3752] is decreased. In addition, the phosphorylation of Zap70 is impaired following CD3 activation [Id., citing Pereira, B I et al. Nature Immunol. (2020) 21:684-694; Lanna, A. et al. Nature Immunol. (2014) 15:965-72]; phosphorylation of Zap-70 is required to initiate T cell receptor signaling [Yan, Q. et al. Mol. Cell Biol. (2013) 33 (11): 2188-2201]. Senescent T cells, when stimulated with anti-CD3 plus anti-CD28, especially those isolated from old individuals, produce significantly lower amounts of IL-2, interferon gamma (IFN-γ), tumor necrosis factor alpha (TNF-α), and granzyme B than do other types of T cells [Zhang, J. et al. EBioMedicine (2021) 68:103409, citing Henson, S M et al. Eur. J. Immunol. (2015) 45:1441-1451; Song, Y. et al. Aging Cell (2018) 17]. Moreover, TCRβ chain diversity roughly declines linearly with age, especially in senescent CD8+ T cells [Id., citing Britanova, O V et al. J. Immunol. (2014) 192:2689-2698; Bjorkstrom, N K et al. Blood (2012) 120:3455-3465]. These findings led to the conclusion that senescent T cells probably dampen TCR-dependent antigen-specific killing.

Senescent T cells also upregulate the expression of NK cell receptors (NKRs), including NKG2A/C and killer cell lectin like receptor G1 (KLRG-1) [Id., citing Barbarin, A. et al. Front. Immunol. (2017) 8:316; Percira, B I et al. Nature Immunol. (2020) 21:684-694]. On NK cells, NKG2C delivers activating signals through immunoreceptor tyrosine-based activation motifs at the cytoplasmic tails of DAP12 transmembrane proteins [Ma, M. et al. Front. Immunol. (2017) 8:1176, citing Call, M E et al. Nat. Immunol. (2010) 11:1023-1029], while NKG2A appears to inhibit NK activation via immunoreceptor tyrosine-based inhibitory motifs in the cytoplasm [Id., citing Lanier, LL. Annu. Rev. Immunol. (1998) 16:359-63]. KLRGI plays an inhibitory role in human NK cells and T cells [Yang, X. et al. BMC Cancer (2021) 21:752].

Senescent T cells display higher levels of CD107a, granzyme B, and perforin than do other subsets with no stimulation [Zhang, J. et al. EBioMedicine (2021) 68:103409, citing Song, Y. et al. Aging Cell (2018) 17] and under NKG2D stimulation [Id., citing Pereira, B I et al. Nature Immunol. (2020) 21:684-694]. In vitro experiments have shown that senescent T cells kill tumor cells independent of TCR, with the same efficiency as natural killer (NK) cells [Id., citing Pereira, B I et al. Nature Immunol. (2020) 21:684-694]. This evidence led to the conclusion that although antigen specific killing is lost, senescent T cells with strong nonspecific killing potential fight antitumor immunity to some extent.

T Cell Anergy

Anergy, which is generally described as an induced hyporesponsive state with low IL-2 production or incomplete activation to which naïve T cells fall upon low co-stimulatory and/or high co-inhibitory stimulation, is another dysfunctional state. [Crespo, J. et al. Curr. Opin Immunol. (2013) 25 (2): 214-221].

The evidence for T cell anergy in the tumor context has been indirect. A core problem has been a lack of positive markers to characterize a loss of function state of T cells. Nonetheless, the following observations support that T cell anergy can be an important phenomenon in cancer:

First, there is an active imbalance between stimulatory and inhibitory B7 family members in the tumor microenvironment [Id., citing Zou, W. Nature Rev. Cancer (2005) 5:263-74; Pardoll, D M. Nat. Rev. Cancer (2012) 12:252-264; Zou W. and Chen, L. Nat. Rev. Immunol. (2008) 8:467-477; Blank, C. et al. Cancer Res. (2004) 64:1140-1145]. Human tumors and tumor associated antigen presenting cells (APCs) often express high levels of B7-H1 (CD274 or PD-L1), B7-H2 (CD275 or ICOS-L), B7-H3 (CD276), B7-H4 (B7S1 or B7x), and B7-DC (CD273 or PD-L2) with low-to-absent expression of B7.1 (CD80) and B7.2 (CD86) [Id., citing Zou W. and Chen, L. Nat. Rev. Immunol. (2008) 8:467-77; Blank, C. et al. Cancer Res. (2004) 64:1140-1145; Curiel, T J et al. Nat. Med. (2003) 9:562-567; Kryczek, I. et al. J. Exp. Med. (2006) 203:871-881]. This indicates a poor co-stimulatory, high co-inhibitory and therefore anergy-promoting environment.

Second, animal model studies have shown that introduction of B7.1 into tumors by transfection or blockade of inhibitory B7 family members can reduce tumor growth or result in spontaneous tumor rejection in vivo [Id., citing Zou W. and Chen, L. Nat. Rev. Immunol. (2008) 8:467-77; Blank, C. et al. Cancer Res. (2004) 64:1140-1145; Curiel, T J et al. Nat. Med. (2003) 9:562-567; Kryczek, I. et al. J. Exp. Med. (2006) 203:871-881; Chen, L. et al. Cell (1992) 71:1093-1102; Gajewski, TF. J. Immunol. (1996) 156:465-72].

Third, homeostatic proliferation of anti-tumor T cells in a lymphopenic host both reverses anergy and promotes tumor rejection in vivo [Id., citing Brown, I E et al. J. Immunol. (2006) 177:4521-4529].

Fourth, there is evidence indicating antigen specific, T cell-intrinsic dysfunction in the tumor microenvironment [Id., citing Nazareth, M R et al. J. Immunol. (20007) 178:5552-5562; Broderick, L. et al. Clin. Immunol. (2006) 118:159-169].

Based on this evidence, it has been suggested that T cell anergy may be a functional mechanism in patients with cancer. However, the relative impact of T cell anergy on tumor immunity remains to be defined.

Cellular and molecular mechanisms controlling T cell anergy are insufficiently understood. It is generally accepted that T cells that are presented antigen along with suboptimal CD28 co-stimulation [Id., citing Schwartz, R H. Science (1990) 248:1349-1356; Schwartz, R H. (2003) 21:305-334] and/or high co-inhibition [Id., citing Greenwald, R J et al. Immunity (2001) 14:145-55] result in anergic phenotypes, as characterized by their low IL-2 production and cell cycle arrest at the G1/S phase. Early growth response gene 2 (Egr2) may be a central transcription factor that regulates the T cell anergic state [Id., citing Zeng, Y. et al. J. Exp. Med. (2012) 209 (12): 2157-2163].

It has been suggested that the anergy program is initiated by improper mTOR and Ras/MAPK signaling in the cell, a pathway which lies directly downstream of TCR/CD28 engagement. Specifically, the sole binding of TCR by MHC promotes Ca2+ imbalance on T cells and retention of active-RAP-1 in the cytosol, an imbalance that would normally be corrected by co-stimulation through CD28 (Ras/MAPK) [Id., citing Boussiotis, V A et al. Science (1997) 278:124-128; Dolmetsch, R E et al. Nature (1998) 392: 93393-6]. The effects of this imbalance on the genetic reprogramming of these cells have been hypothesized to be mediated by NFAT homodimer formation and transcription of anergy-inducing genes [Id., citing Anandasabapathy, N. et al. Immunity (2003) 18:535-547; Soto-Nieves, N. et al. J. Exp. Med. (2009) 206:867-876]. The E3 ubiquitin ligase family can affect PI3K, mTOR, and Ras/MAPK signaling pathways and help to actively maintain anergy [Id., citing Anandasabapathy, N. et al. Immunity (2003) 18:535-547; Jeon, M S et al. Immunity (2004) 21:167-177; Mueller, D L. Nat. Immunol. (2004) 5:883-890]. Epigenetic factors such as IKAROS (through acetylation), an inhibitory C-type lectin with an intracellular immunoreceptor tyrosine-based inhibitory motif (ITIM), and Sirt1 are involved in histone modifications that promote T cell anergy [Id., citing Gao, B. et al Proc. Natl Acad. Sci. USA (2012) 109:899-904; Bandyopadhyay, S. et al. Blood (2007) 109:2878-2886]. Thus, anergy may be the combined result of factors that negatively regulate proximal TCR-coupled signal transduction, together with a program of active transcriptional silencing that is reinforced through epigenetic mechanisms [Id., citing Wells, AD. J. Immunol. (2009) 182:7331-7341].

Tumor Microenvironment

The TME comprises cellular components, noncellular components and signaling molecules [Arneth, B. Medicina (2020) 56:15, citing Spill, F. et al. Curr. Opin. Biotechnol. (2016) 40:41-48; Del Prete, A. et al. Curr. Opin. Pharmacol. (2017) 35:40-47]. The cellular components include endothelial cells, which play a role in tumor development and tumor cell protection from the immune system; immune cells, such as granulocytes, lymphocytes and macrophages, which are involved in various immune responses and activities, such as inflammatory reactions orchestrated by the tumor to promote survival; and fibroblasts, which allow cancer cells to migrate from the primary tumor location into the bloodstream for systemic metastasis and provide a passage for endothelial cells undergoing angiogenesis in the tumor. The extracellular matrix (ECM), which is mainly secreted by cancer-associated fibroblasts (CAFs), which produce more ECM proteins than normal fibroblasts, is composed of various macromolecules, including collagens, glycoproteins (fibronectin and laminins), proteoglycans and polysaccharides with different physical and biological properties. [Brassart-Pasco, S. et al. Front. Oncology (2020) 10:397]. Interstitial matrix, primarily synthesized by stromal cells, is rich in fibrillary collagens and proteoglycans. CAF secretome analyses show an increased secretion of bone morphogenetic protein (BMP) 1, thrombospondin-1 and elastin interface 2 [Id. citing Santi, A. et al. Proteomics (2018) 18: e1700167; Socovich, A M and Naba, A. Semin. Cell Dev. Biol. (2019) 89:157-166]. Several splice variants of fibronectin ED-A and ED-B and tenascins C and W may be secreted by CAFs. [Id., citing Grahovac, J. and Wells, A. Lab Investig. (2014) 94:31-40].

Tumor cells can influence the microenvironment through the release of extracellular paracrine signals that induce peripheral immune tolerance and support tumor angiogenesis [Arneth, B. Medicina (2020) 56:15, citing Korneev, K V et al. Cytokine (2017) 89:127-135]. The composition and structure of the TME is known to vary among cancer types and among patients. [Id., citing Bussard, K. et al. Breast Cancer Res. (2016) 18:84].

Cellular interactions in the TME also affect cancer development and progression. Within the heterogeneous TME, T cells are a major part of the immune infiltrate. [Zhang, Z. et al. Frontiers Cell & Devel. Biol. (2020) 8:17]. The intratumoral T cell populations comprise naïve T cells, memory T cells, effector T cells, and Tregs. [Id., citing Hashimoto, M. et al. Annu. Rev. Med. (2018) 69:301-18]. In a murine model, the tumor-specific T cell dysfunctional exhaustion state was found to be initiated early after tumor initiation and antigen encounter. [Id., citing Schictinger, A. et al., Immunity (2016): 45: 389-401]. Dysfunctional CD8+ T cells are characterized by a loss of effector functions, such as cytotoxicity and proliferation. In addition, the upregulation of immune checkpoints and changes in transcriptional and metabolic molecules have been described as hallmarks of T cell dysfunction. Emerging evidence indicates that epigenetic states, including DNA methylation and histone modifications, and chromatin landscapes are closely associated with the functional state of dysfunctional or exhausted CD8+ T cells. [Id., citing Pauken, K E et al. Science (2016) 342:1242454; Sen, D R et al. Science (2016) 354:1165-1169; Kartikasari, A E R et al. Front. Immunol. 9:3109].

In many hematological cancers, the bone marrow tumor microenvironment (BMME) is known to upregulate anti-apoptotic mechanisms in tumor cells through tight cross-talk between MSCs and tumor cells; tumor cell lysis by T and NK cells also is largely mediated via activation of extrinsic and intrinsic apoptotic pathways [Rasche, L. et al. N. Kroger, et al, eds. Chapter 4 in The EBMT/EHA CAR-T Cell Handbook (2002) doi.org/10.1007/978-3-030-94353-0_4, citing Hanabuchi, S. et al. Proc. Natl Acad. Sci. 1994 91(1)]:4930-4; Falschlehner, C. et al. Immunology (2009) 127 (2): 145-54; Carneiro, BA and E1-Deiry, W S. Nat. Rev. Clin. Oncol. (2020) 17 (7): 395-417; Culen, S P et al. Cell Death Differ. (2010) 17 (4): 616-23; Sutton, V R et al. J. Exp. Med. (2000) 192 (10): 1403-1414]. Myeloma cell-bone marrow mesenchymal stromal cell (BMMSC) interactions have been reported to protect myeloma cells from conventional cytotoxic T cells and from daratumumab (DARZALEX®) redirected NK cells [Id., citing McMillin, D W et al. Blood (2012) 119 (15): e131-8; de Haart, S J et al. Clin. Cancer Res. (2013) 19 (20): 5591-601; de Haart, S J et al. Haematologica (2016) 101 (8): e339-e342].

The importance of the tumor stroma in the efficacy of CAR-T cells. These studies were extended to CAR-T cells by testing a panel of nine different myeloma-reactive CAR-T cells that were reactive to three different myeloma-associated antigens (CD138, B Cell Maturation Antigen (BCMA), and CD38) with different target affinities and with different costimulatory domains (CD28, 4-1BB, or CD28 plus 4-1BB [Id., citing Holthof, L. et al. Clin. Cancer Res. (2021) 27 (13): 3793-803]. In the absence of BMMSCs, $BCMA^{bb2121}$ CAR-T cells, high affinity CD38 CAR-T cells, and intermediate affinity CD38 CAR-T cells containing CD28 costimulatory domains showed high levels of anti-myeloma cell lysis, whereas other CAR-T cells showed moderate cytotoxic activity against myeloma cells. BMMSCs did not modulate the lytic activity of highly lytic CAR-T cells but readily protected myeloma cells against all other CAR-T cells with intermediate killing capacity. Overall, a strong inverse correlation was demonstrated between the lytic capacity of the CAR-T cells and the extent of BMMSC-mediated protection. Furthermore, the BMMSC-mediated protection of myeloma cells from these CAR-T cells was readily abrogated by inhibition of survivin (an apoptosis inhibitor), myeloid cell leukemia 1 (MCL-1), and X-linked inhibitor of apoptosis (XIAP) using the small molecule surviving inhibitor FL118. These results confirmed that BMMSC-mediated immune resistance was mediated by negative regulation of apoptotic pathways. In addition, in a solid tumor mouse model, destruction of the tumor stroma contributed to eradication of large tumors by HER2-specific CAR-T cells (Id., citing Textor, A. et al. Cancer Res. (2014) 74 (23): 6796-6805).

Current Challenges of CAR-T Therapy

Toxicities with CAR-T cells can be classified as on-target (likely to achieve the intended outcome at the target) or off-target (adverse effects resulting from modulation of other targets). The longest running clinical experience in the CAR-T cell field has been with CD19-directed CAR T cells, for which two on-target toxicities, cytokine release syndrome (CRS) and immune effector cell associated neurotoxicity syndrome (ICANS) have been described. [Finck, A V et al. Nat. Med. (2022) 28 (4): 678-689, citing Lee, D W et al. Biol. Blood Marrow Transpl. (2019) 25:625-638]. CRS and ICANS toxicities, while now regarded as a class effect of CAR-T cells as they have been observed in patients treated with CAR-T cells targeting CD19, BCMA, and many other cell surface structures [Id., citing Lateau, C A et al.

Cancer Cell (2021) 39:1553-1557] may be more of a feature of increasingly potent therapies. Also, the expression of targets in healthy patients may not be the same as in patients with cancer.

Cytokine release syndrome (CRS) is a potentially life-threatening, systemic inflammatory response observed following administration of antibodies and adoptive T cell therapies, including CAR-T cell therapy. With immune activation, an associated increase in a wide array of systemic proinflammatory cytokines, such as IL-6, C-reactive protein (CRP), ferritin, and IL-2, occurs, which coincides with peak-T cell expansion. Severity can vary from mild symptoms including fever, myalgia, and fatigue, to severe symptoms including but not limited to acute respiratory distress syndrome, hypotension, disseminated intravascular coagulation, and/or renal and liver toxicities. [Shalabi, H. et al. Chapter 12 in Novel Designs of Early Phase Trials for Cancer Therapeutics (2018) Academic Press, pages 175-191].

ICANS was initially thought to result from a cascade of off-target effects due to systemic inflammation and cytokine release [Finck, A V et al. Nat. Med. (2022) 28 (4): 678-689, citing Taraseviciute, A. et al. Cancer Discov. (2018) 8:750-63]; however, some aspects of the syndrome may be related to the expression of CD19 in pericytes in the central nervous system [Id., citing Parker, K R et al. Cell (2020) 183:126-142], which was unexpected since CD19 initially was described as a B-lineage-restricted protein.

On-target, off-tumor toxicity can occur because most tumor-associated antigens are not tumor-specific but are only overexpressed on tumor cells. Although target antigens are expressed on both tumor and normal cells, not all CAR-T cell therapies exhibit observable on-target off-tumor effects. [Han, et al. J. Hematol. & Oncol. (2919) 12:128, citing Brown, C E et al. Clin. Cancer Res. (2015) 21 (18): 4062-4072; Katz, S C et al. Clin. Cancer Res. (2015) 21 (14): 3149-3150; Klampatsa, A. et al. Cancers (Basel) (2017) 9 (9): 115; Kakarla, S. et al. Mol. Ther. (2013) 21 (8): 1611-1620; Wang, L C et al. Cancer Immunol. Res. (2014) 2 (2): 154-166]. During solid tumor treatment, on-target, off-tumor toxicities following the infusion of CAR-T cells can cause serious adverse events or be lethal. [Han, X. et al. J. Hematol & Oncol. (2019) 12:128, citing Morgan, R A et al. Mol. Ther. (2010) 18 (4): 843-851; Lamers, C H et al. J. Clin. Oncol. (2006) 24 (13): 20-22; Tran, E. et al. J. Exp. Med. (2013) 210 (6): 1125-1135].

Disease relapse after CAR-T cell infusions. There are two main forms of disease relapse: antigen-positive relapse in the early phase and antigen escape relapse in a later phase. The disease relapse of antigen-positive cells is closely related to CAR-T cell persistence, meaning how long the functional CAR-T cells exist after infusion into the subject. CAR-T cell persistence is a major challenge. Preclinical and clinical trials have shown that the 4-1BB (CD137) costimulatory domain induced longer-term persistence of CAR-T cells than did CD28 [Id., citing Zhao, Z. et al. Cancer Cell (2015) 28 (4): 415-428; Kachenderfer, J N et al. J. Clin. Oncol. (2015) 33 (6): 540-549].

Antigen escape, including antigen loss or down regulation, also can drive disease relapse following CAR-T immunotherapy. Complete antigen loss is not necessary for CAR-T cell resistance, and in some cases, a reduction in antigen density is sufficient for tumor cells to evade CAR-T cells [Id., citing Fry, T J et al. Nat. Med. (2018) 24 (10:20-28]. Investigators have shown that combinatorial multi-antigen targeted strategies could effectively prevent the tumor escape caused by low antigen density that results from CAR-T cell trogocytosis [Id., citing Hamich, M. et al. Nature (2019) 568 (7750): 112-116]. Immune escape caused by low antigen level and/or heterogeneous expression is a cause of solid tumor resistance to CAR-T cells.

Optimization of CAR design. Optimization of the CAR design is equally important for better persistence and overall treatment efficacy.

The concepts of Boolean Logic gates have been applied to CAR-T cell design primarily as a tool for increasing specificity by integrating signals from two or more target antigens. Such studies have focused on AND gates (where two target antigens are required for full activation to limit toxicity), OR gates (involving two equally powered CARs against alternate target antigens in the same tumor) and NOT gates (an off-signal associated with a target antigen present on normal tissue as a means to limit off-target toxicity). A CAR with an intracellular domain providing signal 2 but no signal 1 is also referred to as a chimeric co-stimulatory receptor (CCR) and is said to provide “co-stimulation in trans,” thereby enhancing proliferation and survival without an effect on cytotoxicity. [Gavriil, A. et al. Cancers (2020) 12:2326, citing Kloss, C C et al. Nat. Biotechnol. (2013) 31:71-75; Lanitis, E. et al. Cancer Immunol. Res. (2013) 1:43-53].

Several paired target antigens have been evaluated using AND gate approaches in preclinical models [Gavriil, A. et al. Cancers (2020) 12:2326, citing Wilkie, S. et al. J. Clin. Immunol. (2012) 32:1059-1070; Kloss, C C et al. Nat. Biotechnol. (2013) 31:71-75]. Several groups have further designed bi-specific CARS, which utilize the OR-gate circuit. [Id., citing Zah, E. et al. Cancer Immunol. Res. (2016) 4:498-508; Munter, S D et al. Int. J. Mol. Sci. (2018) 19:403]. The NOT gate logic has been applied to generate CARs coupled with an immune-inhibitory signal (iCAR), such as PD-1 or CTLA-4, to divert off-target immunotherapy responses [Id., citing Fedorov, V D, et al. Sci. Transl. Med. (2013) 5: 215ra172].

The basic logic principles above have been extended to the concept of the sequential AND gate, whereby engagement with one target antigen triggers the expression of a CAR against a second target antigen. Since the first antigen does not provide activating T cell signals, and the CAR against the second antigen is not expressed until the T cell reaches the tumor, this arrangement potentially can limit both tonic signaling and exhaustion, as well as off-target toxicity. [Id., citing Morsut, L. et al. Cell (2016) 164:780-791; Roybal, K T et al. Cell (2016) 167:419-432; Roybal, K T et al. Cell (2016) 164:770-779].

Immune checkpoint blockade is another approach to overcome tumor-associated immune suppression [Finck, A V et al. Nat. Med. (2022) 28 (4): 678-89, citing Rafiq, S. et al. Nat. Biotechnol. (2018) 36:847-856] and revitalize T cells [Id., citing Xia, Y. et al. Blood Rev. (2016) 30:189-200]. In clinical trials, the combination of the PD-1 immune checkpoint inhibitor pembrolizumab (KEYTRUDA®) with lesothelin-targeting CAR-T cells further enhanced the persistence and function of the latter in patients with malignant pleural diseases [Id., citing Adusumillli, P S et al. Cancer Discov. (2021) 11:2748-2763]. One study demonstrated that two CARs, one targeting EGFRvIII and the other targeting IL-13Ra2, preferred different checkpoint blockades within the same tumor model [Id., citing Yin, Y. et al. Mol. Ther. Oncolytics (2018) 11:20-38]. An alternative approach is to engineer CAR-T cells to produce bispecific antibodies, as shown in a preclinical study for the treatment of glioblastoma. [Id., citing Choi, B D et al. Nat. Biotechnol. (2019) 37:1049-1058].

Adoptive cellular immunotherapy with engineered chimeric antigen receptor (CAR)-T cells has transformed the treatment of hematological malignancies [Weber, E W et al. Cell (2020) 181:46-62; Lim, W A and June, C H. Cell (2017) 168:724-740]. However, relapse remains a major challenge to over 50% of patients who initially respond to CAR-T cell therapies. In addition, CAR-T cells are less effective in treating solid tumors [Cappell, K M and Kochenderfer, JN. Nat. Rev. Clin. Oncol. (2023) 20:359-371]. The diminished efficacy of CAR-T therapy can be ascribed to long-term exposure of CAR-T cells to tumor antigen and tumor microenvironment, leading to T cell dysfunction/exhaustion Ruella, M N. et al. Nat. Rev. Drug Discov. (2023) 22:976-995]. CAR-T cell exhaustion is manifested as induction of inhibitory mechanisms, attenuated effector function, failure to acquire memory cell characteristics, and poor in vivo persistence. Drivers of T cell exhaustion include key transcription factors (TFs), such as nuclear factor of activated T cell (NFAT), thymus high-mobility group box protein (TOX), and nuclear receptor group 4a (NR4A), which act together to induce the expression of multiple inhibitory receptors, such as programmed cell death 1 (PD1), lymphocyte activation gene 3 (LAG3), T cell immunoglobulin domain and mucin domain 3 (TIM3) and cytotoxic T lymphocyte antigen 4 (CTLA4) [Mognol, G P et al. Proc. Natl Acad. Sci. USA (2017) 114: E2776-E2785]. Therefore, there is an urgent need to identify approaches to prevent or mitigate CAR-T cell exhaustion, enhance CAR-T cell function, and improve CAR-T cell persistence.

Efforts to enhance CAR-T function have focused on DNA sequence-specific transcription factors (TFs) or epigenetic regulators that modify DNA per se or histones. Loss-of-function approaches such as triple deletion of NT4A family members (Nr4a1, Nr4a2, and Nr4a3) [Chen, J. et al. Nature (2019) 567:530-534]. or ablation of BLIMP1 TF [Yung, I Y. Sci. Transl. Med. (2022) 14: cabn7336], TET2 (a methylcytosine dioxygenase that facilitates DNA demethylation) [Fraietta, J A et al., Nature (2018) 558:307-312; Jain, N. et al. Nature (2023) 615:315-322] DNMT3A (de novo DNA methyl transferase that catalyzes DNA methylation) [Prinzing, B. et al. Sci. Transl. Med. (2021) 13: cabh0272, or SUV39H1 (a histone methyl transferase that catalyzes H3K9me3) [Jain, N. et al. Cancer Discov. (2024) 14:142-157] in CAR-T cells result in enhanced tumor control.

Conversely, gain-of-function via overexpression of TFs, including c-JUN [Lynn, R C et al. Nature (2019) 576:293-300], BATF [Sco, H. et al. Nat. Immunol. (2021) 22:983-995] and FOXO1 Chan, J D et al. Nature (2024) 629:201-210; Doan, A E et al. Nature (2024) 629:211-218] in CAR-T cells also show beneficial effects on curtailing tumor growth. The potency of each approach differed depending on the models used, and it remains unknown if these strategies could be effectively translated into clinic therapeutics and patient care. Such uncertainties necessitate novel approaches to boost CAR-T cell functions.

For example, studies show that the transcription factor FOXO1 is responsible for promoting memory and restraining exhaustion in human CAR-T cells. [Doan, A E et al. Nature (2024) 629:211-218]. Pharmacological inhibition or gene editing of endogenous FOXO1 diminished the expression of memory-associated genes, promoted an exhaustion-like phenotype and impaired the anti-tumor activity of CAR-T cells. Overexpression of FOXO1 induced a gene-expression program consistent with T cell memory and increased chromatin accessibility at FOXO1-binding motifs. CAR-T cells that overexpressed FOXO1 retained their function, memory potential and metabolic fitness in settings of chronic stimulation and exhibited enhanced persistence and tumor control in vivo. [Id.]

Overexpression of TCF1 (encoded by TCF7) did not enforce canonical memory programs or enhance the potency of CAR-T cells. $TCF1^{OE}$ and $FOXO1^{OE}$ cells that were serially rechallenged with Nalm6 leukemia both exhibited enhanced cytokine secretion compared with controls, but only $FOXO1^{OE}$ increased CD8 proliferation and memory marker expression while suppressing the levels of TOX. In contrast, $TCF1^{OE}$ increased the expression of TOX and CD39 relative to controls expressing the truncated rat nerve growth factor receptor (tNGFR) marker alone, consistent with a more exhausted or effector-like phenotype.

Tle Proteins

TFs do not act alone and require cofactors to achieve regulatory specificity, stability, and transcriptional output; this is particularly important for TFs such as Runx3, which are stably expressed throughout the CD8+ T cell differentiation process [Zhao, X. et al. Nature Immunol. (2024) 25:294-306, citing Pipkin, M E. Immunol. Rev. (300): 100-124; Shan, Q. et al. Nature Immunol. (2017) 18:931-939]. One such cofactor, Transducin-Like Enhancer of split (Tle) protein, interacts with many immune function-related transcription factors including Tcf1/Lef1, Runx 1/Runx3, Myc and Blimp1 [Id., citing Orian, A. et al. Proc. Natl Acad. Sci. USA (2007) 104:15771-15776; Ren, B. et al. Genes & Development (1999) 13:125-137; Zhao, X. et al. Nat. Rev. Immunol. (2022) 22:147-157; Sco, W. and Taniuchi, I. Mol Cells (2020) 43:107-113].

Tle proteins are the mammalian homologues of *Drosophila* Groucho transcriptional repressor. There are four mammalian Tle genes, Tle1-4, which encode full-length Tle proteins; these Tle proteins have both unique and redundant functions in development of multiple organs, including hematopoiesis [Id., citing Turki-Judeh, W. and Courey, AJ. Curr Top. Dev. Biol. (2012) 98:65-96; Buscarlet, M. and Stifani, S. Trends in Cell Biol. (2007) 17:353-361; Jennings, B H and Ish-Horowicz, D., Genome Biol. (2008) 9:205; Gasperowicz, M. and Otto, Fl. J. cell Biochem. (2005) 95:670-687]. In T lineage cells, TLE3 is most abundantly expressed, followed by Tle4 and Tle1, with Tle2 at a barely detectable level [Id., citing Xing, S. et al. J. Exp. Med. (2018) 215:2211-2226]. Tle1, TLE3, and Tle4 are critically required for CD8+ T cell lineage choice during thymic development, in a gene-dose dependent manner [Id., citing Xing, S. et al. J. Exp. Med. (2018) 215:2211-2226]. Functional analyses collectively demonstrated that TLE3 supports effector memory T cell fate and targeting TLE3 instead promotes central memory T cell formation.

The Tle proteins contain five defined domains, with the N-terminal glutamine-rich domain (namely, Q domain) and C-terminal tryptophan-aspartate (WD)—repeat domain responsible for most of protein-protein interactions (Xing, S. et al. Exp. Med. (2018) 215 (8): 2211-2226, citing Buscarlet, M. and Stifani, S. Trends Cell Biol. (2007) 17:353-361; Turki-Judeh, W. and Courcy, A. J. Curr. Top. Dev. Biol. (2012) 98:65-96]. The full-length Tcf1 and Lef1 contain an N-terminal β-catenin binding domain, C-terminal high-mobility-group (HMG) DNA binding domain, and a context-dependent regulatory (CRD) domain that harbors histone deacetylase activity (Xing, S. et al. Nat. Immunol. (2016a) 17:695-703]. Both CRD and HMG domains in Tcf1 and Lef1 contribute to interaction with the Q domain in Tle proteins [Id., citing (Arce, L. et al., (2009) BMC Cancer 9:159; Chodaparambil, J V et al. EMBO J. (2014) 33:719-731]. On the other hand, both Runx 1 and Runx3 use their conserved C-terminus VWRPY motifs to interact with the WD-repeat domain in Tle proteins (Id., citing Levanon, D. et al. Proc. Natl Acad. Sci. USA (1998) 95:11590-11595].

All Tle proteins interact with Tcf1 and Lef1 downstream of the Wnt signaling pathway [Xing, S. et al. Exp. Med. (2018) 215 (8): 2211-2226, citing Brantjes, H J., et al., Nucleic Acids Res. (2001) 29:1410-1419; Daniels, D L and Weis, W I. Nat. Struct. Mol. Biol. (2005) 12:364-371; Staal, F J T and Sen, J M Eur. J. Immunol. (2008) 38:1788-1794)] suggestive of involvement in T cell development and function [Id., citing Xuc, H H and Zhao, DM Ann. N.Y. Acad. Sci. (2012) 1247:16-33; Steinke, F C and Xue, H H, Immunol. Res. (2014) 59:45-55]. Tle1 has been shown to bind Runx 1 [Id., citing Levanon, D. et al. Proc. Natl Acad. Sci. USA (1998) 95:11590-11595], which is essential for the generation and maintenance of hematopoictic stem/progenitor cells (HSPCs) [Id., citing Cai, X. et al. Cell Stem Cell (2015) 17:165-177]. In line with such broadly interacting partners, germline deletion of Tle4 in mice causes a profound reduction in cellularity of hematopoietic cells including HSPCs and B cells (Id., citing Wheat, J C et al. PLOS One (2014) 9: e105557].

In a recent study [Zhao, X. et al. Nature Immunol. (2024) 25:294-306) our group analyzed Tle genes in CD8+ T cell responses to acute viral infection. While ablating all three Tle 1, 3, 4 genes abrogates differentiation of effector CD8+ T (Teff) cells, TLE3 shows non-redundant roles in regulating memory CD8+ T (Tmem) lineage stability without affecting Tmem cell pool size. Induced deletion of TLE3 accelerates formation of CD62L+ central Tmem (TCM) at the expense of CD62L-effector Tmem ($T_{EM}$) cells. This effect is not a phenocopy of ablating any of its partner TFs (Tcf1, Runx3 or Tbet), and likely results from specific disruption of Tle-sensitive TF complexes, highlighting unique integrative functions by TLE3. On the mechanistic side, key observations include: (1) besides its known co-repressor roles, TLE3 functions as a transcriptional coactivator, where TLE3 establishes/maintains a chromatin open state to induce its target gene expression; 2) TLE33 engages Tbet as a novel partner TF in Teff and Tmem cells, to form complexes with its known partners, such as Runx3; (3) while its expression is relatively stable, TLE3 is dynamically redistributed in the Teff and Tmem cell genome, representing a novel means/pattern of gene regulation.

Building on these findings, we reasoned that gain-of-function for TLE3 may confer advantages to anti-tumor immunity. Because ablation of TLE3 showed both 'preferred" and 'unwanted' regulatory effects and Tle3 has distinctive functional domains, we further reasoned that TLE functions can be uncoupled through molecular engineering and utilized to improve anti-tumor immunity. The present disclosure is a result of this approach.

SUMMARY OF THE INVENTION

According to one aspect, the present disclosure provides a chimeric antigen receptor (CAR) immunotherapy for treating a hematologic cancer comprising: (a) genetically modifying a population of immune effector cells comprising T cell receptors (TCRs) to stably express at least one CAR, wherein the ectodomain of the CAR specifically binds a cancer antigen; (b) expanding the population of CAR-containing immune effector cells in the presence of one or more cytokines in vitro to achieve a therapeutic dose, wherein the population of CAR-containing immune effector cells expresses a nonexhausted memory T cell phenotype; and (c) infusing eligible subjects with the CAR-containing immune effector memory T cell phenotype population of cells as needed until all cancer in the body is destroyed.

According to some embodiments of the CAR immunotherapy, the hematologic cancer is a leukemia, a lymphoma or a myeloma.

According to some embodiments of the CAR immunotherapy, the CAR comprises an extracellular antigen recognition domain, a spacer/hinge region and transmembrane domain, and an intracellular signal transduction domain, wherein the intracellular signal transduction domain of the CAR comprises 4-1BB; a CD3ζ T cell activation chain; and a genetically engineered TLE3 molecule.

According to some embodiments of the CAR immunotherapy, the engineered TLE3 molecule is derived from a wild type TLE3 comprising, in order, an N-terminal Q domain, a GP domain, a CcN domain, an SP domain and a C terminal WDR domain; or the engineered TLE3 molecule is a truncated TLE3 protein; or the engineered TLE3 molecule is a C-terminus truncated TLE3 (TLE3ΔWDR) protein.

According to some embodiments of the CAR immunotherapy, expression of the engineered TLE molecule is ectopic.

According to some embodiments of the CAR immunotherapy, the target antigen of the CAR is CD19; the target antigen of the CAR is CD20; the target antigen of the CAR is CD22; the target antigen of the CAR is NKG2D-1; the target antigen of the CAR is CD33; the target antigen of the CAR is BCMA, or the target antigen of the CAR is CD123.

According to some embodiments of the CAR immunotherapy, the CAR-containing population of immune effector cells recognizes two or more tumor associated antigens simultaneously.

According to some embodiments of the CAR immunotherapy, the immune effector cell population engineered to express the CAR comprising a TLE3 construct by lentiviral transduction is a CD3+ T cell population; and the T cell population comprises CD4+ T cells, CD8+ T cells, or both.

According to some embodiments of the CAR immunotherapy, the immune effector cell engineered to express the CAR comprising a TLE3 construct by lentiviral transduction adapted from the CAR-T design is an NK cell.

According to some embodiments of the CAR immunotherapy, the source of the immune effector cell is peripheral blood or umbilical cord blood; or the population of immune effector cells is autologous to the subject; or the population of immune effector cells is allogeneic to the subject.

According to some embodiments of the CAR immunotherapy, when the engineered TLE3 molecule is a C-terminus truncated TLE3 (TLE3ΔWDR) protein, compared to a no-TLE3 CAR immune effector control, expression of the TLE3ΔWDR construct in CAR-containing immune effector cells enhances CAR-immune effector cell function despite chronic antigen stimulation; and/or expression of the TLE3ΔWDR construct in stimulated CAR-containing immune effector cells promotes activation of genes that promote anti-tumor activity and also represses genes involved in excessive effector function, exhaustion or both; and/or expression of the TLE3ΔWDR construct in stimulated CAR-containing immune effector cells reduces expression of at least one inhibitory receptor comprising PD-1, CTLA-4, LAG3, TIGIT, or a combination thereof; and/or expression of the CAR-TLE3ΔWDR construct in stimulated CAR-containing immune effector cells induces transcriptomic changes comprising differential expression of genes that enhance the anti-tumor response and/or promotes proliferation of the CAR-containing immune effector cells;

enhances persistence of the CAR-containing immune effector cells and maintains immune homeostasis despite chronic antigen stimulation; and/or expression of the CAR-TLE3ΔWDR construct in stimulated CAR-containing immune effector cells reprograms the immune effector cells to acquire stem-like, memory cell characteristics including production of IFN-γ and TNF, expression of TCF-1 or both, and/or expression of the TLE3ΔWDR construct in CAR-containing immune effector cells enhances CAR-immune effector cell function after rechallenge with the cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fec.

FIG. 1A and FIG. 1B depict generation of CAR-T cells expressing engineered TLE3. FIG. 1A is a diagram showing TLE protein structure (Taken from Buscarlet and Stifani, Trends in Cell Biol. (2007) 17:353-361], designated domains in WT and engineered TLE proteins. FIG. 1B is a diagram showing human CD19-directed chimeric antigen receptor (CAR) protein, linked to engineered TLE3 protein via P2A peptide, which allows simultaneous translation of both proteins.

FIG. 2A, FIG. 2B, FIG. 2C, and FIG. 2D show that TLE3ΔWDR expression enhances leukemia control by CAR-T cells and promotes survival. FIG. 2A is a diagram showing key steps of the generation of engineered CAR-T cells from healthy donors. FIG. 2B shows the study design using a xenograft of Raji leukemic and CAR-T cells into highly immunodeficient NSG mice. FIG. 2C shows longitudinal tracking of leukemic burden in NSG recipients via in vivo imaging. Images are representative of 6 independent experiments. FIG. 2D shows a Kaplan-Meier survival curve of NSG recipients. Data are pooled results from 2 independent experiments, and the p values were obtained by log-rank (Mantel-Cox) statistical analysis.

FIG. 3A, FIG. 3B, FIG. 3C, and FIG. 3D show that TLE3ΔWDR expression confers growth and survival advantages to CAR-T cells. FIG. 3A shows immunoblotting of endogenous (Endo.) WT TLE3 and engineered TLE3ΔWDR in CAR-T cells, with detection of β-actin as a loading control. FIG. 3B shows tracking CAR-T cell accumulation over extended culture ex vivo. Established control or TLE3ΔWDR+ CAR-T cells (12 days after initial activation) were sort-purified and seeded in 24-well plate at 5×10E5 cell/well in the presence of IL-2 (10 ng/ml), IL-7 (5 ng/ml) and IL-15 (5 ng/ml). FIG. 3C shows the result of PCA of RNA-seq libraries of CAR-T cells from two healthy donors. The established CAR-T cells were cultured with or without Raji cells (at 1:9 ratio) for 48 hrs and then sort-purified for RNA-seq analysis. FIG. 3D shows numbers of differentially expressed genes (DEGs) that were common to both donor-derived CAR-T cells. Up- and down-regulated genes in TLE3ΔWDR+ CAR-T cells were defined as TLE3ΔWDR-induced and -repressed genes, respectively.

FIG. 4A shows detection of CAR-T cells in peripheral blood cells of NSG recipients at the indicated time windows. FIG. 4B shows detection of CD4+ vs CD8+ CAR-T cell distribution in the peripheral blood cells. Data are means±s.d. from two independent experiments, with individual data points shown. , p<0.01; *, p<0.001 by student's t-test. NRD, not reliably detected, because of the low frequency of CAR-T cells.

FIG. 5A, FIG. 5B, and FIG. 5C show that TLE3ΔWDR limits CAR-T cell exhaustion at an early response stage in vivo. On 12 days post-tumor implantation (dpt), splenocytes were harvested from NSG recipients, and analyzed for CD4+ and CD8+ CAR-T cell numbers (FIG. 5A), and expression of PD1, TIM3 and LAG3 in the CAR-T cells (FIG. 5B). FIG. 5C. Cumulative data on frequency of $TIM3^{hi}$PD1+, $TIM3^{lo}$PD1+, and PD1¬– subsets in splenic CAR-T cells. Data in A and C are means±s.d. from two independent experiments, with individual data points shown. *, p<0.05; , p<0.01; *, p<0.001; ns, not statistically significant by student's t-test.

FIG. 6A shows the occurrence of high leukemia burden in NSG recipient mice on 30 days post-tumor implantation (dpt), as detected with in vivo imaging. For examples, please refer to FIG. 2B, where all recipients of control CAR-T and the 5th recipient (on the far right of the panel) of TLE3ΔWDR+ CAR-T cells were considered to have high leukemia burden, while leukemia in the rest of TLE3ΔWDR+ CAR-T cell recipients were below detection limited and considered 'cured'. Data are cumulative from 3 independent experiments. FIG. 6B shows CAR-T cell numbers in recipient spleens on 30 dpt. The differences between control and TLE3ΔWDR+ CAR-T cell numbers were not statistically significant and therefore unmarked. FIG. 6C shows detection of PD1 and TIM3 expression in CAR-T cells, where TLE3ΔWDR+ CAR-T cells were from the 'leukemia-cured' recipients. FIG. 6D shows cumulative data of relative expression of coinhibitory receptors in CD8+ (top) and CD4+ CAR-T cells (bottom), where the average of geometric mean fluorescence intensity (gMFI) for each receptor in control CAR-T cells was set as 1, and all samples were then normalized to the average in the same experiment. This approach allows direct comparison across different experiments. Data in FIG. 6B and FIG. 6D are means±s.d. from two independent experiments , p<0.01; *, p<0.001 by student's t-test.

FIG. 7A shows detection of TOX and TCF1 expression CAR-T cells via intranuclear staining. FIG. 7B shows detection of cytokine production by CAR-T cells. On 30 days post-tumor implantation (dpt), splenocytes were stimulated with phorbol myristate acetate (PMA) and ionomycin in the presence of Golgi plug and Golgi stop for 5 hours, and detected for IFN-γ, TNF-α and IL-2 via intracellular staining. IFN-γ+ cells were then gated for further analysis of TNF-α and IL-2 production. FIG. 7C shows profiles of cytokine production in CAR-T cells, where cells producing all three cytokines are marked as "triple", those producing IFN-γ and TNF-α as "double", and those producing IFN-γ only as "single" producers. Data are means±s.d. from two independent experiments.

FIG. 8A shows a Kaplan-Meier survival curve of the rechallenged recipients. Data are pooled results from 2-3 independent experiments, and the p values were determined with log-rank (Mantel-Cox) statistical analysis. FIG. 8B shows longitudinal tracking of leukemia burden in rechallenged mice harboring TLE3ΔWDR+ CAR-T cells via in vivo imaging. Data are representative from 3 experiments. FIG. 8C. Tracking of frequency of leukemia-responding TIM3$^{hi}$PD1+ subset in TLE3ΔWDR+ CAR-T cells in the peripheral blood cells. The day of injection of high-dose Raji cells was designated as day 0 in the graph.

FIG. 11A, FIG. 11B and FIG. 11C shows that TLE3ΔWDR reprograms CAR-T cells to acquire molecular features of memory T cells from an early response stage in vivo. On 12dpt, control or TLE3ΔWDR+ CAR-T cells were sort-purified from NSG recipient spleens and were analyzed with CITE-seq. FIG. 11A is a uniform manifold approximation and projection (UMAP) plot of scRNA-seq data on CD8+ CAR-T cells, with each dot representing a single cell and all five clusters identified with Seurat in distinct colors. FIG. 11B is a bar graph showing distribution of control and TLE3ΔWDR+ CAR-T cells in each cluster defined in A. FIG. 11C is a heat map showing expression of select characteristic genes for indicated functional programs, with each column corresponding to a single cell and the color scale representing z-score transformed transcript levels.

DETAILED DESCRIPTION OF THE INVENTION

Glossary

Figure 3C:
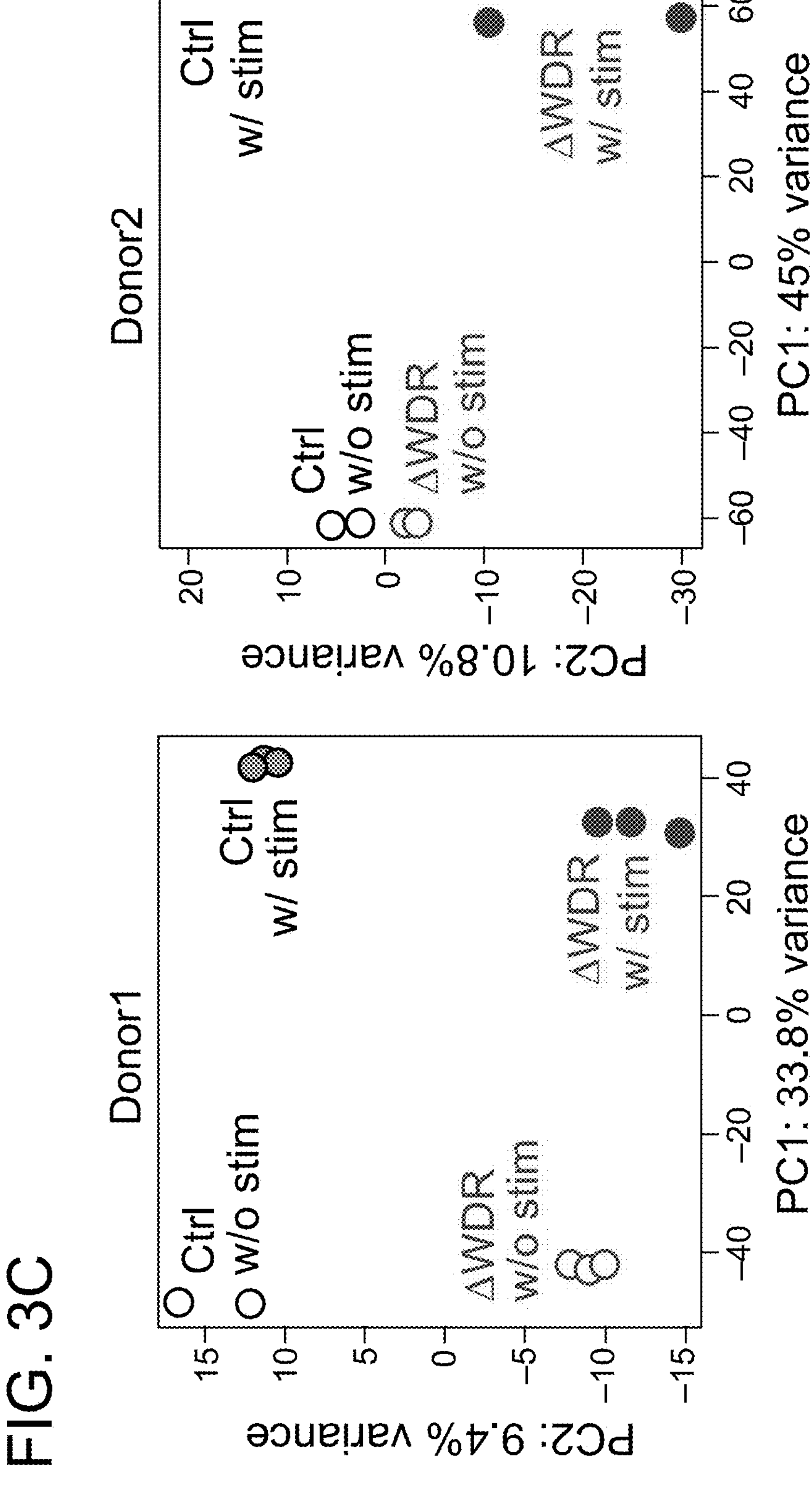

The terms "4-1BB" or "CD137" or "tumor necrosis factor receptor super family 9" as used herein refer to an inducible costimulatory receptor expressed on activated T and natural killer (NK) cells. [Chester, C. et al. Blood (2018) 131 (1): 49-57]. There is widespread expression of 4-1BB throughout the hematopoietic and nonhematopoietic compartments. 4-1BB is expressed on activated monocytes and NK cells, dendritic cells (DCs), neutrophils, eosinophils and mast cells. [Id., citing Wilcox, R A et al. J. Immunol. (2002) 168 (9): 4262-4267; Heinisch I V, et al. Eur. J. Immunol. (2000) 39 (120): 3441-3446; Schwarz, H. et al. Blood (1995) 85 (4): 1043-1052].

On T cells, 4-1BB is transiently expressed after T-cell receptor engagement and, when 4-1BB is engaged by its natural or artificial ligand, it provides CD28-independent costimulation resulting in enhanced proliferation and TH1 cytokine production. [Id., citing DeBenedetto, M A e al. J. Immunol. (1997) 158 (2): 551-9; Saoullli, K. et al. J. Exp. Med. (1998) 187 (11): 1849-1862]. The major biological ligand of 4-1BB, 4-1BBL, is expressed on activated APCs, including dendritic cells (DCs) and macrophages and B cells [Id., citing Goodwin, R G et al. Eur. J. Immunol. (1993) 23 (10): 2631-2641; Alderson, M R et al. Eur. J. Immunol. (1994) 24 (9): 2219-2227; Futagawa, T. et al. Intl Immunol. (2002) 14 (3): 275-286; Pollok, K E et al. Eur. J. Immunol. (1994) 24 (2): 367074]. Ligation of 4-1BB recruits TNFR-associated factor (TRAF) 1 and TRAF2 and induces signaling through the master transcription factor NF-κB and MAPKs. [Id., citing Lee, D Y et al. PLOS One (2013) 8 (7): e69677; Vinay, D S and Kwon, B S. Semin. Immunol. (1998) 10 (6): 481-489]. Upon ligation with agonist mAbs, 4-1BB rapidly internalizes to an endosomal compartment from which it keeps signaling through this pathway. [Id., citing Bradley, J R and Pober, J S. Oncogene (2001) 20 (44): 6482-6491; Kim, C M et al. Sci Rep. (2016) 6 (1): 25526]. 4-1BB signaling ultimately contributes to the secretion of IL-2 and IFN-γ and upregulation of the antiapoptotic Bcl-2 family members Bcl-xL and Bfl-1, which provide strong protection against activation-induced T cell death. [Id., citing Hurtado, J C et al. J. Immunol. (1997) 158 (6): 2600-2609 sec. Lee, H-W et al. J. Immunol. (2002) 169 (9): 4882-4888; Maus, M V et al. Nat. Biotechnol. (2002) 20 (2): 143-148; Takahashi, C. et al. J. Immunol. (1999) 162 (9): 5037-5040]. Even though 4-1BB and CD28 costimulation are said to be functionally independent, CD28 costimulation is a powerful stimulus for 4-1BB upregulation.

Upon Fc-receptor triggering, NK cells upregulate 4-1BB and increase cytotoxic function in response to 4-1BB agonism, but 4-1BB agonism on resting NK cells may reduce NK cell frequency and compromise NK cell cytotoxic function. [Id., citing Choi, B K et al. J. Immunol. (2010) 185 (30): 1404-1411; Lee, S—H and Hahm, D. J. Immunol. (2016) 196 (1 suppl.) Abstract 61.4; Chester, C. et al. Cancer Immunol. Immunother. (2016) 65 (10): 1243-1248]. Endothelial cells also can upregulate 4-1BB following stimulation with TNF alpha, lipopolysaccharide, and IL-1beta. Expression of 4-1BB along blood vessel walls at the sites of inflammation, chiefly including tumor microvasculature and atherosclerotic areas, suggests that 4-1BB may mediate leukocyte extravasation and migration. [Id., citing Drenkard, D. et al. FASEB J. (2007) 21 (20:456-463; Broll, K. et al. Am J. Clin. Pathol. (2001) 115 (4): 543-549; Teijeira, A. et al. FASEB J. (2012) 26 (8): 3380-3392]. Tregs also express 4-1BB, but its role on this immune subset remains poorly understood. [Id., citing Smith, S E et al. Cancer Immunol. Immunother. (2011) 60 (12): 1775-87; Zhang, P. et al. Scand. J. Immunol. (2007) 66 (4): 435-440].

Endothelial cells in hypoxic blood vessels within tumors can upregulate 4-1BB in a hypoxia-inducible factor 1-alpha mediated fashion. [Id., citing Palazon, A. et al. Cancer Res. (2011) 71 (30:801-11]. In this compartment, anti-4-1BB antibodies give rise to an increased expression of homing receptors for T-cell infiltration. 4-1BB signaling can break and reverse established anergy in cytotoxic T lymphocytes. 4-1BB signaling also plays a role in restoring the functionality of exhausted CD8+ T cells. [Id., citing Williams, J B et al. J. Exp. Med. (2017) 214 (2): 381-400]. On NK cells, 4-1BB signaling can increase antibody-dependent cell mediated cytotoxicity. Agonistic monoclonal antibodies targeting 4-1BB can lead to tumor clearance and durable antitumor immunity. [Id. citing Kohrt, H E et al. Blood (2011) 117 (8): 2423-2432; Kohrt, H E et al. J. Clin. Invest. (2012) 122 (3): 1066-1075; Kohrt, H E et al. J. Clin. Invest. (2014) 124 (6): 2668-2682].

The term "adaptive response" refers to an immune response mediated by uniquely specific recognition of a non-self entity by lymphocytes whose activation leads to elimination of the entity and the production of specific memory lymphocytes.

The term "adoptive immunotherapy" also known as "cellular immunotherapy" is a type of immunotherapy in which T cells are given to a recipient patient to help the body fight diseases. Types of adoptive cell therapy include chimeric antigen receptor (CAR) T-cell therapy and tumor-infiltrating lymphocyte (TIL) therapy.

The term "adaptor protein" as used herein refers to a protein that contains a series of protein-binding sites that link respective interaction partners to each other and facilitate the generation of larger signaling complexes.

The term "adverse event" or "AE" as used herein refers to an unfavorable medical event that occurs in a subject who is given a therapeutic product but does not necessarily have a causal relationship with the treatment. An adverse event may be any adverse and unwanted sign (including an abnormal laboratory result), symptom, or temporary illness associated with the use of the product, whether or not it is related to the product. The correlation between adverse events and test medications is either affirmative, likely related, may be relevant, may be irrelevant, and certainly not relevant. The severity of adverse events according to the National Cancer Institute's Common Terminology Criteria for Adverse Events (CTCAE) ranges from Mild (Grade 1), to Moderate (grade 2); to Severe (Grade 3), to Life-Threatening (Grade 4); to Death (grade 5).

The term "allele" as used herein refers to any of one or more alternative forms of a given gene.

The term "allogeneic" as used herein refers to being derived from a genetically different individual of the same species.

The term "amplicon" as used herein refers to the end product of a replicated or amplified piece of DNA.

The term "anergy" as used herein refers to a state of lymphocyte nonresponsiveness to specific antigen induced by an encounter of the lymphocyte with cognate antigen under less-than-optimal conditions, such as in the absence of costimulation.

As used herein, the term "antibody" includes, by way of example, both naturally occurring and non-naturally occurring antibodies. Specifically, the term "antibody" includes polyclonal antibodies and monoclonal antibodies, and fragments thereof. Furthermore, the term "antibody" includes chimeric antibodies and wholly synthetic antibodies, and fragments thereof.

As used herein, the term "antibody" is used in the broadest sense and encompasses various antibody structures, including but not limited to monoclonal antibodies, polyclonal antibodies, antibody fragments, chimeric antibodies and wholly synthetic antibodies as long as they exhibit the desired antigen-binding activity. In nature, antibodies are serum proteins the molecules of which possess small areas of their surface that are complementary to small chemical groupings on their targets. These complementary regions (referred to as the antibody combining sites or antigen binding sites) of which there are at least two per whole antibody molecule, and in some types of antibody molecules ten, eight, or in some species as many as 12, may react with their corresponding complementary region on an antigen (the antigenic determinant or epitope) to link several molecules of multivalent antigen together to form a lattice. The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, K and 2; individual molecules of immunoglobulin generally are only one or the other. In mammals, there are five classes of antibodies, IgA, IgD, IgE, IgG, and IgM, each with its own class of heavy chain. All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifested at many levels. Brought down to the molecular level, "specificity" means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur; this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy ($V_H$) and light ($V_L$=$V_\kappa$ and $V_\lambda$) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human $V_L$ chains with the heavy chain variable region ($V_H$) domain of a mouse monoclonal antibody reactive with an antigen of interest; (ii) selecting half-human Fabs on that antigen (iii) using the selected $V_L$ genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1 antibody molecule in the mouse myeloma.

The term antibody may include an oligoclonal antibody, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody, and an antibody that can be labeled in soluble or bound form, as well as fragments, variants or derivatives thereof, either alone or in combination with other amino acid sequences provided by known techniques.

An antibody may be from any species. The term antibody also includes binding fragments of the antibodies of the invention. Binding fragments of an antibody can be produced by recombinant DNA techniques, or by enzymatic or chemical cleavage of intact antibodies. Exemplary fragments include Fv, Fab, Fab', single stranded antibody (svFC), dimeric variable region (Diabody) and di-sulfide stabilized variable region (dsFv). Structural and functional domains can be identified by comparison of the nucleotide and/or amino acid sequence data to public or proprietary sequence databases. For example, computerized comparison methods can be used to identify sequence motifs or predicted protein conformation domains that occur in other proteins of known structure and/or function. Methods to identify protein sequences that fold into a known three-dimensional structure are known. See, for example, Bowie et al. Science 253:164 (1991), which is incorporated by reference in its entirety. An antibody other than a "bispecific" or "bifunctional" antibody is understood to have each of its binding sites identical.

The term "antibody construct" as used herein refers to a polypeptide comprising one or more the antigen-binding portions linked to a linker polypeptide or an immunoglobulin constant domain. Linker polypeptides comprise two or more amino acid residues joined by peptide bonds and are used to link one or more antigen-binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Human IgG heavy chain and light chain constant domain amino acid sequences are known in the art. Antibody portions, such as Fab and F(ab') 2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

The term "antigen" as used herein refers to a molecule containing one or more epitopes (either linear, conformational or both) that will stimulate a host's immune-system to make a humoral and/or cellular antigen-specific response. The term is used interchangeably with the term "epitope." Normally, a B-cell epitope will include at least about 5 amino acids but can be as small as 3-4 amino acids. A T-cell epitope, such as a CTL epitope, will include at least about 7-9 amino acids, and a helper T-cell epitope will include at least about 12-20 amino acids. Normally, an epitope will include between about 7 and 15 amino acids, such as, 7, 8, 9, 10, 11, 12, 13, 14, or 15 amino acids. The term includes polypeptides which include modifications, such as deletions, additions and substitutions (generally conservative in nature) as compared to a native sequence, as long as the protein maintains the ability to elicit an immunological response, as defined herein. These modifications may be deliberate, as through site-directed mutagenesis, or may be accidental, such as through mutations of hosts which produce the antigens.

The term "antigen binding site" as used herein refers to the structure formed at the amino-terminal ends (variable domains) of the light and heavy chains of an antibody, which are folded to form 3-dimensional (globular) variable domains, $V_H$ and $V_L$. The antigen binding site makes physical contact with the antigen and binds it noncovalently. The antigen specificity of the site is determined by its shape and the amino acids present.

The term "antigen presentation" as used herein, generally refers to the display to a T cell of antigen on the surface of a cell, e.g., in the form of peptide fragments bound to MHC molecules.

As used herein, the term "antigen presenting cell (APC)" refers to a class of cells capable of displaying on its surface ("presenting") one or more antigens in the form of peptide-MHC complexes recognizable by specific effector cells of the immune system, and thereby inducing an effective cellular immune response against the antigen or antigens being presented. Examples of professional APCs are dendritic cells and macrophages, although any cell expressing MHC Class I or II molecules can potentially present a peptide antigen. An APC can be an "artificial APC," meaning a cell that is engineered to present one or more antigens. Before a T cell can recognize a foreign protein, the protein must be processed inside an antigen presenting cell or target cell so that it can be displayed as peptide-MHC complexes on the cell surface.

As used herein the term "antigen processing" refers to the intracellular degradation of foreign proteins into peptides that can bind to MHC molecules for presentation to T cells.

The term "AP-1" as used herein refers to a heterodimeric transcription factor formed as one of the outcomes of intracellular signaling via the antigen receptors of lymphocytes and the toll like receptors (TLRs) of cells of innate immunity. Most often AP-1 contains one Fos-family member and one Jun-family member. AP-1 mainly activates the expression of genes for cytokines and chemokines.

The term "apheresis" as used herein refers to a medical technology in which the blood of a donor or patient is passed through an apparatus that separates out one particular constituent and returns the remainder back to the donor or patient's circulation. Leukapheresis is one type of apheresis where leukocytes (white blood cells) are selectively removed.

The terms "apoptosis" or "programmed cell death" refer to a highly regulated and active process that contributes to biologic homeostasis comprising a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways.

The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to death domain (DD) containing receptors like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits inhibitor of apoptosis (IAP) proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome c is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNase (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation, can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. [Loberg, R D, et al., J. Biol. Chem. (2002) 277 (44): 41667-41673]. It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon aggregation and mitochondrial localization, induces cytochrome c release. Akt is a critical regulator of GSK-3, and phosphorylation and inactivation of GSK-3 may mediate some of the antiapoptotic effects of Akt.

The term "assay for transposase-accessible chromatin with sequencing" or "ATAC-Seq" as used herein refers to a popular method for determining chromatin accessibility across the genome. By sequencing regions of open chromatin, ATAC-Seq can help uncover how chromatin packaging and other factors affect gene expression.

The term "autologous" as used herein refer to being present in or derived from an individual's own tissues.

The term "B7 molecules" as used herein refers to cell surface proteins on specialized APCs, such as dendritic cells, which are the major costimulatory molecules for T cells. B7.1 (CD80) and B7.2 (CD86) are closely related members of the immunoglobulin superfamily, and both bind to CD28 and CTLA-4 proteins on T cells.

The term "basic leucine zipper ATF-like transcription factor" ("Batf) refers to a bZIP transcription factor that plays an important role in regulating differentiation and function in many lymphocyte lineages [Kurachi, M. et al. Nature Immunol. (2014) 15 (4): 373-383, citing Schraml B U, et al. Nature. 2009; 460 (7253): 405-409. Betz B C, et al. J Exp Med. 2010; 207 (5): 933-942, 16; Ise W, et al. Nat Immunol. 2011; 12 (6): 536-543, Murphy T L, et al. Nat Rev Immunol. 2013; 13 (7): 499-509, Grigoryan G, et al. Nature. 2009; 458 (7240): 859-864]. In the CD8+ T cell lineage, increased expression of BATF in exhausted CD8+ T cells suppresses their effector function [Quigley M, et al. Nat Med. 2010; 16 (10): 1147-1151]. In the CD4+ T cell lineage, BATF is required for the differentiation of interleukin 17 (IL-17)-producing helper T cells (TH17) [Id., citing Schraml B U, et al. Nature. 2009; 460 (7253): 405-409], where it binds co-operatively with the transcription factor IRF4 [Glasmacher E, et al. Science. 2012; 338(6109):975-980, Li P., et al. Nature. 2012; 490(7421):543-546, Ciofani M, et al. Cell. 2012; 151 (2): 289-303] and its dimerization partners c-Jun, JunB and JunD [Id., citing Grigoryan G, et al. Nature. 2009; 458(7240):859-864]. BATF is also important for the development of follicular helper T cells (TFH) by regulating the transcription factors Bcl-6 and c-Maf [Id., citing Betz B C, Jordan-Williams K L, Wang C, Kang S G, Liao J, Logan M R, et al. Batf coordinates multiple aspects of B and T cell function required for normal antibody responses. J Exp Med. 2010; 207(5):933-942, Ise W, Kohyama M, Schraml B U, Zhang T, Schwer B, Basu U, et al. The transcription factor BATF controls the global regulators of class-switch recombination in both B cells and T cells. Nat Immunol. 2011; 12(6):536-543]. In addition, BATF is required for class-switch recombination in B cells and to regulate activation-induced cytidine deaminase [Id., citing Ise W, Kohyama M, Schraml B U, Zhang T, Schwer B, Basu U, et al. The transcription factor BATF controls the global regulators of class-switch recombination in both B cells and T cells. Nat Immunol. 2011; 12(6):536-543] as well as DNA damage checkpoint in hematopoietic stem cell (HSC) self-renewal [Id., citing Wang J, Sun Q, Morita Y, Jiang H, Groß A, Lechel A, et al. A differentiation checkpoint limits hematopoietic stem cell self-renewal in response to DNA damage. Cell. 2012; 148(5):1001-101423.

The term "binding" and its various grammatical forms means a lasting attraction between chemical substances.

The term "binding specificity" as used herein involves both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system a molecule interacts with its targets or partners differentially, thereby impacting them distinctively depending on the identity of individual targets or partners.

The term "biocompatible" as used herein refers to causing no clinically relevant tissue irritation, injury, toxic reaction, or immunological reaction to living tissue.

The term "biodegradable" as used herein refers to material that will break down actively or passively over time by simple chemical processes, by action of body enzymes or by other similar biological activity mechanisms.

As used herein, the term "biomarker" (or "biosignature") refers to a peptide, protein, nucleic acid, antibody, gene, metabolite, or any other substance used as an indicator of a biologic state. It is a characteristic that is measured objectively and evaluated as a cellular or molecular indicator of normal biologic processes, pathogenic processes, or pharmacologic responses to a therapeutic intervention. Once a proposed biomarker has been validated, it may be used to diagnose disease risk, presence of disease in an individual, or to tailor treatments for the disease in an individual (choices of treatment or administration regimes). In evaluating potential therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The terms "cancer" or "malignancy" as used herein refer to diseases in which abnormal cells divide without control and can invade nearby tissues. Cancer cells also can spread to other parts of the body through the blood and lymph systems.

The term "CD19" as used herein refers to a 95 kd transmembrane glycoprotein belonging to the immunoglobulin (Ig) superfamily. It is encoded by the 7.41 kilobyte CD19 gene located on the short arm of chromosome 16, 16p11.2. The gene contains 15 exons and codes for the CD19 molecule with 556 amino acids. Structurally, the gene contains an unusually short 5'-untranslated region. The proximal cd19 promoter lacks a TATA box, and its major start sites are found within 50 bp of the initiation codon. CD19 is classified as a type I transmembrane protein, with a single transmembrane domain, a cytoplasmic C-terminus, and extracellular N-terminus. No significant homology exists between CD19 and other known proteins. The extracellular element contains two C2-type Ig-like domains divided by a smaller potential disulfide linked non-Ig-like domain, as well as N-linked carbohydrate addition sites. The highly conserved cytoplasmic domain consists of 242 amino acids with nine tyrosine residues near the C-terminus [9-11]. Multiple studies have come to suggest that the biologic functions of CD19 are dependent on three cytoplasmic tyrosine residues—Y391, Y482 and Y513. CD19 is critically involved in establishing intrinsic B cell signaling thresholds through modulating both B cell receptor (BCR)-dependent and independent signaling. It plays roles in the antigen-independent development as well as the immunoglobulin-induced activation of B cells. [Wang, K. et al. Exptl Hematology & Oncology (2012) 1: art. 36].

The term "CD20" as used herein refers to a 33-37 kDa non-glycosylated protein expressed on the surface of normal and malignant B lymphocytes. It belongs to the MS4A (membrane-spanning 4-domain family A) protein family. CD20 protein consists of four hydrophobic transmembrane domains, one intracellular and two extracellular domains (large and small loops) with both N- and C-termini residing within the cytosol. Three CD20 isoforms (33, 35 and 37 kDa) resulting from different phosphorylation have been identified, and CD20 phosphorylation was reported to be higher in proliferating malignant B cells than in resting B cells. Normally, CD20 does not form hetero-oligomers, 18 but exists on the cell surface as homodimeric and homotetrameric oligomers associated with other cell-surface and cytoplasmic proteins contributing to the signal transduction. CD20 is also known to be physically coupled to major histocompatibility complex class II (MHCII), CD40 molecule, BCR, and the C-terminal src kinase-binding protein (CBP) that interacts with Src kinases such as LYN, FYN, and LCK. [Pavlasova, G. and Mraz, M. Haematologica (2020) 105 (6): 1494-1506]. It may be found in higher than normal amounts in patients with certain types of B-cell lymphomas and leukemias.

The term "CD22" as used herein refers to a surface molecule expressed early during the ontogeny of B cells in the bone marrow and spleen that can be found on B cells isolated from the different lymphoid compartments in humans. CD22 is an inhibitory coreceptor of the B-cell receptor (BCR) and plays a critical role in establishing signaling thresholds for B-cell activation. CD22 is expressed by most blasts from the majority (60-90%) of B-cell acute lymphoblastic leukemia (B-ALL). [Lanza,. et al. Cancers (Basel) (2020) 12 (20:303].

The term "CD33" as used herein refers to a myeloid cell surface antigen that is not expressed on blood stem cells or within the hematopoietic system, but that can be expressed on the surface of natural B-lymphocytes, activated T-lymphocytes, and natural killer (NK) cells.

The term "CD123" as used herein refers to the α chain of the interleukin 3 receptor, which is a cytokine receptor overexpressed in multiple hematolymphoid neoplasms, including acute myeloid leukemia, blastic plasmacytoid dendritic cell neoplasm, acute lymphoblastic leukemia, hairy cell leukemia, and systemic mastocytosis. CD123 expression is upregulated in leukemic stem cells relative to non-neoplastic hematopoietic stem cells.

The terms "cell line" and "cultured cell line" are used interchangeably to refer to cells of a single type that have been adapted to grow continuously in the laboratory.

As used herein, the term "cell growth" is the process by which cells accumulate mass and increase in physical size. There are many different examples in nature of how cells can grow. In some cases, cell size is proportional to DNA content. For instance, continued DNA replication in the absence of cell division (called endoreplication) results in increased cell size. Megakaryoblasts, which mature into granular megakaryocytes, the platelet-producing cells of bone marrow, typically grow this way. By a different strategy, adipocytes can grow to approximately 85 to 120 μm by accumulating intracellular lipids. In contrast to endoreplication or lipid accumulation, some terminally differentiated cells, such as neurons and cardiac muscle cells, cease dividing and grow without increasing their DNA content. These cells proportionately increase their macromolecule content (largely protein) to a point necessary to perform their specialized functions. This involves coordination between extracellular cues from nutrients and growth factors and intracellular signaling networks responsible for controlling cellular energy availability and macromolecular synthesis. Perhaps the most tightly regulated cell growth occurs in dividing cells, where cell growth and cell division are clearly separable processes. Dividing cells generally must increase in size with each passage through the cell division cycle to ensure that a consistent average cell size is maintained. For a typical dividing mammalian cell, growth occurs in the G1 phase of the cell cycle and is tightly coordinated with S phase (DNA synthesis) and M phase (mitosis). The combined influence of growth factors, hormones, and nutrient availability provides the external cues for cells to grow. [Guertin, D. A., Sabatini, D. M., "Cell Growth," in The Molecular Basis of Cancer (4th Edn) Mendelsohn, J. et al Eds, Saunders (2015), 179-190].

As used herein, the term "cell proliferation" refers to the process that results in an increase of the number of cells and is defined by the balance between cell divisions and cell loss through cell death or differentiation.

The term "chemical bond" as used herein refers to an attractive force between atoms strong enough to permit the combined aggregate to function as a unit.

As used herein, the term "chemokine" refers to a class of chemotactic cytokines that orchestrate migration and positioning of immune cells within the tissues. Chemokines bind to seven transmembrane G protein-coupled receptors that trigger intracellular signaling that drives cell polarization, adhesion, and migration [Vilgelm, A E and Richmond, A. Front. Immunol. (2019) doi.org/10.3389/fimmu.2019.00333, citing Griffith, J W et al. Annu. Rev. Immunol. (2014) 32:659-702; Nagarsheth, N. et al. Nat. Rev. Immunol. (2017) 17:559-572]. They are divided into four families based upon structure: CXC, CC, CX3C, and C chemokines. The receptors follow a similar nomenclature system, based upon the family of chemokines to which they bind. In addition, there is a family of atypical chemokine receptors that do not directly couple to G proteins but are reported to have a variety of roles in development, homeostasis, inflammatory disease, infection, and cancer [Id., citing Nibbs, RJ, Graham, GJ. Nat. Rev. Immunol. (2013) 13:815-829].

The term "CCR7" as used herein refers to a receptor for the constitutive chemokines CC chemokine ligand (CCL)-19 and CCL21, which are produced by stomal cells in the T cell zone of the spleen, lymph nodes and Peyer's patches. [Unsoeld, H. et al. J. Immunol. (2002) 169 (2): 638-641, citing Butcher, E C et al. Adv. Immunol. (1999) 72:209; Cyster, J G. Science (1999) 286:2098; Sallusto, F., et al. Annu. Rev. Immunol. 1 (2000) 18:593] This enables naïve T cells to migrate to T cell areas of lymphoid organs in search of antigen presented by dendritic cells. [Id., citing Gunn, M D et al. J. Exp. Med. (12999) 189:451; Forster, R. et al. Cell (1999) 99:23] In humans, CCR7 has been described as a defining factor for two different types of memory T cells, termed central and effector memory T cells [Id., citing Sallusto, F. et al. Nature (1999) 401:708]. Central memory cells express CCR7 and represent a nonpolarized Ag-experienced cell population that lacks immediate effector cell functions. In contrast, effector memory cells have down-regulated CCR7 and are capable of immediately producing cytokines after Ag recognition.

The term "CD62L" as used herein refers to L-selectin, a leukocyte adhesion molecule associated with differentiating naïve and activated/memory T cells. It has been demonstrated that naive T cells express a $CD62L^{hi}CD44^{lo}$ phenotype, whereas memory T cells exhibit a $CD62L^{lo}CD44^{hi}$phenotype. [Gerberick, G F et al. Toxicology and Applied Pharmacol. (1997) 146 (1): 1-10].

The term "CITE-Seq" or "cellular indexing of transcriptomes and epitopes" as used herein refers to a sequencing-based method that uses unique oligonucleotide-tagged antibodies to identify surface proteins. The oligo-conjugated antibodies combined with single-cell library preparation solutions use barcodes to link proteome and transcriptome profiles to single cells.

The term "clonal expansion" as used herein refers to rapid proliferation of a specific cell type.

The term "cluster analysis" as used herein in the context of clonal expansion, is a computational method used to group together cells or DNA sequences that share a high degree of similarity, allowing researchers to identify populations of cells originating from a single progenitor cell (a clone), indicating clonal expansion.

The term "CTLA-4" or "cytotoxic T-lymphocyte-associated antigen 4" or "CD152" as used herein refers to an inhibitory receptor and immune checkpoint that aids in maintaining self-antigen immunity by dampening T cell responses. It is a counterreceptor to costimulatory molecule CD28.

The term "cofactor" as used herein refers to a regulatory protein factor that typically is unable to bind to DNA itself and is recruited to enhancers by sequence-specific transcription factors (TFs). Cofactors can have enzymatic functions (for example, they can catalyze post-translational modifications of proteins) and can mediate the regulatory function of the enhancers. [Zabidi, M A and Stark, A. Trends Genet. (2016) 32 (12): 801-14].

The term "cognate" signifies two biomolecules that typically interact, e.g., a receptor and its cognate ligand.

The term "compatible" as used herein refers to components of a composition that are capable of being combined with each other in a manner such that there is no interaction that would substantially reduce the efficacy of the composition under ordinary use conditions.

The terms "complete response" or "complete remission" or "CR" as used herein refer to the disappearance of all signs of cancer in response to treatment. This does not always mean the cancer has been cured.

The term "component" as used herein, is meant to refer to a constituent part, element or ingredient.

The term "composition" as used herein, is meant to refer to a material formed by a mixture of two or more substances.

As used herein, the term "condition" as used herein, is meant to refer to a variety of health states and is meant to include disorders or diseases caused by any underlying mechanism or disorder.

As used herein, the term "contact" and its various grammatical forms is meant to refer to a state or condition of touching or of immediate or local proximity. Contacting a composition to a target destination may occur by any means of administration known to the skilled artisan.

The term "core-promoter" or "minimal promoter" as used herein refers to a short sequence around the transcription start site (TSS) that can direct the recruitment of RNA Polymerase II (Pol II) and transcription initiation. Core-promoters typically have low basal activities in the absence of enhancers. [Zabidi, M A and Stark, A. Trends Genet. (2016) 32 (12): 801-814].

The term "costimulation" as used herein refers to the second signal required for completion of lymphocyte activation and prevention of anergy, which is supplied by engagement of CD 28 by CD 80 and CD 86 (T cells) and of CD 40 by CD 40 Ligand (B cells).

The term "costimulatory molecule" as used herein refers to molecules that are displayed on the cell surface that have a role in enhancing the activation of a T cell that is already being stimulated through its TCR. For example, HLA proteins, which present foreign antigen to the T cell receptor, require costimulatory proteins which bind to complementary receptors on the T cell's surface to result in enhanced activation of the T cell. Co-stimulatory molecules are highly active immunomodulatory proteins that play a critical role in the development and maintenance of an adaptive immune response (Kaufman and Wolchok eds., General Principles of Tumor Immunotherapy (2007) Chpt 5, 67-121). The two signal hypothesis of T cell response involves the interaction between an antigen bound to an HLA molecule and with its cognate T cell receptor (TCR), and an interaction of a co-stimulatory molecule and its ligand. Specialized APCs, which are carriers of a co-stimulatory second signal, can activate T cell responses following binding of the HLA molecule with TCR. In contrast, somatic tissues do not express the second signal and thereby induce T cell unresponsiveness [Kaufman and Wolchok eds., General Principles of Tumor Immunotherapy (2007) Chpt 5, 67-121]. Many of the co-stimulatory molecules involved in the two-signal model can be blocked by co-inhibitory molecules that are expressed by normal tissue (Id.). In fact, many types of interacting immunomodulatory molecules expressed on a wide variety of tissues may exert both stimulatory and inhibitory functions depending on the immunologic context (Id.).

The term "co-stimulatory receptor" as used herein refers to a cell surface receptor on naïve lymphocytes through which they receive signals in addition to those received through the antigen receptor, and which are necessary for the full activation of the lymphocyte. Examples are CD 30 and CD 40 on B cells and CD 27 and CD 28 on T cells.

The term "cross-dressing" as used herein refers to a pathway for cross-presentation. In cross-dressing, dendritic cells acquire preformed MHC class I molecules in complex with antigens from other cells by the process of trogocytosis [Yewdell, J W and Dolan, B P, "Cross-dressers turn on T cells". Nature (2011) 471 (7340): 581-582, citing Joly, E. and Hudrisier, D. Nature Immunol. (2003) 4:815; Herrera O B et al. J. Immunol. (2004) 173:4828-4837] or through gap junctions. This allows antigen presentation by acceptor dendritic cells to occur immediately, without any processing. Cross-dressing is used to activate memory T cells, but not naïve T cells, in response to viral infection [Id., citing Wakins, L M and Bevan, M J. Nature (2011) 471:629-632].

The term "cross-presentation" as used herein refers to a process by which proteins taken up by dendritic cells from the extracellular milieu can give rise to peptides presented by MHC class I molecules. It enables antigens from extracellular sources to be presented by MHC class I molecules and to activate CD8 T cells.

The term "cross-priming" as used herein refers to activation of CD8 T cells by dendritic cells in which the antigenic peptide presented by MHC class I molecules is derived from an exogenous protein (i.e., by cross-presentation), rather than produced within the dendritic cells directly (cf. direct presentation).

The terms "CCTC-binding factor" or "CTCF" as used herein refers to a highly conserved zinc finger protein that can function as a transcriptional activator, a repressor or an insulator protein, blocking the communication between enhancers and promoters. CTCF can also recruit other transcription factors while bound to chromatin domain boundaries. The three-dimensional organization of the eukaryotic genome dictates its function, and CTCF serves as one of the core architectural proteins that help establish this organization. The mapping of CTCF-binding sites in diverse species has revealed that the genome is covered with CTCF-binding sites. [Kim, S. et al. Exp. & Molec. Med. (2015) 47: e166].

The term "culture" and its other grammatical forms as used herein, is meant to refer to a process whereby a population of cells is grown and proliferated on a substrate in an artificial medium.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines. Non-limiting examples of cytokines include e.g., IL-1, IL-2, IL-3, IL-4, IL-5, IL-6, IL-7, IL-8, IL-9, IL-10, IL-11, IL-12/IL-23 P40, IL13, IL-15, IL-15/IL15-RA, IL-17, IL-18, IL-21, IL-23, TGF-β, IFNγ, GM-CSF, Groα, MCP-1 and TNF-α.

The term "cytotoxic T lymphocytes" (CTLs) as used herein refers to effector CD8+ T cells. Cytotoxic T cells kill by inducing their targets to undergo apoptosis/programmed cell death via extrinsic and intrinsic pathways.

The term "CX3CR1" as used herein refers to CX3C chemokine receptor 1, which is a marker of T cell differentiation. It was found that $CX3CR1^+$ $CD8^+$ T cells were the progeny of $CX3CR1^-CD8^+$ T cells and exhibited robust cytotoxicity in anti-viral immunity [Yamauchi, T. et al. Nature Communic. (2021) 12: article 1402, citing Bottcher, J P et al. Nat. Commun. (2015) 6:8306; Gerlach, C. et al. Immunity (2016) 45:1270-1284].

The term "dendritic cells" (or "DCs") as used herein refers to professional antigen presenting cells, which induce naïve T cell activation and effector differentiation. [Patente, T A, et al., Frontiers Immunol. (2019) doi.org/10.3389/fimmu.2018.03176]. Human DCs are identified by their high expression of major histocompatibility complex (MHC) class II molecules (MHC-II) and of CD11c, both of which are found on other cells, like lymphocytes, monocytes and macrophages [Id., citing Carlens J, et al. J Immunol. (2009) 183:5600-7; Drutman S B, et al. J Immunol. (2012) 188: 3603-3610; Hochweller K, S et al. Eur J Immunol. (2008) 38:2776-2783; Huleatt J W, Lefrançois L. J Immunol. (1995) 154:5684-5693; Rubtsov A V, et al. Blood (2011) 118:1305-1315; Probst H C, et al. Clin Exp Immunol. (2005) 141:398-404; Vermaclen K, Pauwels R. Cytometry (2004) 61A: 170-177]. DCs express many other molecules which allow their classification into various subtypes. Although some of the DC subtypes were originally described as macrophages, DC and macrophages have distinct characteristics [Id., citing Delamarre L, Science (2005) 307:1630-1634; Geissmann F, et al. Science (2010) 327:656-661; van Montfoort N, et al. Proc Natl Acad Sci USA. (2009) 106: 6730-6735] and ontogeny, so that, currently, little doubt remains that they belong to distinct lineages [Id., citing Haniffa M, et al. (2013) 120:1-49; Hashimoto D, et al. Immunity (2013) 38:792-804; Hettinger J, et al. Nat Immunol. (2013) 14:821-830; McGovern N, et al. Immunity (2014) 41:465-477; Naik S H, et al. Nature (2013) 496:229-232; Schulz C, et al. Science (2012) 336:86-90; Schraml B U, et al. Cell (2013) 154:843-858; Wang J, et al. Mol Med Rep. (2017) 16:6787-6793; Yona S, et al. Immunity (2013) 38:79-91].

The term "derived from" as used herein encompasses any method for receiving, obtaining, or modifying something from a source of origin.

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like. "Assay markers" are measurable components whose presence or absence can be detected and correlated to a particular detectable response.

The term "detectable response" as used herein, is meant to refer to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "direct presentation" as used herein refers to the process by which proteins produced within a given cell give rise to peptides presented by MHC class I molecules. This may refer to APCs (such as dendritic cells), or to nonimmune cells that will become the targets of CTLs.

The term "detection limit" as used herein refers to the smallest amount or concentration of an analyte in a test sample that can reliably be distinguished from the baseline.

The term "differential gene expression" as used herein refers to an observed difference or change in expression level of a gene between two experimental conditions that is statistically significant.

The term "differentiate" and its various grammatical forms as used herein refer to the process of development with an increase in the level of organization or complexity of a cell or tissue, accompanied with a more specialized function.

The terms "disease progression" or "progressive disease" as used herein refers to a cancer that continues to grow or spread.

The term "domain" as used herein refers to a region of a protein with a characteristic tertiary structure and function and to any of the three-dimensional subunits of a protein that together make up its tertiary structure formed by folding its linear peptide chain.

The term "dose" as used herein, is meant to refer to the quantity of a therapeutic substance prescribed to be taken at one time. The term "maximum tolerated dose" as used herein is meant to refer to the highest dose of a drug or treatment that does not cause unacceptable side effects.

The term "dose escalation study" as used herein refers to a type of study where enrolled patients receive different doses of an investigational agent to determine the recommended phase 2 dose.

The term "dose limiting toxicities" as used herein refers to side effects of a treatment that are serious enough to prevent an increase in dose of that treatment.

The term "ectopic gene expression" refers to expression of a gene in a place or at a time in which it is not expressed in nature.

The term "effective dose" as used herein generally refers to that amount of therapeutic agent sufficient to induce a therapeutic effect. An effective dose may refer to the amount of the therapeutic agent sufficient to delay or minimize the onset of symptoms. An effective dose may also refer to the amount of the therapeutic agent that provides a therapeutic benefit in the treatment or management of a disease, disorder or condition. Further, an effective dose is the amount with respect to a therapeutic agent alone, or in combination with other therapies, which provides a therapeutic benefit in the treatment or management of a disease. An effective dose may also be the amount sufficient to enhance the subject's (e.g., a human's) own immune response. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease and/or reduces the severity of symptoms.

For any therapeutic agent described herein the effective dose may be initially determined from preliminary in vitro studies and/or animal models. A therapeutically effective dose may also be determined from human data. The applied dose may be adjusted based on the relative bioavailability and potency of the administered agent. Adjusting the dose to achieve maximal efficacy based on the methods described above and other well-known methods is within the capabilities of the ordinarily skilled artisan.

General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where an agent's plasma concentration can be measured and related to the therapeutic window, additional guidance for dosage modification can be obtained.

The term "effector cell" as used herein refers to a cell that carries out a final response or function. The main effector cells of the immune system, for example, are activated lymphocytes and phagocytes.

The term "effector functions" as used herein refers to the actions taken by effector cells and antibodies to eliminate foreign entities, and includes, without limitation, cytokine secretion, cytotoxicity, and antibody-mediated clearance.

The term "eligible subject" as used herein refers to a subject that satisfies the requirements to be treated with the immunotherapy of the present disclosure under the professional judgment of the patient's physician. Eligibility criteria may include the subject's age, type and stage of cancer, current health status, medical history, and previous treatments.

The term "enhancer" as used herein refers to a sequence of several tens to hundreds of base pairs that boosts transcription from a target core-promoter in a cell-type-specific manner and independent of the enhancer's relative orientation and distance. Enhancers and core-promoters are two major classes of cis-regulatory elements. [Zabidi, M A and Stark, A. Trends Genet. (2016) 32 (12): 801-814].

The term "enrich" as used herein refers to increasing the proportion of a desired substance, for example, to increase the relative frequency of a subtype of cell compared to its natural frequency in a cell population. Positive selection, negative selection, or both are generally considered necessary to any enrichment scheme. Exemplary selection methods include, without limitation, magnetic separation and FACS.

The term "epigenetic marks" as used herein refer to DNA methylation, histone modifications, chromatin remodeling and microRNA.

The term "epigenetics" as used herein refers to a stably heritable phenotype resulting from changes in a chromosome without alterations in the DNA sequence.

The term "exclusion criteria" as used herein refers to specify characteristics that disqualify subjects from clinical studies and often include factors such as comorbidities or concomitant treatment or factors that could mask the effect of the study treatment.

The term "exon" as used herein refers to nucleic acid coding sequences of an RNA transcript, or the DNA encoding it, that are translated into protein.

The terms "expand" or "amplify" as used herein with respect to cells refers to increasing in cell number.

As used herein, the term "expression" and its other grammatical forms refers to production of an observable phenotype by a gene, usually by directing the synthesis of a protein. It includes the biosynthesis of mRNA, polypeptide biosynthesis, polypeptide activation, e.g., by post-translational modification, or an activation of expression by changing the subcellular location or by recruitment to chromatin.

The term "flow cytometry" as used herein, is meant to refer to a tool for interrogating the phenotype and characteristics of cells. It senses cells or particles as they move in a liquid stream through a laser (light amplification by stimulated emission of radiation)/light beam past a sensing area. The relative light-scattering and color-discriminated fluorescence of the microscopic particles is measured. Flow analysis and differentiation of the cells is based on size, granularity, and whether the cell is carrying fluorescent molecules in the form of either antibodies or dyes. As the cell passes through the laser beam, light is scattered in all directions, and the light scattered in the forward direction at low angles (0.5°-10°, inclusive) from the axis is proportional to the square of the radius of a sphere and so to the size of the cell or particle. Light may enter the cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogenous population (Marion G. Macey, Flow cytometry: principles and applications, Humana Press, 2007). Fluorescence-activated cell sorting (FACS), which allows isolation of distinct cell populations too similar in physical characteristics to be separated by size or density, uses fluorescent tags to detect surface proteins that are differentially expressed, allowing fine distinctions to be made among physically homogeneous populations of cells.

The term "forkhead box, subgroup O (FOXO) transcription factors" as used herein refers to a subfamily of a conserved FOX protein family which regulates gene expression, consisting of FOXO1, FOXO3, FOXO4, and FOX06 in mammals. They bind to DNA through the FoxO-recognized element in the C-terminal basic region of the forkhead DNA-binding domain. Following forkhead binding to DNA, target gene expression is repressed or activated through multiple protein-DNA contacts with the primary recognition site located at α-helix H3. [Dai, S. et al. Nucleic Acids Res.

(2021) 49 (18): 10235-10249]. FOXOs control cellular homeostasis, such as stress resistance, cell cycle, cell differentiation, apoptosis, proteostasis, intracellular signaling, metabolism, and autophagy. FOXOs are well known for their functions in oxidative and redox regulation downstream of the insulin/insulin-like growth factor-1 (IGF-1) signaling (IIS) pathway. The pI3K pathway is an important regulator of FOXO activity. FOXOs also play critical functions in DNA damage repair.

The term "gene" as used herein refers to a region of DNA that includes the entire functional unit encompassing coding DNA sequences, noncoding regulatory DNA sequences, and introns, which controls a discrete hereditary characteristic, usually corresponding to a single protein or RNA.

The term "gene activator protein" as used herein refers to a gene regulatory protein that when bound to its regulatory sequence in DNA activates transcription.

The term "gene editing" as used herein refers to alteration of the genetic material of a living organism by inserting, replacing, or deleting a DNA sequence, typically with the goal of improving some characteristic of the organism.

The term "gene expression" as used herein refers to the process by which information encoded in a gene is turned into a function. This mostly occurs via the transcription of RNA molecules that code for proteins or non-coding RNA molecules that serve other functions. Eukaryotic gene expression is regulated by genomic enhancers that recruit transcription factors and cofactors to activate transcription from target core-promoters.

The term "gene fusion" or "fusion gene" as used herein refers to a hybrid gene that is formed from the abnormal combination of two chromosomes The formation of fusion genes in cells can occur through multiple mechanisms. In the most common scenario, a fusion gene is formed via somatic chromosomal rearrangement. The four basic types of chromosomal rearrangement are deletions, translocations, tandem duplications, and inversions. For example, in hematologic cancers, in chronic myelogenous leukemia patients an interchromosomal translocation produces a chimeric BCR-ABL1 transcript that encodes a constitutively active form of ABL kinase; an interchromosomal translocation in acute lymphocytic leukemia produces the fusion gene ETV6-RUNX1; and an interchromosomal translocation in acute myeloid leukemia produces a RUNX1-ETO chimeric protein. [Annala, M. et al. Cancer Lett. (2013) 340 (2): 192-200].

The term "gene regulatory protein" as used herein refers to any protein that binds to a specific DNA sequence to alter the expression of a gene.

The term "gene repressor protein" as used herein refers to a gene regulatory protein that prevents the initiation of transcription.

The term "general transcription factor" as used herein refers to any of the proteins whose assembly around the TATA box indicates where a genetic sequence can be read and decoded, which is required for the initiation of transcription of most eukaryotic genes.

The term "graft versus host disease" or "GVHD" as used herein refers to an attack on the tissues of a graft recipient by mature T cells from a nonidentical donor, which can cause a variety of symptoms, sometimes severe.

The term "graft versus tumor effect" as used herein refers to immune reactivity mediated by donor T cells against the recipient's tumor cells.

The term "granzyme B" or "GZMB" as used herein refers to a caspase-like serine proteinase that is released by recently activated CD8+ T cells. Resting CD8+ memory cells are granzyme B negative. [Nowacki, T M et al. Cell Immunol. (2007) 247 (1): 36-48].

The term "haploidentical" as used herein refers to half-matched donors. A haploidentical donor is usually an individual's mother, father, or child. Parents are always a half-match for their children. Siblings (brothers or sisters) have a 50% (1 out of 2) chance of being a half-match for each other.

The term "hashtag antibody" as used herein refers to an antibody targeting cell surface proteins that is conjugated to a barcode allowing researchers to identify and pool different samples of cells for analysis simultaneously that can be de-multiplexed during analysis.

The term "healthy subject" or "healthy donor" or "healthy adult donor" as used herein refers to a subject having no signs or symptoms of a cancer.

The term "hematologic cancer" as used herein refers to a cancer that begins in blood-forming tissue. Examples of hematologic cancer are a cancer that begins in blood-forming tissue, such as the bone marrow (e.g. a leukemia), a cancer that begins in cells of the immune system (a lymphoma), and a cancer that arises in plasma cells (e.g., multiple myeloma).

The term "IL7R" as used herein refers to the receptor for the cytokine interkeukin-7. One of the principal roles of IL-7 is to promote the survival of both naïve and memory T cells. Expression of the IL7R following infection is thought to contribute to the dynamic changes in the quantitative T cell response during the expansion and contraction phases of an immune response [Colpitts, S L et al. J. Immunol. (2009) 182 (9): 5702-5711, citing Schluns, K S et al. Nat. Immunol. (2000) 1:426-432; Schluns, K S and Lefrancois, L. Nat. Rev. Immunol. (2003) 3:269-279]. For example, at the peak of the expansion phase to an acute viral or bacterial infection, the majority of the antigen-specific cells are IL7Rlow, and they are destined to be a short-lived population that can execute effector function and need not be maintained after the pathogen is cleared [Id., citing Schluns, K S et al. Nat. Immunol. (2000) 1:426-432; Kaech, S M et al. Nat. Immunol. (2003) 4:1191-1198; Huster, K M et al. Proc. Natl Acad. Sci. USA (2004) 101:5610-5615]. On the other hand, after contraction occurs, the remaining antigen-specific T cells express high levels of the IL7R, which promotes their continued maintenance.

As used herein, the term "immune checkpoints" refers to the array of inhibitory pathways necessary for maintaining self-tolerance and that modulate the duration and extent of immune responses to minimize damage to normal tissue. In T cells, the ultimate amplitude and quality of the immune response, which is initiated through antigen recognition by the TCR, is regulated by a balance between co-stimulatory and inhibitory signals (immune checkpoints). [Pardoll, D M. Nat. Rev. Cancer (2012) 12 (4): 252-264]. Immune checkpoint molecules such as PD-1, PD-L1, and CTLA-4 are cell surface signaling receptors that play a role in modulating the T-cell response in the tumor microenvironment. Tumor cells have been shown to utilize these checkpoints to their benefit by up-regulating their expression and activity. With the tumor cell's ability to commandeer some immune checkpoint pathways as a mechanism of immune resistance, it has been hypothesized that checkpoint inhibitors that bind to molecules of immune cells to activate or inactivate them may relieve their inhibition of an immune response. Immune checkpoint inhibitors have been reported to block discrete checkpoints in an active host immune response allowing an endogenous anti-cancer immune response to be sustained. Recent discoveries have identified immune checkpoints or targets, like PD-1, PD-L1, PD-L2, CTLA-4, TIGIT, TIM-3, LAG-3, CCR4, OX40, OX40L, IDO, and A2AR, as proteins responsible for immune evasion.

The terms "immune escape" or "immune evasion" as used herein refers to a strategy to evade a host's immune response. It is characterized by the inability of the immune system to eliminate transformed cells prior to and after tumor development. The host's contribution is manifested by its inability to recognize antigens expressed by tumor cells, a phenomenon known as "host ignorance." It happens because of defects in both the innate and adaptive arms of the immune system. The tumor's contribution is manifested by the adaptation of tumor cells to evade the immune system or by developing a microenvironment that suppresses the immune system. [Qian J. et al. (2011) Immune Escape. In: Schwab M. (eds) Encyclopedia of Cancer. Springer, Berlin, Heidelberg. https://doi.org/10.1007/978-3-642-16483-5_2975].

The term "immune homeostasis" refers to the delicate and finely regulated balance of appropriate immune activation and suppression in tissues and organs, driven by a myriad of cellular players and chemical factors. [da Gama Duarte, J. et al. Immunology and Cell Biology (2018) 96:497-506]

The terms "immune response" and "immune-mediated" are used interchangeably herein to refer to any functional expression of a subject's immune system, against either foreign or self-antigens, whether the consequences of these reactions are beneficial or harmful to the subject. The term "immunological response" to an antigen or composition as used herein is meant to refer to the development in a subject of a humoral and/or a cellular immune response to an antigen. For purposes of the present disclosure, a "humoral immune response" refers to an immune response mediated by antibody molecules, while a "cellular immune response" is one mediated by T-lymphocytes and/or other white blood cells. One aspect of cellular immunity involves an antigen-specific response by cytolytic T lymphocytes ("CTL's"). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. The term "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of T cells, suppressor T-cells and/or γδ T-cells directed specifically to an antigen or antigens present in the composition of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

The term "immune phenotype" or "immunotype" as used herein refers to the collective frequency of various immune cell populations and their functional responses to stimuli (cell signaling and antibody responses). [See Kaczorowski, K J et al. Proc. Nat. Acad. Sci. USA (2017) doi/10.1073/pnas. 1705065114]

The terms "immune surveillance" and "immunological surveillance" are used interchangeably to refer to a monitoring process by the immune system to detect and destroy infected and neoplastically transformed cells in the body.

The term "immune system" as used herein refers to the body's system of defenses against disease, which comprises the innate immune system and the adaptive immune system. The innate immune system provides a non-specific first line of defense against pathogens. It comprises physical barriers (e.g. the skin) and both cellular (granulocytes, natural killer cells) and humoral (complement system) defense mechanisms. The reaction of the innate immune system is immediate, but unlike the adaptive immune system, it does not provide permanent immunity against pathogens. The adaptive immune response is the response of the vertebrate immune system to a specific antigen that typically generates immunological memory.

The term "immunological synapse" ("IS") as used herein refers to a highly structured body that functions to concentrate T cell signaling in a defined area. It is associated with the selective recruitment of signaling molecules and exclusion of negative regulators. The synapse is stabilized by a ring of adhesion molecules, including, for example, LFA1, which binds to ICAM1 on the APC. The immune synapse modulates TCR signaling by several mechanisms. In the earliest stages of immune synapse formation, TCR-containing microclusters are recruited to the central molecular cluster. The TCR responds to two distinct pMHC ligands (agonist and self-peptide-MHC) in co-agonism rather than nonspecific TCR-MHC interactions, which adds to the overall binding strength of the TCR-p-MHC complex. The strength of the TCR-p-MHC interactions has a role in determining the influence of coreceptors that are recruited to the immune synapse (e.g., CD8). The immune synapse also modulates TCR signaling by regulating interactions between kinases in the TCR pathway and their substrates. [Morris, G. and Allen, P M. Nature Immunol. (2012) doi: 10.1038/nm.2190].

Studies have shown that expression of CD5 increases according to the magnitude of the signal delivered by the TCR. Consequently, CD5 is an activation marker of T cells, and CD5 expression reflects the heterogeneity of the signal strength associated with each individual TCR within a polyclonal T cell population. [Voisinne, G. et al. Front. Immunol. (2018) 9:2900]. In homeostasis, high expression of CD5 is considered a surrogate for TCR affinity for self-p-MHC and is positively correlated with expression of the IL-7 receptor. [Morris, G P and Allen, P M. Nature Immunol. (2012) doi: 10.1038/ni.2190]. Another model, termed "coreceptor tuning" proposes a mechanism for the adjustment of homeostasis in the periphery whereby expression of the Il-7 receptor and CD8 are reciprocally regulated. [Morris, G P and Allen, P M. Nature Immunol. (2012) doi: 10.1038/ni.2190].

The T cell signaling pathway includes proximate signaling (including phosphorylation of the invariant signaling protein CD3 and early signaling molecules, calcium-mediated signaling (release of intracellular Ca2+ stores and influx of extracellular Ca2+), and GTPase Ras-MAPK signaling. [Morris, G P and Allen, P M. Nature Immunol. (2012) doi: 10.1038/ni.2190]

T cell activation is mediated through highly organized and dynamic interaction of TCRs with MHC-peptide complexes at the IS. A mature IS is an aggregation of TCR-based signalosomes (meaning multimolecular complexes) that induce T cell responses and is defined by three concentric rings of clustered molecules. The inner circle is termed the central supramolecular activation cluster (cSMAC) where TCR signaling takes place. The cSMAC contains most of the TCR-MHC peptide complexes, CD28, PKC-theta and Lck, whereas the peripheral SMAC (pSMAC) contains proteins involved in cell adhesion, such as integrin LFA-1, cytoskeletal linker talin, and ICAM1. Larger molecules, such as CD43 and CD45, are excluded from the pSMAC and make up the distal SMAC (dSMAC). Inhibitory and costimulatory molecules, such as PD-1, CTLA-4, and ICOS also are aggregated at the region of the IS and play crucial roles in the regulation of T cell activation. [Watanabe, K. et al. Front. Immunol. (2018) 9:2486, citing Yokosuka, T. et al. Immunity (2010) 33:326-39]. Secretion of lytic granules occurs within a secretary synapse between CTLs and target cells. The secretory synapse has two separate and distinct domains in cSMAC: one is a signaling domain, which contains the signaling proteins, and another is a secretory domain for exocytosis of cytokines, perforins and granzymes. The transient polarization and docking of the centrosome to the plasma membrane, which is controlled by Lck signaling, has an important role in the mechanism of directing this secretion. [Id., citing Stinchcombe, J C et al. Nature (2006) 443:462-465; Tsun, A. et al. J. Cell Biol. (2011) 192:663-674].

The intracellular signaling downstream of CARs and the mechanisms of the IS formed by CARS have not been extensively studied. It has been demonstrated that CAR clustering, ZAP70 recruitment to IS, and exclusion of CD45 outside of IS occur between CD19-specific CAR-T cells and target cells that is similar to TCR activation. Downstream signaling molecules of the TCR, such as CD3zeta, LAT, Lck and ZAP70 are phosphorylated after CD19-CAR-T cell activation by autologous CD19 B cells [Id., citing Karlsson, H. et al. PLOS ONE (2015) 10: e0144787]. The CAR IS does not present a systematic bull's eye structure, which is a characteristic feature of TCR IS. Organization of the actin ring is poor, and actin may not be completely diminished at the center of CAR IS [Id., citing Xiong, W. et al. Mol. Ther. (2018) 26:963-975]. LFA-1 is disorganized and CAR-tumor antigen complexes form microclusters that are randomly distributed at the CAR immunological synapse [Id., citing Davenport, A J et al. Proc. Natl Acad. Sci. USA (2018) 115: E2068-76]. While the TCR IS requires 5-10 min to form the bull's eye structure, the CAR IS might not need to form these stable structures because the disorganized multifocal pattern of the CAR IS is sufficient to rapidly induce proximal signaling, which occurs within a short period of time (<2 min). The rapid but short duration of proximal signaling of the CAR IS also induces a rapid microtubule organizing center (MTOC) to the IS and accelerates the delivery of cytotoxic granules including perforin and granzymes, to the IS [Id., citing Davenport, A J et al. Proc. Natl Acad. Sci. USA (2018) 115: E2068-E2076].

The term "immunotherapy" as used herein refers to measures taken using immunological methods and principles to target the hyper or hyo-immune state of an organism, intervene or adjust the organism's immune function artificially, and strengthen or attenuate the immune response to treat disease. It enhances the immune system's ability to recognize, target and eliminate cancer cells in the body. [Zhang, Z. et al. Front. Immunol. (2021) 12:672356; Barbari, C. et al. Intl J. Mol. Sci. (2020) 21:5009]. Some types of immunotherapy only target certain cells of the immune system. Others affect the immune system in a general way.

The term "inflammation" as used herein refers to the physiologic process by which vascularized tissues respond to injury. Sec, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity.

The term "inhibitor of DNA binding protein 2" or "Id2" as used herein refers to a small helix-loop-helix transcription factor that transcriptionally and epigenetically regulates the generation of Slamf6$^+$ progenitor exhausted ($T_{ex}^{prog}$) CD8$^+$ T cells and their conversion to Tim-3$^+$ terminally exhausted ($T_{ex}^{tem}$) CD8$^+$ T cells. [Li, Y. et al. Cellular & Molecular Immunol. (2024) 21:292-308].

The term "inhibitor receptor lymphocyte activation gene-3" or "LAG-3" as used herein refers to a member of the immunoglobulin superfamily ("IgSF") that binds to major histocompatibility complex (MHC) class II. LAG-3 expression on tumor infiltrating lymphocytes (TILs) is associated with tumor-mediated immune suppression.

The term "innate response" as used herein refers to non-specific and broadly specific mechanisms that deter entry or promote elimination of foreign entities. These include physical, chemical and molecular barriers that exclude antigens in a totally nonspecific way; and soluble and membrane bound factors that recognize a limited number of molecular patterns that are common to a wide variety of pathogens or produced by host cells under stress.

The term "insulator" as used herein refers to DNA elements that can block regulatory enhancer-core-promoter communication, typically by the recruitment of insulator proteins, such as CTCF, and thus demarcate the range of enhancer activity and define TAD borders. [Zabidi, M A and Stark, A. Trends Genet. (2016) 32 (12): 801-814].

The term "intron" as used herein refers to a noncoding region of a eukaryotic gene that is transcribed into an RNA molecule but is then excised by RNA splicing and does not remain in the final mature mRNA molecule following transcription of that gene.

The term "Kaplan-Meier survival curve" or "survival curve" as used herein refers to the probability of surviving in a given length of time while considering time in many small intervals. It is commonly used to analyze time-toevent (survival) data, such as the time until death or the time until a specific event occurs. Time is plotted on the x-axis and the survival rate is plotted on the y-axis. Each subject is characterized by three variables: (1) their serial time; (2) their status at the end of their serial time (occurrence of an event of interest or censored); and (3) the study group they are in. The term "serial time" refers to the clinical course duration for each subject having a beginning and an end along the timeline of the complete study. An "interval", which is graphed as a horizontal line, is the serial time duration of known survival. An interval therefore is terminated only by the event of interest. "Censoring" means the total survival time for that subject cannot be accurately determined; this can happen when something negative for the study occurs, such as the subject drops out, is lost to follow-up, or required data is not available, or, conversely, something good happens, such as the study ends before the subject had the event of interest occur. Censoring can occur within the study or terminally at the end. Censored subjects are indicated as tick marks; these do not terminate the interval. [Rich, J T., et al. Otolaryngol. Head Neck Surg. (2010) 143 (3): 331-336]. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of an event are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "killer cell lectin-like receptor subfamily G, member 1" or "KLRG1" as used herein refers to a signaling molecule acquired as T cells become terminally differentiated. [Gattinoni, L. et al. Nature Reviews Cancer (2012) 12:671-684].

The term "leukemia" is a broad term for cancers of the blood cells. The type of leukemia depends on the type of blood cell that becomes cancerous and whether it grows quickly or slowly.

Like other cancers, leukemia is characterized by a succession of mutations in genes that regulate the processes of cellular division, death and differentiation leading to the progressive shift of cells from normal to malignant state [Sak, K. & Evaraus, H., Curr. Genomics (2017) 18 (1): 3-26]. Hematopoietic cancers often emerge in consequence of the uncontrolled growth and accumulation of immature blasts, since cellular differentiation is typically blocked at a particular maturation stage leading to the deficiency of normal functional blood cells and causing numerous serious symptoms [Id.].

Leukemia consists of a heterogeneous group of hematological malignancies affecting the cells of all hematopoietic lineages [Id., citing Mahbub, A. A. et al. Anticancer Agents med. Chem. (2013) 13 (10): 1601-1613; Qin, Y. et al. Eur. J. Pharm. Sci. (2012) 45 (5): 648-656; Kikuchi, H. et al. Intl J. Oncol. (2013) 43 (6): 1976-1984]. Examples of leukemias include, without limitation, acute lymphoblastic leukemia (also called acute lymphocytic leukemia and ALL), acute myelogenous leukemia (also called acute myeloblastic leukemia, acute myeloid leukemia, acute nonlymphocytic leukemia, AML, and ANLL), acute myeloid leukemia with myelodysplasia, acute promyelocytic leukemia (also called APL), chronic eosinophilic leukemia; chronic granulocytic leukemia (also called chronic myelogenous leukemia, chronic myeloid leukemia, and CML), erythroleukemia; mast cell leukemia; and hairy cell leukemia.

The term "linker for activation of T cells" or "LAT" as used herein refers to a signaling adaptor protein at the immune synapse. Once phosphorylated by ZAP70, LAT recruits cytosolic adaptors including SH2 domain-containing leukocyte phosphoprotein of 76 kDa (SLP76), growth factor receptor-bound protein 2 (GRB2), GRB2-related adaptor protein (GRAP2), as well as enzymes like Phospholipase C (PLCγ1) and IL-2 inducible T cell kinase (ITK).

The term "Lck" or "p56Ick" as used herein refers to a Src family kinase recruited to phosphorylate CD3 ITAMs during immune synapse maturation. [Ehrlich, L. I. R. et al. Immunity (2002) 17 (6): 809-822].

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens. This commitment, which exists before the first contact of the immune system with a given antigen, is expressed by the presence on the lymphocyte's surface membrane of receptors specific for determinants (epitopes) on the antigen. Each lymphocyte possesses a population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions. Lymphocytes are much more common in the lymphatic system, and include B cells, T cells, natural killer T (NKT) cells, and natural killer (NK) cells. There are two broad categories of lymphocytes, namely T cells and B cells. T-cells are responsible for cell-mediated immunity whereas B-cells are responsible for humoral immunity (relating to antibodies). T-cells are so-named because these lymphocytes mature in the thymus; B-cells mature in bone marrow. B cells make antibodies that bind to pathogens to enable their destruction. CD4+ (helper) T cells coordinate the immune response. CD8+ (cytotoxic) T cells, NKT, and Natural Killer (NK) cells are able to kill cells of the body that are, e.g., infected by a virus or display a recognized antigenic sequence.

The term "lymphocyte activation" or "activation" refers to stimulation of lymphocytes by specific antigens, nonspecific mitogens, or allogeneic cells resulting in synthesis of RNA, protein and DNA and production of lymphokines, the soluble product of lymphocytes; it is followed by proliferation and differentiation of various effector and memory cells. For example, a mature B cell can be activated by an encounter with an antigen that expresses epitopes that are recognized by its cell surface immunoglobulin (lg). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. Full responsiveness of a T cell requires, in addition to receptor engagement, an accessory cell-delivered costimulatory activity, e.g., engagement of CD28 on the T cell by CD80 and/or CD86 on the antigen presenting cell (APC).

The term "lymphodepletion" as used herein refers to a short course of chemotherapy to kill T cells. It creates a favorable immune environment for CAR T cells, which improves their expansion, persistence and clinical activity while reducing the potential for anti-CAR immune responses. [Wagner, D L et al. Nat. Rev. Clin. Oncol. (2021) 18 (6): 379-393].

The term "lymphoid enhancer binding factor" or "Lef1" as used herein refers to a gene that encodes a transcription factor that shares homology with high mobility group (HMG) protein-1. The HMG proteins are known to interact with a minor groove of the DNA double-helix and thus bend DNA to modulate DNA structure. [Shan, Q. et al. Nature Communic. (2021) 12:5863, citing Grosschedl, R. et al. Trends Genet. (1994) 10:94-100]. Lef1 binds a minimal TCRα enhancer and induce a sharp bend in DNA in vitro; the DNA bending facilitates interaction of Ets and Runx family transcription factors that bind to sequences flanking the Lef1 site. {Id., citing Giese, K. et al. Genes Dev. (1995) 9:995-1008; Love, J J et al. Nature (1995) 376:791-795].

The term "lymphoma" as used herein refers to a cancer of the lymphatic system, which includes the lymph nodes, spleen, thymus gland, and bone marrow that initiates from the malignant transformation of a single lymphocyte. Examples include Hodgkin's lymphoma, non-Hodgkin's lymphoma, cutaneous B cell lymphoma; cutaneous T cell lymphoma and Waldenstrom macroglobulinemia. Lymphomas almost always depend on surrounding stromal cells for survival and growth factors as well as vital intercellular contacts and so are generally restricted to sites within tissues. From its initiation site, a lymphoma tends to spread to additional secondary lymphoid tissues and eventually to non-lymphoid organs. Occasionally, a lymphoma cell undergoes additional mutations that allow it to survive and circulate in the blood, i.e., it becomes a leukemic cell. The disease then may be called a "leukemia/lymphoma." [Mak, T W et al. Ch. 20 Hematopoictic cancers, in Primer to the Immune response (2014) Elsevier, Inc., pp. 573-574]. The progression of any lymphoma can be described in four stages:

In Stage I, one or more diseased lymph nodes are present in a single group of lymph nodes in a lymphoid tissue of the body.

In stage 2, diseased lymph nodes are present in more than one group of lymph nodes, but all diseased nodes are contained either above or below the diaphragm. Tumor cells may also be present in a single organ near an affected node.

In stage III, diseased lymph nodes are present in two or more groups on both sides of the diaphragm. Tumor cells also may be present in the spleen and/or another organ near an affected node.

In stage IV, there is wide dissemination of tumor cells into multiple lymph nodes, bone marrow, liver and multiple organs. [Mak, T W et al. Ch. 20 Hematopoietic cancers, in Primer to the Immune response (2014) Elsevier, Inc., pp. 573-574]

Lymphomas display a tumor microenvironment (TME), with huge differences amongst the various forms. Hodgkin lymphoma (HL), both classic HL and nodular lymphocyte predominant HL, as well as several T cell lymphoma entities, such as angioimmunoblastic T-cell lymphomas (AITL), predominantly (>80% of the tumor mass) consist of TME cells. In indolent B-cell lymphomas, such as follicular lymphoma (FL) or marginal zone lymphomas, the TME constitutes about 50% of the cellular mass. In aggressive lymphomas, such as diffuse large B-cell lymphomas (CLBCL), the proportion of the TME varies and is generally lower. In Burkitt lymphoma, plasmablastic lymphoma and lymphoblastic T cell and B cell lymphomas, the TME is barely existent. [Menter, T. & Tzankov, A. Pathobiology (2019) 86:225-36].

The term "macrophage" as used herein refers to a mononuclear, actively phagocytic cell arising from monocytic stem cells in the bone marrow. These cells are widely distributed in the body and vary in morphology and motility. Phagocytic activity is typically mediated by serum recognition factors, including certain immunoglobulins and components of the complement system, but also may be nonspecific. Macrophages also are involved in both the production of antibodies and in cell-mediated immune responses, particularly in presenting antigens to lymphocytes. They secrete a variety of immunoregulatory molecules.

The terms "Major Histocompatibility Complex (MHC), MHC-like molecule" and "HLA" are used interchangeably herein to refer to cell-surface molecules that display a molecular fraction known as an epitope or an antigen and mediate interactions of leukocytes with other leukocyte or body cells. MHCs are encoded by a large gene group and can be organized into three subgroups-class I, class II, and class III. In humans, the MHC gene complex is called HLA ("Human leukocyte antigen"); in mice, it is called H-2 (for "histocompatibility"). Both species have three main MHC class I genes, which are called HLA-A, HLA-B, and HLA-C in humans, and H2-K, H2-D and H2-L in the mouse. These encode the α chain of the respective MHC class I proteins. The other subunit of an MHC class I molecule is β2-microglobulin. The class II region includes the genes for the α and β chains (designated A and B) of the MHC class II molecules HLA-DR, HLA-DP, and HLA-DQ in humans. Also in the MHC class II region are the genes for the TAP1:TAP2 peptide transporter, the PSMB (or LMP) genes that encode proteasome subunits, the genes encoding the DMα and BMβ chains (DMA and DMB), the genes encoding the α and β chains of the DO molecule (DOA and DOB, respectively), and the gene encoding tapasin (TAPBP). The class II genes encode various other proteins with functions in immunity. The DMA and DMB genes encoding the subunits of the HLA-DM molecule that catalyzes peptide binding to MHC class II molecules are related to the MHC class II genes, as are the DOA and DOB genes that encode the subunits of the regulatory HLA-DO molecule. [Janeway's Immunobiology. 9th ed., GS, Garland Science, Taylor & Francis Group, 2017. pps. 232-233]. In humans, there are three MHC class II isotypes, HLA-DR, HLA-DP, and HLA-DQ, encoded by α and β chain genes within the Human Leukocyte Antigen (HLA) locus on chromosome 6 [Wosen, J E et al. Front. Immunol. (2018) doi. 10.3389/fimmu.2018.02144].

The term "MHC restriction" as used herein refers to the requirement that APCs or target cells express MHC molecules that a T cell recognizes as self for the T cell to respond to the antigen presented by that APC or target cell (T cells will only recognize antigens presented by their own MHC molecules). For example, CD8 T cells bind class I MHCs which are expressed on most cells in the body, and CD4 T cells bind class II MHCs which are only expressed on specialized APCs.

As used herein, the terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "marker gene analysis" as used herein refers to amplicon-based sequencing or metabarcoding where the transcript levels of a gene in a specific cluster is sufficiently higher than those in other clusters so that the gene can be used as a "marker" to identify the cluster.

The term "mediated", and its various grammatical forms as used herein refers to depending on, acting by or connected through some intervening agency.

The term "memory cells" as used herein refers to B and T lymphocytes generated during a primary immune response that remain in a quiescent state until fully activated by a subsequent exposure to specific antigen (secondary immune response). Memory cells generally are more sensitive than naïve lymphocytes to antigen and respond rapidly on re-exposure to the antigen that originally induced them. During an immune response, naïve T cells ($T_N$) are primed by antigen-presenting cells (APCs). Depending on the strength and quality of stimulatory signals, proliferating T cells progress along a differentiation pathway that culminates in the generation of terminally differentiated short-lived effector T ($T_{EFF}$) cells. When antigenic and inflammatory stimuli cease, primed T cells become quiescent and enter the memory stem cell ($T_{SCM}$), central memory ($T_{CM}$) cell or effector memory ($T_{EM}$) cell pools, depending on the signal strength received. $T_{SCM}$ cells possess stem cell-like attributes to a greater extent than any other memory lymphocyte population. Although both $T_{CM}$ and $T_{EM}$ cells can also undergo self-renewal, the capacity to form diverse progeny is progressively restricted, so that only $T_{SC}$ cells can generate all three memory subsets and $T_{EFF}$ cells; $T_{CM}$ cells can give rise to $T_{CM}$, $T_{EM}$ and $T_{EFF}$ cells, and $T_{EM}$ cells can only produce themselves and $T_{EFF}$ cells. [Gattinoni, L. et al. Nature Revs. Cancer 12 (2012) 671-684].

The term "modulate" and its other grammatical forms as used herein means to regulate, alter, adapt, or adjust to a certain measure or proportion.

The term "molecule" as used herein refers to a chemical unit composed of one or more atoms connected by chemical bonds. The term "myeloma" as used herein refers to a plasma cell tumor that secretes large quantities of an Ig protein of usually unknown specificity. When tumors are present in multiple body sites, the disease is referred to as multiple myeloma (MM). Normal plasma cells cannot divide and so die soon after secreting antigen-specific antibody. In contrast, cancerous plasma cells divide uncontrollably and express huge quantities of antibodies or single Ig chains of unknown antigenic specificity.

As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "naïve T cell" as used herein refers to a T cell that has not previously been exposed to an antigen. Naïve T cells are conventionally defined by co-expression of the RA isoform of the transmembrane phosphatase CD45, the lymph node homing molecules L-selectin (CD62L) and CCR7, and the costimulatory receptors CD27 and CD28. [De Rosa, S C et al. Nature Med. (2001) 7:245-248].

The term "natural killer (NK) cells" as used herein refers to lymphocytes in the same family as T and B cells, classified as group I innate lymphocytes. They can kill tumor cells without any priming or prior activation, in contrast to cytotoxic T cells, which need priming by antigen presenting cells. NK cells secrete cytokines such as IFNγ and TNFα, which act on other immune cells, like macrophages and dendritic cells, to enhance the immune response. Activating receptors on the NK cell surface recognize molecules expressed on the surface of cancer cells and infected cells and switch on the NK cell. Inhibitory receptors act as a check on NK cell killing. Most normal healthy cells express MHCI receptors, which mark them as "self." Inhibitory receptors on the surface of the NK cell recognize cognate MHCI, which switches off the NK cell, preventing it from killing. Once the decision is made to kill, the NK cell releases cytotoxic granules containing perforin and granzymes, which leads to lysis of the target cell. Natural killer reactivity, including cytokine secretion and cytotoxicity, is controlled by a balance of several germline encoded inhibitory and activating receptors such as killer immunoglobulin-like receptors (KIRs) and natural cytotoxicity receptors (NCRs). The presence of the MHC Class I molecule on target cells serves as one such inhibitory ligand for MHC Class I-specific receptors, the Killer cell Immunoglobulin-like Receptor (KIR), on NK cells. Engagement of KIR receptors blocks NK activation and, paradoxically, preserves their ability to respond to successive encounters by triggering inactivating signals. Therefore, if a KIR can sufficiently bind to MHC Class I, this engagement may override the signal for killing and allows the target cell to live. In contrast, if the NK cell is unable to sufficiently bind to MHC Class I on the target cell, killing of the target cell may proceed. Consequently, those tumors which express low MHC Class I and which are thought to be capable of evading a T-cell-mediated attack may be susceptible to an NK cell-mediated immune response instead.

The term "neoantigens" as used herein refers to newly formed antigens generated by tumor cells as a result of various tumor-specific alterations, such as genomic mutation, dysregulated RNA splicing, disordered post-translational modification, and integrated viral open reading frames. Leukemia and sarcoma (which are among the cancers with the lowest predicted single nucleotide variant (SNV) burden) express gene fusions and splice variant transcripts shared across multiple tumors. [Smith, C C et asl. Nature Reviews Cancer (2019) 19:465-478].

The term "Next Generation Sequencing" or "NGS" as used herein refers to a method of parallel sequencing. For instance, a nucleic acid (e.g., DNA) sample is obtained and prepared into a library (meaning a collection of nucleic acid fragments from the sample). The library is prepared by fragmenting the DNA or RNA sample. Fragmentation can be performed by physical (e.g., sheared by acoustics, nebulization, centrifugal force, needles, or hydrodynamics) or enzymatic (e.g., site-specific or non-specific nucleases) methods. According to some embodiments, the fragments are about 200 bp, about 20 bp, about 300 bp, or about 350 bp in length. The DNA or RNA samples are repaired at the ends (e.g., blunt-ended) and then A-tailed (e.g., an adenosine is added to the 3' end resulting in an overhang). Adapters (which are short pieces of DNA around 80 bases in length) are ligated to each end to flank either side of the sequence of interest. Adapters include sequences, such as barcodes to uniquely tag each molecule in a given sample library, restriction sites, and primer sequences to bind general sequencing primers.

The term "NKG2D" as used herein refers to an activating receptor expressed by all NK cells and subsets of T cells (γδ T cells, CD8+ T cells and CD4+ T cells) in humans. It is encoded by the KLRK1 gene (killer cell lectin-like receptor subfamily K, member 1). The NKG2D receptor functions as an activating receptor by virtue of its interactions with the signaling adaptor dimer DAP10 in humans and with DAP10 and DAP12 in mice [Raulet, D H et al. Annu. Rev. Immunol. (2013) 31:4123-4141, citing Champsaur, M. and Lanier, L L. Immunol. Rev. (2010) 235:267-285; Wu, J. et al. Science (1999) 285:730-732]. When the receptor is ligated, DAP10 provides signals that recruit the p85 subunit of phosphatidylinositol 3-kinase (PI3K) and a complex of GRB2 and VAV1. Engagement of NKG2D on NK cells induces degranulation and cytokine production. However, engagement of NKG2D provides an enhancing or co-stimulatory signal for the activation of CD8+ T cells and probably other T cells.

NKG2D binds to several different ligands, all of which are homologous to MHC class I molecules but have no known role in antigen presentation [Id., citing Raulet, D H. Nat. Rev. Immunol. (2003) 3:781-790; Champsaur, M. and Lanier, L L. Immunol. Rev. (2010) 235:267-285; Eagle, R A and Trowsdale, J. Nat. Rev. Immunol. (2007) 7:737-744; Machuldova, A. ct al. Front. Immunol. (2021) 12:651751, citing Stephens, HA. Trends Immunol. (2001) 22 (7): 378-385]. Like MHC proteins, they exhibit considerable allelic variation. In humans, the NKG2D ligands include MHC class I chain-related protein A (MICA) and MHC class I chain-related protein B (MICB), both encoded by genes in the MHC, and up to six different proteins called Unique long (UL) 16-binding proteins (ULBPs), also known as retinoic acid early transcript 1 (RAET1) proteins. Like MHC proteins, the NKG2D ligands exhibit considerable allelic variation.

All NKG2D ligands are encoded by distinct genes in the host's own genome, i.e., the ligands are self-proteins. NKG2D ligands are expressed poorly or not at all by most normal cells but are upregulated in transformed/cancer cells, virus-infected cells, and, in some cases, stressed cells. This type of recognition process, in which self-coded ligands for activating receptors are induced on unhealthy cells, has been termed "induced self-recognition [Id. citing Diefenbach, A. and Raulet, D H. Immunol. Rev. (2001) 181:170-184], which is distinct from "missing self-recognition", a phenomenon in which loss of MHC ligands for NK inhibitory receptors sensitizes cells for elimination by NK cells. Various cellular pathways activated because of cellular stress, infection, or tumorigenesis regulate expression of the NKG2D ligands.

The structures of NKG2D-ligand complexes indicate that NKG2D binds diagonally over the α1 and α2 helices of the ligands, much as T-cell receptors bind over MHC molecules. Despite the poor homology of different ligands, some of the key residues that interact with NKG2D are conserved, and the NKG2D residues involved in binding are similar in the different structures.

The term "non-expanded" as used herein, is meant to refer to a cell population that has not been grown in culture (in vitro) to increase the number of cells in the cell population.

The term "nuclear factor of activated T cells proteins" or "NFAT proteins" refers to a family of transcription factors whose activation is controlled by calcineurin, a calcium dependent phosphatase. During periods of sustained elevations of calcium, calcineurin dephosphorylates NFATC1-C4, allowing NFAT to translocate to the nucleus. This nuclear translocation is blocked by cyclosporine A (CSA), which blocks calcineurin activity. Once in the nucleus, NFAT binds to consensus DNA sites and controls gene transcription. Originally identified in T cells as inducers of cytokine gene expression, NFAT proteins play varied roles in cells outside of the immune system. [Horsley, V. and Pavlath, G K. J. Cell Biol. (2002) 156 (5): 771-774].

The term "objective response rate" or "ORR" as used herein refers to the percentage of people in a study or treatment group who have a partial response or complete response to the treatment within a certain period of time.

The term "overall survival" as used herein refers to the length of time from either the date of diagnosis or the start of treatment for a disease, such as cancer, that patients diagnosed with the disease are still alive.

The term "PD-1" or "programmed cell death protein 1" as used herein refers to an inhibitory receptor expressed on the surface of activated T cells. Its ligands, PD-L1 and PD-L2, are expressed on the surface of DCs or macrophages. PD-1 and its ligands PD-L1/PL-L2 act as co-inhibitory factors that can limit the development of the T cell response. PD-L1 is overexpressed on tumor cells or on non-transformed cells in the tumor microenvironment [Pardoll, D M. Nat. Rev. Cancer (2012) 12:252-264]. PD-L1 expressed on the tumor cells binds to PD-1 receptors on the activated T cells, which leads to the inhibition of the cytotoxic T cells. These deactivated T cells remain inhibited in the tumor microenvironment.

The term "partial response" or "PR" as used herein refers to a decrease in the size of a tumor or in the extent of cancer in the body in response to treatment.

The term "peptide" is used herein to designate a series of amino acid residues, connected one to the other typically by peptide bonds between the alpha-amino and carbonyl groups of the adjacent amino acids. Peptides are typically 9 amino acids in length but can be as short as 8 amino acids in length, and as long as 14 amino acids in length. A series of amino acids are considered an "oligopeptide" when the amino acid length is greater than about 14 amino acids in length, typically up to about 30 to 40 residues in length. When the amino acid residue length exceeds 40 amino acid residues, the series of amino acid residues is termed a "polypeptide".

As used herein, the term "perforin" as used herein refers to a molecule that can insert into the membrane of target cells and promote lysis of those target cells. Perforin-mediated lysis is enhanced by enzymes called granzymes.

The terms "peripheral blood mononuclear cells" or "PBMCs" are used interchangeably herein to refer to blood cells having a single round nucleus such as, for example, a lymphocyte or a monocyte. PBMCs are a critical component in the immune system's responses to infections.

The term "phenotype" as used herein refers to qualitative and quantitative observable characteristics of cells. A cell's phenotype is the culmination of several cellular processes through a complex network of molecular interactions that ultimately result in a unique morphological signature. Clinical, biochemical and imaging methodologies can be used to refine and characterize a phenotype.

The term "PRDM1" or "PR domain-containing 1 with ZNF domain" or "BLIMP-1" as used herein refers to a gene that encodes a transcriptional regulator of effector T cell differentiation. [Gattinoni, L. et al. Nature Reviews Cancer (2012) 12:671-684].

The term "pre-initiation complex" or "PIC" as used herein refers to an assembly of proteins, including polymerase II and general transcription factors, that first nucleates at the core-promoter before transcription initiation and makes polymerase II transcription competent.

The terms “posttranslational modification”, “PTMs” or “covalent modifications” as used herein refers to the breaking or generation of covalent bonds on the backbones or amino acid side chains of proteins. More than 650 types of protein modifications, such as the most well-known phosphorylation, acetylation, methylation, ubiquitination, glycosylation, acylation, cysteine oxidation, SUMOylation, ADP-ribosylation, neddylation, citrullination, and carbamylation, have been described, and the inventory is still increasing. [Zhong, Q. et al. Med Comm. (2020) 4 (30): e261, citing Ramazi, S. and Zhiri, J. Database (Oxford) (2021) 2021: baab012; Wang, H. et al. Cancer Gene Ther. (2023) 30 (4): 529-47].

Most PTMs are dynamically reversible, and the addition and removal of the PTMs are enzymatically regulated. [Id., citing Macek, B. et al. Nat. Rev. Microbiol. (2019) 17 (11): 651-664] These protein modifications occur faster than the synthesis of new proteins, which allows cells or organisms to respond rapidly to changes in the surrounding environment [Id., citing Conibear, AC Nat. Rev. Chem. (2020) 4 (120:674-695]. By changing protein conformation, activity, charges and stability and interactions with DNA, RNA, and other proteins within and between cells, PTMs ultimately alter the phenotypes and biological functions of cells [Id., citing Liddy, K A et al. Genome Med. (2013) 5 (2): 20] and participate in the regulation of numerous cellular processes and pathways, such as cell cycle [Id., citing Chen, L. et al. Signal Transduct. Target Ther. (2020) 5 (1): 90] cell differentiation [Id., citing Shvedunova, M. and Akhtar, A. Nat. Rev. Mol. Cell Biol. (*2022) 23 (50:329-49], transcriptional regulation, [Id., citing Nozaki, T. and Kanai, M. Acc. Che. Res. (2021) 54 (9): 2313-2322], cell metabolism [Id., citing Humphrey, S H et al. Trends Endocrinol. Metab. (2015) 26 (12): 676-87], immunity [Liu, J. et al. Immunity (2016) 45 (1): 15-30; signal transduction [Id., citing Guccione, E. and Richard, S. Nat. Rev. Mol. Cell Biol. (2019) 20 (10): 642-657], and autophagy [[Id., citing Polletta, L. et al. Autophagy (2015) 11 (20:253-270]. For example, phosphorylation is involved in cell signal transduction and the cell cycle [Id., citing Ubersax, J A and Ferrell, JE, Jr. Nat. Rev. Mol. Cell Biol. (2007) 8 (70:530-541]; acetylation and methylation are associated with transcriptional regulation and cell metabolism [Id., citing Choudhary, C. et al. Science (2009) 325 (5942): 834-840; Wu, Q. et al. Nat. Rev. Drug Discov. (2021) 20 (7): 509-530]; glycosylation plays an important role in protein folding and cell adhesion [Id., citing Ohtsubo, K. and Marth, JD. Cell (2006) 126 (5): 855-867]; and ubiquitination regulates protein degradation and localization [Id., citing Meyer-Schwesinger, C. Nat. Rev. Nephrol. (2019) 15 (7): 393-411].

The term “priming” as used herein refers to the first encounter with a given antigen, which generates a primary adaptive immune response. The term “unprimed cells” (also referred to as virgin, naïve, or inexperienced cells) as used herein refers to T cells and B cells that have generated an antigen receptor (TCR for T cells, BCR for B cells) of a particular specificity, but have never encountered the antigen. For example, before helper T cells and B cells can interact to produce specific antibody, the antigen-specific T cell precursors must be primed.

Priming involves several steps: antigen uptake, processing, and cell surface expression bound to class II MHC molecules by an antigen presenting cell, recirculation and antigen-specific trapping of helper T cell precursors in lymphoid tissue, and T cell proliferation and differentiation. [Janeway, C A, Jr., “The priming of helper T cells, Semin. Immunol. (1989) 1(1):13-20]. Helper T cells express CD4, but not all CD4 T cells are helper cells. Id. The signals required for clonal expansion of helper T cells differ from those required by other CD4 T cells. The critical antigen-presenting cell for helper T cell priming appears to be a macrophage; and the critical second signal for helper T cell growth is the macrophage product interleukin 1 (IL-1). Id. If the primed T cells and/or B cells receive a second, co-stimulatory signal, they become activated T cells or B cells.

The term “progression” as used herein refers to the course of disease as it becomes worse or spreads in the body.

The term “progression-free survival” or PFS” as used herein refers to the length of time during and after the treatment of the disease that a patient lives with the disease, but it does not get worse.

The term “proliferate” and its various grammatical forms as used herein is meant to refer to the process that results in an increase of the number of cells, and is defined by the balance between cell division and cell loss through cell death or differentiation.

The term “promoter” as used herein refers to a sequence several kbs upstream of TSSs (transcription start signals) that can autonomously drive transcription. This functionality and the fact that some promoters can activate transcription from a distal core-promoter in reporter assays is in line with promoters consisting of a core-promoter and a proximal or overlapping enhancer.

The term “promoter-proximal tethering elements” as used herein refers to sequences proximal to the core-promoter that enable or facilitate its interaction with enhancers.

The term “promoter-targeting sequences” as used herein refers to sequences proximal to enhancers that enable or facilitate their interactions with core-promoters.

The term “recurrent cancer” or “recurrence” means a cancer that has come back, usually after a period during which the cancer could not be detected. The cancer may come back to the same place as the primary tumor or to another place in the body.

The term “refractory cancer” or “resistant cancer” means a cancer that does not respond to treatment. The cancer may be resistant at the beginning of treatment, or it may become resistant during treatment.

The term “relapse” refers to the return of a disease or the signs and symptoms of a disease after a period of improvement.

The terms “relapse-free survival” (RFS) or “disease-free survival” (DFS) mean the length of time after primary treatment for a cancer ends that the subject or patient survives without any signs or symptoms of that cancer.

The term “repertoire” as used herein refers to the collection of immune cells that respond to a particular foreign substance (e.g., pathogen). The repertoire recognizing a molecule would be the sum of the repertoires responding against all the component epitopes of the molecule. Likewise, the repertoire against an organism or cell would be the sum of all the repertoires against all the molecules from the pathogen or cell.

The term “RNA-seq” as used herein refers to a process of creating short sequencing reads from RNA molecules. The steps consist of first converting the RNA into cDNA; then (optionally) amplifying the cDNA by PCR; and finally fragmenting the cDNA into short pieces/fragments. After the sequencing library is prepared, the fragments are used as input for next-generation sequencing. The resulting sequence reads contained in FASTQ files are then aligned to a known reference sequence. [Deshpande, D., et al. Frontiers Genetics (2023) 14: 997383].

The term "RUNX" as used herein refers to an evolutionary conserved family of transcription factors (TFs) that are best known for their roles in the regulation of the expression of genes involved in embryonic development and cell differentiation. All three Runx genes have two alternative promoters, proximal (P2) and distal (P1), and the transcripts also undergo alternative splicing, giving rise to multiple isoforms and producing diffuse bands on Western blots. The patterns of the isoform expression are cell type-specific, time-dependent and nonredundant. As with other TFs, Runx proteins are subject to post-translational modifications that affect Runx cellular localization, stability, DNA-binding affinity and ability to interact with other proteins—sumoylation [Korinfskaya, S. et al. Front. Immunol. (2021) 12:701924, citing Lee, J W et al. in Advances in Exptl Med & Biol. New York LLC: Springer (2017) pp. 321-332], acetylation, phosphorylation [Id., citing Tanaka, T. et al. Mol. Cell Biol. (1996) 16:3967-3979; Kim, H R et al. J. Cell Biochem. (2008) 105:1048-1058; Goh, Y M et al. J. Biol. Chem. (2010) 285:10122-10129], ribosylation [Id., citing Tay, L S et al. Cell Rep. (2018) 24:1747-1755], methylation [Id., citing Zhao, X. et al. Genes Dev. (2008) 22:640-653; Herglotz, J. et al. Oncogene (2013) 32:2565-2575] and ubiquitination [Id., citing Zhang, M. et al. J. Cell Sci. (2009) 122:1382-9]. For example, methylated RUNX1 has increased transcription activation potency [Id., citing Zhao, X et al. Genes Dev. (2008) 22:640-53], whereas poly (ADP)-ribosylation of RUNX1 and RUNX3 enables interaction with the helicase BLM (Bloom syndrome protein) in response to DNA damage in the context of Fanconi anemia [Id., citing Tay, L S et al. Cell Rep. (2018) 24:1747-1755]. Runx proteins share the ability to dimerize with the transcription factor CBF beta (CBFβ) [Id., citing Wang, S. et al. Mol. Cell Biol. (1993) 13:3324-Heterodimerization of Runx proteins increases their ability to bind DNA and protects them from ubiquitination [Id., citing Tahirov, T H and Bushweller, J. Mol Cell Biol. (1993) 13:3324-39]. Additionally, CBFβ controls the translation of RUNX1 [Id., citing Malik, N. et al. Nat. Commun. (2019) 10:1-15]. CBFβ does not have DNA binding activity itself but is instead recruited to DNA by all members of the Runx family through physical interactions [Id., citing Huang, G. et al. EMBO J. (2001) 20:723-733]. Among the TFs that cooperate and/or compete with the Runx proteins upon DNA binding are members of the ETS family, which positively and/or negatively regulates the expression of genes involved in signaling pathways, development, cell proliferation, differentiation, migration, apoptosis, invasion and metastasis [Id., citing Mao, S. et al. Mol. Cell Biol. (1999) 19:3635-3644; Kar, A. and Gutierrez-Hartman, Crit. Rev. Biochem. Mol. Biol. (2013) 48 (6): 522-43], Kruppel-like factor 4 [KLF4], an evolutionarily conserved zinc finger-containing transcription factor that regulates diverse cellular processes such as cell growth, proliferation, and differentiation [Id., citing Liu, S. et al. Haematologica (2019) 104:1597-1607; Ghaleb, A M and Yang, V W. Gene (2017) 611:27-37], nuclear factor of activated T cell [NFAT; Id., citing Gabriel, C H et al. J. Biol. Chem. (2016) 291:24172-24187], activator protein-1 [AP-1; Id., citing D'Alonzo, R C et al. J. Biol. Chem (2002) 277:816-822; Hess, J. et al. J. Biol. Chem. (2001) 276: 20029-200238], STAT5 [Ogawa, S. et al. Biochem. (2008) 143:695-709] and many others. Runx proteins can repress or activate genes through direct and/or indirect interactions with chromatin modifiers Id., citing Taniuchi, I. and Littman, DR. Oncogene (2004) 23:4341-4345].

The term "scFv" as used herein refers to a class of engineered functional antibodies generated by the fusion of the variable heavy (VH) and variable light (VH) domains of an immunoglobulin through a short polypeptide linker.

The term "sign" as used herein refers to a healthcare provider's evidence of disease.

The term "Signal transducer and activator of transcription 3" or "STAT3" as used herein refers to a transcription factor that is activated downstream of a large range of cell surface receptors. It forms part of a family of proteins that also includes STAT1, 2, 4, 5A, 5B, and 6, which are activated in a similar manner downstream of surface receptors. Binding of their ligand by these receptors leads to the activation of receptor-associated Janus activating kinases (JAKs). The activated JAKs then phosphorylate the receptor providing docking sites for STATs, which in turn become tyrosine phosphorylated. This leads to the formation of homodimers or heterodimers, followed by translocation to the nucleus where the dimers bind to DNA and induce transcription of a broad range of target genes [Deenick, E K., et al. Front. Immunol. (2018) 9: doi.org/10.3389/fimmu.2018.00168, O'Shea, J J., et al. N. Engl. J. Med. (2013) 368 (20): 161-170; Shuai, K. and Liu, B. Nat. Rev. Immunol. (2003) 3 (11): 900-911]. Many of the cytokine receptors that lead to STAT3 activation are expressed by lymphocytes including those for IL-6, IL-10, IL-21, IL-23, and IFNs. STAT3 plays a central role in regulation of immune responses. Loss of function (LOF) mutations in STAT3 cause the primary immunodeficiency autosomal dominant hyper IgE syndrome (ADHIES), which is characterized by defects in both T and B cells [Id., citing Holland, S M., et al. N. Engl. J. Med. (2007) 357 (16): 1608-1619; Minegishi, Y., et al. Nature (2007) 448 (7157): 1058-1062]. Gain of function (GOF) mutations in STAT3 have been identified in patients who presented with early onset autoimmunity as well as immunodeficiency [Id., citing Flanagan, S E., et al. Nat. Genet. (2014) 46 (8): 812-814; Haapaniemi, E M et al. Blood (2015) 125 (4): 639-648; Milner, J D., et al. Blood (2015) 125 (40): 59159-9].

The term "solid tumor" as used herein refers to an abnormal mass of tissue that usually does not contain cysts or liquid areas. Solid tumors may be benign (a growth that does not invade nearby tissue or spread to other parts of the body) or malignant (meaning to grow in an uncontrolled way; malignant tumors can invade nearby tissues and spread to other parts of the body through the blood and lymph system). Different types of solid tumors are named for the type of cells that form them. Types of solid tumors are sarcomas, carcinomas, and lymphomas; leukemias (cancers of the blood) generally do not form solid tumors.

A carcinoma is a cancer that begins in the skin or in tissues that line or cover internal organs. An adenocarcinoma is a cancer that forms in the glandular tissue that lines certain internal organs and makes and releases substances in the body, such as mucus, digestive juices, and other fluids. Most cancers of the breast, lung, esophagus, stomach, colon, rectum, pancreas, prostate, and uterus are adenocarcinomas.

A lymphoma is a malignant solid neoplasm of the lymphoid system, which produces immune cells. Abnormal lymphocytes become lymphoma cells, which multiply and collect in the lymph nodes. Over time, these cancerous cells impair the immune system. There are two categories of lymphomas: Hodgkin lymphoma and non-Hodgkin lymphoma. About 12 percent of people with lymphoma have Hodgkin lymphoma. Most non-Hodgkin lymphomas are B-cell lymphomas, and either grow quickly (high-grade) or slowly (low-grade). There are over a dozen types of B-cell non-Hodgkin lymphomas. The rest are T-cell lymphomas.

Hodgkin's lymphoma is a lymphoma in which the tumor mass is made up of a reactive infiltrate of nontransformed lymphocytes, macrophages and fibroblasts plus scattered, malignant Reed-Sternberg cells. Reed-Sternberg cells are large, abnormal lymphocytes that may contain more than one nucleus, are clonal in their growth and are the tumor cells of the malignant mass. While of the B-cell lineage, they lack common B-cell specific surface markers such as CD19 and CD79a as well as Ig gene transcripts [Hertel, C B et al. Oncogene (2002) 21:4908-4920]. Hodgkin lymphoma most commonly affects lymph nodes in the neck or in the area between the lungs and behind the breastbone. It can also begin in groups of lymph nodes under an arm, in the groin, or in the abdomen or pelvis. If it spreads, it may spread to the lung, spleen liver, bone marrow or bone.

There are two major categories of Hodgkin lymphoma: classical Hodgkin lymphoma, which is divided into 4 subtypes based on the appearance of lymph node structure and cells, and nodular lymphocyte-predominant Hodgkin lymphoma.

Classical Hodgkin lymphoma (cHL) represents about 95% of cases of Hodgkin lymphoma. It is diagnosed when characteristic abnormal lymphocytes, (Reed-Sternberg cells) are found. There are 4 subtypes of cHL. Nodular sclerosis Hodgkin lymphoma, the most common subtype of cHL, affects up to 80% of people diagnosed with cHL. It is most common in young adults, especially women. In addition to Reed-Sternberg cells, there are bands of connective tissue (called fibrosis) found in the lymph node. This type of lymphoma often affects the lymph nodes in the mediastinum.

Non-Hodgkin's lymphoma (NHL) is a heterogeneous group of lymphomas in which the solid tumor mass consists almost entirely of malignant lymphocytes. [Mak, T W et al. Ch. 20 Hematopoietic cancers, in Primer to the Immune response (2014) Elsevier, Inc., pp. 573-574] NHL may be described by how quickly the cancer is growing. An "indolent or low-grade lymphoma' is a type of lymphoma that tends to grow and spread slowly and has few symptoms. When indolent lymphoma is in stages 1 and 2, it is called localized disease. An "aggressive lymphoma" "high-grade lymphoma" or intermediate-grade lymphoma" is a type of lymphoma that grows and spreads quickly and has severe symptoms. In children, aggressive non-Hodgkin lymphoma is more common. Some types of lymphoma cannot be easily classified as indolent or aggressive.

There are more than 60 NHL subtypes of NHL that tend to mimic stages of normal B cell differentiation. [Mancuso, S. et al. Immunity & Aging (2018) 15:22]. Diffuse large B-cell lymphoma (DLBCL) is the most common form of lymphoma representing about 30% of NHL in the US. It is an aggressive form of NHL that involves organs other than the lymph nodes about 40% of the time. DLBCL includes germinal center and non-germinal center DLBCL. Follicular lymphoma (FL) is the second most common form of lymphoma in the United States and Europe, representing about 20% of people with NHL. It usually begins in the lymph nodes, is most often indolent, and grows very slowly. Mantle cell lymphoma represents about 5-7% of individuals with NHL. It is an aggressive (fast-growing) type of B-cell non-Hodgkin lymphoma that usually occurs in middle-aged or older adults is marked by small- to medium-size cancer cells that may be in the lymph nodes, spleen, bone marrow, blood, and gastrointestinal system.

Small lymphocytic lymphoma, which represents about 5% of individuals with NHL, is the same disease as B-cell chronic lymphocytic leukemia (CLL), without a significant amount of disease in the blood. It is considered an indolent lymphoma.

Burkitt lymphoma/Burkitt cell leukemia is a very rare and aggressive form of lymphoma that occurs most often in children and young adults. The disease may affect the jaw, central nervous system, bowel, kidneys, ovaries, or other organs. There are three forms: endemic (which occurs commonly in Africa, appears most often in the jawbones of children, and is usually associated with infection with EBV); sporadic (which occurs throughout the world), and immunodeficiency-related (which is most often seen in AIDS patients). This subtype often has abnormalities involving the MYC gene, which can contribute to cancer growth.

T cell lymphomas make up approximately 10% 1-15% of lymphoid malignancies. [Armitage, J. O. Am. J. Hematol. (2017) 92 (7): 706-715]. The frequency of these lymphomas varies geographically, with the highest incidence in parts of Asia. T-cell lymphomas can be divided into those of precursor T-cells (i.e., precursor T-lymphoblastic lymphoma) and those arising in more mature T-cells, with the latter termed peripheral T-cell lymphomas (PTCLs). The aggressive PTCLs are associated with a short survival. These can be subdivided into those of primarily nodal origin and those that typically present in specific extranodal sites and are often associated with characteristic clinical syndromes. [Armitage, J. O. Am. J. Hematol. (2017) 92 (7): 706-715]

Adult T-cell lymphoma/leukemia (human T cell lymphotropic virus type I positive) is caused by the human T-cell lymphotropic virus type 1. It is an aggressive disease that often involves the bone and skin. Lymphoma cells are often found in the blood.

A sarcoma is a type of cancer that begins in bone or in the soft tissues of the body, including cartilage, fat, muscle, blood vessels, fibrous tissue, or other connective or supportive tissue. Bone and soft tissue sarcomas are the main types of sarcoma. Soft tissue sarcomas can develop in soft tissues like fat, muscle, nerves, fibrous tissues, blood vessels, or deep skin tissues. They can be found in any part of the body. Most of them start in the arms or legs. They can also be found in the trunk, head and neck area, internal organs, and the retroperitoneum. The different types of sarcoma are based on where the cancer forms. For example, osteosarcoma forms in bone, liposarcoma forms in fat, and rhabdomyosarcoma forms in muscle.

The term "splice-site variant" or "splice-site mutation" as used herein refers to a genetic alteration in the DNA sequence that occurs at the boundary of an exon and an intron (splice site). This change can disrupt RNA splicing resulting in the loss of exons or the inclusion of introns and an altered protein-coding sequence.

As used herein, the term "stimulate" in any of its grammatical forms as used herein is meant to refer to inducing activation or increasing activity.

The term "stimulate an immune cell" or "stimulating an immune cell" as used herein is meant to refer to a process (e.g., involving a signaling event or stimulus) causing or resulting in a cellular response, such as activation and/or expansion, of an immune cell, e.g. a CD8+ T cell.

The terms "subject" or "individual" or "patient" are used interchangeably to refer to a member of an animal species of mammalian origin, including but not limited to, mouse, rat, cat, goat, sheep, horse, hamster, ferret, pig, dog, guinea pig, rabbit and a primate, such as, for example, a monkey, ape, or human.

The phrase "subject in need thereof" as used herein refers to an eligible patient that (i) will be administered an immunotherapy according to the present disclosure, (ii) is receiving at least one immunotherapy according to the present disclosure; or (iii) has received at least one immunotherapy according to the present disclosure, unless the context and usage of the phrase indicates otherwise.

The term "symptom" as used herein refers to a patient's subjective evidence of disease.

The terms "T cell" or "T lymphocyte" are used interchangeably to refer to cells that mediate a wide range of immunologic functions, including the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on their expression of specific cell surface molecules and the secretion of cytokines. T cells recognize antigens on the surface of antigen presenting cells (APCs) and mediate their functions by interacting with, and altering, the behavior of these APCs. T cells can also be classified based on their function as helper T cells; T cells involved in inducing cellular immunity; suppressor T cells; and cytotoxic T cells. T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adaptor proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. The ultimate amplitude and quality of the T cell immune response, which is initiated through antigen recognition by the TCR, is regulated by a balance between co-stimulatory and inhibitory signals (immune checkpoints).

Although the lineage relationship between T cell subsets remains controversial, T cells cluster in populations that can be arranged as a progressive continuum based on phenotypic, functional and transcriptional attributes. T lymphocytes transition through progressive stages of differentiation that are characterized by a stepwise loss of functional and therapeutic potential in an order from naive T ($T_N$) cells to T memory stem cells ($T_{SCM}$) (the most immature antigen-experienced T cells), to T central memory ($T_{CM}$) Cells, which Patrol Central Lymphoid Organs, to T effector memory ($T_{EM}$) cells, which patrol peripheral tissues. In contrast to $T_N$ cells, memory T cells are capable of rapidly releasing cytokines on restimulation. $T_{CM}$ cells more efficiently secrete IL-2 and $T_{EM}$ have an increased capacity for IFNγ release and cytotoxicity. All antigen-experienced T cells upregulate the common IL-2 and IL-15β receptor (IL-2Rβ) conferring the ability to undergo homeostatic proliferation in response to IL-15, and also display high amounts of CD95 (also known as FAS), a receptor that provides cither costimulatory or pro-apoptotic signals depending on the efficiency of CD95 signaling complex formation and on which particular intracellular signaling proteins are part of the complex. [Gattinoni, L. et al. Nature Revs. Cancer 12:671-684].

The term "T cell antigen" as used herein is meant to refer to a protein, lipid (for CD1) or fragment thereof which can be processed into a peptide that can bind to either Class I MHC, Class II MHC, non-classical MHC, or CDI family molecules (collectively antigen presenting molecules), and, in this combination, can engage a T cell receptor on a T cell.

The term "T cell epitope" as used herein is meant to refer to a short peptide molecule that binds to a class I or II MHC molecule and that is subsequently recognized by a T cell. T cell epitopes that bind to class I MHC molecules are typically 8-14 amino acids in length, and most typically 9 amino acids in length. T cell epitopes that bind to class II MHC molecules are typically 12-20 amino acids in length. In the case of epitopes that bind to class II MHC molecules, the same T cell epitope may share a common core segment, but differ in the length of the carboxy- and amino-terminal flanking sequences due to the fact that ends of the peptide molecule are not buried in the structure of the class II MHC molecule peptide-binding cleft as they are in the class I MHC molecule peptide-binding cleft.

The term "T cell factor 1" or (TCF-1), encoded by Tcf7, as used herein refers to the key transcription factor of the canonical Wnt signaling pathway. TCF1 and its homolog LEFI are known as effector transcription factors downstream of the WNT signaling pathway and are essential for early T cell development. TCF1 is required for the self-renewal of stem-like CD8+ T cells generated in response to viral or tumor antigens, and for preserving heightened responses to checkpoint blockade immunotherapy. In the helper T cell lineages, TCF1 is indispensable for the differentiation of T follicular helper and T follicular regulatory cells and crucially regulates immunosuppressive functions of regulatory T cells. Mechanistic investigations have also identified TCF1 as the first transcription factor that directly modifies histone acetylation, with the capacity to bridge transcriptional and epigenetic regulation. [Shan, Q. et al. Nature Communic. (2021) 12:5863, citing Zhao, X. et al. Nat. Rev. Immunol. (2022) 22:147-157].

The term "T cell receptor" (TCR) as used herein refers to a complex of integral membrane proteins that participates in the activation of T cells in response to an antigen. The TCR expressed by the majority of T cells consisting of a heterodimer of α and β chains. A small group of T cells express receptors made of γ and δ chains. Among the α/β T cells are two sublineages: those that express the coreceptor molecule CD4 (CD4+ cells), and those that express CD8 (CD8+ cells). These cells differ in how they recognize antigen and in their effector and regulatory functions. The TCR is composed of four distinct signal transducing subunits (CD3-gamma (γ), -delta (δ), -epsilon-(ε), and zeta (ζ)) that share a common functional sequence, the immunoreceptor tyrosine-based activation motif (ITAM) [Shores, E W et al. J. Exp. Med. (1997) 185 (5): 893-900, citing Robey, E. and Fowlkes, BJ. Annu. Rev. Immunol. (1994) 12:675-705] within their intracytoplasmic domains [Id., citing Reth, M. Nature (Lond) (1989): 338: 383-384; Samelson, L E and Klausner, R D. J Biol. Chem. (1992) 267:24913-24916]. After TCR engagement, phosphorylation of ITAMs leads to the recruitment of SH2 domain-containing proteins (e.g., tyrosine kinases) to the TCR complex and initiation of the T cell activation cascade [Id., citing Samelson, L E and Klausner, R D. J Biol. Chem. (1992) 267:24913-24916; Weiss, A., and Littman, D R. Cell (1994) 76:263-274; Irving, B A and Weiss, A. Cell (1991) 64:891-901; Romeo, C. et al. Cell (1992) 68:889-897]. The CD3 subunits each contain a single ITAM, whereas & contains three ITAMs within its longer cytoplasmic tail. ITAM sequences are conserved but nonidentical. Irving et al constructed a chimeric protein linking the extracellular and transmembrane domains of CD8 to the cytoplasmic domain of the zeta chain and demonstrated that the CD8/zeta chimera was expressed independently of the TCR and was capable of transducing signals that, by criteria of early and late activation, were indistinguishable from those generated by the intact TCR. [Irving, B A and Weiss, A. Cell (1991) 64:891-901]. Their data showed that CD8/zeta can activate the appropriate signal transduction pathways in the absence of CD3 gamma, delta, and epsilon, and suggested that the role of CD3 zeta is to couple the TCR to intracellular signal transduction mechanisms.

The term "helper T cells" or "$T_H$" cells as used herein refers to effector CD4 T cells that stimulate or "help" B cells to make antibody in response to antigenic challenge. $T_H2$, $T_H1$ and the $T_{FH}$ subsets of effector CD4 T cells can perform this function.

The term "T follicular helper ($T_{FH}$) cells" as used herein refers to a distinct subset of CD4+ T lymphocytes, specialized in B cell help and in regulation of antibody responses. They develop within secondary lymphoid organs (SLO) and can be identified based on their unique surface phenotype, cytokine secretion profile, and signature transcription factor. They support B cells to produce high-affinity antibodies toward antigens to develop a robust humoral immune response and are crucial for the generation of B cell memory. They are essential for infectious disease control and optimal antibody responses after vaccination. Stringent control of their production and function is critically important, both for the induction of an optimal humoral response against thymus-dependent antigens but also for the prevention of self-reactivity. [Gensous, N. et al. Front. Immunol. (2018) doi.org/10.3389/fimmu.2018.01637).

The term "$T_H1$ cells" as used herein refers to a lineage of CD4+ effector T cells that promotes cell-mediated immune responses and is required for host defense against intracellular viral and bacterial pathogens. They are mainly involved in activating macrophages but can also help stimulate B cells to produce antibody. $T_H1$ cells secrete IFN-gamma, IL-2, IL-10, and TNF-alpha/beta. IL-12 and IFN-γ make naive CD4+ T cells highly express T-bet and STAT4 and differentiate to $T_H1$ cells. [Zhang, Y. et al. Adv. Exp. Med. Bio. (2014) 841:15-44].

The term "$T_H2$ cells" as used herein refers to a lineage of CD4+ effector T cells that secrete IL-4, IL-5, IL-9, IL-13, and IL-17E/IL-25. These cells are required for humoral or antibody-mediated immunity and play an important role in coordinating the immune response to large extracellular pathogens. IL-4 makes naive CD4+ T cells highly express STAT6 and GATA3 and differentiate to TH2 cells. (Zhang, Y. et al. Adv. Exp. Med. Bio. (2014) 841:15-44).

The term "$T_H17$ cells" as used herein refers to a CD4+ T-cell subset characterized by production of interleukin-17 (IL-17). IL-17 is a highly inflammatory cytokine with robust effects on stromal cells in many tissues, resulting in production of inflammatory cytokines and recruitment of leukocytes, especially neutrophils, thus creating a link between innate and adaptive immunity. [Tesmer, L A, et al., Immunol. Rev. (2008) 223:87-113]. The key transcription factor in TH17 cell development is RORγt.

The term "TATA box" as used herein refers to an A/T rich sequence located about 25-30 nucleotides upstream of the transcription start site in the promoter region of many eukaryotic genes involved in binding RNA polymerase via a TATA binding protein.

The term "T-bet" as used herein refers to a $T_H1$ cell transcription factor. Differential expression of the $T_H1$ cell transcription factor T bet and a closely related T-box family transcription factor, factor particularly in CD8+ T cells, Eomesodermin (Eomes) facilitates the cooperative maintenance of the pool of antiviral CD8+ T cells during chronic viral infection. [Paley, M A et al., Science (2012) 338:1220-1225]. During chronic infections, T-bet is reduced in virus-specific CD8+ T cells; this reduction correlates with T cell dysfunction. In contrast, Eomes mRNA expression is up-regulated in exhausted CD8+ T cells during chronic infection. [Id.]

The term "Tpex" as used herein refers to progenitors or precursors of exhausted T cells. [Utzschneider, D T et al. Nature Immunol. (2020) 21:1256-1266].

The term "Treg" or "regulatory T cells" as used herein refers to effector CD4 T cells that inhibit T cell responses and are involved in controlling immune reactions and preventing autoimmunity. The natural regulatory T cell lineage that is produced in the thymus is one subset. The induced regulatory T cells that differentiate from naïve CD4 T cells in the periphery in certain cytokine environments is another subset. Tregs are most commonly identified as CD3+CD4+CD25+FoxP3+ cells in both mice and humans. Additional cell surface markers include CD39, 5' Nucleotidase/CD73, CTLA-4, GITR, LAG-3, LRRC32, and Neuropilin-1. Tregs can also be identified based on the secretion of immunosuppressive cytokines including TGF-beta, IL-10, and IL-35. Cell surface molecules CTLA-4, LAG-3, and neuropilin-1 (Nrp1) impair dendritic cell (DC)-mediated conventional T cell activation: CTLA-4 and LAG-3 outcompete CD28 and T cell receptor expressed on conventional T cells for binding to CD80/86 and MHC class II on DCs, and Nrp1 stabilizes DC—Treg contact, thereby preventing antigen presentation to conventional T cells [Ikebuchi, R. et al. Front. Immunol. (2019) doi.org/10.3389/fimmu.2019.01098].

The term "therapeutic effect" as used herein is meant to refer to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

The term "therapeutic window" as used herein is meant to refer to a concentration range that provides therapeutic efficacy without unacceptable toxicity. In a drug context, following administration of a dose of a therapeutic agent/drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

The treatment of solid tumors by CAR-T cells is complex, multifactorial and has a narrower therapeutic window than does the targeting of CD19 for the treatment of B cell leukemia and non-Hodgkin lymphoma. [Watanabe, et al. Front. Immunol. (2018) 9:2486]. Possible approaches to expand the therapeutic window of CAR-T cell therapy include:

(1) optimizing CAR affinity and sensing (with the caveat that increasing the affinity of CAR-T cells may reduce or prevent serial killing, promote T cell exhaustion, decrease the generation and persistence of $T_{CM}$ and $T_{EFF}$ [Watanabe, citing Caserta, S. et al. J. Immunol. (2010) 185:6545-6554] or increase the loss of T cells through activation-induced cell death [Id., citing Engels, B. et al. Mol. Ther. (2012) 20:652-660]; and/or combinatorial antigen recognition through two different antigens on tumor cells. In one such example, CAR-1 can drive only the activation signal (signal 1 of CD35, and CAR2 can drive only co-stimulation (signal 2) through costimulatory molecules (AND logic gated CAR) or OR logic gated CAR [Id., citing Wilkie, S. et al. J. Clin. Immunol. (2012) 32:105-170; Kloss, C C et al. Nat. Biotechnol. (2013) 31:71-75; Grada, Z. et al. Mol. Ther. Nucleic Acids (2013) 2: e105; Hegde, M. et al. Mol Ther. (2013) 21:2087-2101; Hegde, M. et al. J. Clin. Invest. (2016) 126:3036-3052].

(2) optimizing immunological synapse formation, e.g., CD28 plus 4-1BB based third generation CARs have been found superior to CD28 based second generation CARs as measured by immunosynapse structure, signaling and function [Id., citing Xiong, W. et al. Mol. Ther. (2018) 26:963-975].

(3) combination therapies for overcoming tumor heterogeneity and thereby expanding the therapeutic window using oncolytic viruses [Id., citing Watanabe, K. et al. JCI Insight (2018) 3:99573; Nishio, N. et al. Cancer Res. (2014) 4:5195-5205; Rosewell, Shaw, A. et al. Mol. Ther. (2017) 25:2440-2451; Wing, A. et al. Cancer Immunol. Res. (2018) 6:605-616].

(4) local delivery of CAR-T cells and therapeutic agents into the tumor bed [Id., citing Tchou, J. et al. Cancer Immunol. Res. (2017) 5:1152-1161].

(5) induction of target antigen expression [Id., citing Garnett, C T et al. Cancer Res. (2004) 64:7985-7994; Hiraga, J. et al. Blood (2009) 113:4885-4893]; or (6) other modifications to enhance safety.

The term "TIGIT" as used herein refers to a member of the Ig super family and an immune inhibitory receptor.

The term "TIM-3" as used herein refers to a transmembrane protein and immune checkpoint receptor. It is associated with tumor-mediated immune suppression.

The term "tissue-resident memory T cell" or "$T_{RM}$" as used herein refers to memory lymphocytes that do not migrate after taking up residence in barrier tissues, where they are retained long term. They appear to be specialized for rapid effector function after restimulation with antigen or cytokines at sites of pathogen entry.

The term "tolerance" as used herein refers to a failure to respond to a particular antigen. Tolerance mechanisms that operate in the thymus before the maturation and circulation of T cells are referred to as "central tolerance." Not all antigens of which T cells need to be tolerant are expressed in the thymus, and therefore central tolerance mechanisms alone are insufficient. Additional tolerance mechanisms exist to restrain the numbers and or function of T cells that are reactive to developmental or food antigens, which are not typically expressed. Tolerance acquired by mature circulating T cells in the peripheral tissues is called "peripheral tolerance."

The term "toll-like receptors" or "TLR" as used herein refers to membrane bound pattern recognition receptors (PRRs) that bind to pathogen products.

The terms "Topically Associating Domains" or "TADs" refers to self-associating, loop-like domains that contain interacting cis-regulatory elements and target genes. The term "TAD boundaries" as used herein refers to insulator elements that restrict interactions of cis-regulatory sequences, such as enhancers, to target genes. [McArthur, E. and Capra, JA. Am. J. Hum. Genet. (2021) 108 (2): 269-283].

The terms "TOX" or "thymocytes selection-associated HMG BOX" as used herein refers to a member of a family of transcriptional factors that contain the highly conserved high mobility group box (HMG-box) region. Increasing studies have shown that TOX is involved in maintaining tumors and promoting T cell exhaustion. [Liang, C. et al. Biomark Res. (2021) 9:20].

The term "toxicity" as used herein refers to the degree to which a substance can harm humans or animals. Acute toxicity involves harmful effects in an organism through a single or short-term exposure.

Figure 9:
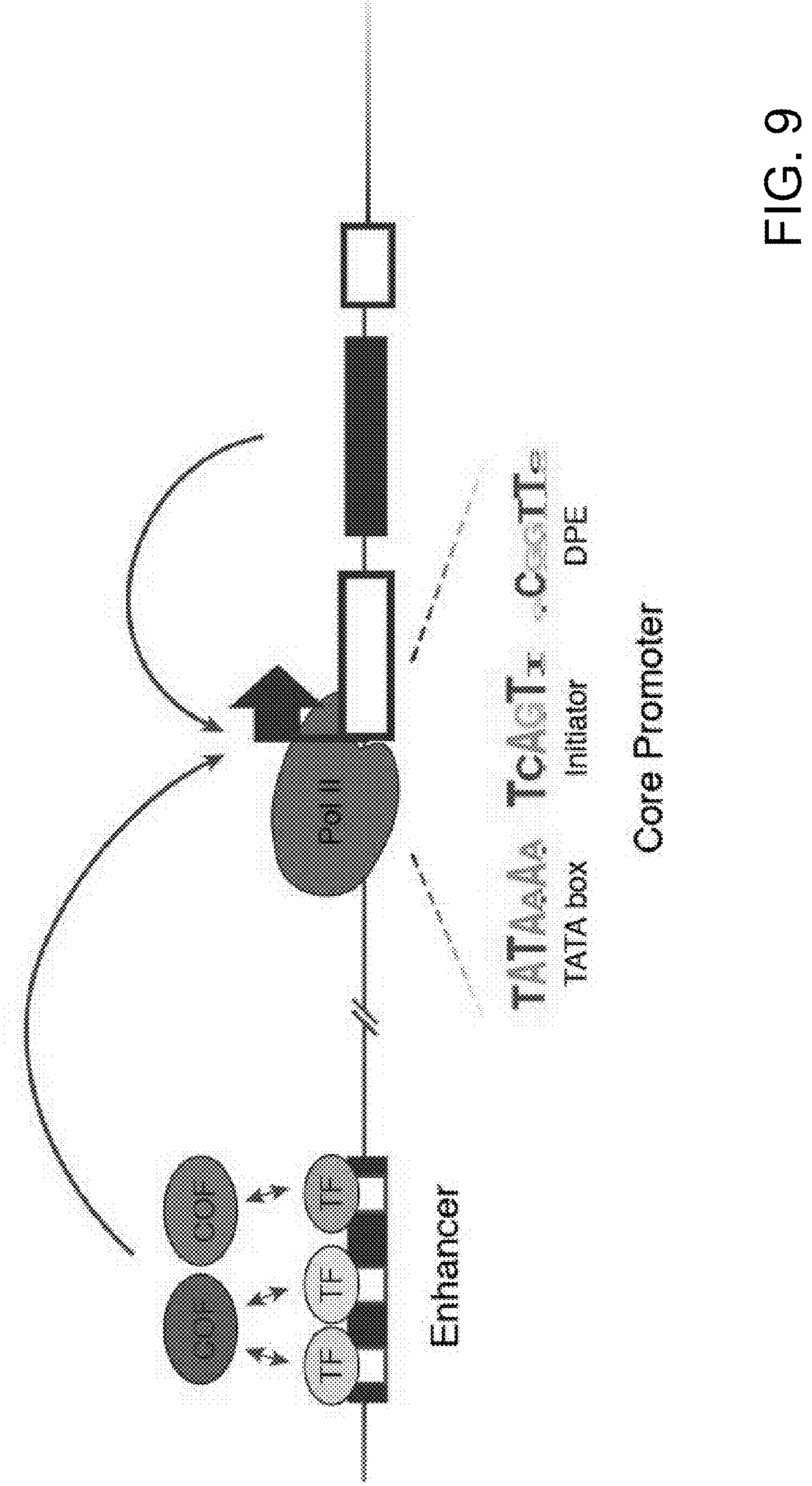
FIG. 9 is a schematic of gene expression regulation by genomic enhancers, which contain binding sites for sequence-specific transcription factors (TFs). The transcription factors recruit cofactors (COFs) that mediate the regulatory communication between the core promoter and the enhancer. Core-promoters typically contain characteristic core-promoter elements or motifs, for example, TATA box, Initiator or Downstream Promoter Element (SPE). Core promoters encompass short sequences of about 100 base pairs surrounding the transcription start site, where Polymerase II (Pol II) assembles and initiates transcription. [Taken from Zabidi, M A and Stark, A. Trends Genet. (2016) 32 (12): 801-14].

The terms "transcription" or "DNA transcription" are used interchangeably herein to refer to copying of one strand of DNA into a complementary RNA sequence by the enzyme RNA polymerase II (Pol II). Transcription initiates within core-promoters, short sequences of around 100 base pairs (bps) surrounding the transcription start sites (TSSs) at the 5' start of genes. Core-promoters recruit Pol II, assemble the Pre-Initiation Complex (PIC) and dictate the accurate position of initiation and direction of transcription [Zabidi, M A and Stark, A. Trends Genet. (2016) 32 (12): 801-814, citing Roeder, RG. Trends in Biochemical Sci. (1996) 21:327-335]. Typically, however, core-promoters on their own cannot support efficient transcription and exhibit only low basal activities. Instead, their cell-type-specific activities are typically determined by enhancers, the second key type of transcriptional regulatory elements [Id., citing Spitz, F. Furlong, E E M. Nat. Rev. Genct. (2012) 13:613-626; Shlyueva, D. et al. Nat. Rev. Genet. (2014) 13:613-626]. Enhancers are genomic DNA elements of up to several hundred bps in length, which contain short transcription factor (TF) recognition sequences or binding sites. Through these sites, combinations of TFs are recruited to enhancers and in turn recruit cofactors with a variety of biochemical functions [FIG. 9, taken from Zabidi, M A and Stark, A. Trends Genet. (2016) 32 (12): 801-814]. Through the combined activating or repressive cues of the different TFs and cofactors, enhancers exert their overall regulatory function to control transcription from target core-promoters irrespective of their orientation and distance [Id., citing Banerji, J. et al. Cell (1981) 27:299-308]. Since enhancers can act over short and long distances, i.e. their positions with respect to their target core-promoters can be arbitrary, they do not always regulate the nearest gene.

The term "transcriptional control" as used herein refers to control of gene expression by controlling when and how often a gene is transcribed.

The term "transcription factor" as used herein refers to a protein required to initiate or regulate transcription in eukaryotes. This includes both gene regulatory proteins as well as the general transcription factors.

The term "transduction" as used herein refers to a process whereby foreign DNA is introduced into another cell via a viral vector.

The term "transfection" as used herein refers to the process of introducing a foreign DNA molecule into a eukaryotic cell by nonviral methods.

The terms "treat" or "treating" include abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder (s) in patients that have previously had the disorder(s); and (e) limiting recurrence of symptoms in patients that were previously asymptomatic for the disorder(s).

The term "trogocytosis" as used herein refers to a cellular process whereby a cell acquires a membrane fragment from another cell in a contact-dependent manner allowing for the transfer of surface proteins with functional integrity. [Mattei, F. et al. Science (2022) 25 (10): 105110; doi.org/10.1016/j.isci.2022.105110].

The term "tumor associated antigen" or "TAA" refers to a protein or other molecule that has elevated levels on tumor cells but that is also expressed at lower levels on healthy cells.

The term "tumor associated macrophages" or "TAMs" as used herein refers to an immunosuppressive macrophage subtype found in the tumor microenvironment that is involved in the progression and metastasis of cancer. TAMs are broadly considered M2-like, which can be further classified into the M2a phenotype (induced by IL-4 or IL-13), M2b phenotype (IL-10 high, IL-12 low) and M2c phenotype (TNF-α low) according to distinct signal stimuli. They produce abundant growth factors, extracellular matrix (ECM) remodeling molecules and cytokines for the regulation of cancer proliferation via noncoding RNAs, exosomes and epigenetics [Yan, S. and Wan, G. The FEBS Journal (2021) 288 (21): 6174-6186, citing Qian, B Z and Pollard, J W. (Cell (2010) 141:39-51]. Activated M2 macrophages distinctively express arginase 1 (ARG1). TAMs can demonstrate direct inhibition on the cytotoxicity of T-lymphocytes through multiple mechanisms and characteristics of tumor evolution, including immune checkpoint engagement via expression, production of inhibitory cytokines [such as IL-10 and transforming growth factor (TGF)-β] and metabolic activities consisting of depletion of 1-arginine (or other metabolites) and the production of reactive oxygen species (ROS). The suppressive immune response renders cancer cells capable of escaping from immune surveillance.

The term "tumor infiltrating lymphocytes" or "TILs" as used herein refers to a heterogeneous lymphocyte population mainly composed of T lymphocytes that may consist of numerous antitumor effector and/or regulatory T cells (Tregs) that have invaded a tumor tissue; TILs are key players in the host's immune response to a tumor. [Wang, J. et al. BMC Cancer (2020) 20:731].

The term "tumor microenvironment" or "TME" as used herein refers to the dynamic and complex ecosystem in which tumor cells exist.

The term "TME macrophages" as used herein refers to macrophages that arise primarily from bone marrow-derived monocytes that are recruited by tumor or stroma-derived chemokines such as colony-stimulating factor 1 (CSF1; also known as M-CSF) and CCL2, to the tumor microenvironment. M1 and M2 phenotypes are differentiated in response to different signal stimuli and are polarized according to the TME, exhibiting strong plasticity, such that macrophages adopt context-dependent phenotypes when stimulated [Yan, S. and Wan, G. The FEBS Journal (2021) 288 (21): 6174-6186, citing Murry, P J and Wynn, TA. Nat. Rev. Immunol. (2011) 11:723-737]. Antitumorigenic MI macrophages express high levels of tumor necrosis factor (TNF), inducible nitric oxide synthase (iNOS; also known as NOS2) and major histocompatibility complex (MHC) class II molecules, whereas pro-tumorigenic M2 macrophages are marked with high levels of arginase 1 (ARG1), interleukin (IL)-10, CD163, CD204 or CD206 expression. The activation of primary macrophages into MI or M2 phenotype is mainly induced by interferon-regulatory factor/signal transducer and activator of transcription (STAT) signaling pathways [Id., citing Waqas, S F H et al. in Nuclear Receptors: Methods and Experimental Protocols, M Z Badr. Ed., Springer, New York, NY, pp. 211-224].

The term "tumor specific antigens" or ("TSA") refers to a protein or other molecule found on cancer cells only.

The terms "tumorigenesis" "oncogenesis" and "carcinogenesis" are used interchangeably to refer to the transformation of normal cells into cells-of-origin (COOs) and the development of cells-of-origin into tumors.

The term "Uniform Manifold Approximation and Projection" or "UMAP" as used herein refers to a dimensionality reduction technique that constructs a high dimensional graph representation of data and then creates a low-dimensional graph to be as structurally similar as possible. This results in the creation of two new parameters UMAP 1 and UMAP 2. UMAP captures local relationships within a cluster as well as global relationships between distinct clusters.

The term "variable (V) domain" as used herein refers to the structural unit of an immunoglobulin or TCR chain that is encoded by the corresponding variable (V) exon.

The term "variable (V) region" as used herein refers to the highly variable N-terminal portion of an Ig or TCR molecule composed of the variable domain that contains the antigen binding site.

The term "wild-type" as used herein refers to the typical form of an organism, strain, gene, protein, nucleic acid, or characteristic as it occurs in nature. "Wild-type" refers to the most common phenotype in the natural population. The terms "wild-type" and "naturally occurring" are used interchangeably.

The term "zeta-chain-associated protein kinase 70" or "ZAP-70" as used herein refers to a non-src family protein kinase that associates with phosphorylated CD3 zeta chain and plays an important role in TCR-CD3 complex signaling. The main substrate of ZAP70 is the transmembrane adaptor LAT.

EMBODIMENTS

According to one aspect, the present disclosure provides a chimeric antigen receptor (CAR) immunotherapy for treating a hematologic cancer comprising (a) genetically modifying a population of immune effector cells comprising T cell receptors (TCRs) to stably express at least one chimeric antigen receptor (CAR), wherein the ectodomain of the CAR specifically binds a cancer antigen;

(b) expanding the population of CAR-containing immune effector cells in the presence of one or more cytokines in vitro to achieve a therapeutic dose, wherein the population of CAR-containing immune effector cells exhibits a nonexhausted memory T cell phenotype;

(c) infusing eligible subjects with the CAR-containing immune effector memory T cell phenotype population of cells as needed until the hematologic cancer in the body is destroyed.

TCRs expressed on the surface of T lymphocytes can only recognize a peptide antigen presented to them through MHCs by antigen-presenting cells (APCs). However, monoclonal antibodies can recognize and bind cell surface-expressed antigens that are not presented by MHCs.

According to some embodiments, the hematologic cancer is a leukemia, a lymphoma or a myeloma.

According to some embodiments, the hematologic cancer is a leukemia. Examples include acute lymphoblastic leukemia (also called acute lymphocytic leukemia and ALL), acute myelogenous leukemia (also called acute myeloblastic leukemia, acute myeloid leukemia, acute nonlymphocytic leukemia, AML, and ANLL), acute myeloid leukemia with myelodysplasia, acute promyelocytic leukemia (also called APL), chronic eosinophilic leukemia; chronic granulocytic leukemia (also called chronic myelogenous leukemia, chronic myeloid leukemia, and CML), erythroleukemia; mast cell leukemia; and hairy cell leukemia.

According to some embodiments, the hematologic cancer is a lymphoma. Examples include Hodgkin's lymphoma, non-Hodgkin's lymphoma, cutaneous B cell lymphoma; cutaneous T cell lymphoma and Waldenstrom macroglobulinemia. According to some embodiments, the hematologic cancer is a leukemia/lymphoma.

According to some embodiments, the hematologic cancer is a myeloma. According to some embodiments, the hematologic cancer is a monoclonal gammopathy of undetermined significance, a smoldering multiple myeloma, or a multiple myeloma (MM). The progression of MM, a B cell malignancy, begins with the precursor pathogenic state of monoclonal gammopathy of undetermined significance ("MGUS"). In the absence of clinical symptoms, MGUS is diagnosed by quantifying the amount of immunoglobulin (Ig) present in both the bloodstream and bone marrow (BM), specifically with a plasma cell population of <10% in the BM. The Ig protein produced by the malignant plasma cell is called a paraprotein, IgM paraprotein, para-IgM or M protein. Evidence indicates that MGUS, previously characterized by myeloma cell growth without bone destruction or other organ involvement, is in fact associated with alterations in the bone. Epidemiologic evidence has shown that patients with MGUS suffer from a significantly increased fracture risk, and that the prevalence of MGUS is increased in patients with osteoporosis. [Fairfield, H. et al., Ann. NY Acad. Sci. (2016) 1364 (1): 32-51, citing Drake, M T. J. Bone Miner. Res. (2014) 29:2529-33] It has been demonstrated that the onset of MGUS is concurrent with the deterioration of both auxiliary and appendicular microarchitecture leading to skeletal fragility [Id., citing Drake, M T. J. Bone Miner. Res. (2014) 29:2529-33]. The disease state transitions into either smoldering MM (SMM) or MM (if clinically manifested), with a plasma cell content exceeding 10%, [Fairfield, H. et al., Ann. NY Acad. Sci. (2016) 1364 (1): 32-51, citing Berenson, J R et al. Br. J. Haematol. (2010) 150:28-38].

Smoldering multiple myeloma (SMM) is an intermediate clinical stage between MGUS and MM. It is classified as having high serum or urinary monoclonal protein as well as clonal BM plasma cells in the range of 10-60%, in the absence of additional myeloma-defining events [Id., citing Glavey, S V & Ghobrial, I M. Expert Rev. Hematol. (2015) 8:273-5] such as hypercalcemia, renal insufficiency, anemia, or bone lesions. [Id., citing Rajkumar, S V et al. Lancet Oncol. (2014) 15: e538-3548]. MGUS progresses to MM at a rate of 1-2% of patients per year; this transition is likely influenced by the presence of mutational diversity or clonality of MM cell populations as well as changes in the local BM and other systemic factors [Id., citing Jemal, A. et al. C A Cancer J. Clin. (2009) 59:1-25; Pawlyn, C. et al. Blood (2015) 125 (5): 831-840; Barlogic, B. et al. Blood (2004) 103:20-32; Rollig, C. et al. Lancet (2014) 385]. MM cells are thought to initially create a plasmacytoma, a single tumor, and then develop into multiple lesions to form the disease of multiple myeloma. [Id., citing Lorsbach, R B et al. Am. J. Clin. Pathol. (2011) 136:168-182].

MM results in osteolytic lesions and fractures. In the disease state, bone healing is limited due to increased osteoclastic and decreased osteoblastic activity, as well as an MM-induced forward-feedback cycle where bone-embedded growth factors further enhance tumor progression as bone is resorbed. [Fairfield, H. et al., Ann. NY Acad. Sci. (2016) 1364 (1): 32-51]. MM is characterized by dissemination of multiple tumor cells throughout the bone marrow (BM). A hallmark of MM is heterogeneous chromosomal aberrations and numerous mutations in a range of genes, both of which make the disease very difficult to target therapeutically. [Id., citing Morgan, G J et al. Nat. Rev. Cancer (2012) 12:335-348].

According to some embodiments, the CAR comprises an extracellular antigen recognition domain, a spacer/hinge region and transmembrane domain, and an intracellular signal transduction domain. According to some embodiments, for each antigen, the extracellular antigen recognition domain comprises a single-chain variable fragment (scFv) derived from a monoclonal antibody specific for that antigen. According to some embodiments, each CAR is specific for a tumor associated antigen or a tumor specific antigen. According to some embodiments, the tumor specific antigen is a tumor neoantigen.

According to some embodiments, the intracellular signal transduction domain of the CAR comprises 4-1BB. According to some embodiments, the intracellular signal transduction domain comprises a CD3ζ T cell activation chain. According to some embodiments, the intracellular signal transduction domain of the CAR comprises 4-1BB and a CD3ζ T cell activation chain. According to some embodiments, the intracellular signal transduction domain comprises an engineered TLE3. According to some embodiments, the engineered TLE3 is ectopically expressed. According to some embodiments, the CD35 T cell activation domain comprises a bicistronically linked green fluorescent protein (GFP) as an expression marker.

According to some embodiments, the TLE3 molecule is a wild type TLE3 comprising, in order, an N-terminal Q domain, a GP domain, a CcN domain, an SP domain and a C terminal WDR domain. According to some embodiments, an engineered TLE3 molecule is a truncated TLE3 protein. According to some embodiments, the engineered TLE3 molecule is a C-terminus truncated TLE3 (TLE3ΔWDR) protein.

According to some embodiments, the target antigen is CD19. According to some embodiments, the target antigen is CD20. According to some embodiments, the target antigen is CD22. According to some embodiments, the target antigen is NKG2D-1. According to some embodiments, the target antigen is CD33. According to some embodiments, the target antigen is BCMA. According to some embodiments, the target antigen is CD123. According to some embodiments, the target antigen is a cancer neoantigen. According to some embodiments, the target antigen comprises a splice-site mutation. According to some embodiments, the target antigen comprises a gene fusion mutation.

Approved commercial CD19-CAR-T cell products include Kymriah® for treating relapsed and refractory ALL and diffuse large B cell lymphoma (DLBCL), a form of non-Hodgkin lymphoma; Yescarta® (axicabtagene ciloleucel), for treating certain types of large B-cell lymphoma and follicular lymphoma in adults; and Tecartus® (Brexucabtagene autoleucel) for treating adults with mantle cell lymphoma or acute lymphoblastic leukemia.

According to some embodiments, populations of CAR-containing immune effector cells that target different tumor antigens can be mixed. According to some embodiments, the CAR containing population of immune effector cells recognizes two or more tumor associated antigens simultaneously, for example, CD19 and CD20, CD19 and CD22, CD19 and NKG2D-1; CD19 and CD33, CD19 and BCMA, CD19 and CD123; CD20 and CD22; CD20 and NKG2D-1; CD20 and CD33; CD20 and BCMA, CD20 and CD123; CD22 and CD33; CD22 and BCMA; CD22 and NKG2D-1; CD22 and CD123; etc. According to some embodiments, the anti-cancer specificity of the CAR-containing immune effector cell population is enhanced by activating the cells in response to cancer antigens while inhibiting the cells in response to HLA-DR. [Fei, F. et al. Molecular Therapy (2022) 30 (3): 1215-1226].

An optimal CAR will specifically bind an antigen expressed exclusively in tumor cells to form an effective immunological synapse leading to downstream T-cell signaling and a potent and specific anti-tumor effect.

According to some embodiments, the immune effector cell population engineered to express the CAR comprising a TLE3 construct by lentiviral transduction is a CD3+ T cell population. According to some embodiments, the T cell population comprises CD4+ T cells, CD8+ T cells, or both.

According to some embodiments, the immune effector cell engineered to express the CAR comprising a TLE3 construct by lentiviral transduction adapted from the CAR-T design is an NK cell.

NK cells are innate effector lymphocytes that also can exhibit features of memory-like or adaptive response [Valeri, A. et al. Front. Immunol. (2022) 13:953849, citing [Foley, B. et al. Blood (2012) 119 (11) 2665-2674; Romee, R. et al. Sci. Transl. Med. (2016) 8 (357): 357ra123; Sun J C et al. Nature (92009) 457 (7229): 557-561]. NK cells identify and rapidly discriminate and kill virally infected, stressed, or senescent cells and control several types of tumor cells and metastases [Id., citing Pereira, B I et al. Nat. Commun. (2019) 10 (10): 2387; Lopez-Soto, A. et al. Cancer Cell (2017) 32 (2): 135-154; Shimasaki, N. et al. Nat. Rev. Drug Discovery (2020) 19 (3): 200-18]. Traditionally, human NK cells have been subclassified into immature immunomodulatory NK cells ($CD56^{bright}CD16^{-/dim}$) and the mature NK cell ($CD56^{dim}CD16^{bright}$) subset, which mediates the cytolytic function [Id., citing Freud, A G et al. Immunity (2017) 47 5): 820-33; Melsen, J E, et al. Front. Immunol. (2016) 7:262].

NK cells have a short lifespan in vivo and release a different spectrum of cytokines and growth factors (e.g, TNF-α, IFN-γ, GM-CSF, and IL-3) during NK cell killing than do T cells. [Id., citing Zhang, Y. et al. Immunology (2007) 121 (2): 258-265; Kilingemann, H. Oncoimmunology (2014) 3: e28147]. In contrast to T cells, adoptive NK or CAR-NK therapy does not cause serious adverse events, such as on-target off-tumor toxicities, cytokine release syndrome (CRS), or immune effector cell-associated neurotoxicity syndrome (ICANS), which may increase hospitalization length and raise therapy cost [Id., citing Olson, J A et al. Blood (2010) 115 (21): 4293-4301; Shah, N. et al. Br. J. Haematol. (2017) 177 (3): 457-466; Liu, E. et al. N. Engl. J. Med. (2020) 382 (6): 545-553].

CAR-NK cells have potential advantages. For example, allogeneic NK products surpass the expensive and lengthy procedure of autologous CAR-T manufacturing [Id., citing Tyagarajan, S. et al. Mol. Ther. Methods Clin. Dev. (2020) 16:136-144]. Allogenic NK and CAR-NK cells constitute an "off-the-shelf" product for immunotherapy that can be applied to different patients and generated from multiple sources [Id., citing Olson, J A, et al. Blood (2010) 115 (21) 4293-4301; Shah, N. et al. Br. J. Haematol. (2017) 177 (3): 457-466; Liu, E. et al. N. Engl. J. Med. (2020) 382 (6): 545-453; Ruggeri, L. et al. Science (2002) 295 (5562): 2097-2100]. This potential arises due to their minimal risk to cause graft-versus-host disease (GvHD). Furthermore, NK cells are functionally similar to CD8+ T cells but do not require prior sensitization and lack TCR expression, thereby their responses are not human leukocyte antigen (HLA)-restricted. Instead, NK cell function depends on the balance between activating and inhibitory signaling generated by several germline-encoded receptors [Id., citing Sivori, S. et al. Cell Mol. Immunol. (2019) 16 (5): 430-441; Xie, G. et al. EBioMedicine (2020) 59:102975]. NK cells retain CAR-independent killing capacity through these innate receptors even in a tumor escape scenario characterized by CAR antigen loss or down-regulation. NK cells could eliminate tumor cells through CD16-mediated antibody-dependent cell-mediated cytotoxicity (ADCC), direct target killing by cytolytic granules, (e.g. perforin and granzymes), or via engagement of death receptors (e.g. FASL or TRAIL) [Id., citing Prager, I. et al. J. Exp. Med. (2019) 216 (9): 2113-2127]. Additionally, NK cells efficiently produce cytokines and chemokines that modulate other immune mediators of cytotoxicity [Id., citing Dunn, G P et al. Nat. Rev. Immunol. (2006) 6 (11): 836-848].

CAR-NK immunotherapy is not without drawbacks. For example, NK cell ex vivo expansion can entail fratricide, by which cells recognize receptors or ligands on the surface of their siblings and trigger a cytotoxic activity against them. Because several mechanisms can lead to fratricide during NK or CAR-NK cell expansion, strategies are being developed to avoid fratricidal events that result in lower yields and diminished efficacy of CAR-NK cells in vivo and to prevent host system rejection. Since donor NK cell recognition and rejection by the host immune system may potentially reduce allogenic CAR-NK cell persistence in the clinical setting and low persistence in vivo could cause early relapses due to the disappearance of CAR-NK therapy, an extension in the effector longevity may be beneficial to boost CAR-NK cell efficacy. Similarly, because a short lifespan limits NK cell proliferation and expansion ex vivo during manufacturing, making it harder to achieve sufficient cell numbers for immunotherapy doses and diminishing the time for NK cell optimization by genetic engineering, an extension in the effector longevity may be beneficial. It is known that tumor cells release soluble ligands that can bind activating and inhibitory receptors expressed in NK cells to promote their dysfunction. For example, soluble NKG2D-L (sNKG2D-L) generated by proteolytic shedding decreases the expression of NKG2D, reducing NK cell antitumor potency and well-known soluble factors present in the TME of most cancers, such as certain interleukins, enzymes, and metabolites impact NK cell effectiveness. [Hilpert, J. et al. J. Immunol. (2012) 189 (3): 1360-1371; Jinushi, M. et al. Proc. Natl Acad. Sci. USA (2008) 105 (4): 1285-1290].

Kong, et al. Front. Immunol. (2024) 15:1384039 reported the following 36 ongoing CAR-NK clinical trials focusing on hematological malignances:

| Clinical Trial Identifier | NK Cell Target | Cancer |
|---|---|---|
| NCT02742727 | CD7 | Hematological Malignancy |
| NCT05739227 | CD19 | Acute Lymphoblastic Leukemia, B-cell Lymphoma, Chronic Lymphocytic Leukemia |
| NCT06045091 | BCMA | Multiple Myeloma, Plasma Cell Leukemia |
| NCT05574608 | CD123 | Refractory/Relapsed Acute Myeloid Leukemia |
| NCT03056339 | CD19 | B-Lymphoid Malignancies, Acute Lymphocytic Leukemia, Chronic Lymphocytic Leukemia, Non-Hodgkin Lymphoma |
| NCT04639739 | CD19 | Non-Hodgkin Lymphoma |
| NCT03579927 | CD19 | Hematological Malignancy |
| NCT05336409 | CD19 | B-Cell Malignancies, Indolent Non-Hodgkin Lymphoma, Aggressive Non-Hodgkin Lymphoma |
| NCT06006403 | CD123 | Acute Myeloid Leukemia, Blastic Plasmacytoid Dendritic Cell Neoplasm, Relapsed/Refractory Leukemia |
| NCT05645601 | CD19 | Adult Relapsed/Refractory B-cell Hematologic Malignancies |
| NCT04623944 | NKG2D | Relapsed/Refractory Acute Myeloid Leukemia, Refractory Myelodysplastic Syndromes |
| NCT05215015 | CD33/CLL1 | Acute Myeloid Leukemia |
| NCT05563545 | CD19 | Acute Lymphoblastic Leukemia |
| NCT04796675 | CD19 | Acute Lymphocytic Leukemia, Chronic Lymphocytic Leukemia, Non-Hodgkin Lymphoma |
| NCT05008575 | CD33 | Acute Myeloid Leukemia |
| NCT03692767 | CD22 | Refractory B-Cell Lymphoma |
| NCT05570188 | CD19 | B-cell Lymphoma, B-cell Leukemia |
| NCT03690310 | CD19 | Refractory B-Cell Lymphoma |
| NCT05734898 | NKG2D | Acute Myeloid Leukemia |
| NCT05842707 | CD19/CD70 | Refractory/ Relapsed B-cell Non-Hodgkin Lymphoma |
| NCT03940833 | BCMA | Multiple Myeloma |
| NCT05667155 | CD19/CD70 | B-cell Non-Hodgkin Lymphoma |
| NCT05652530 | BCMA | Multiple Myeloma |
| NCT05092451 | CD70 | B-Cell Lymphoma, Myelodysplastic Syndromes, Acute Myeloid Leukemia |
| NCT02944162 | CD33 | Acute Myelogenous Leukemia, Acute Myeloid Leukemia |
| NCT05110742 | CD5 | Hematological Malignancy |
| NCT04887012 | CD19 | B-cell Non-Hodgkin Lymphoma |
| NCT05182073 | BCMA | Multiple Myeloma |
| NCT03824964 | CD19/CD22 | Refractory B-Cell Lymphoma |
| NCT05654038 | CD19 | B-Cell Lymphoblastic Leukemia, Lymphoma |
| NCT05247957 | NKG2D | Relapsed or Refractory Acute Myeloid Leukemia |
| NCT05472558 | CD19 | B-cell Non-Hodgkin Lymphoma |

Preparation of Mononuclear Immune Effector Cells

Human PBMCs can be isolated from the buffy coat layer of a whole blood sample using Ficoll-Paque® density gradient centrifugation. Specific cell types can be enriched by negative cell selection. For example, according to some embodiments, CD3+ T cells can be isolated by negative selection, e.g., using Miltenyi Pan T-cell Isolation Kit, human (130-096-535). Non-target cells, i.e., monocytes, neutrophils, eosinophils, B cells, stem cells, dendritic cells, NK cells, granulocytes, and erythroid cells are labeled using a cocktail of biotin-conjugated antibodies. The cocktail contains antibodies against antigens of the non-target cells, e.g., CD14 (macrophages), CD15 (human myeloid cells; granulocytes, macrophages), CD16 (NK cells), CD19 (B cells), CD34 (HSCs, EPCs, ECs), CD36 (macrophages), CD56 (NK cells), CD123 (pDCs, basophils, myeloid progenitors), and CD235a (glycophorin A on RBC precursors). Subsequently, non-target cells are magnetically labelled with the Pan T Cell MicroBead Cocktail. The non-T cells then are retained in a MAXS Column placed in a MACS Separator, while the unlabeled T cells pass through the column and are collected as the enriched, unlabeled T cell fraction.

Similarly, according to some embodiments, CD16+ CD56+NK cells can be isolated from human PBMCs by negative selection. Non-target cells, i.e., monocytes, neutrophils, eosinophils, B cells, stem cells dendritic cells, T cells, granulocytes, and erythroid cells are labeled using a cocktail of biotin-conjugated antibodies. The cocktail contains antibodies against CD3 (T cells), CD14 (macrophages), CD15 (human myeloid cells, granulocytes, macrophages), CD34 (HSCs, EPCs, ECs), CD36 (macrophages), CD123 (pDCs, basophils, myeloid progenitors), CD199 (naïve CD8+ T cells), and CD235a (glycophorin A on RBC precursors). Subsequently, non-target cells are magnetically labelled with the Pan T Cell MicroBead Cocktail. The non-NK cells are retained in a MAXS Column placed in a MACS Separator, while the unlabeled NK cells pass through the column and are collected as the enriched, unlabeled NK cell fraction.

According to some embodiments, the immune effector cell is derived from peripheral blood of the subject. According to some embodiments, the immune effector cell is derived from and is therefore autologous to the subject.

According to some embodiments, the immune effector cell is derived from a normal healthy subject and is therefore allogeneic to the subject.

According to some embodiments, the immune effector cell is derived from umbilical cord blood (UCB). More than 85% of UCB derived T cells have a naive phenotype, allowing them to induce fewer graft versus host disease during transplantation [Kwoczek, J. et al. Transfusion (2018) 58:88-99]. Moreover, they express significantly lower markers of exhaustion (PD1, LAG3, TIM3) in comparison to PB-derived T cells, allowing them to have long-term persistence and efficiency. [Cael, B. et al., Cancers (2022) 14:3168, citing Lin, Y. et al. Stem Cell Invest. (2019) 6:35].

According to some embodiments, expression of the TLE3ΔWDR construct in CAR-containing immune effector cells enhances CAR-immune effector cell function despite chronic antigen stimulation. According to some embodiments, expression of the TLE3ΔWDR construct in stimulated CAR-containing immune effector cells in vitro promotes activation of genes that promote anti-tumor activity and also represses genes involved in excessive effector function, exhaustion or both. According to some embodiments, ectopic expression of the TLE3ΔWDR construct in stimulated CAR-containing immune effector cells reduces expression of at least one inhibitory receptor comprising PD-1, CTLA-4, LAG3; TIGIT, or a combination thereof compared to a CAR-immune effector cell that does not overexpress Tle3 (control). According to some embodiments, expression of the CAR-TLE3ΔWDR construct in stimulated CAR-containing immune effector cells induces transcriptomic changes comprising differential expression of genes that enhance the anti-tumor response comprising proliferation of the CAR-containing immune effector cells; enhances persistence of the CAR-containing immune effector cells while maintaining immune homeostasis despite chronic antigen stimulation.

According to some embodiments, expression of the CAR-TLE3ΔWDR construct in stimulated CAR-containing immune effector cells reprograms the immune effector cells to acquire stem-like, memory cell characteristics including production of IFN and TNF, expression of TCF-1 or both.

According to some embodiments, expression of the TLE3ΔWDR construct in CAR-containing immune effector cells enhances CAR-immune effector cell function after rechallenge with the cancer, compared to a no-TLE3-CAR immune effector cell control.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates, which may need to be independently confirmed.

EXAMPLES

The following examples are put forth so as to provide those of ordinary skill in the art with a complete disclosure and description of how to make and use the invention of the present disclosure and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Building on our long-standing interest in Tcf1/Lef1 and Runx3 TFs in T cells (16-19), we investigated their cofactors, Transducin-Like Enhancer of split (TLE) proteins, the mammalian homologs of *Drosophila* Groucho transcriptional corepressor [Turki-Judeh, A. and Courey, J. Curr. Top. Dev. Biol. (2012) 98:65-96; Buscarlet, M. and Stifani, S. Trends in Cell Biol. (2007) 17:353-361; Jennings, BH and Ish-Horowicz, D. Genome Biol. (2008) 9:205; Gasperowicz, M. and Otto, F. J. Cellular Biochem. (2005) 95:670-687].

TLE cofactors interact with 1) Tcf/Lef TFs through its N-terminal glutamine-rich Q domain to counter Wnt activity, 2) Runx TFs through its C-terminal WD-repeat (WDR) domain, and 3) Hdac1 through the Gly-Pro-rich GP domain to exert its repressive function [Turki-Judeh, W. and Courcy, AJ. Curr. Top. Dev. Biol. (2012) 98:65-96; Chen, G. et al. Genes & Development (1999) 13:2218-2230] (FIG. 1A). In mammals, there are 4 TLE genes (TLE1-4) that encode full-length proteins. In T cells, TLE3 is most abundantly expressed, followed by TLE4 and TLE1. In our previous study [Xing, S. et al. J. Exp. Med. (2018) 215:2211-2226], we demonstrated that TLE cofactors are differentially partitioned into distinct TF complexes, with TLE-Runx3 complex instructing CD8+ lineage choice during thymic development and TLE-Tcf/Lef complex protecting naïve CD8+ T cell identity, where TLE genes showed redundant and gene-dose effect, with TLE3 exerting a more dominant function.

Recently, we analyzed TLE genes in CD8+ T cell responses to acute viral infection [Zhao, X. et al. Nature Immunol. (2024) 25:294-306]. While ablating all three TLE1,3,4 genes abrogates differentiation of effector CD8+ T ($T_{eff}$) cells, TLE3 shows non-redundant roles in regulating memory CD8+ T ($T_{mem}$) lineage stability without affecting $T_{mem}$ cell pool size. Induced deletion of TLE3 accelerates formation of CD62L+ central Tmem ($T_{em}$) at the expense of CD62L—effector Tmem ($T_{em}$) cells. Notably, this effect is not a phenocopy of ablating any of its partner TFs (Tcf1, Runx3 or Tbet), and likely results from specific disruption of TLE3-sensitive TF complexes. On the mechanistic side, key observations include: 1) besides its known corepressor roles, TLE3 functions as a transcriptional coactivator, where TLE3 establishes/maintains chromatin open state to induce its target gene expression; 2) TLE3 engages Tbet as a novel partner TF in $T_{eff}$ and $T_{mem}$ cells, to form complexes with its known partners such as Runx3) while its expression is relatively stable, TLE3 is dynamically redistributed in $T_{eff}$ and $T_{mem}$ cell genome, representing a novel means/pattern of gene regulation. We propose that the TLE transcription cofactors exert their unique regulatory roles in T cell biology by integrating the action of multiple TF pathways.

Generation of CAR-T Cells Expressing Engineered TLE Proteins.

Building on the concept that TLE cofactors function as TF integrators, we reasoned that gain-of-function for TLE3 may reprogram the fate of activated T cells, boosting Tmem formation, persistence and recall capacity. We further reasoned that molecular engineering of TLE3 may skew partner TF utilization, leading to its function uncoupling and boosting its preferred regulatory effects in CAR-T cells. Therefore, we engineered human TLE3 to make TLE3ΔQ protein that lacks N-terminal Tcf1-interacting Q domain and TLE3ΔWDR protein that lacks C-terminal Runx3-interacting WDR domain. The domain structure of wild type TLE3 protein and the resulting engineered TLE molecules are shown in FIG. 1A. TLE3 utilizes different functional domains to engage distinct partner TFs. The N-terminal side (the Q domain) interacts with TCF-1, the GP domain interacts with Hdac1, and the C-terminal WDR domain interacts with Runx3. The Cen domain functions in nuclear localization and phosphorylation, the SP domain functions in phosphorylation.

Using a codon-optimization method, we synthesized CD19-BBz-CAR that consists of anti-hCD19 single-chain variable fragment (scFv), a 4-1BB costimulatory domain and a CD3ζ T cell activation domain along with bicistronically linked green fluorescent protein (GFP) as an expression marker [Id., citing Porter, D L et al. New Engl. J. Med. (2011) 365:725-733]. We further engineered the hCD19-CAR to co-express TLE3ΔQ or TLE3ΔWDR via P2A peptide in the same lentiviral expression construct. A schematic of the construct is shown in FIG. 1B.

We then activated T cells from healthy donors using anti-CD3 and anti-CD28 antibodies, followed by lentiviral transduction to express a control CAR without TLE3, TLE3ΔQ or TLE3ΔWDR CAR in T cells as shown schematically in FIG. 2A. The CAR-T cells were enriched by sorting for GFP+ cells and further expanded in the present of cytokines including IL-2, IL-7, and IL-15 to obtain CAR-T cells for in vivo assessment.

Example 2. Ectopic Expression of TLE3-ΔWDR but not TLE3-ΔQ Improves Leukemia Control As shown schematically in FIG. 2B, we used these CAR-T cells in a xenograft mouse model. We first inoculated Raji Burkitt's lymphoma cells i.v. into NSG mice (0.25 million lymphoma cells/mouse), and 3 days later, infused control CAR-T cells or those expressing Tle3ΔQ or Tle3ΔWDR (0.5 million CAR-T cells/mouse).

The Raji cells express firefly luciferase, allowing tracking of tumor growth in live mice through in vivo imaging. Conventional CAR T cells curtailed tumor growth by 15 day post tumor inoculation (dpt), compared with the no CAR-T group, but did not fully control tumor expansion at later time points (28 dpt). In contrast, TLE3ΔWDR+ CAR-T cells kept the tumors under the detection limit in most cases till 28 dpt, while TLE3ΔQ+ CAR-T cells showed impaired anti-tumor activity (FIG. 2C). By 36 dpt, while recipients of control and TLE3ΔQ+ CAR-T cells had succumbed to the lymphoma, most recipients of TLE3ΔWDR+ CAR-T cells survived (FIG. 2D), without overt signs of xeno-GVHD. These data demonstrate that ectopic expression of TLE3ΔWDR but not Tle3ΔQ in CAR-T cells enhanced their anti-tumor activity and conferred robust protection against leukemia growth.

Example 3. TLE3-ΔWDR Promotes CAR-T Cell Expansion and Survival Ex Vivo

To investigate the beneficial effect of ectopic TLE3ΔWDR expression, we first validated TLE3 expression in CAR-T cells by immunoblotting. As shown in FIG. 3A, endogenous TLE3 was detected in both control and TLE3ΔWDR+ CAR-T cells, while the C-terminus-truncated TLE3ΔWDR was only detected in the latter.

Because CD8+ CAR-T cells outgrew CD4+ CAR-T cells in vivo, especially after TLE3ΔWDR expression (see below), we focused our ex vivo analysis on CD8+ CAR-T cells. Prolonged ex vivo culture of established CAR-T cells showed that TLE3ΔWDR+ CAR-T cells continued to expand over-time, while control CAR-T cells had limited numerical gain (FIG. 3B), suggesting that TLE3ΔWDR expression conferred growth advantages to CAR-T cells ex vivo.

To determine if and how TLE3ΔWDR expression reprograms CAR-T cells on a molecular level, we performed RNA-seq analysis of control and TLE3ΔWDR+ CAR-T cells before and after ex vivo stimulation with Raji cells for 48 hrs.

To extract reproducible transcriptomic changes induced by TLE3ΔWDR expression, CAR-T cells were generated from two healthy donors, each in 2-3 technical replicates. Principal component analysis (PCA) reduces the number of dimensions in large datasets to principal components that retain most of the original information. It does this by transforming potentially correlated variables into a smaller set of variables, called principal components.

Figure 3D:
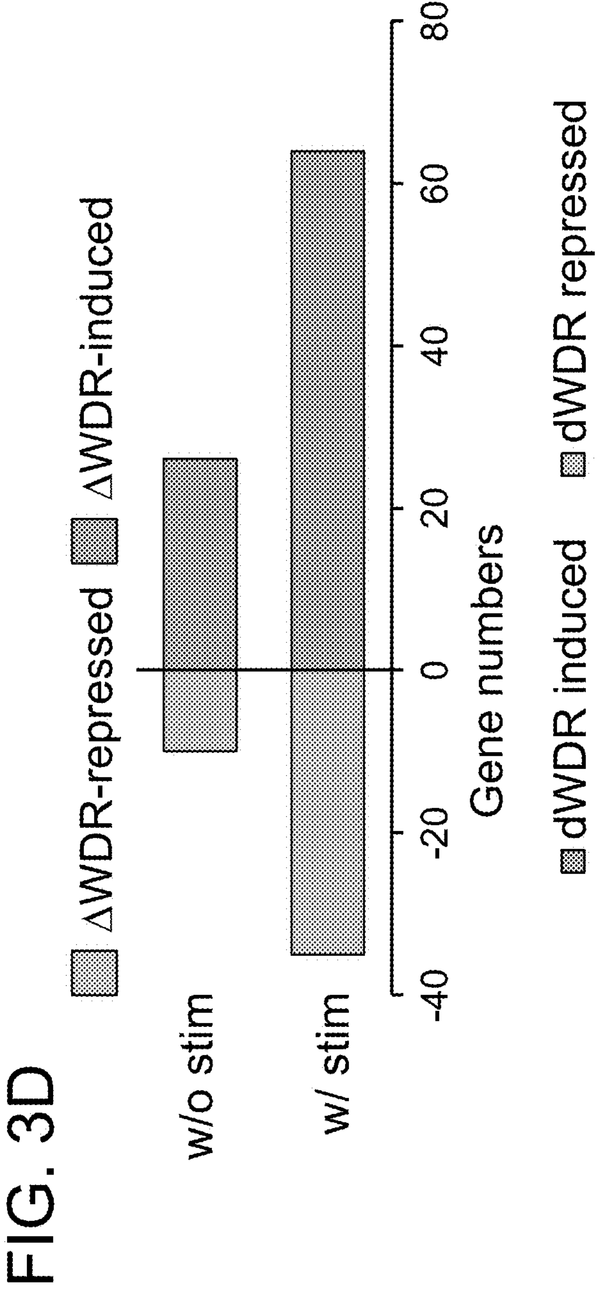
Figure 3E:
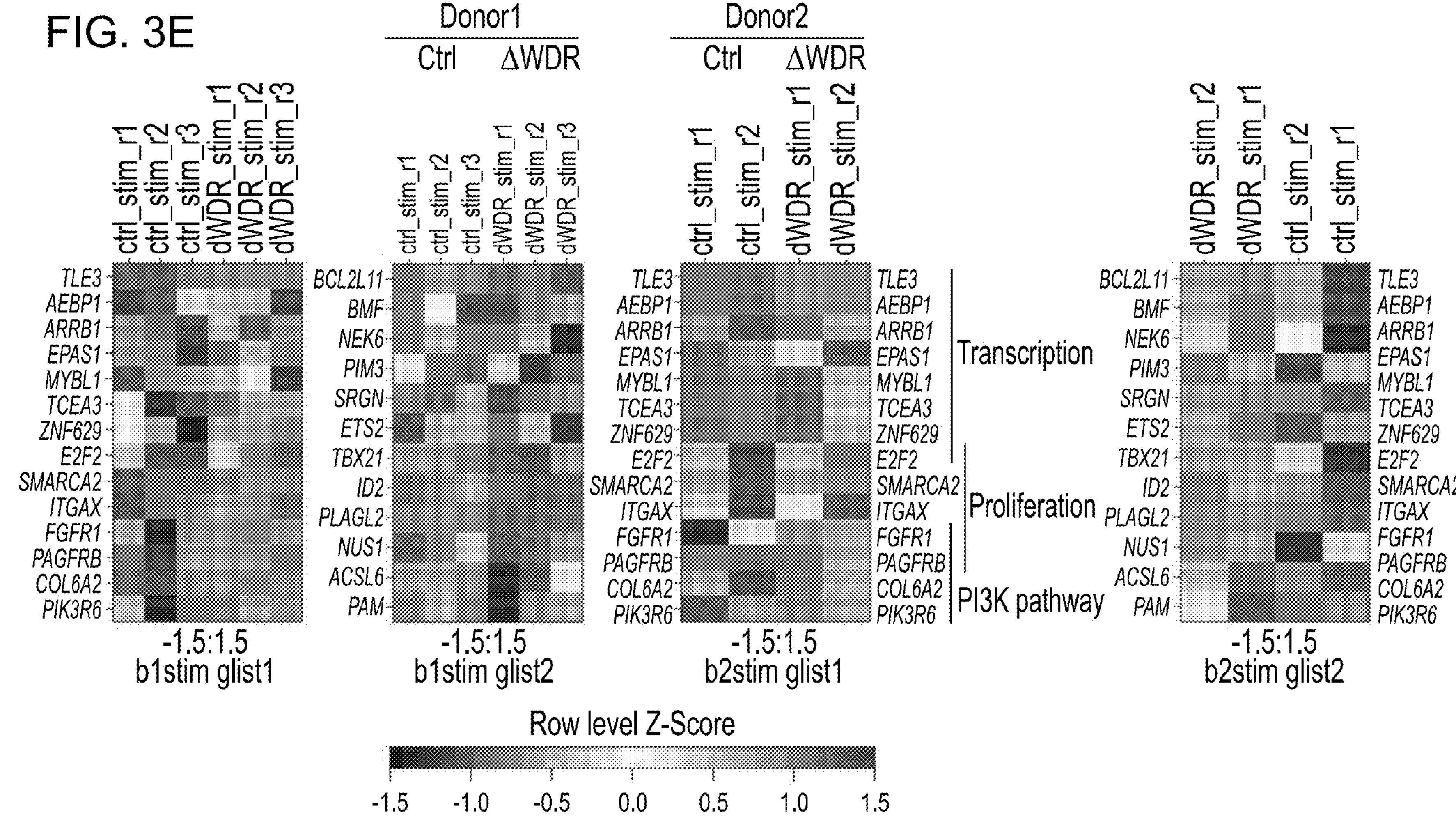
FIG. 3E and FIG. 3F are heatmaps showing select TLE3ΔWDR-induced (FIG. 3E) and -repressed (FIG. 3F) genes, with key functional annotation marked on the right. Color scale represents z-score transformed transcript levels.

Principal component analysis showed that ex vivo stimulation with Raji cells causes strong transcriptomic diversification in CAR-T cells, and the differences between control and TLE3ΔWDR+ CAR-T cells were more evident after stimulation in both donors (FIG. 3C). By the criteria of ≥1.25 fold changes and false discovery rate <0.1, we identified differentially expressed genes (DEGs) between control and TLE3ΔWDR+ CAR-T cells before and after stimulation. Upon extracting common DEGs between the two donors, there were higher numbers of DEGs after stimulation than those before stimulation (FIG. 3D). TLE3ΔWDR+ CAR-T cells had higher TLE3 expression as expected (FIG. 3E, top row).

Common methods for gene (protein) functional analysis include metabolic signaling pathway analysis and Gene Ontology (GO) analysis. Gene ontology (GO) analysis categorizes gene functions into three major classes: Biological Process (BP), Molecular Function (MF), and Cellular Component (CC). Functional annotation is the process of attaching biological information to sequences of genes or proteins. The basic level of annotation is using sequence alignment tool BLAST for finding similarities, and then annotating genes or proteins based on that. Functional annotation consists of three main steps: identifying portions of the genome that do not code for proteins; identifying elements on the genome, a process called gene prediction; and attaching biological information to these elements. Functional annotation analysis involves annotating genes with GO terms and pathway information.

Functional annotation analysis showed that TLE3ΔWDR expression induced expression of several transcription regulators including EPAS1 (encoding hypoxia-inducible factor 2α, HIF2α), which promotes anti-tumor activity by tumor-infiltrating CD8+ T cells [Likanan, I. et al. J. Clin. Invest. (2021) 131] (FIG. 3E). TLE3ΔWDR induced cell cycle regulators, such as E2F2 that promotes G1-S phase transition [Johnson, D G and Schneier-Broussard, R. Front. Biosci. (1998) 3: d447-448]. and SMACA2 that encodes BRM in SWI/SNF chromatin remodeling complex and contributes to self-renewal of neural stem cells [Gao, F. et al. Molecular Cell (2019) 75:891-904] (FIG. 3E). The SWI/SNF chromatin remodeling complex functions by displacing nucleosomes near important regulatory sites which can facilitate transcription factor binding and thus promote gene activation in both uni- and multi-cellular eukaryotes [Church, M C and Workman, J L. Biochem. Soc. Trans. (2024) 52 (30:1327-37, citing [Owen-Hughes, T. et al. Science (1996) 273:513-16; Cote, J. et al. Science (1994) 265:53-60; Hirschhorn, J N et al. Genes Dev. (1992) 6:2288-98; Kruger, W. et al. Genes Dev. (1995) 9:2770-9; Imbalzano, A N et al. Nature (1994) 370:481-85; Kwon, H. et al. Nature (1994) 370:477-81; Wang, W. et al. EMBO J. (1996) 15:5370-82; Khavari, P A et al. Nature (1993) 366:170-74; Hodges, C. et al. Cold Spring Harb. Perspect. Med. (2016) 6: a026930]. TLE3ΔWDR also induced several genes in the PI3K pathway, which is intimately linked to a pro-survival effect [Pungsrinont, T. et al. Int. J. Mol. Sci. (2021) 22] (FIG. 3E).

Figure 3F:
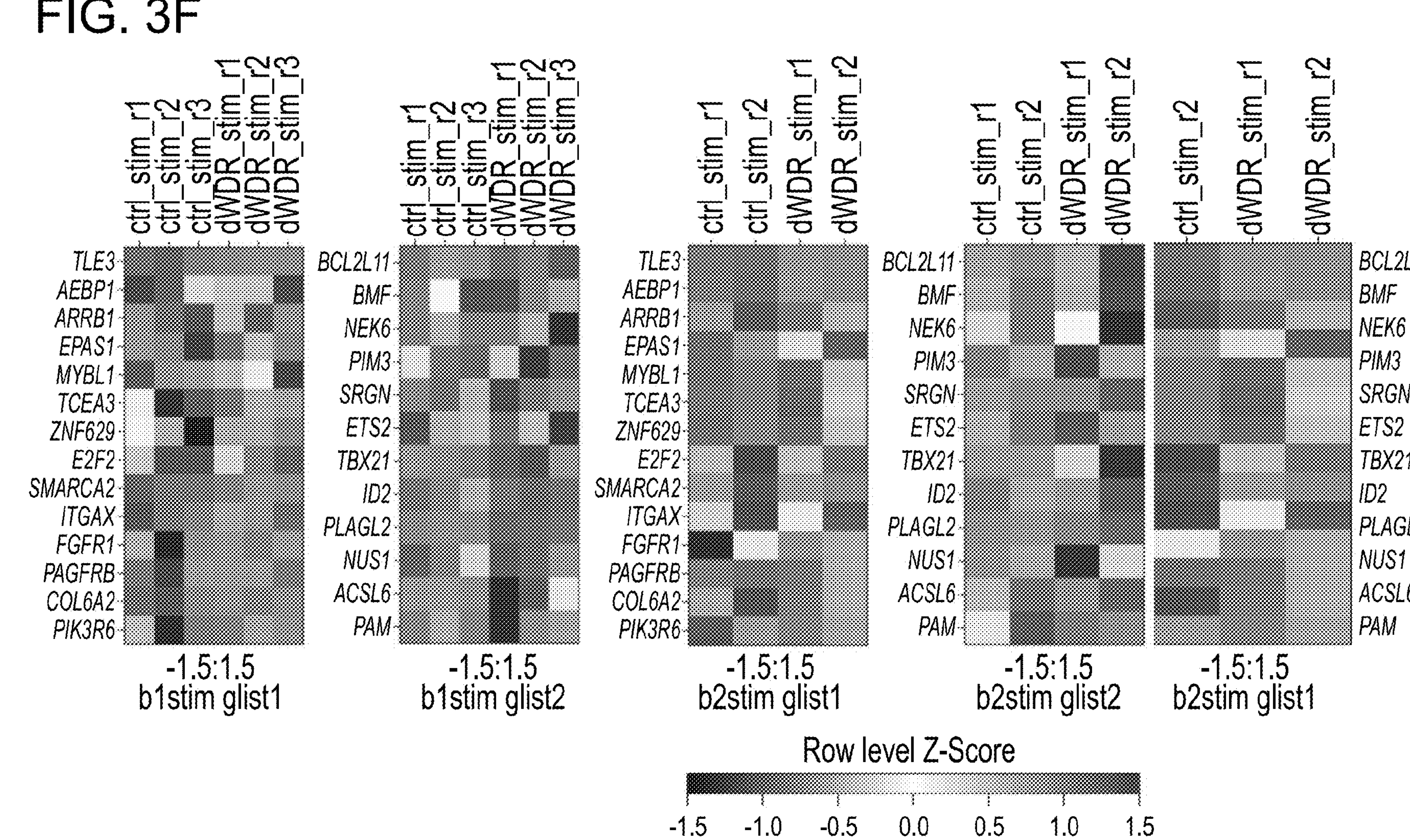

On the other hand, TLE3ΔWDR expression repressed other genes that are involved in apoptosis, effector functions and lipid metabolism (FIG. 3F). Of particular interest was BCL2L11, which encodes BIM proapoptotic protein [Sionov, R V et al. Oncotarget (2015) 6:23058-23134], which was the sole gene that was repressed in TLE3ΔWDR+ CAR-T cells before stimulation. TBX21 (encoding T-BET) and ID2 promote effector T cell differentiation [Yang, C Y et al. Nature Immunol. (2011) 12:1221-1229; Intlekofer, A M et al. Nature Immunol. (2005) 6:1236-1244; Kaech, S M and Cui, W. Nat. Rev. Immunol. (2012) 12:749-761], and their repression by TLE3ΔWDR likely prevented excessive effector function and/or CAR-T cell exhaustion. Collectively, these data suggest that TLE3ΔWDR expression reprogrammed CAR-T cells to gain advantages in proliferation and survival, while maintaining more balanced effector functions.

Example 4. TLE3ΔWDR Amplifies CAR-T Cell Responses In Vivo

To further determine the beneficial effect of ectopic TLE3ΔWDR expression in vivo, we tracked CAR-T cells in the peripheral blood of NSG recipient mice. Following the study design depicted in FIG. 2B, we chose 3 time-windows, including early time point 10-12 days post-tumor transplantation (dpt) when the leukemia burden was similar between recipients of control and TLE3ΔWDR+ CAR-T cells, 20-22 dpt and 28-30 dpt when the leukemia was largely cleared in recipients of TLE3ΔWDR+ CAR-T cells, whereas leukemic cells continued to expand in control CAR-T cells (FIG. 2B).

Figures 4A, 4B:
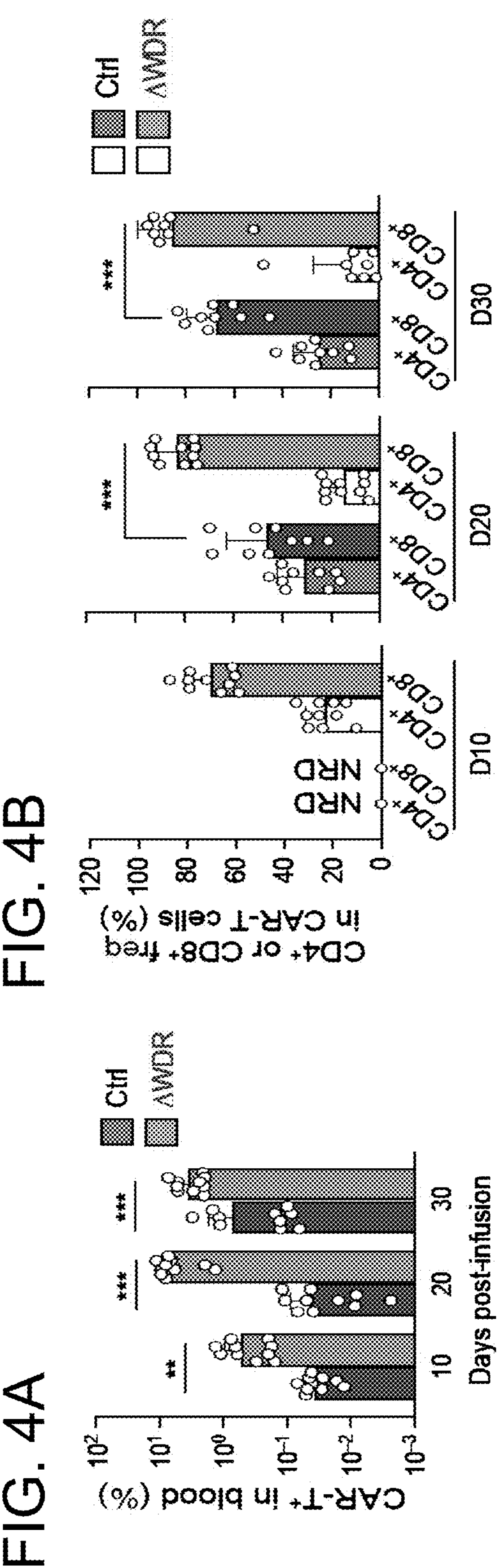
FIG. 4A and FIG. 4B show that TLE3ΔWDR expression amplifies CD8+ CAR– T cell response in vivo.

At 10- and 20-days post-tumor transplantation (dpt), control CAR-T cells were barely detectable, frequently at <0.1% of viable blood cells (FIG. 4A). In contrast, TLE3ΔWDR+ CAR-T cells were more readily detectable in all recipients examined, at approximately 15- and 150-fold higher frequency than control CAR-T cells at 10 and 20 dpt, respectively (FIG. 4A). These data validated the robust growth/survival advantages of TLE3ΔWDR+ CAR-T cells in vivo. On 30 dpt, control CAR-T cells became more detectable, likely as a result of responding to persisting stimulation by leukemic cells (FIG. 4A); TLE3ΔWDR+ CAR-T cells were detected at lower frequencies on 30 dpt compared with 20 dpt, suggesting that they were undergoing contraction because of greatly diminished leukemia burden in these recipients (FIG. 4A). Contraction is a physiological phenomenon for T cell responses to bacterial or acute viral infection [Haring, J S et al. Immunity (2006) 25:19-29].

These data suggest that TLE3ΔWDR+ CAR-T cells did not undergo uncontrolled expansion in numbers, in spite of the growth/survival advantages over control CAR-T cells and retained the ability of physiological contraction in the absence of antigen stimulation. Collectively, TLE3ΔWDR expression amplified the magnitude and changed the kinetics of CAR-T cell response to leukemia.

In the CAR-T production process, the CD4+ and CD8+ T cell ratio could vary due to donor-derived differences and/or introduction of engineered TLE3 molecules. To avoid such pre-existing bias, we generated CD4+ and CD8+ CAR-T cells in parallel and mixed those in a 1:1 ratio for recipient infusion (FIG. 4A). Control CAR-T cells largely maintained the CD4+/CD8+ ratio on 20 dpt but showed biased expansion of CD8+ CAR-T cells on 30 dpt (FIG. 4B). In contrast, TLE3ΔWDR+ CAR-T cells exhibited clear bias toward the CD8+ lineage, with an average CD4+/CD8+ ratio of 1:3 from the early time point, and the CD8+-bias was further amplified over time, showing a CD4+/CD8+ ratio of 1:5.5 on 20 dpt and that of 1:7 on 30 dpt (FIG. 4B). These data indicate that TLE3ΔWDR expression preferentially amplified CD8+ CAR-T cell responses.

Example 5. TLE3DWDR Ameliorates CAR-T Cell Exhaustion In Vivo

Figure 5A:
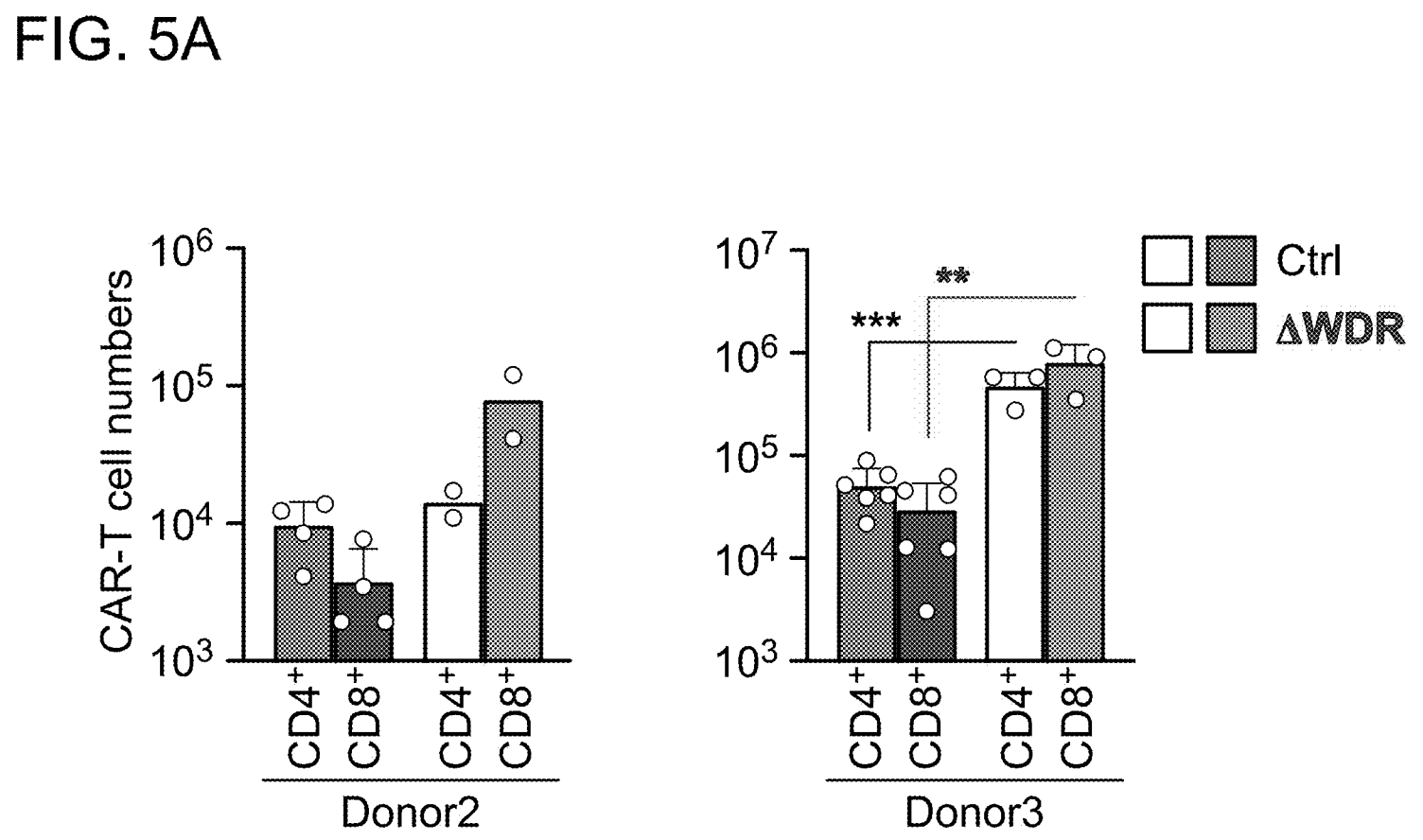
Figure 5B:
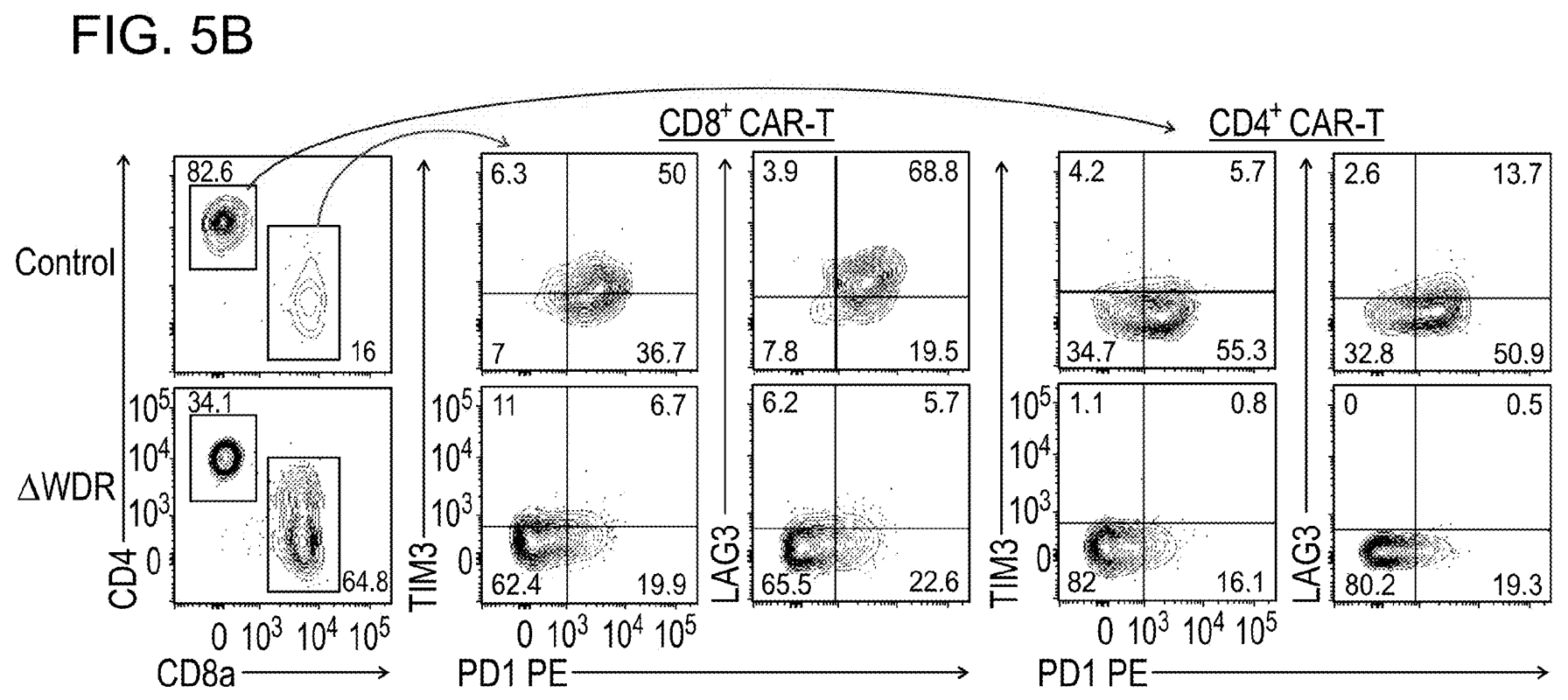
Figure 5C:
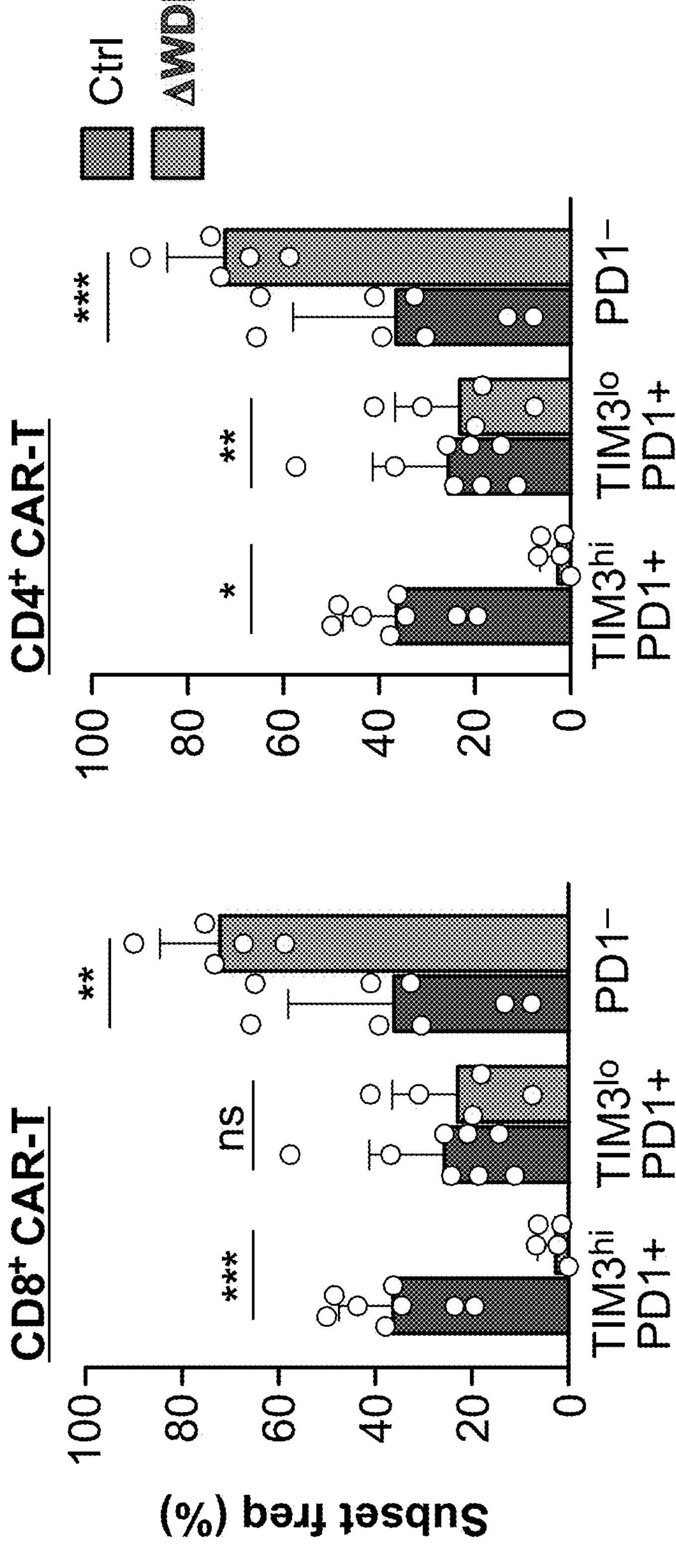

CAR-T cell exhaustion is one of the major factors that compromise their anti-tumor activities. We next examined the expression pattern of coinhibitory receptors in CAR-T cells from the spleens of NSG recipients. We first analyzed 12 dpt when the leukemia burden was similar between recipients of control and TLE3ΔWDR+ CAR-T cells. At this timepoint, control CD8+ CAR-T cells did not gain growth advantage over control CD4+ CAR-T cells in the spleens, while TLE3ΔWDR+ CD8+ CAR-T cells were consistently detected at higher numbers than TLE3ΔWDR+ CD4+ and control CD8+ CAR-T cells (FIG. 5A). The vast majority of control CD8+ CAR-T cells expressed high level of PD1, with a substantial portion co-expressed TIM3 or LAG3; in contrast, a substantially smaller portion of TLE3ΔWDR+ CD8+ CAR-T cells expressed PD1, and both TIM3 and LAG3 expression were greatly diminished in TLE3ΔWDR+ CD8+ CAR-T cells (FIG. 5B, FIG. 5C). On the other hand, TIM3 and LAG3 expression was less pronounced in control CD4+ compared with CD8+ CAR-T cells, and PD1 was expressed at high levels in >50% of CD4+ CAR-T cells; nonetheless, all these coinhibitory receptors showed further reduced expression in TLE3ΔWDR+ CD4+ CAR-T cells (FIG. 5B, FIG. 5C). These data demonstrate that TLE3ΔWDR prevented excessive induction of co-inhibitory receptors in CAR-T cells during the early response stage.

Figures 6A, 6B, 6C, 6D:
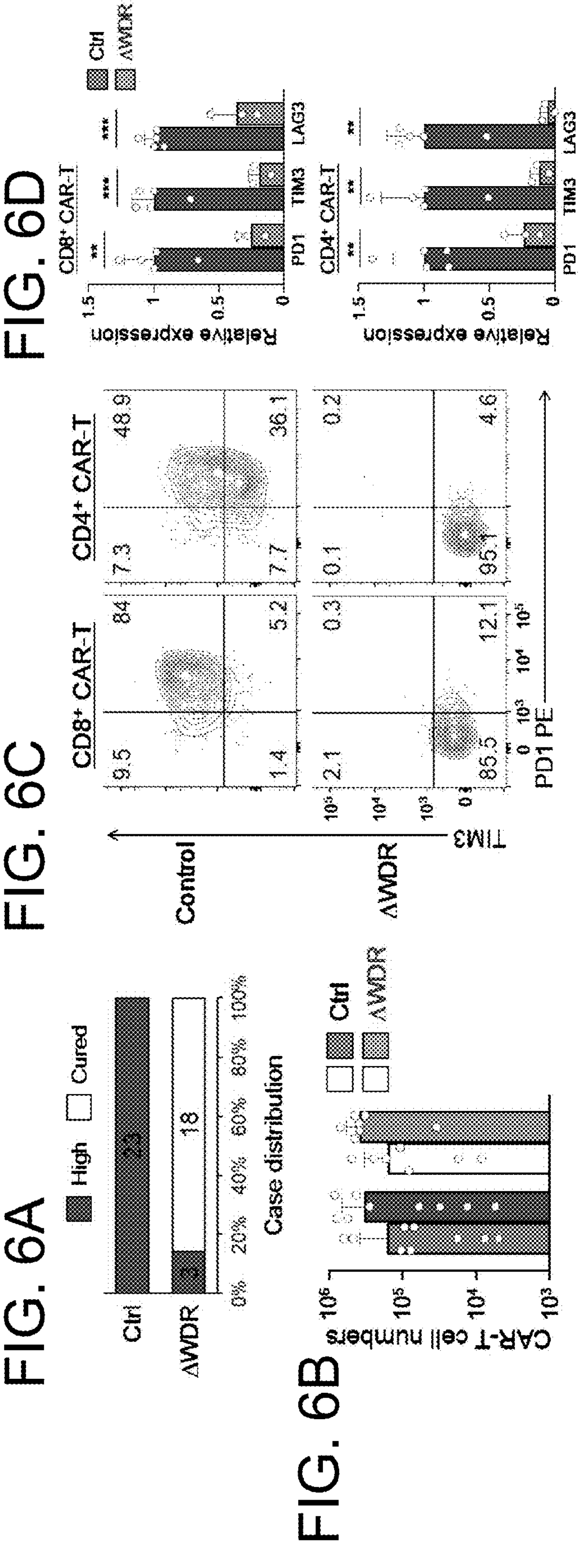
FIG. 6A, FIG. 6B, FIG. 6C and FIG. 6D show that TLE3ΔWDR sustains repression of CAR-T cell exhaustion at late response stage in vivo.

To further determine if Tle3ΔWDR suppressed CAR-T cell exhaustion in long-term, we performed similar analysis at a later time window. By 30 dpt, all NSG recipients of control CAR-T cells showed high leukemic burden, while leukemia was below the detection limit in over 80% of recipients of TLE3ΔWDR+ CAR-T cells (FIG. 6A). In this context, control CAR-T cells showed continued expansion in response to the high leukemia burden, albeit at varied levels (FIG. 6B). On the other hand, TLE3ΔWDR+ CAR-T cells in 'leukemia-cured' recipients were sustained at a readily detectable level, with CD8+ CAR-T cells showing consistently higher numbers and abundance compared with CD4+ CAR-T cells (FIG. 6B).

Phenotypic analysis further showed that control CAR-T cells continued to express high levels of PD1 and TIM3, with control CD8+ CAR-T cells adopting almost uniform $TIM3^{hi}PD1^{+}$ phenotype, as a result of persisting leukemic antigen (FIG. 6C). In key contrast, TLE3ΔWDR+ CAR-T cells had minimal expression of PD1, TIM3 and LAG3 in both CD8+ and CD4+ lineages (FIG. 6C, FIG. 6D). We also analyzed CAR-T cells in the bone marrow at both time windows and observed similar suppression of exhaustion markers by TLE3ΔWDR expression (data not shown). These data indicate that TLE3ΔWDR had the long-term effect of ameliorating CAR-T cell exhaustion.

Example 6. TLE3ΔWDR Promotes Generation of CAR-T Cells with Memory T Cell Characteristics In a productive immune response where antigen is cleared, memory T cells are generated and provide long-term protection Martin, M D and Badovinac, V P. Front. Immunol. (2018) 9:2692; Jameson, S C and Masopust, D. Immunity (2018) 48:214-226]. Our previous studies demonstrated that the transcription factor TCF1 is necessary and sufficient to promote memory CD8+ T cell longevity and recall capacity upon rechallenge with the same antigen [Zhou, X. et al. Immunity (2010) 33:229-240; Shan, Q. et al. Nature Immunol. (2022) 23:386-398]. In T cell response to persisting antigens, TCF1 expression demarcates a subset of exhausted T (Tex) cells that has stem-like, self-renewal capacity and expands rapidly in response to immune checkpoint blockade therapy, known as Tex-stem cells [Zhao, X. et al. Nat. Rev. Immunol. (2022) 22:147-157]. We and others showed that TCF1 is necessary and sufficient for the Tex-stem cell pool in chronic viral infections and tumor microenvironment [Zhao, X. et al. Nat. Rev. Immunol. (2022) 22:147-157; (Im, S J et al. Nature (2016) 537:417-4212; Siddiqui, I. et al. Immunity (2019) 50:195-211 e110; Chen, Z. et al. Immunity (2019) 51:840-855 e845; Shan, Q. et al. Cell Mol. Immunol. (2021) 18:1262-1277].

Figures 7A, 7B, 7C:
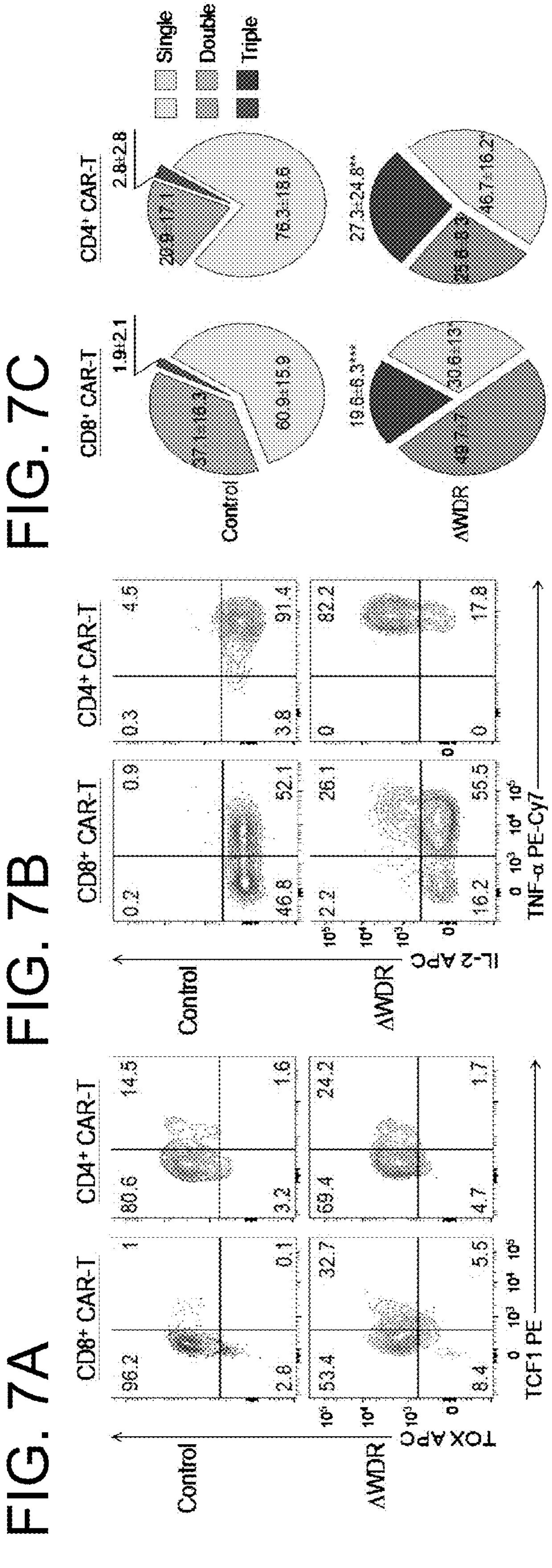
FIG. 7A, FIG. 7B, and FIG. 7C show that TLE3ΔWDR expression promotes stemness and memory T cell features in CAR-T cells.

We therefore examined the expression of TCF1 together with Tex-characteristic TOX in CAR-T cells via intracellular staining. On 30 dpt, almost all control and TLE3ΔWDR+ CAR-T cells were $TOX^{hi}$, consistent with their exposure to persisting antigens (FIG. 7A). Whereas few CD8+ CAR-T cells expressed TCF1, over ⅓ of TLE3ΔWDR+ CD8+ CAR-T cells expressed high levels of TCF1 (FIG. 7A). In addition, TCF1+ population was expanded in TLE3ΔWDR+ CD4+ CAR-T cells compared to their control counterparts (FIG. 7A). These observations suggest that TLE3ΔWDR expression reprogrammed CAR-T cells to acquire stem-like, memory T cell characteristics.

Among memory T cells, IL-2 production is a key feature for central memory T cells which persist longer and show more robust recall response than other memory subsets (Martin, M D and Badovinac, V P. Front. Immunol. (2018) 9:2692; Jameson, S C and Masopust, D. Immunity (2018) 48:214-226]. A hall mark for T cell exhaustion is the diminished capacity of poly-cytokine production, showing early failure to produce IL-2, followed by gradual decline in TNF-α and then IFN-γ production [Blank, C U et al. Nat. Rev. Immunol. (2019) 19:665-674; McLane, L M et al. Annu. Rev. Immunol. (2019) 37:457-495]. On 30 dpt, both control and TLE3ΔWDR+ CAR-T cells retained the capacity of producing IFN-γ. However, among the IFN-γ-producing CAR-T cells, control CD8+ CAR-T cells partially retained the ability of producing TNF-α but failed to generate IL-2; in contrast, IFN-γ-producing TLE3ΔWDR+ CAR-T cells retained robust capacity of generating both cytokines (FIG. 7B, left panels). On the other hand, while control TLE3ΔWDR+ CD4+ CAR-T cells were high producers of TNF-α, only the latter robustly generated IL-2 (FIG. 7B, right panels). As summarized in FIG. 7C, control CAR-T cells were rarely poly-cytokine producers, with approximately ⅓ as IFN-γ+TNF-α+ double cytokine producers, while TLE3ΔWDR expression greatly expanded the proportion of double and poly cytokine producers in CAR-T cells. These data collectively demonstrate that TLE3ΔWDR-expressing CAR-T cells acquired central memory T cell characteristics for long-term persistence and better-preserved functionalities.

Figures 8A, 8B, 8C:
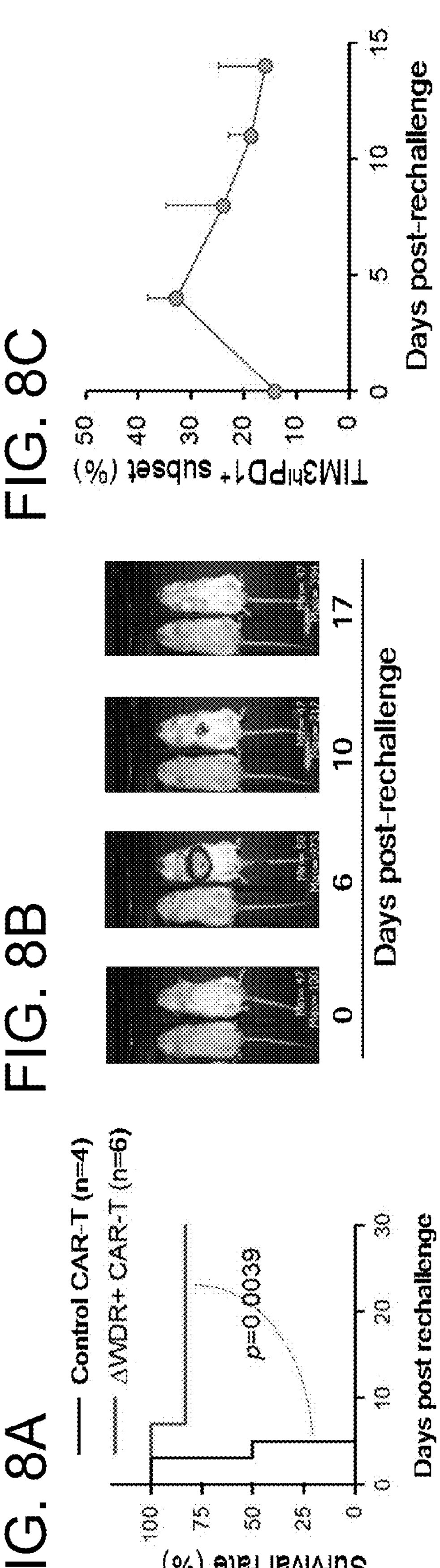
FIG. 8A, FIG. 8B and FIG. 8C show TLE3ΔWDR-expressing CAR-T cells protect against secondary leukemia challenge. The leukemia-bearing NSG mice were infused with control or TLE3ΔWDR+ CAR-T cells as in FIG. 2B. The recipients that survived to 36 days post-tumor implantation (dpt) were rechallenged with 10-20 fold higher dose of Raji leukemic cells.

Example 7. TLE3-ΔWDR+ CAR-T Cells Provide Long-Term Protection Against Leukemia Memory T cells mount robust recall response when re-encountering the same antigen. To test if the memory-like TLE3ΔWDR+ CAR-T cells provided prolonged protection against leukemia, we performed rechallenge assay by injecting 10-20 times higher dose of Raji lymphoma cells over the initial inoculated dose in the primary response (2.5-5 million/mouse). At 36 dpt, only ~¼ of the recipients of control CAR-T cells survived, and the surviving mice all had high leukemia burden (FIG. 2C, FIG. 2D). When rechallenged with excess dose of leukemic cells, the mice rapidly succumbed within 5 days (FIG. 8A). In contrast, most of the recipients of TLE3ΔWDR+ CAR-T cells showed prolonged survival (FIG. 8A). In the rechallenged mice harboring TLE3ΔWDR+ CAR-T cells, leukemia was either below detection limit by in vivo imaging or transiently expanded to detectable levels but was diminished to undetectable levels within 2-3 weeks (FIG. 8B). When monitored in peripheral blood, TLE3ΔWDR+ CAR-T cells showed a transient increase in the TIM3hiPD1+ subset, demonstrating that CAR-T cells responded to leukemia restimulation (FIG. 8C). It is of interest to note that the TIM3hiPD1+ subset fell back to a similar level at later time points as that before rechallenge (FIG. 8C), concordant with leukemia clearance. These observations support the notion that the memory-like TLE3ΔWDR+ CAR-T cells remained highly responsive to secondary challenge and could effectively curtail leukemia relapse.

Conclusion

Figure 10:
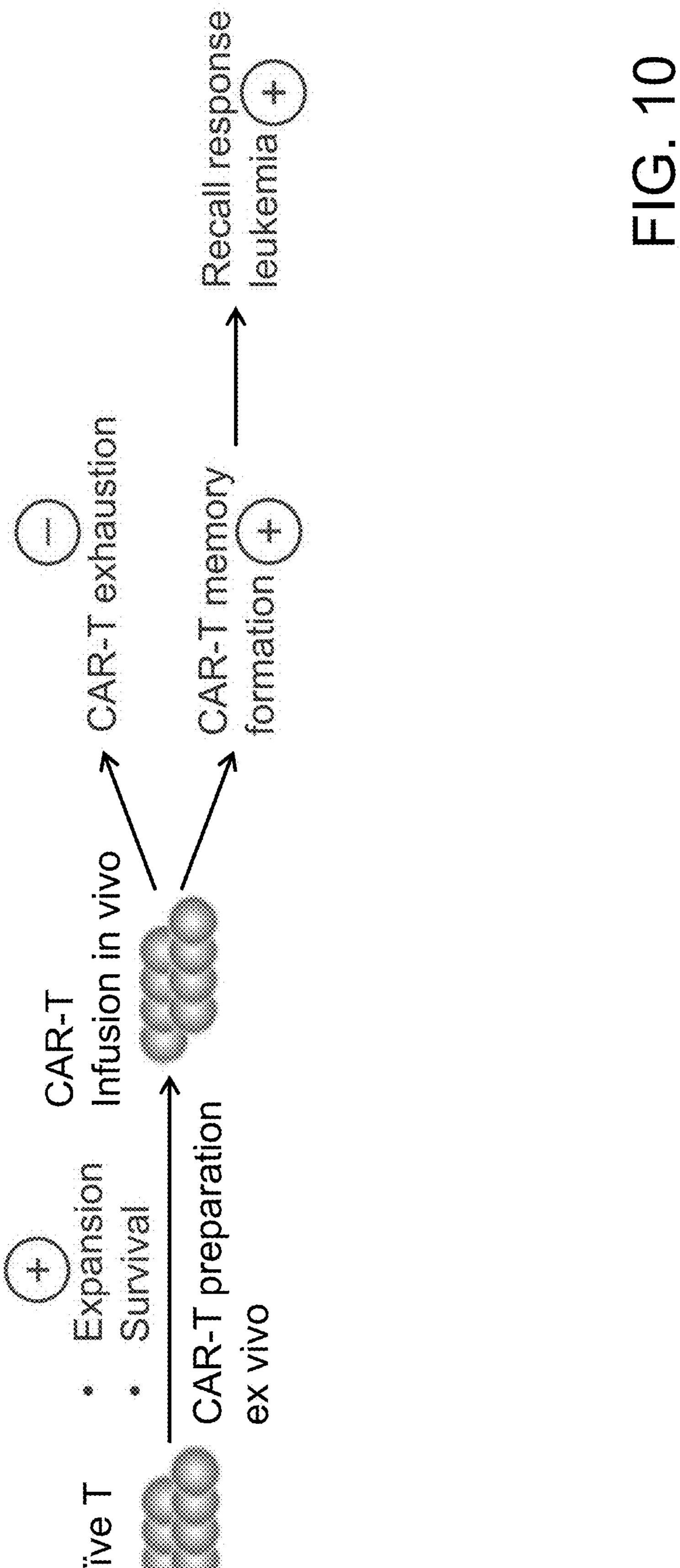
FIG. 10 is a diagram summarizing the beneficial impact on CAR-T cells by ectopic expression of TLE3ΔWDR, where + and − signs denote positive and negative regulation, respectively.

Preventing or reversing T cell exhaustion has been a long sought-after goal, which has profound bearings in improving cancer immunotherapy. Through molecular engineering of the TLE3 transcription cofactor, we identified a TLE3ΔWDR molecule that reprogrammed CAR-T cells and enhanced their anti-tumor activities in a xenograft leukemia model. Ectopic expression of TLE3ΔWDR showed multifaceted beneficial effects on CAR-T cells (FIG. 10). The foremost impact was the suppression of multiple coinhibitory receptors, preventing their downstream signaling leading to CAR-T cell exhaustion; this effect was evident during the early stage of an anti-leukemia response, and was further sustained for long-term after the leukemia burden dropped below the detection limit on in vivo imaging. Secondly, TLE3ΔWDR redirected the CAR-T cell along a different path from exhaustion to memory cell lineage, as featured by elevated expression of TCF1 that promotes stem-like self-renewal and longevity, and by retaining the poly-cytokine producing capacity. These memory-like TLE3ΔWDR-expressing CAR-T cells provided long-term protection over leukemia rechallenge and may hence maintain leukemia remission. Thirdly, TLE3ΔWDR conferred on CAR-T cells advantages in proliferation and survival, which allowed their early and sustained expansion upon encountering leukemia cells. The beneficial effects of overexpressing engineered TLE3ΔWDR were more robust than those of overexpressing c-Jun, Foxo1, and Batf3 reported in the literature [Lynn, R C et al. Nature (2019) 576:293-300; Sco, H. et al. Nat. Immunol. (2021) 22:983-995; Chan, J D et al. Nature (2024) 629:201-210; Doan, A. E. et al. Nature (2024) 629:211-218]. Collectively, our comprehensive functional and molecular analyses demonstrated that TLE3ΔWDR enhances CAR-T cell function in tumor control, long-term persistence, and preventing exhaustion. Our invention represents a novel approach to enhance CAR-T cell function in tumor immunotherapy.

Figure 11A:
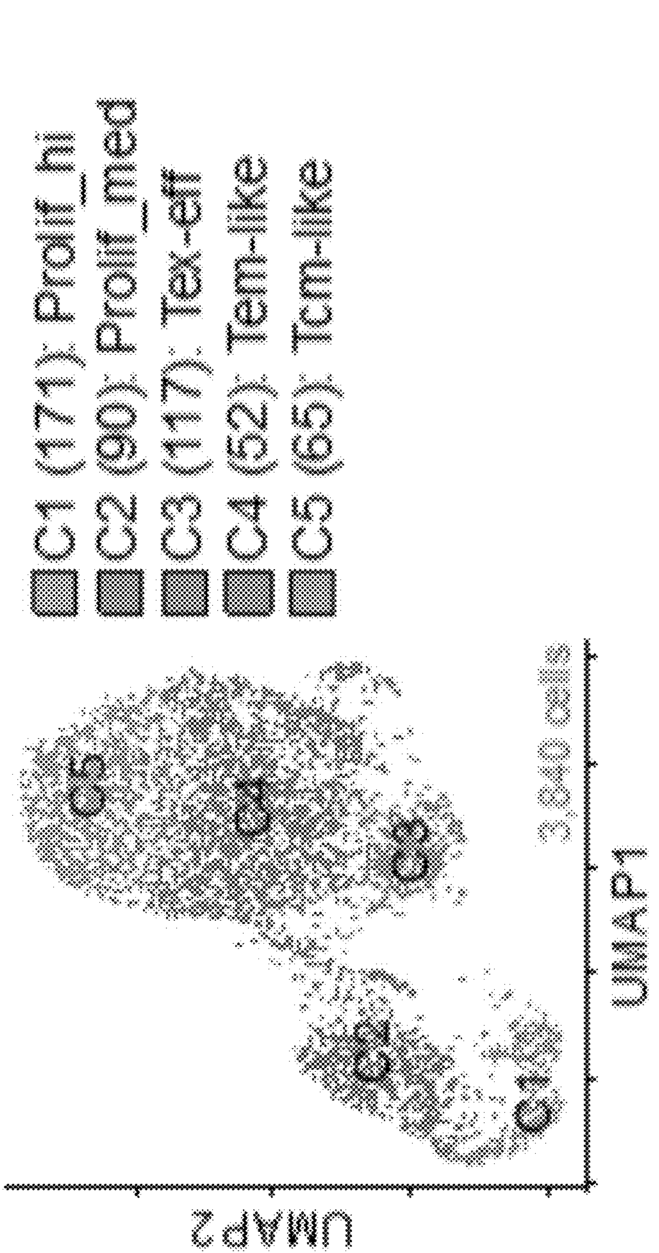

Example 8. TLE3ΔWDR Promotes Acquisition of Memory T Cell Features in CAR-T Cells In Vivo To better define the molecular mechanisms by which TLE3ΔWDR enhances CAR-T cell function, we perform single cell RNA-seq on sort-purified control or TLE3ΔWDR+ CAR-T cells from the spleens of NSG recipient mice on 12 dpt (day post tumor inoculation) when the leukemia burden was similar between recipients of control and TLE3ΔWDR+ CAR-T cells. We took the CITE-seq approach (1) so that each cell type was distinguishable via hashtag antibodies and both cell types were processed in the same reaction for library preparation. This approach avoided batch effect and ensured fair comparison of transcriptomes of control and TLE3ΔWDR+ CAR-T cells. We first focused on CD8+ CAR-T cells, which were resolved into five distinct clusters (FIG. 11A). Marker gene analysis revealed that cluster 1 (C1) and C2 cells were proliferative, expressing high levels of MKI67 (encoding Ki-67, a nuclear marker of cell proliferation) (2) and CDKI (encoding cyclin-dependent kinase 1) (FIG. 11C), which was particularly evident in C1 cells. C3 cells had active expression of genes in the exhaustion program (including TOX and PRDMI transcription factors, LAG3 and HAVCR3/TIM3 co-inhibitory receptors) (3) and genes in the effector program (including TBX21/T-BET, ID2, and RUNX3 transcription factors, GZMB/granzyme B cytotoxic molecule, and KLRG1 and CX3CR 1 markers) (4) (FIG. 11C), hence named Tex-eff cells. In contrast, C5 cells expressed central memory T ($T_{cm}$) cell-characteristic genes, including TCF7/TCF1, LEF1, and EOMES transcription factors, CCR7, SELL/CD62L and IL7R markers (5, 6) (FIG. 11C), hence named $T_{cm}$-like cells. On the other hand, C4 cells had modest features of both C3 $T_{ex\text{-}eff}$ and C5 $T_{cm}$-like cells and were thus considered as effector memory T ($T_{em}$)-like cells.

Figure 11B:
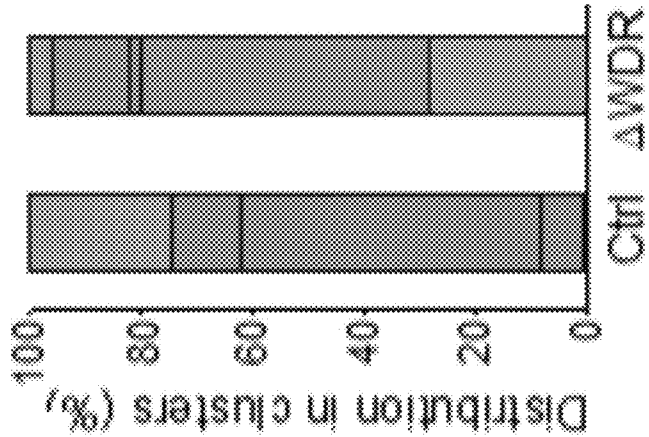

Analysis of CAR-T cell distribution showed that control CAR-T cells were predominantly in C1 and C2 proliferative and C3 Tex-eff clusters, with minor contribution to $T_{em}$-like C4 cells (FIG. 11B). In contrast, TLE3ΔWDR+ CAR-T cells sustained the pool of C2 proliferative cells, greatly expanded the C4 $T_{em}$-like and C5 $T_{cm}$-like at the expense of $T_{ex\text{-}eff}$ cells (FIG. 11B). These data demonstrated that ectopic expression of TLE3ΔWDR resulted in robust molecular rewiring and reprogrammed CAR-T cells to rapidly acquire memory-like features, since the early response stage.

REFERENCES

1. M. Stoeckius et al., Simultaneous epitope and transcriptome measurement in single cells. Nat Methods 14, 865-868 (2017).
2. K. Stamatiou et al., Ki-67 is necessary during DNA replication for fork protection and genome stability. Genome Biol 25, 105 (2024).
3. C. U. Blank et al., Defining 'T cell exhaustion'. Nat Rev Immunol 19, 665-674 (2019).
4. M. Philip, A. Schietinger, CD8 (+) T cell differentiation and dysfunction in cancer. Nat Rev Immunol 22, 209-223 (2022).
5. M. D. Martin, V. P. Badovinac, Defining Memory CD8 T Cell. Front Immunol 9, 2692 (2018).
6. X. Zhao, Q. Shan, H. H. Xue, TCF1 in T cell immunity: a broadened frontier. Nat Rev Immunol 22, 147-157 (2022).

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A chimeric antigen receptor (CAR) immunotherapy for treating a hematologic cancer comprising:

(a) genetically modifying a population of immune effector cells comprising T cell receptors (TCRs) to stably express at least one chimeric antigen receptor (CAR), wherein the ectodomain of the CAR specifically binds a cancer antigen, and wherein the CAR comprises an extracellular antigen recognition domain, a spacer/hinge region and transmembrane domain, and an intracellular signal transduction domain, wherein the intracellular signal transduction domain of the CAR comprises 4-1BB; a CD3ζ T cell activation chain; and a truncated transducer-like enhancer 3 (TLE3) molecule;

(b) expanding the population of CAR-containing immune effector cells in the presence of one or more cytokines in vitro to achieve a therapeutic dose, wherein the population of CAR-containing immune effector cells expresses a non-exhausted memory T cell phenotype; and (c) infusing eligible subjects with the CAR-containing immune effector memory T cell phenotype population of cells as needed until all cancer in the body is destroyed.

2. The CAR-immunotherapy according to claim 1, wherein the hematologic cancer is a leukemia, a lymphoma or a myeloma.

3. The CAR immunotherapy according to claim 1, wherein
the truncated TLE3 molecule is a C-terminus truncated TLE3 (TLE3ΔWDR) protein.

4. The CAR immunotherapy according to claim 3, wherein the CAR is linked to the engineered truncated TLE molecule via P2A peptide, which allows simultaneous translation of both proteins in the same immune effector cell.

5. The CAR immunotherapy according to claim 1, wherein
a) the target antigen of the CAR is CD19;
b) the target antigen of the CAR is CD20;
c) the target antigen of the CAR is CD22;
d) the target antigen of the CAR is NKG2D-1;
e) the target antigen of the CAR is CD33;
f) the target antigen of the CAR is BCMA, or
g) the target antigen of the CAR is CD123.

6. The CAR immunotherapy according to claim 5, wherein the CAR containing population of immune effector cells recognizes two or more tumor associated antigens simultaneously.

7. The CAR immunotherapy according to claim 1 wherein:
a) the immune effector cell population is engineered to express the CAR comprising the truncated TLE3 molecule by lentiviral transduction;
b) the immune effector cell population is a CD3+ T cell population; and
c) the T cell population comprises CD4+ T cells, CD8+ T cells, or both.

8. The CAR immunotherapy according to claim 1, wherein
a) source of the immune effector cell is peripheral blood or umbilical cord blood;
b) the population of immune effector cells is autologous to the subject; or
c) the population of immune effector cells is allogeneic to the subject.

9. The CAR immunotherapy according to claim 1, wherein when the engineered TLE3 molecule is a C-terminus truncated TLE3 (TLE3ΔWDR) protein, compared to a no-TLE3 CAR immune effector control,
a. expression of the TLE3ΔWDR construct in CAR-containing immune effector cells enhances CAR-immune effector cell function despite chronic antigen stimulation; and/or
b. expression of the TLE3ΔWDR construct in stimulated CAR-containing immune effector cells promotes activation of genes that promote anti-tumor activity and also represses genes involved in excessive effector function, exhaustion or both; and/or
c. expression of the TLE3ΔWDR construct in stimulated CAR-containing immune effector cells reduces expression of at least one inhibitory receptor comprising PD-1, CTLA-4, LAG3, TIGIT, or a combination thereof; and/or
d. expression of the CAR-TLE3ΔWDR construct in stimulated CAR-containing immune effector cells induces transcriptomic changes comprising differential expression of genes that enhance the anti-tumor response comprising proliferation of the CAR-containing immune effector cells; enhances persistence of the CAR-containing immune effector cells and maintains immune homeostasis despite chronic antigen stimulation; and/or
e. expression of the CAR-TLE3ΔWDR construct in stimulated CAR-containing immune effector cells reprograms the immune effector cells to acquire stem-like, memory cell characteristics, central memory cell characteristics, effector memory cell characteristics, or a combination thereof including production of IFN and TNF, expression of TCF-1, TOX, or both, and/or
f. expression of the TLE3ΔWDR construct in CAR-containing immune effector cells enhances CAR-immune effector cell function after rechallenge with the cancer.

10. The CAR immunotherapy according to claim 9, wherein the activation of genes that promote anti-tumor activity comprise the activation of TLE3, AEBP1, ARRB1, EPAS1, MYLB1, TCEA3, ZNF629, E2F2, SMARCA2, ITGAX, FGFR1, PAGFRB, COL6A2, PIK3R6, or a combination thereof.

11. The CAR immunotherapy according to claim 9, wherein the repression of genes involved in excessive effector function, exhaustion, or both comprise repression of BCL2L11, BMF, NEK6, PIM3, SRGN, ETS2, TBX21, ID2, PLAGL2, NUS1, ACSL6, PAM, or a combination thereof.

12. The CAR immunotherapy according to claim 4, wherein ectopic expression of the truncated TLE3 molecule is effective to selectively antagonize normal TLE3 activity.

* * * * *